(12) United States Patent
Wurster et al.

(10) Patent No.: US 7,915,443 B2
(45) Date of Patent: Mar. 29, 2011

(54) SULFOXIMINES AS KINASE INHIBITORS

(75) Inventors: Julie A. Wurster, Irvine, CA (US); Clarence Eugene Hull, III, Trabuco Canyon, CA (US); Richard C. Yee, Tustin, CA (US); Sougato Boral, Santa Ana, CA (US); Shimiao Wang, Irvine, CA (US); Thomas C. Malone, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 107 days.

(21) Appl. No.: 11/941,753

(22) Filed: Nov. 16, 2007

(65) Prior Publication Data

US 2009/0099181 A1 Apr. 16, 2009

Related U.S. Application Data

(60) Provisional application No. 60/866,080, filed on Nov. 16, 2006.

(51) Int. Cl.
C07D 211/72 (2006.01)
C07D 241/00 (2006.01)
C07C 331/00 (2006.01)

(52) U.S. Cl. ........ 560/317; 544/336; 546/290; 546/304; 546/316; 546/323

(58) Field of Classification Search .................. 560/317
See application file for complete search history.

(56) References Cited

FOREIGN PATENT DOCUMENTS

| EP | 0023392 | 2/1981 |
|---|---|---|
| EP | 0109575 | 5/1984 |
| WO | WO 00/27823 | 5/2000 |
| WO | WO 02/50071 | 6/2002 |
| WO | WO 2004/014300 | 2/2004 |
| WO | WO 2005/037800 | 4/2005 |
| WO | WO2006044823 | 4/2006 |
| WO | WO2006082373 | 8/2006 |
| WO | WO2006082404 | 8/2006 |
| WO | WO 2006/099974 | 9/2006 |
| WO | WO2006013449 | 10/2006 |
| WO | WO2007075869 | 7/2007 |

OTHER PUBLICATIONS

Patani et. al., "Bioisosterism: A Rational Approach in Drug Design", Chem. Rev. 1996, pp. 3147-3176.*
Hcaplus 1974:504104, "Rearrangement processes in the mass spectra of N-substituted sulfoximines", Whittle et. al., 1974.*
Hcaplus 1975:139783, "N-9o- and p-nitrobenzoyl)-sulfoximine intermediates", Herrmann et. al., 1975.*
Ishihara et al, "Preparation of benzylamine derivatives having excellent ileal bile acid transporter inhibitory activity", Chemical Abstracts Service—XP002477766, 1999.
Suzuki et al, "Preparation of benzene derivatives containing amide moiety as ACC inhibitors activity", XP002477767, STN—1216425-2005.
Matsusawa et al, "Heat-sensitive recording materials containing specific recording materials containing specific color-developing materials", XP002477768, STN—547198-2002.
Konishi et al, "Preparation of styrenecarboxamides as leukotriene antagonists", STN—XP002477769, STN-191363-1994.
Database online, "Pyridyloxybenzamide derivatives as herbicides", XP002477770, STN-522316-1983.
Database Chemcats, "Interchim Intermediates", XP002477771, 2035822323, 2007.

* cited by examiner

*Primary Examiner* — Janet L Andres
*Assistant Examiner* — Heidi Reese
(74) *Attorney, Agent, or Firm* — Joel B. German; Debra D. Condino

(57) ABSTRACT

The present invention relates to organic molecules capable of modulating tyrosine kinase signal transduction in order to regulate, modulate and/or inhibit abnormal cell proliferation.

44 Claims, No Drawings

SULFOXIMINES AS KINASE INHIBITORS

CROSS REFERENCE TO RELATED APPLICATIONS

This application is based on, and claims the benefit of, U.S. Provisional Application No. 60/866,080, filed Nov. 16, 2006, and which is incorporated herein by reference.

BACKGROUND OF THE INVENTION

1. Field of the Invention

The present invention relates to novel compounds capable of modulating, regulating and/or inhibiting tyrosine kinase signal transduction. The present invention is also directed to methods of regulating, modulating or inhibiting tyrosine kinases, whether of the receptor or non-receptor class, for the prevention and/or treatment of disorders related to unregulated tyrosine kinase signal transduction, including cell growth, metabolic, and blood vessel proliferative disorders.

2. Description of the Related Art

Protein tyrosine kinases (PTKs) comprise a large and diverse class of proteins having enzymatic activity. The PTKs play an important role in the control of cell growth and differentiation.

For example, receptor tyrosine kinase mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic homeostasis, and responses to the extracellular microenvironment).

With respect to receptor tyrosine kinases, it has been shown also that tyrosine phosphorylation sites function as high-affinity binding sites for SH2 (src homology) domains of signaling molecules. Several intracellular substrate proteins that associate with receptor tyrosine kinases (RTKs) have been identified. They may be divided into two principal groups: (1) substrates which have a catalytic domain; and (2) substrates which lack such domain but serve as adapters and associate with catalytically active molecules. The specificity of the interactions between receptors or proteins and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

Aberrant expression or mutations in the PTKs have been shown to lead to either uncontrolled cell proliferation (e.g. malignant tumor growth) or to defects in key developmental processes. Consequently, the biomedical community has expended significant resources to discover the specific biological role of members of the PTK family, their function in differentiation processes, their involvement in tumorigenesis and in other diseases, the biochemical mechanisms underlying their signal transduction pathways activated upon ligand stimulation and the development of novel drugs.

Tyrosine kinases can be of the receptor-type (having extracellular, transmembrane and intracellular domains) or the non-receptor type (being wholly intracellular).

The RTKs comprise a large family of transmembrane receptors with diverse biological activities. The intrinsic function of RTKs is activated upon ligand binding, which results in phosphorylation of the receptor and multiple cellular substrates, and subsequently in a variety of cellular responses.

At present, at least nineteen (19) distinct RTK subfamilies have been identified. One RTK subfamily, designated the HER subfamily, is believed to be comprised of EGFR, HER2, HER3 and HER4. Ligands to the Her subfamily of receptors include epithelial growth factor (EGF), TGF-α, amphiregulin, HB-EGF, betacellulin and heregulin.

A second family of RTKs, designated the insulin subfamily, is comprised of the INS-R, the IGF-1R and the IR-R. A third family, the "PDGF" subfamily includes the PDGF α and β receptors, CSFIR, c-kit and FLK-II. Another subfamily of RTKs, identified as the FLK family, is believed to be comprised of the Kinase insert Domain-Receptor fetal liver kinase-1 (KDR/FLK-1), the fetal liver kinase 4 (FLK-4) and the fins-like tyrosine kinase 1 (flt-1). Each of these receptors was initially believed to be receptors for hematopoietic growth factors. Two other subfamilies of RTKs have been designated as the FGF receptor family (FGFR1, FGFR2, FGFR3 and FGFR4) and the Met subfamily (c-met and Ron).

Because of the similarities between the PDGF and FLK subfamilies, the two subfamilies are often considered together. The known RTK subfamilies are identified in Plowman et al, 1994, DN&P 7(6): 334-339, which is incorporated herein by reference.

The non-receptor tyrosine kinases represent a collection of cellular enzymes which lack extracellular and transmembrane sequences. At present, over twenty-four individual non-receptor tyrosine kinases, comprising eleven (11) subfamilies (Src, Frk, Btk, Csk, Abl, Zap70, Fes/Fps, Fak, Jak, Ack and LIMK) have been identified. At present, the Src subfamily of non-receptor tyrosine kinases is comprised of the largest number of PTKs and include Src, Yes, Fyn, Lyn, Lck, Blk, Hck, Fgr and Yrk. The Src subfamily of enzymes has been linked to oncogenesis. A more detailed discussion of non-receptor tyrosine kinases is provided in Bolen, 1993, Oncogen 8: 2025-2031, which is incorporated herein by reference.

Many of the tyrosine kinases, whether an RTK or non-receptor tyrosine kinase, have been found to be involved in cellular signaling pathways leading to cellular signal cascades leading to pathogenic conditions, including cancer, psoriasis and hyper immune response.

In view of the surmised importance of PTKs to the control, regulation and modulation of cell proliferation the diseases and disorders associated with abnormal cell proliferation, many attempts have been made to identify receptor and non-receptor tyrosine kinase "inhibitors" using a variety of approaches, including the use of mutant ligands (U.S. Pat. No. 4,966,849), soluble receptors and antibodies (PCT Application No. WO 94/10202; Kendall & Thomas, 1994, Proc. Nat'l Acad. Sci. 90: 10705-09; Kim, et al, 1993, Nature 362: 841-844), RNA ligands (Jellinek, et al, Biochemistry 33: 10450-56); Takano, et al, 1993, Mol. Bio. Cell 4:358A; Kinsella, et al, 1992, Exp. Cell Res. 199: 56-62; Wright, et al, 1992, J. Cellular Phys. 152: 448-57) and tyrosine kinase inhibitors (PCT Application Nos. WO 94/03427; WO 92/21660; WO 91/15495; WO 94/14808; U.S. Pat. No. 5,330, 992; Mariani, et al, 1994, Proc. Am. Assoc. Cancer Res. 35: 2268).

More recently, attempts have been made to identify small molecules which act as tyrosine kinase inhibitors. For example, bis monocyclic, bicyclic or heterocyclic aryl compounds (PCT Application No. WO 92/20642), vinylene-azaindole derivatives (PCT Application No. WO 94/14808) and 1-cyclopropyl-4-pyridyl-quinolones (U.S. Pat. No. 5,330,992) have been described generally as tyrosine kinase inhibitors. Styryl compounds (U.S. Pat. No. 5,217,999), styryl-substituted pyridyl compounds (U.S. Pat. No. 5,302, 606), certain quinazoline derivatives (EP Application No. 0 566 266 A1), seleoindoles and selenides (PCT Application No. WO 94/03427), tricyclic polyhydroxylic compounds (PCT Application No. WO 92/21660) and benzylphosphonic acid compounds (PCT Application No. WO 91/15495) have been described as compounds for use as tyrosine kinase inhibitors for use in the treatment of cancer.

The identification of effective small compounds which specifically inhibit signal transduction by modulating the activity of receptor and non-receptor tyrosine kinases to regulate and modulate abnormal or inappropriate cell proliferation is therefore desirable and one object of this invention.

In addition, certain small compounds are disclosed in U.S. Pat. Nos. 5,792,783; 5,834,504; 5,883,113; 5,883,116 and 5,886,020 as useful for the treatment of diseases related to unregulated TKS transduction. See also patents and PCT Published Patent Application WO 02/29630; U.S. Pat. Nos. 6,599,173; 6,765,012; 6,699,863; 6,541,504 and 6,747,025. These patents are hereby incorporated by reference in its entirety for the purpose of disclosing starting materials and methods for the preparation thereof, screens and assays to determine a claimed compound's ability to modulate, regulate and/or inhibit cell proliferation, indications which are treatable with said compounds, formulations and routes of administration, effective dosages, etc.

BRIEF SUMMARY OF THE INVENTION

The present invention relates to organic molecules capable of modulating, regulating and/or inhibiting tyrosine kinase signal transduction. Such compounds are useful for the treatment of diseases related to unregulated TKS transduction, including cell proliferative diseases such as cancer, atherosclerosis, restenosis, metabolic diseases such as diabetes, inflammatory diseases such as psoriasis and chronic obstructive pulmonary disease, vascular proliferative disorders such as diabetic retinopathy, age-related macular degeneration and retinopathy of prematurity, autoimmune diseases and transplant rejection.

In one illustrative embodiment, the compounds of the present invention have the following general formula I:

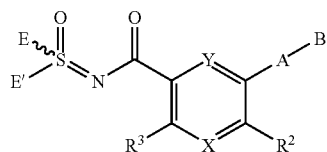

wherein:
X is $CR^4$ or N;
Y is $CR^1$ or N;

$R^1$ is selected from the group consisting of hydrogen, alkyl, halogen, $OR^4$, CN, $NO_2$, $COR^4$, $(CH^2)_aOR^4$, $(CH_2)_aN(R^4)_2$, $C(O)N(R^4)_2$ and $N(R^4)_2$;

$R^2$ is selected from the group consisting of hydrogen, halogen, alkyl, $OR^4$, CN, $NO_2$, $SO_2N(R^4)_2$, $COR^4$, $(CH_2)_aOR^4$, $(CH_2)_aN(R^4)_2$, $C(O)N(R^4)_2$, $N(R^4)_2$ and $N(R^6)(CR^7R^8)_aR^{10}$;

$R^3$ is selected from the group consisting of hydrogen, halogen, alkyl, $OR^4$, CN, $NO_2$, $SO_2N(R^4)_2$, $COR^4$, $(CH_2)_aOR^4$, $(CH_2)_aN(R^4)_2$, $C(O)N(R^4)_2$, $N(R^4)_2$ and $N(R^6)(CR^7R^8)_aR^{10}$;

$R^4$ is hydrogen or $C_1$ to $C_4$ alkyl;

A is selected from the group consisting of C≡C, CH═CH, $CH_2CH_2$, $CH_2O$, $CF_2O$, $OCH_2$, $OCF_2$, O, $N(R^4)$, C(O), $S(O)_e$, $NR^7C(O)$, $C(O)NR^7$ and $N(R^7)C(O)NR^7$;

B is selected from the group consisting of hydrogen, alkyl and alkyloxyalkyl or B may be a 5 or 6 membered carbocyclic aryl or heterocyclic aryl group;

E is a 5 or 6 membered carbocyclic aryl or heterocyclic aryl group;

E' is selected from the group consisting of alkyl, $CF_3$, $(CR^7R^8)_aC(O)OR^{10}$, $(CR^7R^8)_aC(O)N(R^{10})_2$, $(CR^7R^8)_aC(O)N(OR^{10})(R^{10})$, $(CR^7R^8)_a(OR^{10})$, $(CR^7R^8)_aN(R^{10})_2$, and $(CR^7R^8)_aR^{10}$; wherein $R^7$ and $R^8$ are selected from the group consisting of H, halogen, hydroxyl, and alkyl or $CR^7R^8$ may represent a carbocyclic ring of from 3 to 6 carbons; and $R^{10}$ is selected from the group consisting of hydrogen, halogen, alkyl, hydroxyl, hydroxymethyl, carbocyclic aryl, heterocyclic aryl, $(CR^7R^8)_aC(O)OR^6$, $(CR^7R^8)_aC(O)R^6$, $(CR^7R^8)_aC(O)N(R^6)_2$, $(CR^7R^8)_aC(O)N(OR^6)(R^6)$, $(CR^7R^8)_a(OR^6)$, $(CR^7R^8)_aN(R^6)_2$ and $(CR^7R^8)_aR^6$, wherein $R^6$ is selected from the group consisting of hydrogen, carboalkyl, alkylamine, alkylhydroxy, and alkyloxyalkyl or $R^6$ is a 5 or 6 membered carbocyclic or heterocyclic group;

a is 0 or an integer of from 1 to 5;
b is an integer of from 2 to 5;
c is 0 or an integer of from 1 to 4;
d is 0 or an integer of from 1 to 5;
e is 0 or an integer of from 1 to 2 and further including prodrugs, pharmaceutically acceptable salts, racemic mixtures and enantiomers of said compound.

Preferably, B is a carbocyclic aryl or heterocyclic aryl represented by formula II below:

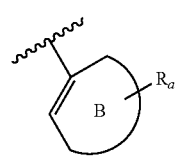

wherein said carbocyclic aryl and heterocyclic aryl groups are selected from the group consisting of:

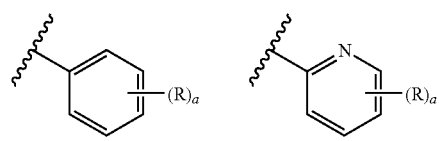

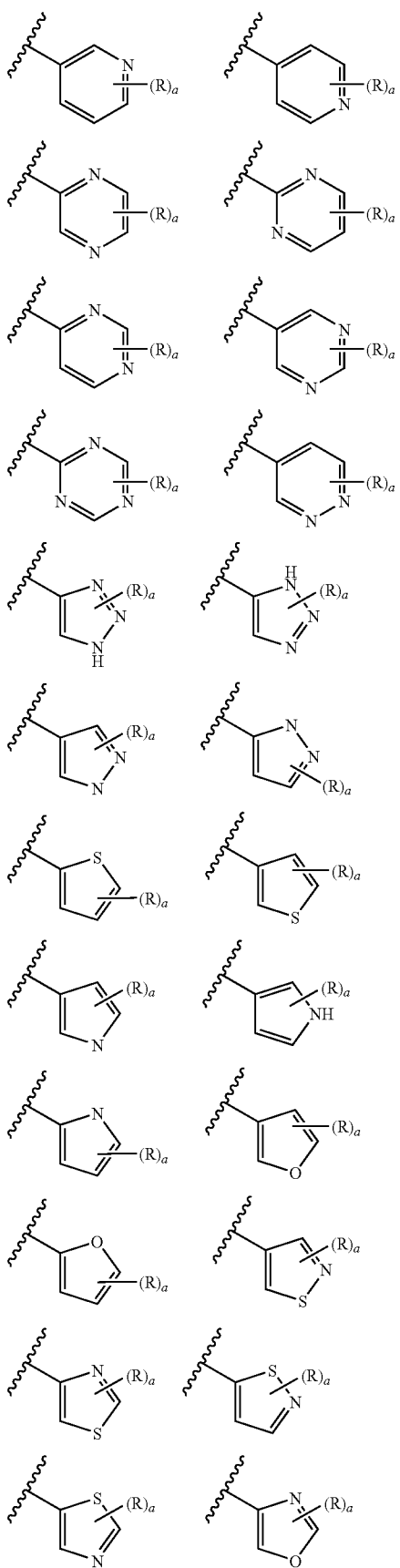

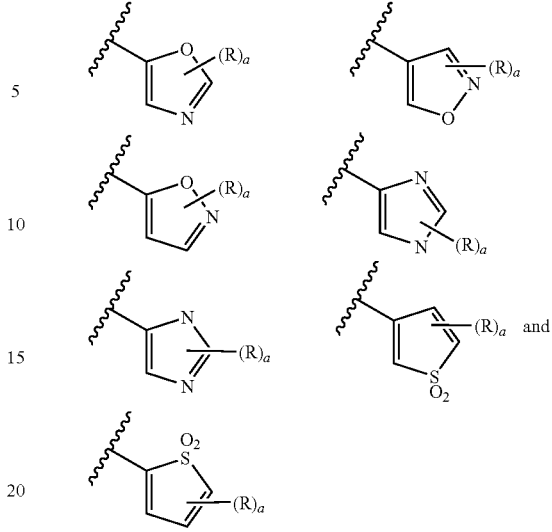

wherein R is selected from the group consisting of halogen, alkyl, $CF_3$, $OCF_3$, $OCF_2H$, $CH_2CN$, CN, $SR^6$, $OP(O)(OR^6)_2$, $OCH_2O$, $HC=N-NH$, $N=CH-S$, $(CR^7R^8)_aC(O)R^6$, $O(CR^7R^8)_aC(O)R^6$, $N(R^6)(CR^7R^8)_aC(O)R^6$, $C(O)(CR^7R^8)_aC(O)R^6$, $S(O)_e(CR^7R^8)_aC(O)R^6$, $(CR^7R^8)_aC(O)OR^6$, $O(CR^7R^8)_aC(O)OR^6$, $N(R^6)(CR^7R^8)_aC(O)OR^6$, $C(O)(CR^7R^8)_aC(O)OR^6$, $S(O)_e(CR^7R^8)_aC(O)OR^6$, $(CR^7R^8)_aC(O)N(R^6)_2$, $O(CR^7R^8)_aC(O)N(R^6)_2$, $N(R^6)(CR^7R^8)_aC(O)N(R^6)_2$, $C(O)(CR^7R^8)_aC(O)N(R^6)_2$, $S(O)_e(CR^7R^8)_aC(O)N(R^6)_2$, $(CR^7R^8)_aN(R^6)C(O)N(R^6)_2$, $O(CR^7R^8)_bN(R^6)C(O)N(R^6)_2$, $N(R^6)(CR^7R^8)_bN(R^6)C(O)N(R^6)_2$, $C(O)(CR^7R^8)_aN(R^6)C(O)N(R^6)_2$, $S(O)_e(CR^7R^8)_aN(R^6)C(O)N(R^6)_2$, $(CR^7R^8)_aC(O)N(OR^6)(R^6)$, $O(CR^7R^8)_aC(O)N(OR^6)(R^6)$, $N(R^6)(CR^7R^8)_aC(O)N(OR^6)(R^6)$, $C(O)(CR^7R^8)_aC(O)N(OR^6)(R^6)$, $S(O)_e(CR^7R^8)_aC(O)N(OR^6)(R^6)$, $(CR^7R^8)_a(OR^6)$, $O(CR^7R^8)_a(OR^6)$, $N(R^6)(CR^7R^8)_a(OR^6)$, $C(O)(CR^7R^8)_a(OR^6)$, $S(O)_a(CR^7R^8)_a(OR^6)$, $(CR^7R^8)N(R^6)_2$, $O(CR^7R^8)_bN(R^6)_2$, $N(R^6)(CR^7R^8)_bN(R^6)_2$, $C(O)(CR^7R^8)_aN(R^6)_2$, $S(O)_e(CR^7R^8)_aN(R^6)_2$, $(CR^7R^8)_aR^6$, $O(CR^7R^8)_aR^6$, $N(R^6)(CR^7R^8)_aR^6$, $C(O)(CR^7R^8)_aR^6$ and, $S(O)_e(CR^7R^8)_aR^6$.

Most preferably $R^6$ is selected from the group consisting of hydrogen, alkyl, dilower alkyl amine or a heterocyclic group represented by the list below or $N(R^6)_2$ may represent a 3 to 7 membered heterocyclic group,

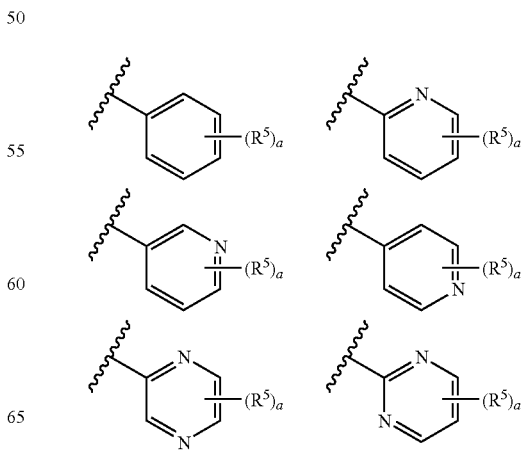

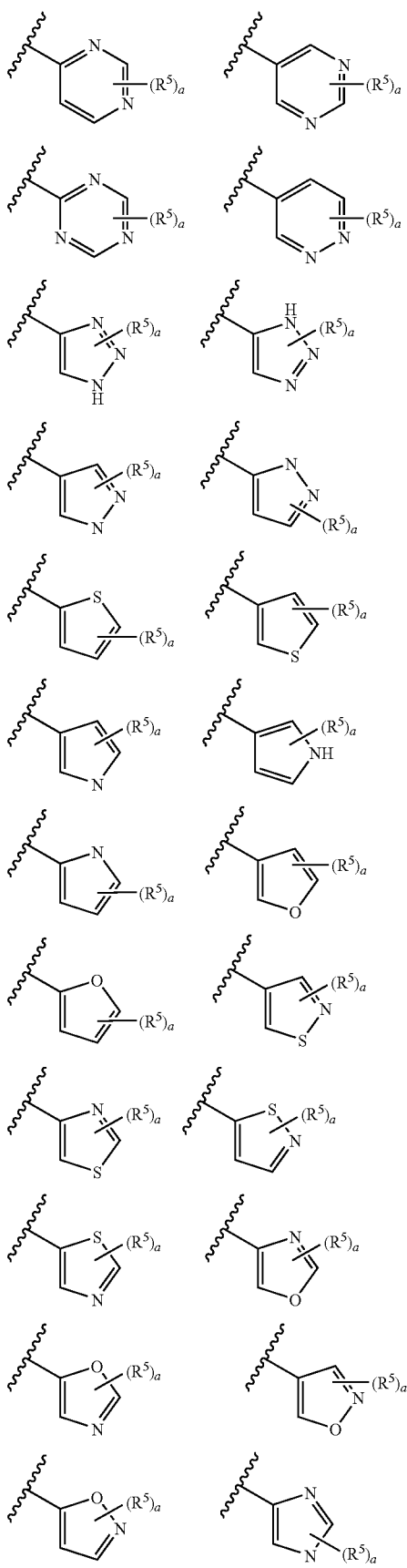
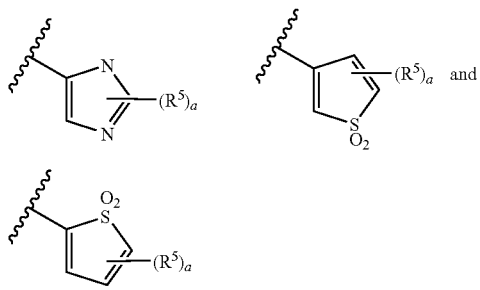
wherein R⁵ is hydrogen, halogen, simple alkyl, $CF_3$, hydroxyl, $OR^7$, $N(R^7)_2$ or NO2.
Preferably, E is a 5 or 6 membered carbocyclic aryl or heterocyclic aryl represented by formula III below:
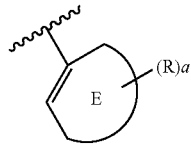
III
wherein said carbocyclic aryl and heterocyclic aryl is selected from the group consisting of:
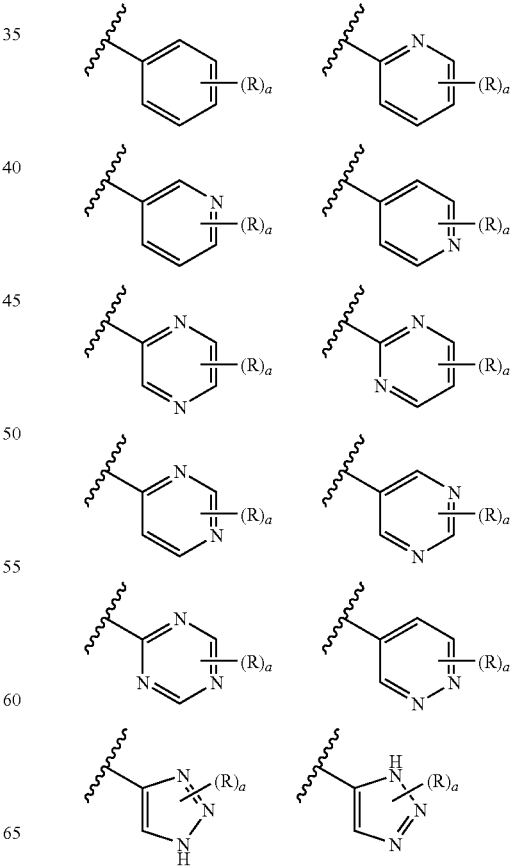

-continued

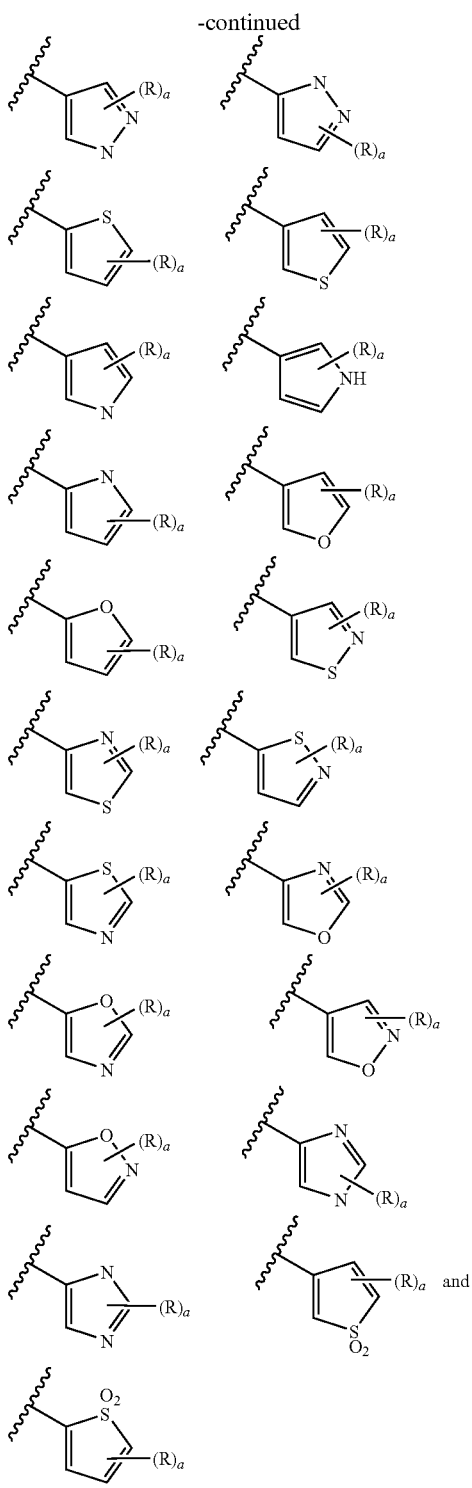

Compounds of formula I below are useful as kinase inhibitors. As such compounds of formula I will be useful for treating diseases related to unregulated tyrosine kinase signal transduction, for example, cancer, blood vessel proliferative disorders, fibrotic disorders, and neurodegenerative diseases. In particular compounds of the present invention are useful for treatment of mesangial cell proliferative disorders and metabolic diseases, diabetic retinopathy, age-related macular degeneration, retinopathy of prematurity, arthritis, restenosis, hepatic cirrhosis, atherosclerosis, psoriasis, diabetes mellitus, wound healing, inflammation and neurodegenerative diseases.

DETAILED DESCRIPTION OF THE INVENTION

The present invention is further directed to pharmaceutical compositions comprising a pharmaceutically effective amount of the above-described compounds and a pharmaceutically acceptable carrier or excipient. Such a composition is believed to modulate signal transduction by a tyrosine kinase, either by inhibition of catalytic activity, affinity to ATP or ability to interact with a substrate.

More particularly, the compositions of the present invention may be included in methods for treating diseases comprising proliferation, fibrotic or metabolic disorders, for example cancer, fibrosis, psoriasis, atherosclerosis, arthritis, and other disorders related to abnormal vasculogenesis and/or angiogenesis, such as diabetic retinopathy.

The following defined terms are used throughout this specification:

"Me" refers to methyl.
"Et" refers to ethyl.
"tBu" refers to t-butyl.
"iPr" refers to i-propyl.
"Ph" refers to phenyl.
"Pharmaceutically acceptable salt" refers to those salts which retain the biological effectiveness and properties of the free bases and which are obtained by reaction with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

"Alkyl" refers to a straight-chain, branched or cyclic saturated aliphatic hydrocarbon. Preferably, the alkyl group has 1 to 12 carbons. More preferably, it is a lower alkyl of from 1 to 7 carbons, most preferably 1 to 4 carbons. Typical alkyl groups include methyl, ethyl, propyl, isopropyl, butyl, isobutyl, tertiary butyl, pentyl, hexyl and the like. The alkyl group may be optionally substituted with one or more substituents are selected from the group consisting of hydroxyl, cyano, alkoxy, =O, =S, $NO_2$, halogen, dimethyl amino, and SH.

"Alkenyl" refers to a straight-chain, branched or cyclic unsaturated hydrocarbon group containing at least one carbon-carbon double bond. Preferably, the alkenyl group has 1 to 12 carbons. More preferably it is a lower alkenyl of from 1 to 7 carbons, most preferably 1 to 4 carbons. The alkenyl group may be optionally substituted with one or more substituents selected from the group consisting of hydroxyl, cyano, alkoxy, =O, =S, $NO_2$, halogen, dimethyl amino, and SH.

"Alkynyl" refers to a straight-chain, branched or cyclic unsaturated hydrocarbon containing at least one carbon-carbon triple bond. Preferably, the alkynyl group has 1 to 12 carbons. More preferably it is a lower alkynyl of from 1 to 7 carbons, most preferably 1 to 4 carbons. The alkynyl group may be optionally substituted with one or more substituents selected from the group consisting of hydroxyl, cyano, alkoxy, =O, =S, $NO_2$, halogen, dimethyl amino, and SH.

"Alkoxyl" refers to an "O-alkyl" group.

"Aryl" refers to an aromatic group which has at least one ring having a conjugated pi electron system and includes carbocyclic aryl, heterocyclic aryl and biaryl groups. The aryl group may be optionally substituted with one or more substituents selected from the group consisting of halogen, trihalomethyl, hydroxyl, SH, OH, $NO_2$, amine, thioether, cyano, alkoxy, alkyl, and amino.

"Alkaryl" refers to an alkyl that is covalently joined to an aryl group. Preferably, the alkyl is a lower alkyl.

"Carbocyclic ring" refers to a substituted or unsubstituted cyclic radical, including cycloalkyl, cycloalkenyl and carbocyclic aryl wherein the ring atoms are carbon and said substituents are selected from the group consisting of hydroxyl, cyano, alkoxy, =O, =S, NO$_2$, halogen, dimethyl amino, and SH.

"Carbocyclic aryl" refers to an aryl group wherein the ring atoms are carbon.

"Heterocyclic ring" refers to a substituted or unsubstituted cyclic radical including cycloalkyl, cycloalkenyl and heterocyclic aryl wherein 1 to 3 of the ring atoms are heteroatoms and the remainder of the ring atoms are carbon substituents are selected from the group consisting of hydroxyl, cyano, alkoxy, =O, =S, NO$_2$, halogen, dimethyl amino, and SH.

"Heterocyclic aryl" refers to an aryl group having from 1 to 3 heteroatoms as ring atoms, the remainder of the ring atoms being carbon. Heteroatoms include oxygen, sulfur, and nitrogen. Thus, heterocyclic aryl groups include furanyl, thienyl, pyridyl, pyrrolyl, N-lower alkyl pyrrolo, pyrimidyl, pyrazinyl, imidazolyl and the like.

"Hydrocarbyl" refers to a hydrocarbon radical having only carbon and hydrogen atoms. Preferably, the hydrocarbyl radical has from 1 to 20 carbon atoms, more preferably from 1 to 12 carbon atoms and most preferably from 1 to 7 carbon atoms.

"Substituted hydrocarbyl" refers to a hydrocarbyl radical wherein one or more, but not all, of the hydrogen and/or the carbon atoms are replaced by a halogen, nitrogen, oxygen, sulfur or phosphorus atom or a radical including a halogen, nitrogen, oxygen, sulfur or phosphorus atom, e.g. fluoro, chloro, cyano, nitro, hydroxyl, phosphate, thiol, etc.

"Amide" refers to —C(O)—NH—R', wherein R' is alkyl, aryl, alkylaryl or hydrogen.

"Thioamide" refers to —C(S)—NH—R', wherein R' is alkyl, aryl, alkylaryl or hydrogen.

"Amine" refers to a —N(R")R'" group, wherein R" and R'" are independently selected from the group consisting of alkyl, aryl, and alkylaryl.

"Thioether" refers to —S—R", wherein R" is alkyl, aryl, or alkylaryl.

"Sulfonyl" refers to —S(O)$_2$—R"", where R"" is aryl, C(CN)=C-aryl, CH$_2$CN, alkylaryl, sulfonamide, NH-alkyl, NH-alkylaryl, or NH-aryl.

The compounds of this invention may be prepared by the general scheme set forth in Scheme 1.

Scheme 1 - General Route to Acyl Sulfoximines

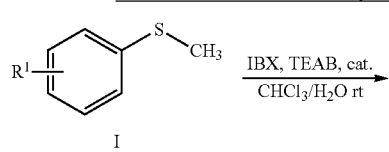

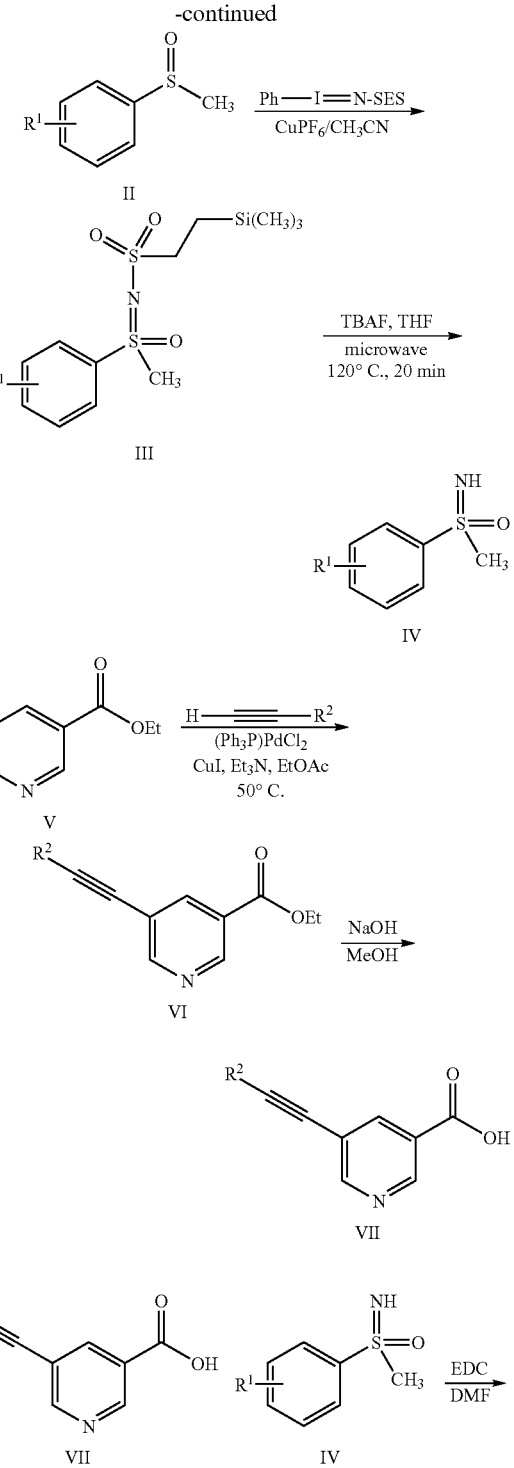

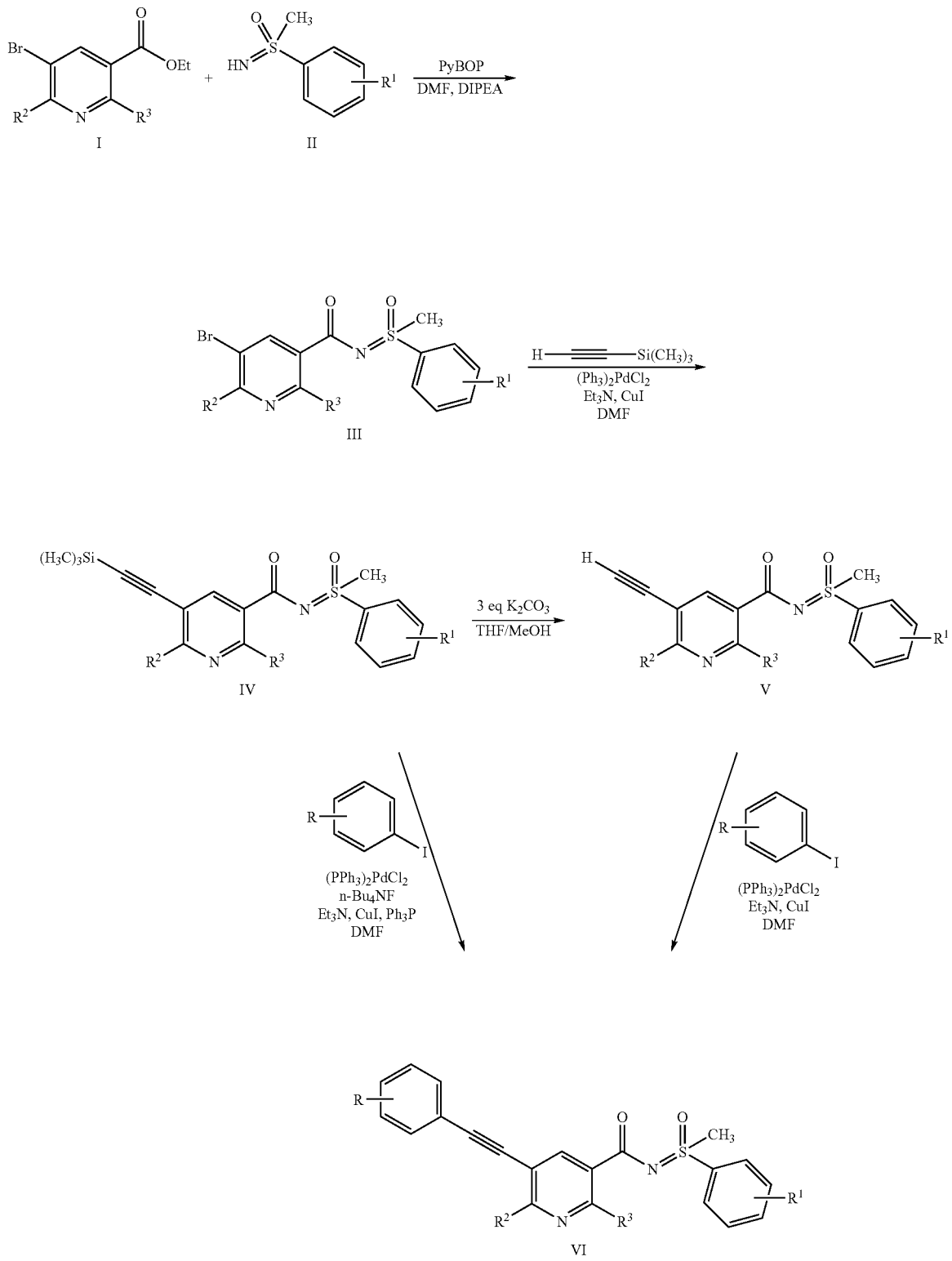

In particular the compounds of the present invention are selected from the compounds of Table 1, Table 2 and Table 2.1 below. In table 1 the compounds of the present invention are exemplified by any combination of Ar¹ and R² attached to the core template illustrated.
TABLE 1
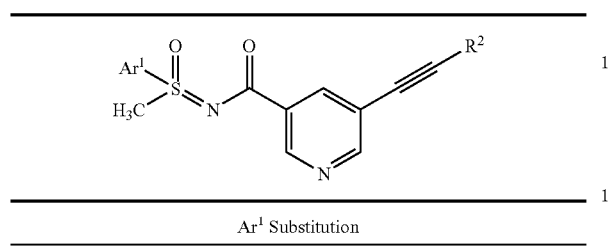
| Ar¹ Substitution |
|---|
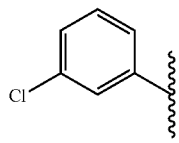
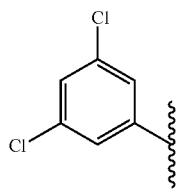
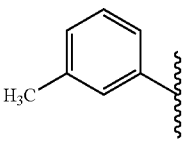
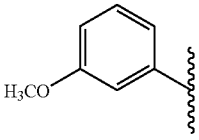
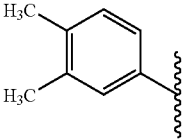
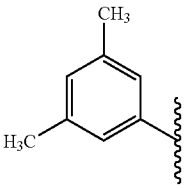
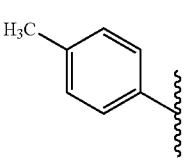
TABLE 1-continued
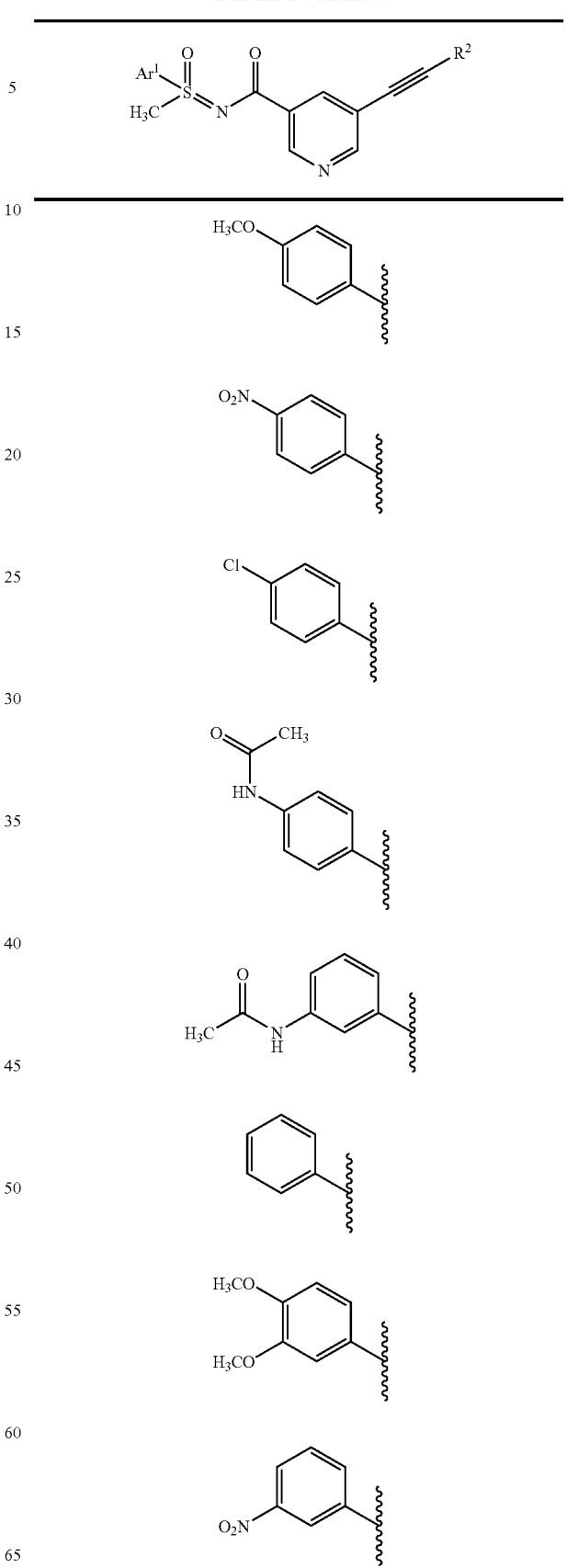

TABLE 1-continued
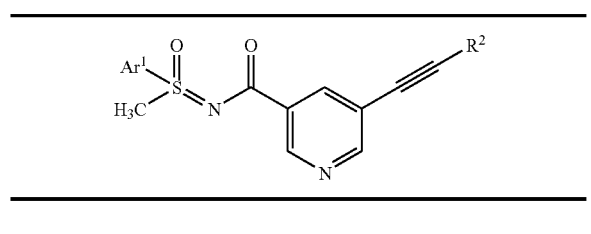
R² Substitution
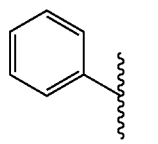
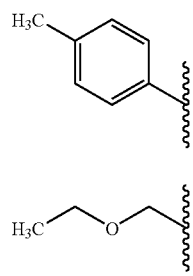
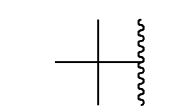
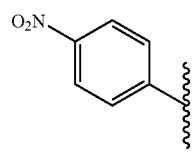
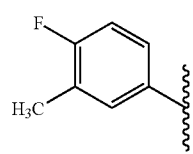
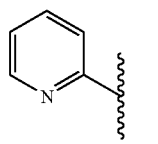
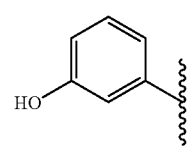
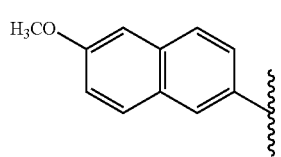
TABLE 1-continued
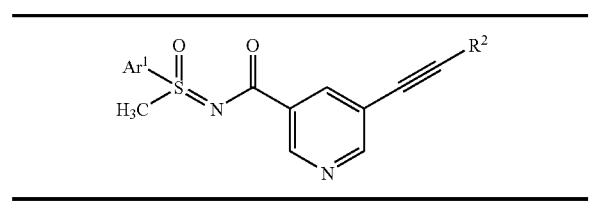
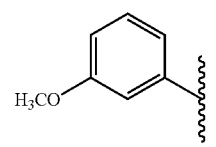
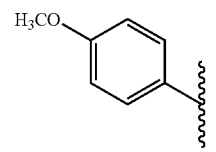
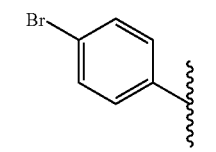
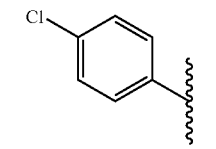
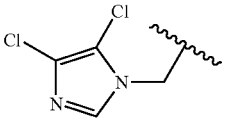
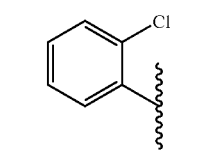
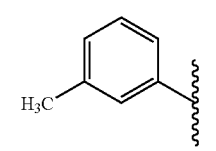
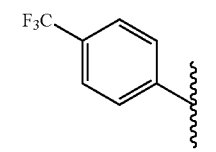
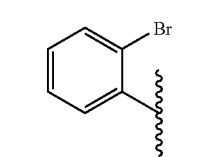

TABLE 1-continued
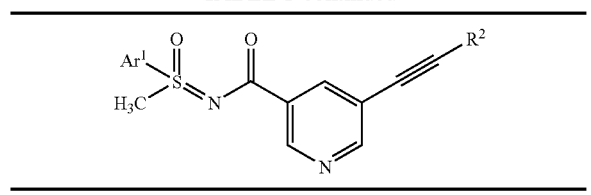
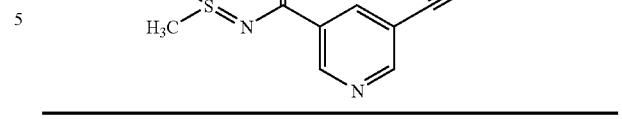
| | |
|---|---|
| 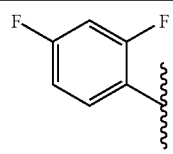 | 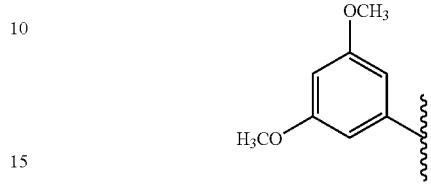 |
| 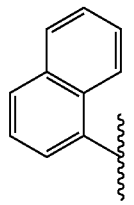 | 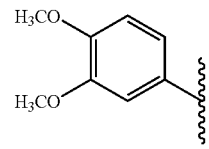 |
| 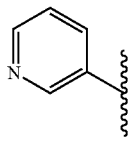 | 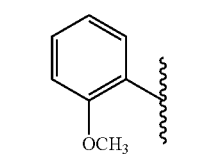 |
| 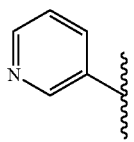 | 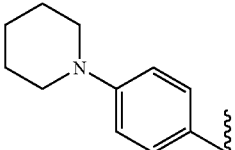 |
| 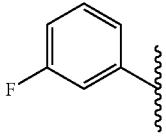 | 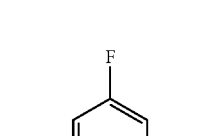 |
| 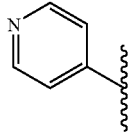 | 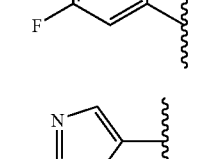 |
| 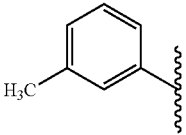 | 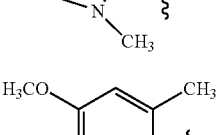 |
| 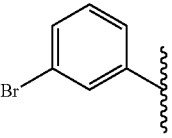 | 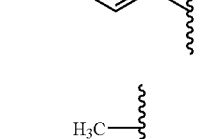 |
| 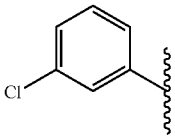 | 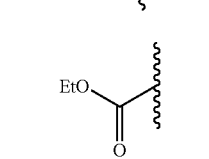 |

TABLE 1-continued
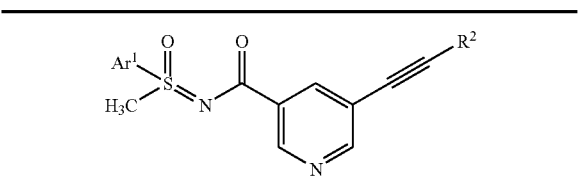
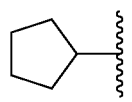
TABLE 1-continued
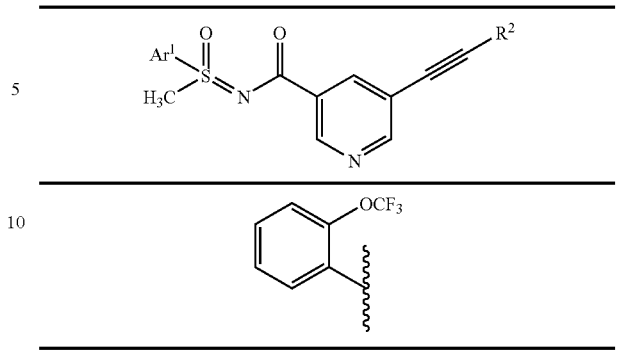
TABLE 2
| Example Number | Structure |
|---|---|
| Example 423 | 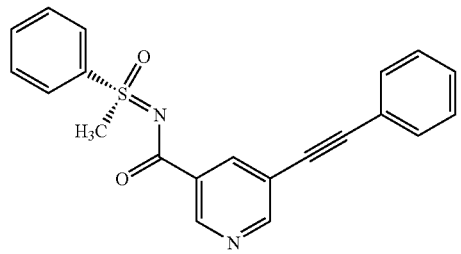 |
| Example 424 | 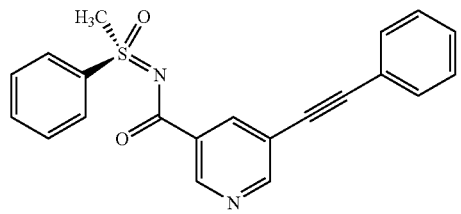 |
| Example 425 | 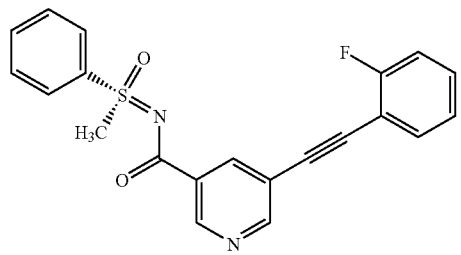 |
| Example 426 | 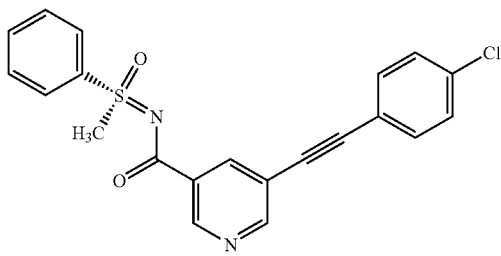 |

TABLE 2-continued

| Example Number | Structure |
|---|---|
| Example 427 | Phenyl-S(=O)(=N-)(CH3) attached via C(=O) to pyridine (3,5-disubstituted), with 5-position bearing C≡C-(3-hydroxyphenyl) |
| Example 428 | Phenyl-S(=O)(=N-)(CH3) attached via C(=O) to pyridine (3,5-disubstituted), with 5-position bearing C≡C-(4-phenoxyphenyl) |
| Example 429 | Phenyl-S(=O)(=N-)(CH3) attached via C(=O) to pyridine (3,5-disubstituted), with 5-position bearing C≡C-Si(CH3)3 |
| Example 430 | Phenyl-S(=O)(=N-)(CH3) attached via C(=O) to pyridine (3,5-disubstituted), with 5-position bearing C≡CH |
| Example 431 | Phenyl-S(=O)(=N-)(CH3) attached via C(=O) to pyridine (3,5-disubstituted), with 5-position bearing C≡C-(4-hydroxyphenyl) |
| Example 432 | Phenyl-S(=O)(=N-)(CH3) attached via C(=O) to pyridine (3,5-disubstituted), with 5-position bearing C≡C-(2-hydroxyphenyl) |

TABLE 2-continued

| Example Number | Structure |
|---|---|
| Example 433 | 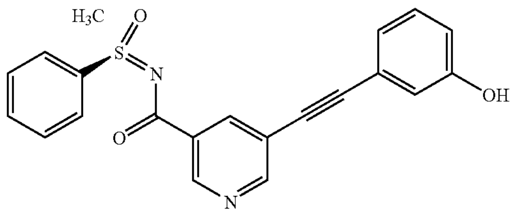 |
| Example 434 | 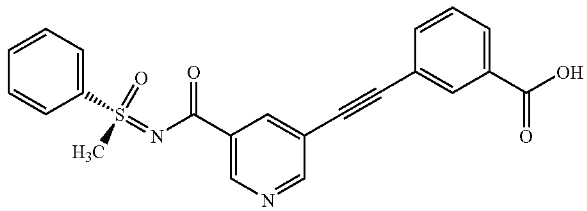 |
| Example 435 | 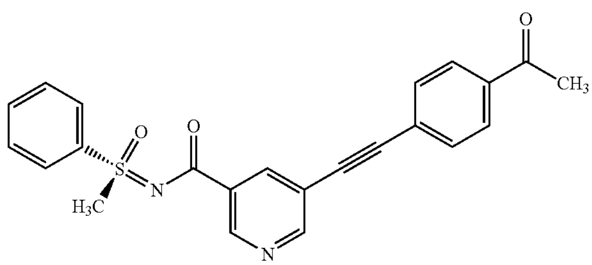 |
| Example 436 | 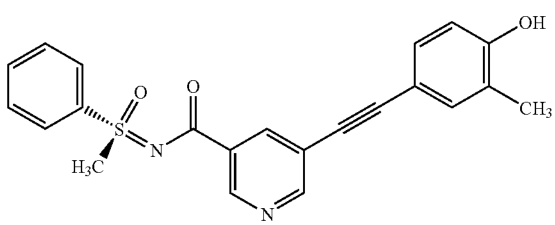 |
| Example 437 | 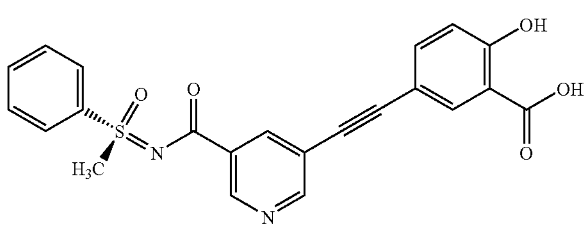 |
| Example 438 | 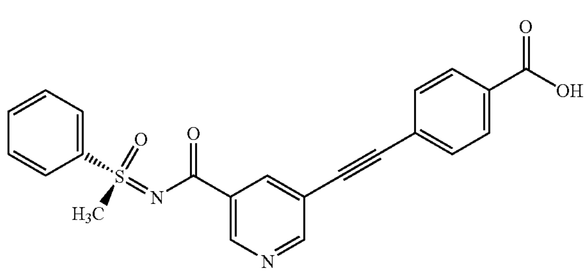 |

TABLE 2-continued

| Example Number | Structure |
|---|---|
| Example 439 | 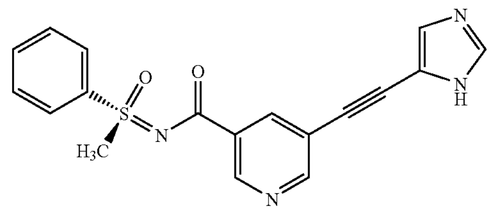 |
| Example 440 | 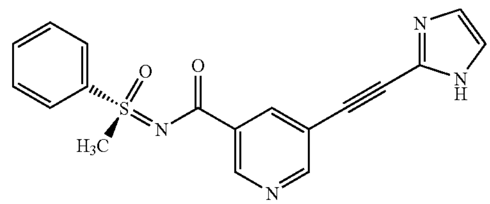 |
| Example 441 | 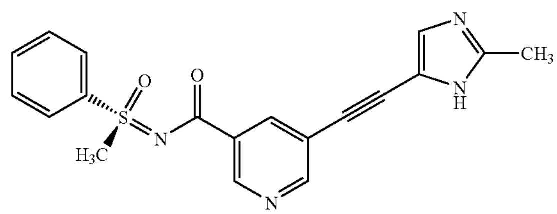 |
| Example 442 | 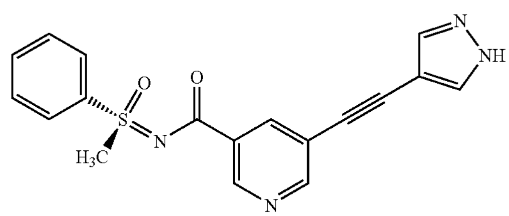 |
| Example 443 | 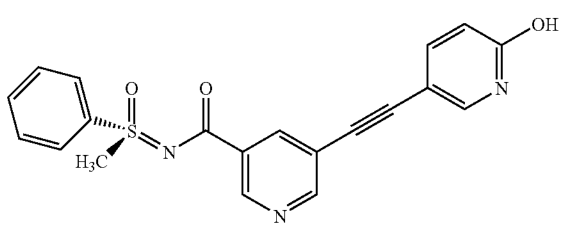 |
| Example 444 | 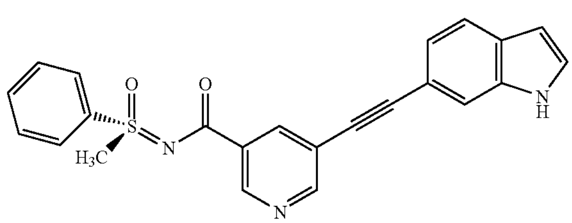 |
| Example 445 | 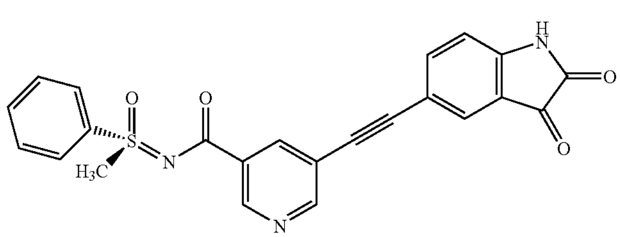 |

TABLE 2-continued

| Example Number | Structure |
|---|---|
| Example 446 | 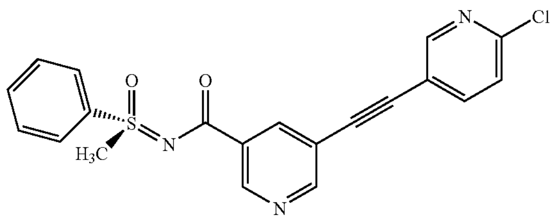 |
| Example 447 | 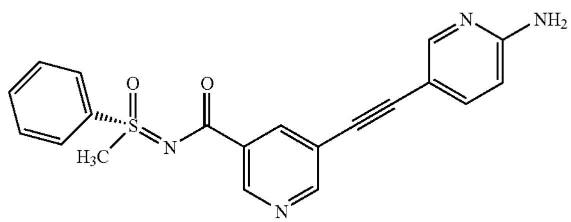 |
| Example 448 | 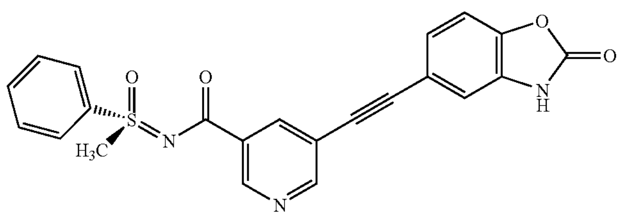 |
| Example 449 | 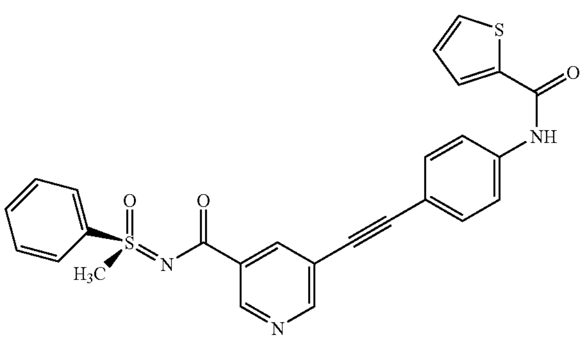 |
| Example 450 | 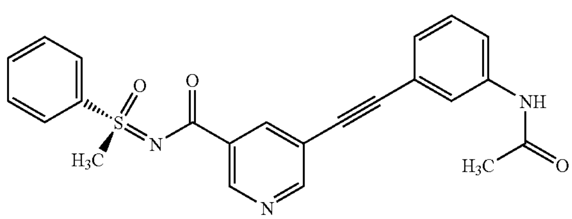 |
| Example 451 | 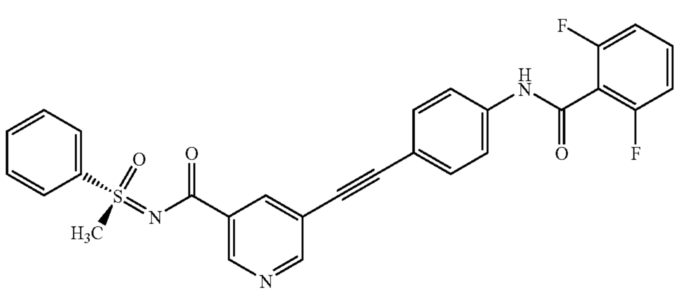 |

TABLE 2-continued

| Example Number | Structure |
|---|---|
| Example 452 | [Structure: phenyl-S(=O)(=N-)(CH3) connected to C(=O)-pyridine-C≡C-phenyl-NH-C(=O)-phenyl-F] |
| Example 453 | [Structure: phenyl-S(=O)(=N-)(CH3) connected to C(=O)-pyridine-C≡C-phenyl-NH-C(=O)-phenyl-CH3] |
| Example 454 | [Structure: phenyl-S(=O)(=N-)(CH3) connected to C(=O)-pyridine-C≡C-phenyl-NH-C(=O)-(2-methylphenyl)] |
| Example 455 | [Structure: phenyl-S(=O)(=N-)(CH3) connected to C(=O)-pyridine-C≡C-phenyl-NH-C(=O)-O-C(CH3)3] |
| Example 456 | [Structure: phenyl-S(=O)(=N-)(CH3) connected to C(=O)-pyridine-C≡C-(3-phenyl)-NH-C(=O)-thiophene] |
| Example 457 | [Structure: phenyl-S(=O)(=N-)(CH3) connected to C(=O)-pyridine-C≡C-(3-phenyl)-NH-C(=O)-(1,3-dimethylpyrazole)] |

TABLE 2-continued
| Example Number | Structure |
|---|---|
| Example 458 | 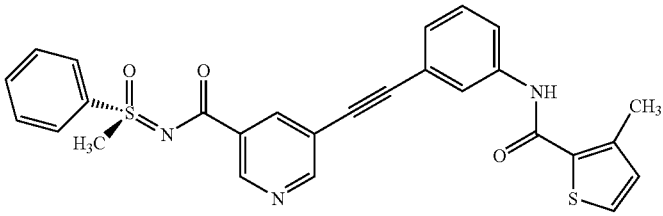 |
| Example 459 | 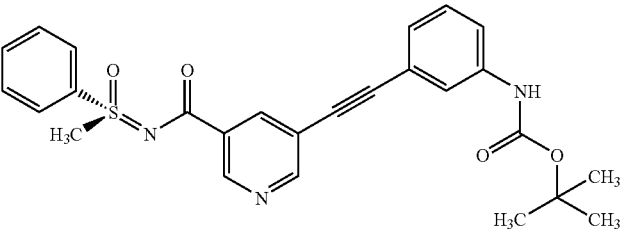 |
| Example 460 | 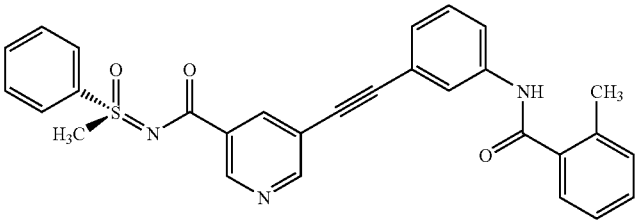 |
| Example 461 | 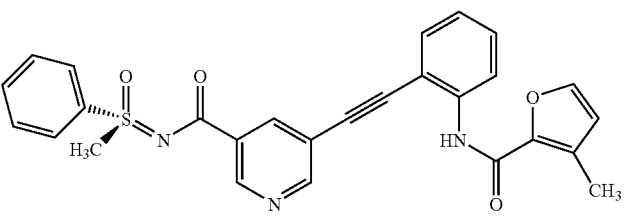 |
| Example 462 | 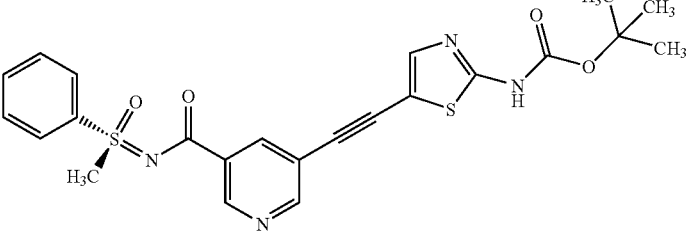 |
| Example 463 | 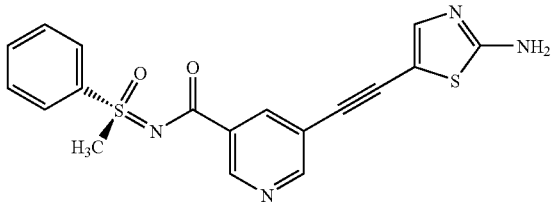 |

TABLE 2-continued

| Example Number | Structure |
|---|---|
| Example 464 | 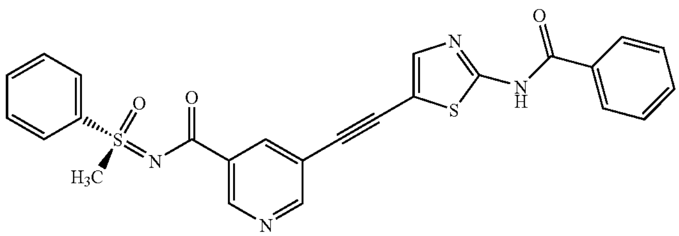 |
| Example 465 | 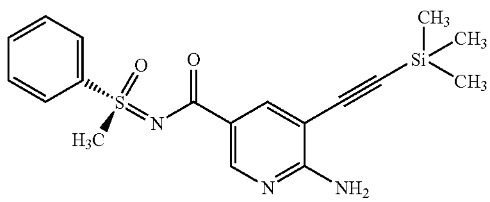 |
| Example 466 | 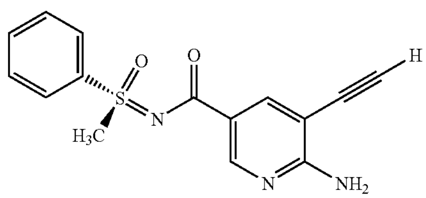 |
| Example 467 | 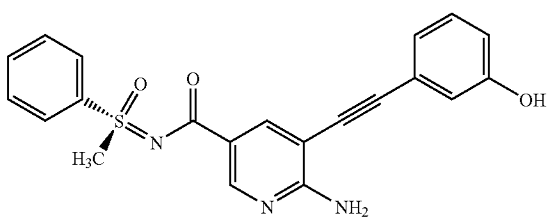 |
| Example 468 | 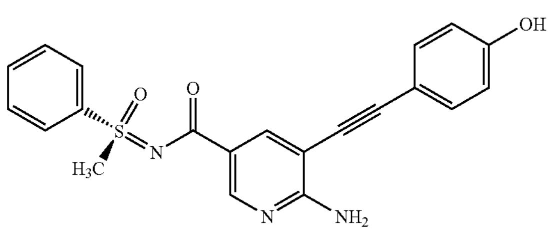 |
| Example 469 | 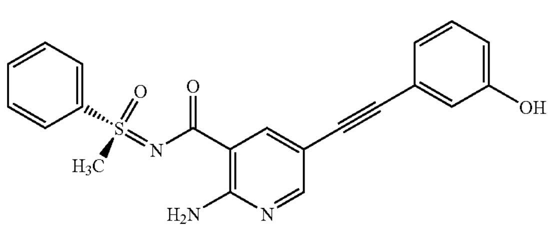 |

TABLE 2-continued

| Example Number | Structure |
|---|---|
| Example 470 | 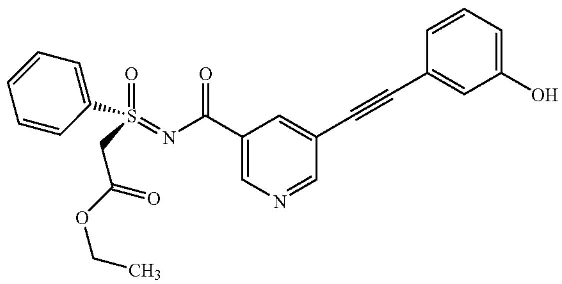 |
| Example 471 | 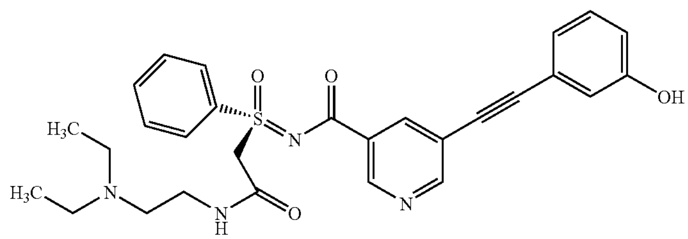 |
| Example 472 | 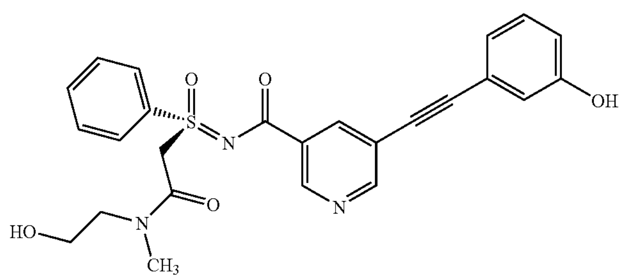 |
| Example 473 | 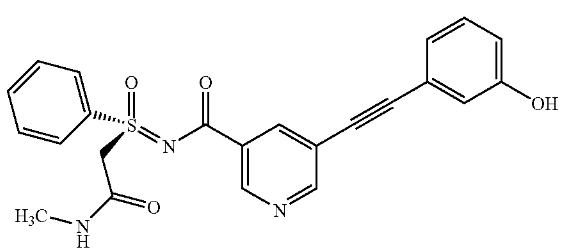 |
| Example 474 | 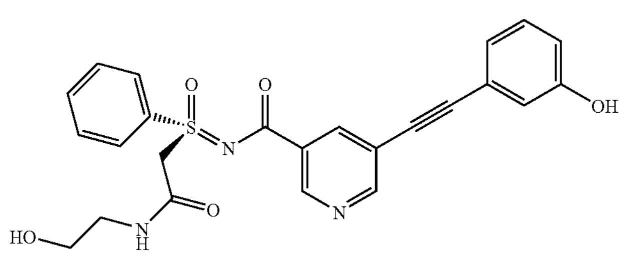 |

TABLE 2-continued

| Example Number | Structure |
|---|---|
| Example 475 | 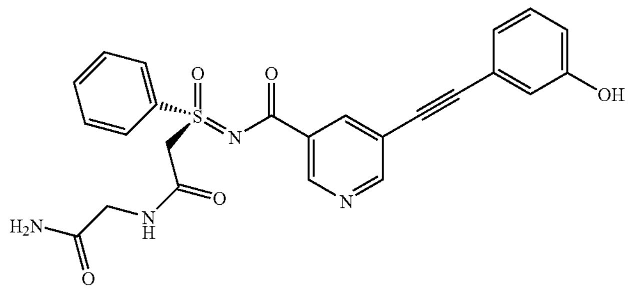 |

TABLE 2-1

| Example # | Structure |
|---|---|
| 476 | 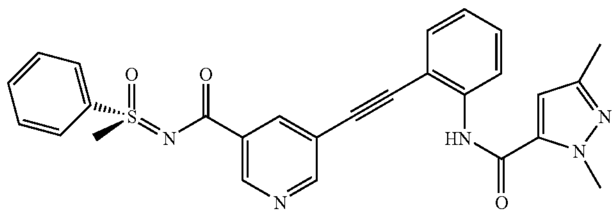 |
| 477 | 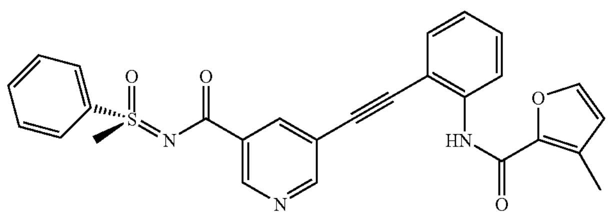 |
| 478 | 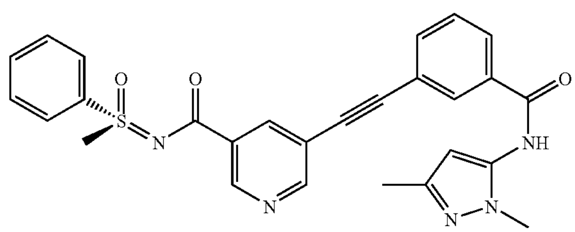 |
| 479 | 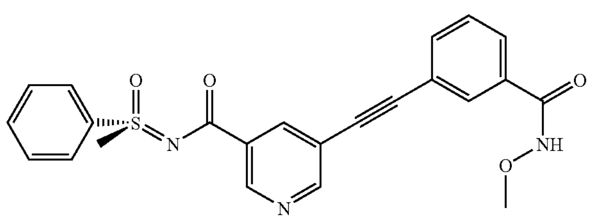 |
| 480 | 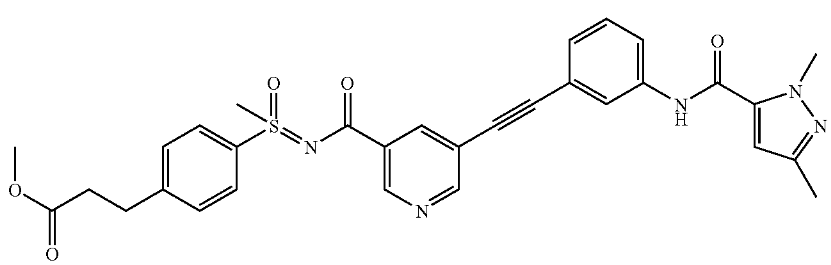 |

TABLE 2-1-continued

| Example # | Structure |
|---|---|
| 481 | 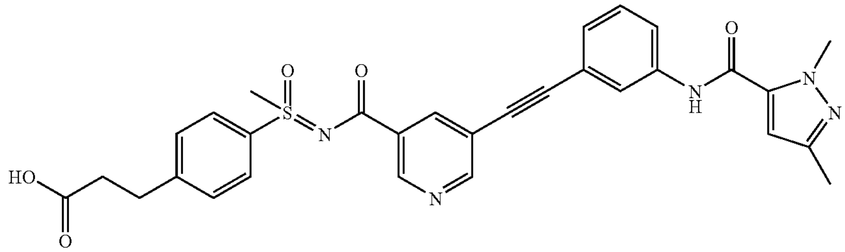 |
| 482 | 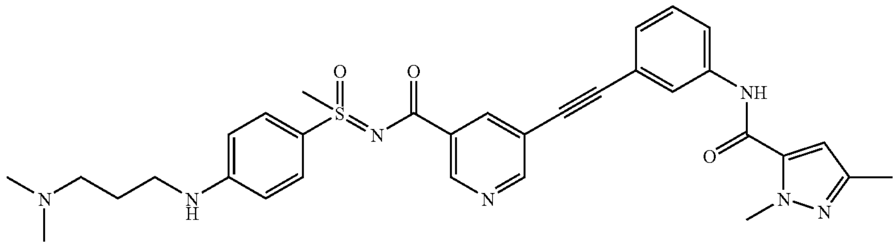 |
| 483 | 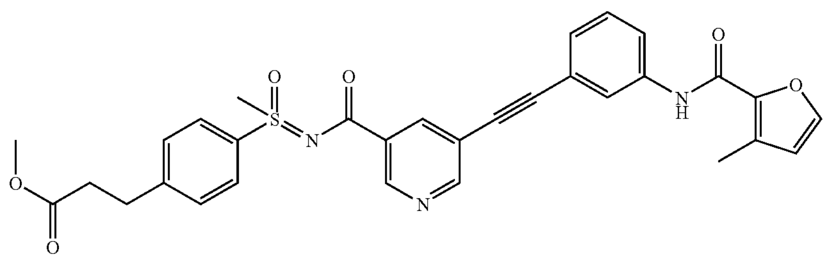 |
| 484 | 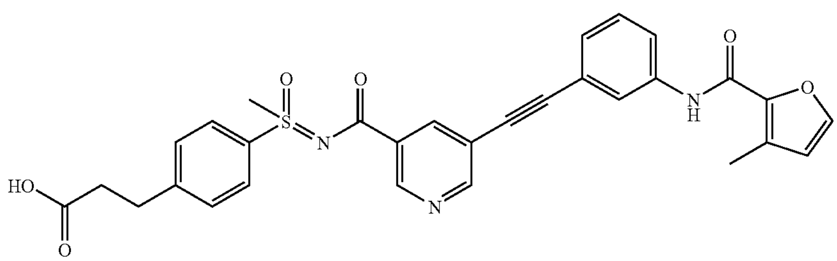 |
| 485 | 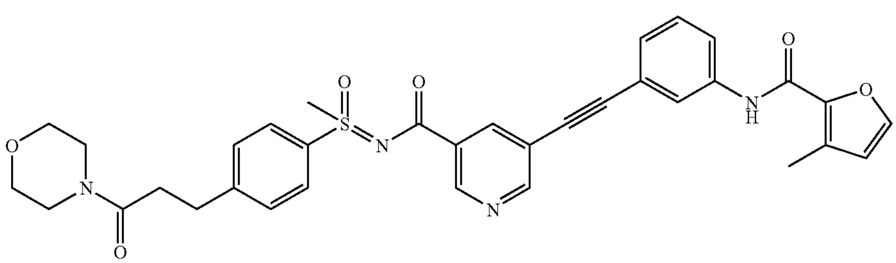 |
| 486 | 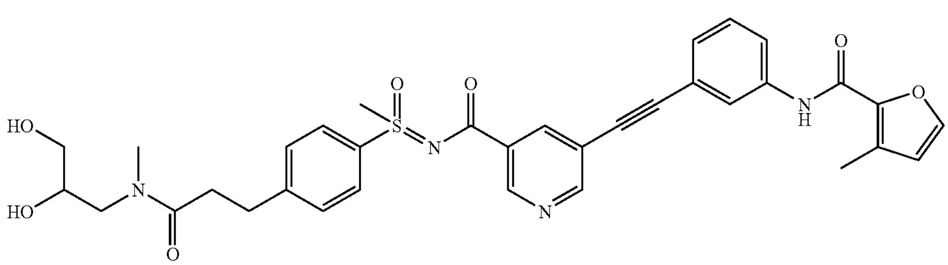 |

TABLE 2-1-continued
| Example # | Structure |
|---|---|
| 487 | 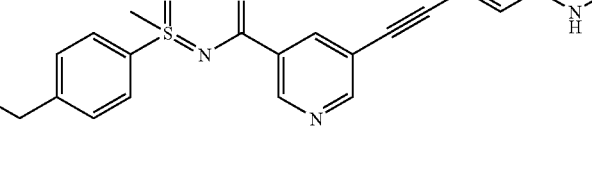 |
| 488 | 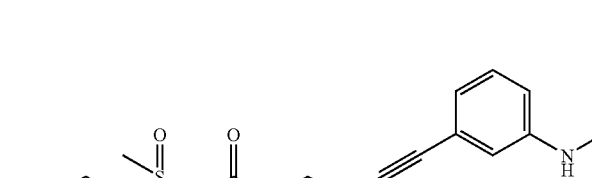 |
| 489 | 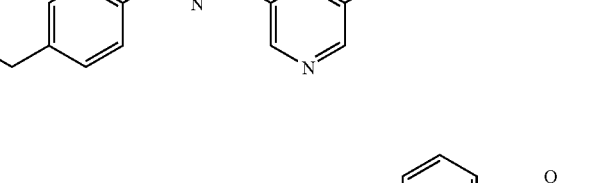 |
| 490 | 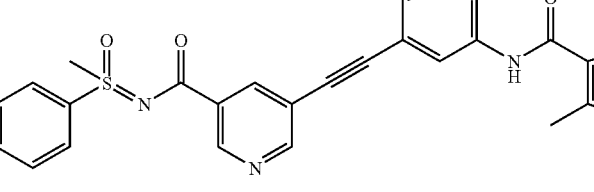 |
| 491 | 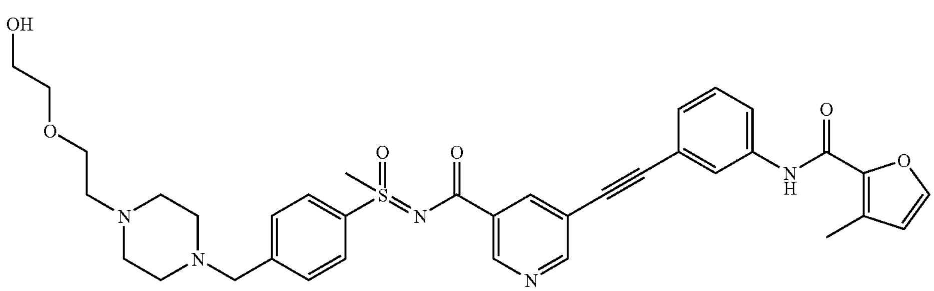 |

TABLE 2-1-continued

| Example # | Structure |
|---|---|
| 492 | 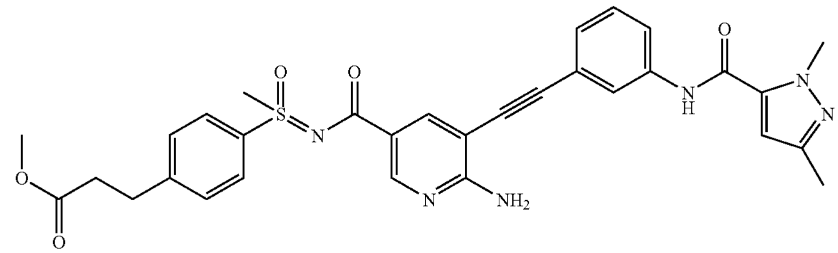 |
| 493 | 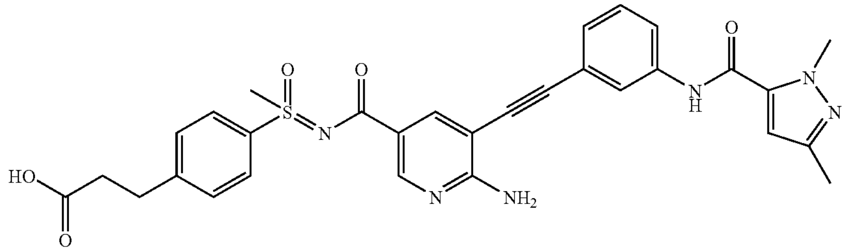 |
| 494 | 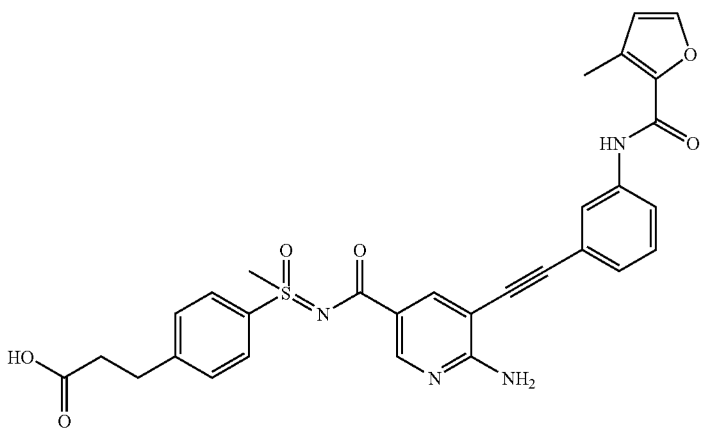 |
| 495 | 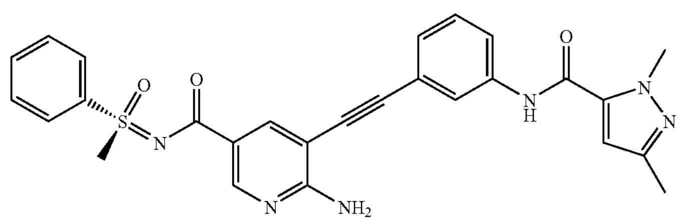 |
| 496 | 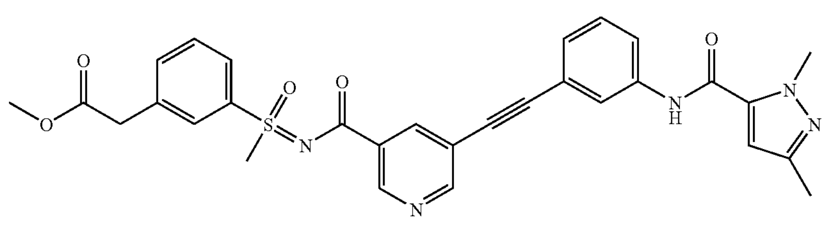 |

TABLE 2-1-continued

| Example # | Structure |
|---|---|
| 497 | 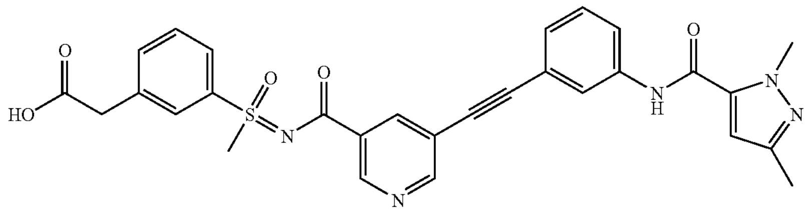 |
| 498 | 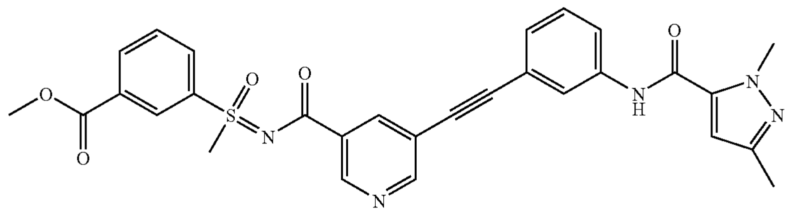 |
| 499 | 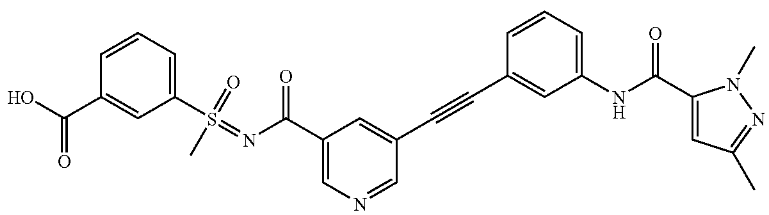 |
| 500 | 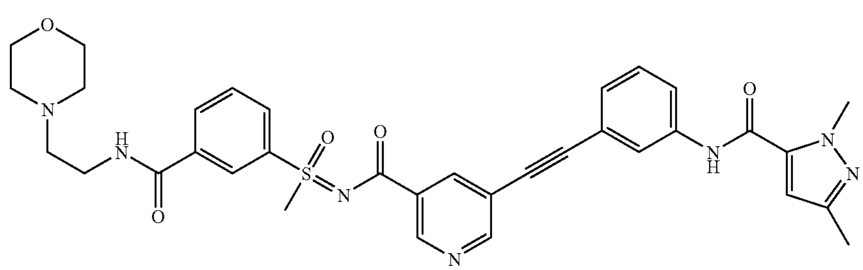 |
| 501 | 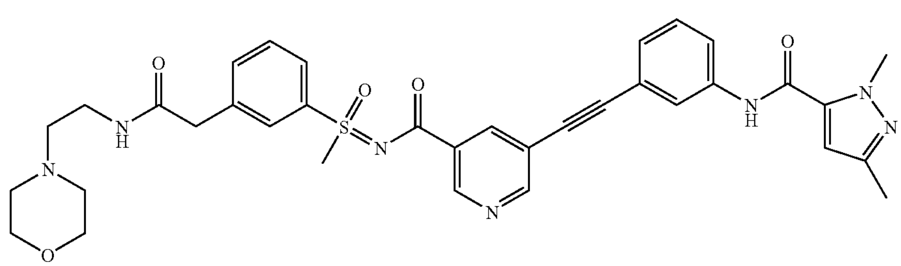 |
| 502 | 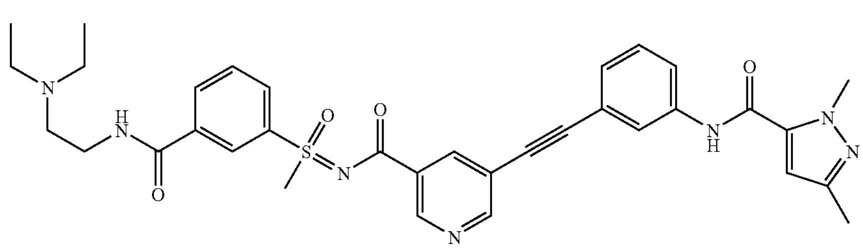 |

TABLE 2-1-continued
| Example # | Structure |
|---|---|
| 503 | 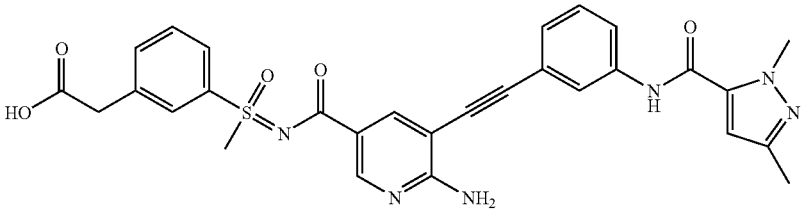 |
| 504 | 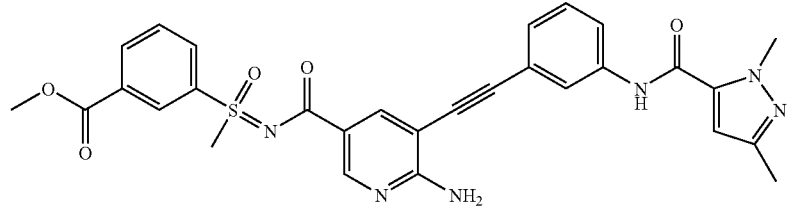 |
| 505 | 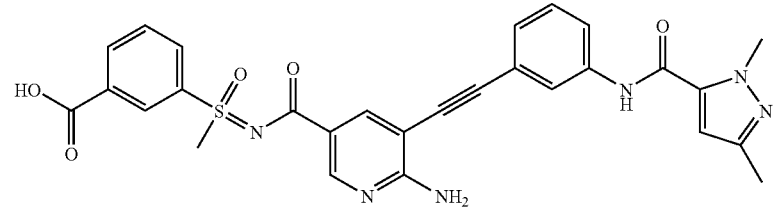 |
| 506 | 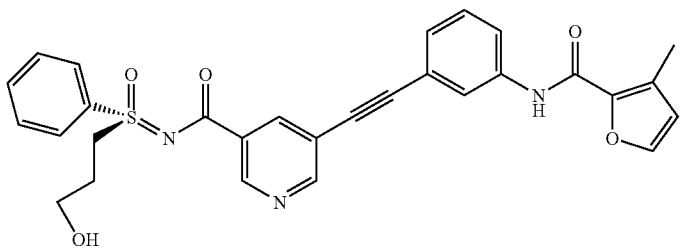 |
| 507 | 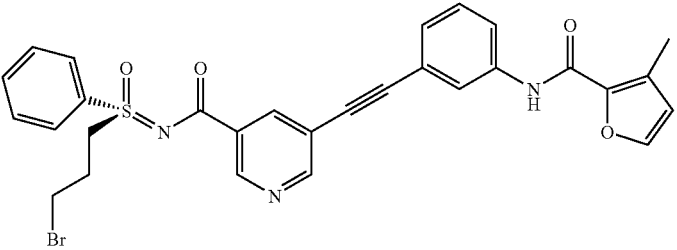 |
| 508 | 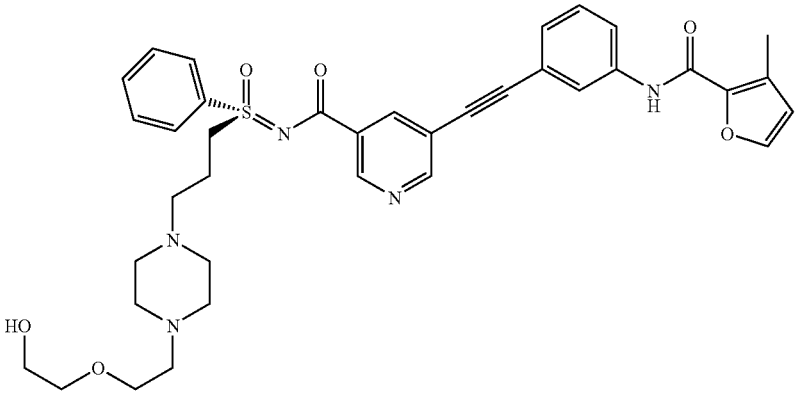 |

TABLE 2-1-continued

| Example # | Structure |
|---|---|
| 509 | 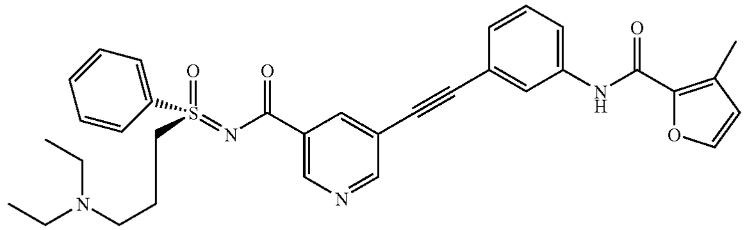 |
| 510 | 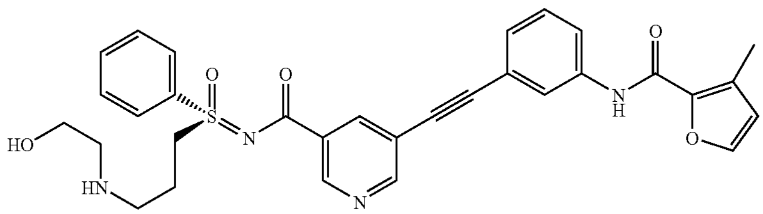 |
| 511 | 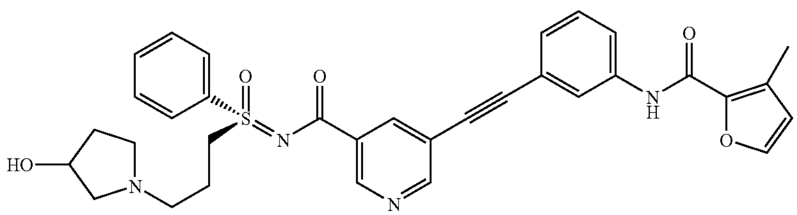 |
| 512 | 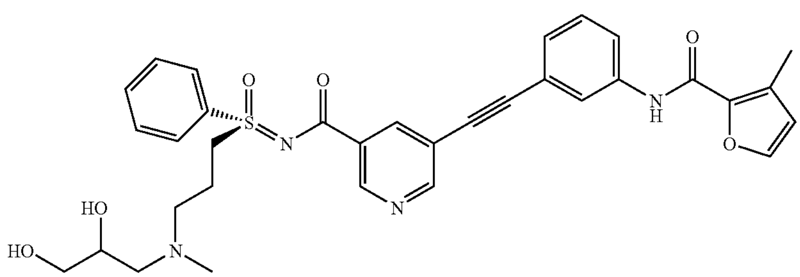 |
| 513 | 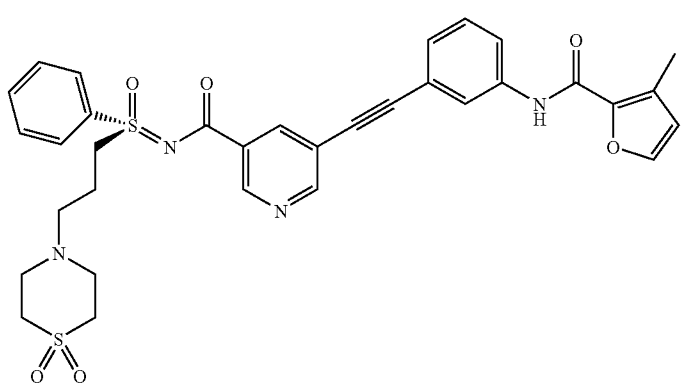 |

TABLE 2-1-continued

| Example # | Structure |
|---|---|
| 514 | 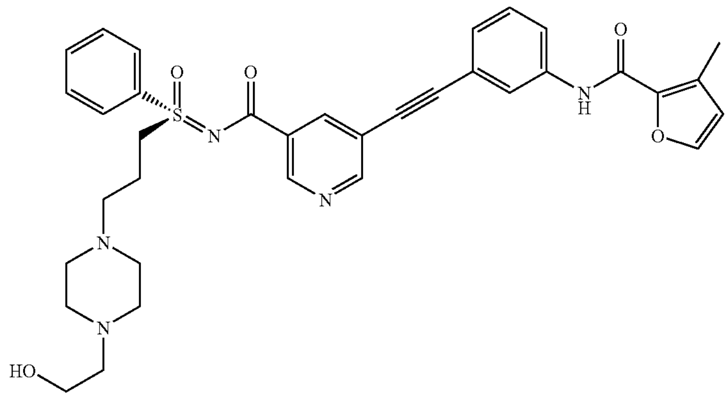 |
| 515 | 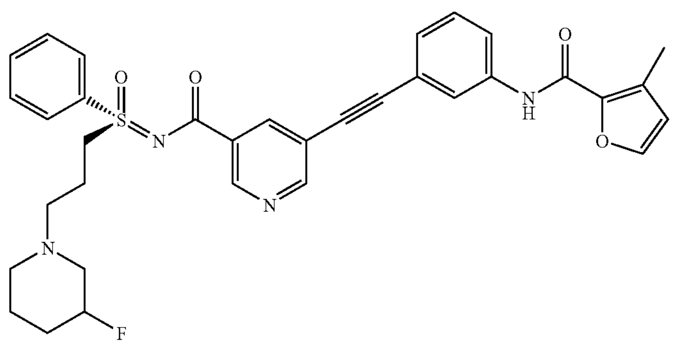 |
| 516 | 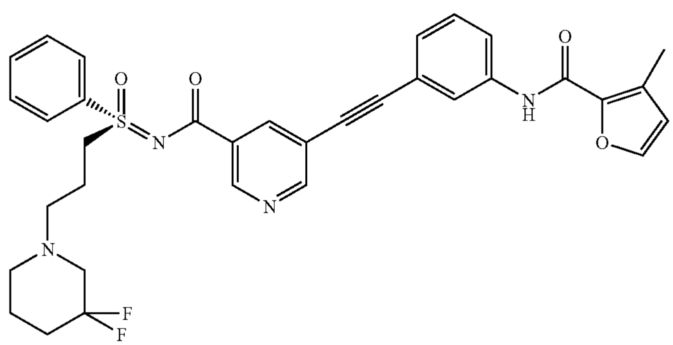 |
| 517 | 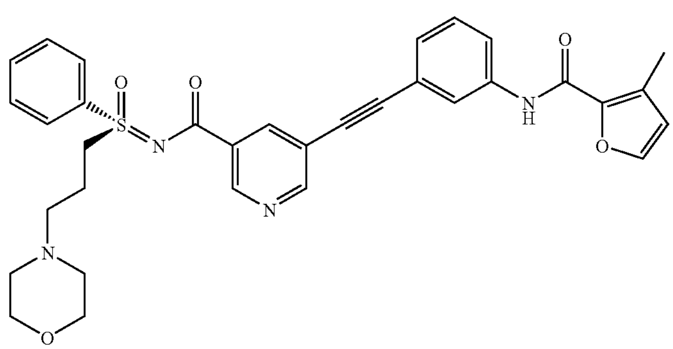 |

TABLE 2-1-continued
| Example # | Structure |
|---|---|
| 518 | 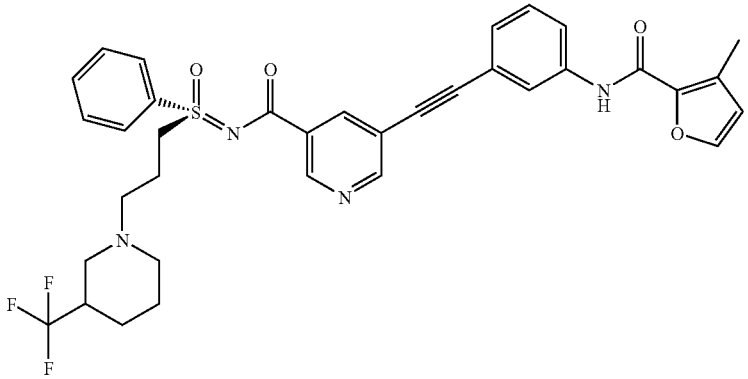 |
| 519 | 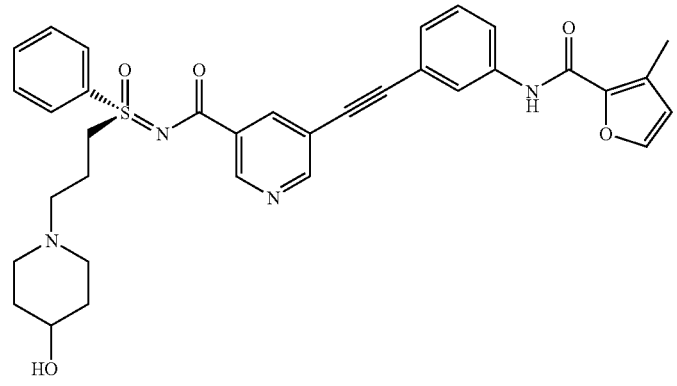 |
| 520 | 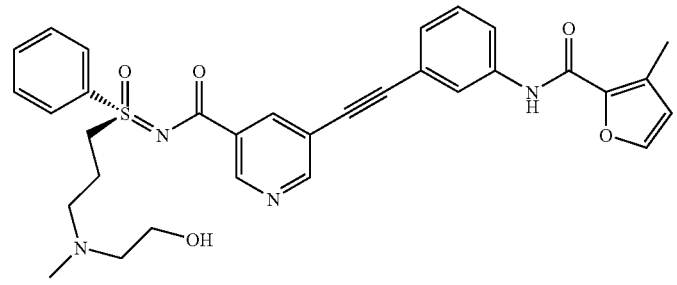 |
| 521 | 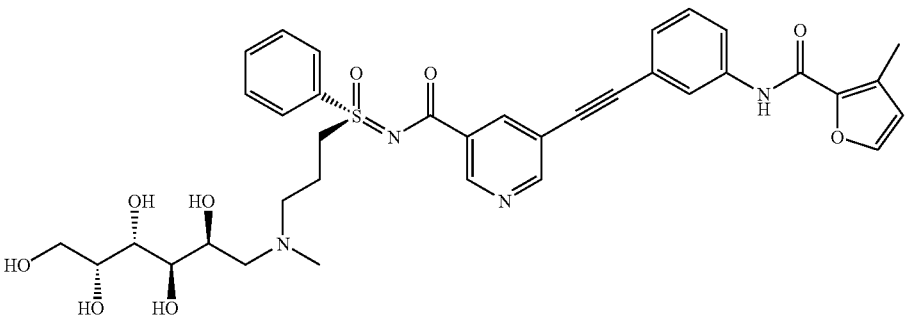 |

TABLE 2-1-continued
| Example # | Structure |
|---|---|
| 522 | 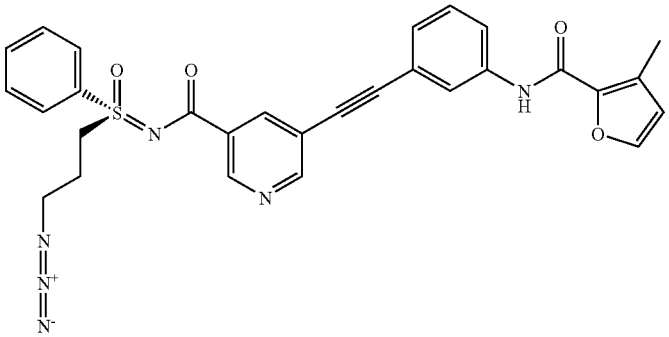 |
| 523 | 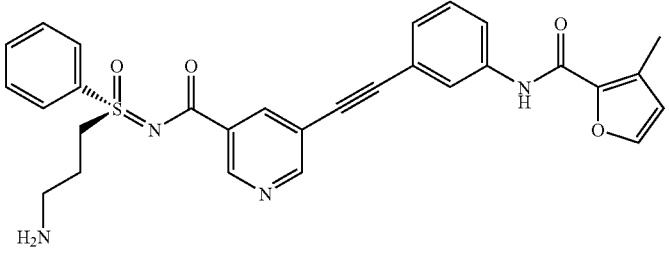 |
| 524 | 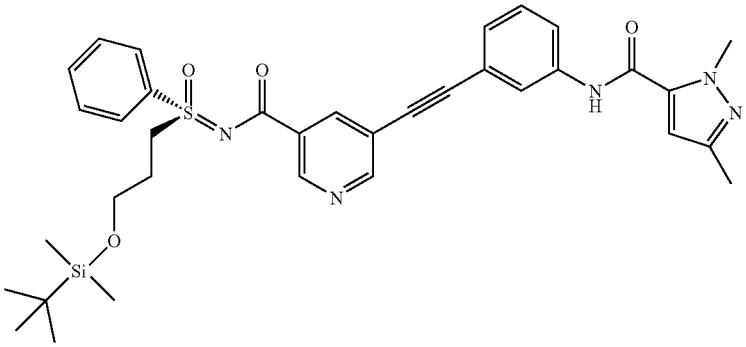 |
| 525 | 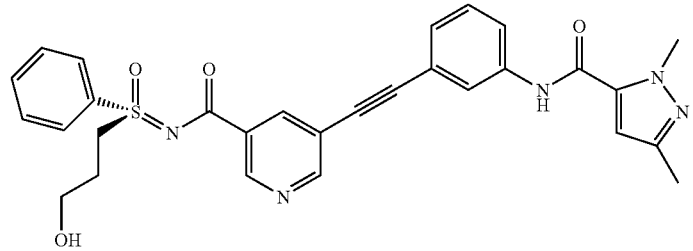 |
| 526 | 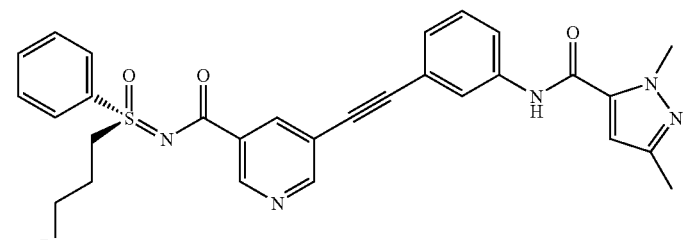 |

TABLE 2-1-continued
| Example # | Structure |
|---|---|
| 527 | 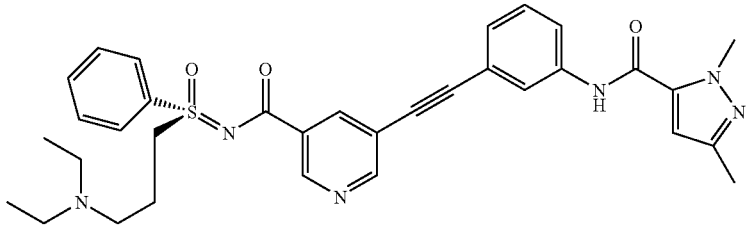 |
| 528 | 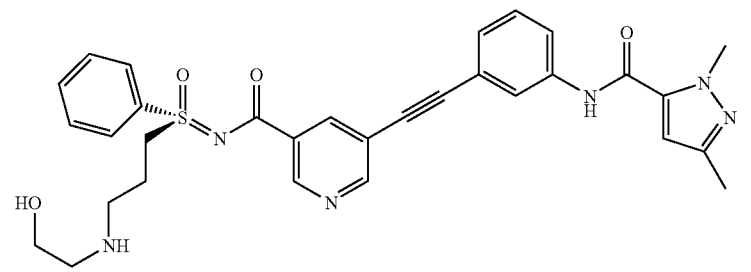 |
| 529 | 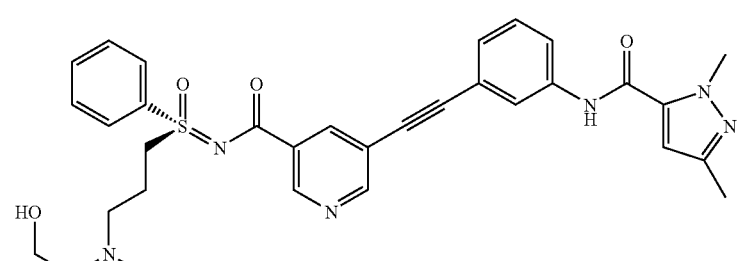 |
| 530 | 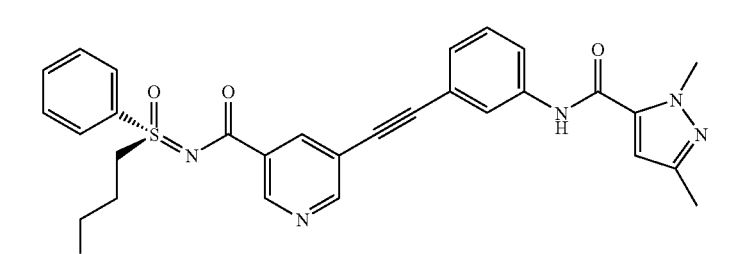 |
| 531 | 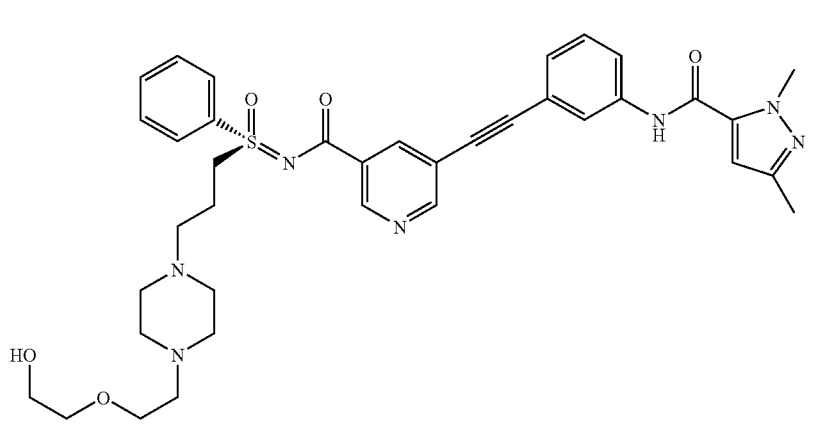 |

TABLE 2-1-continued

| Example # | Structure |
|---|---|
| 532 | 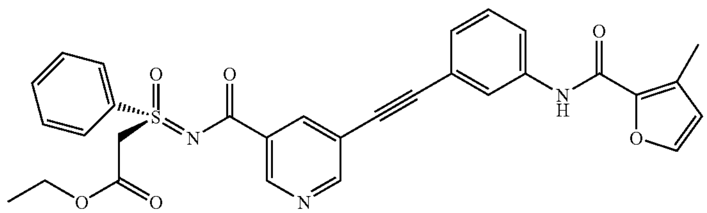 |
| 533 | 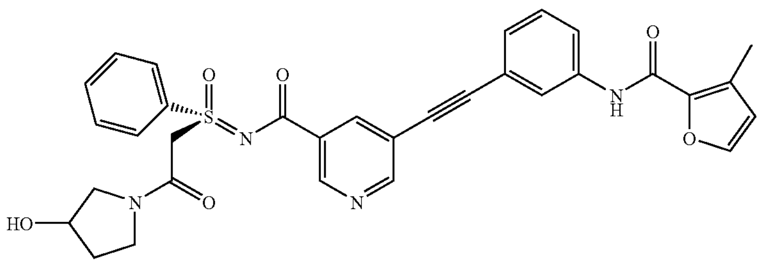 |
| 534 | 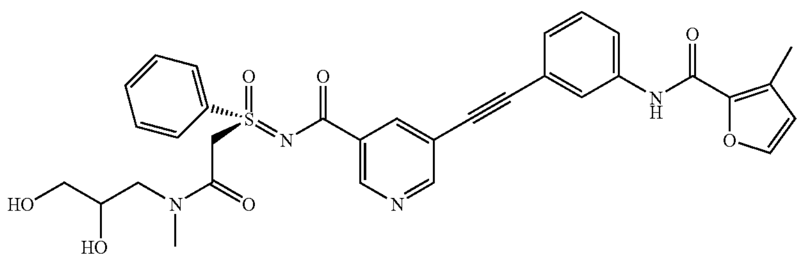 |
| 535 | 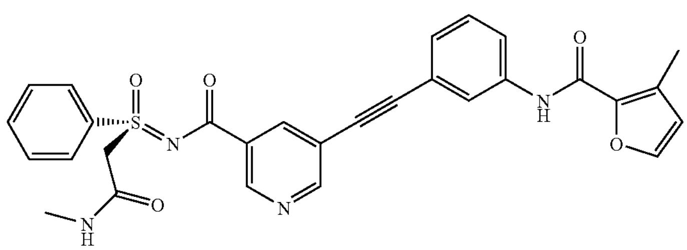 |
| 536 | 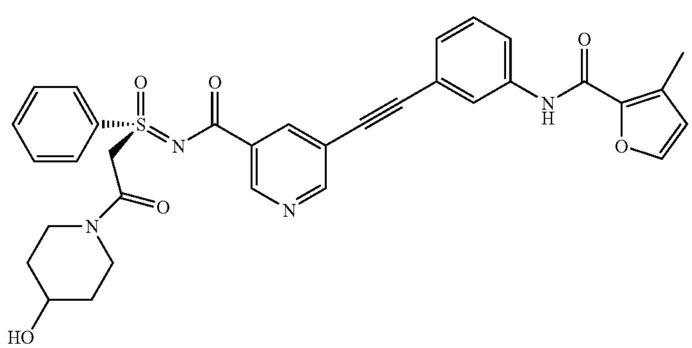 |

TABLE 2-1-continued

| Example # | Structure |
|---|---|
| 537 | 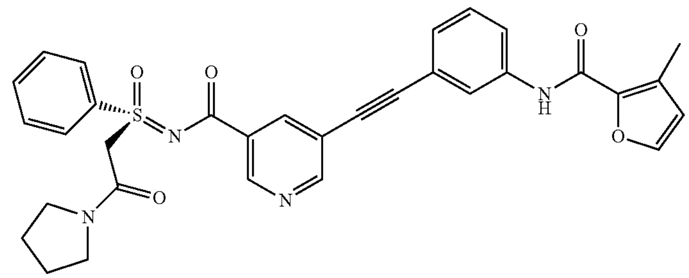 |
| 538 | 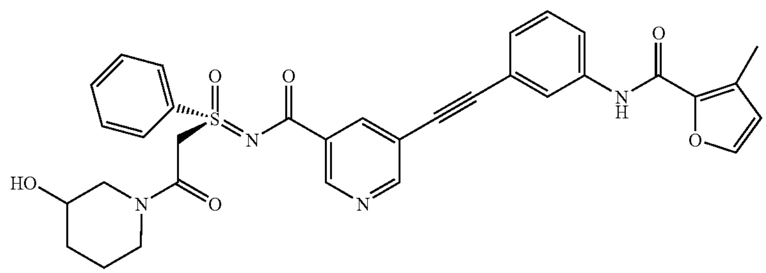 |
| 539 | 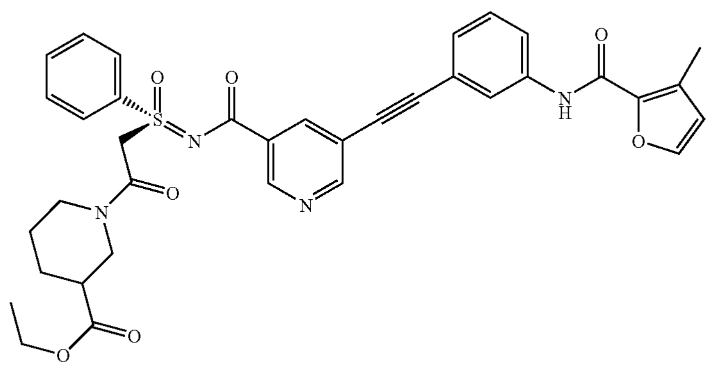 |
| 540 | 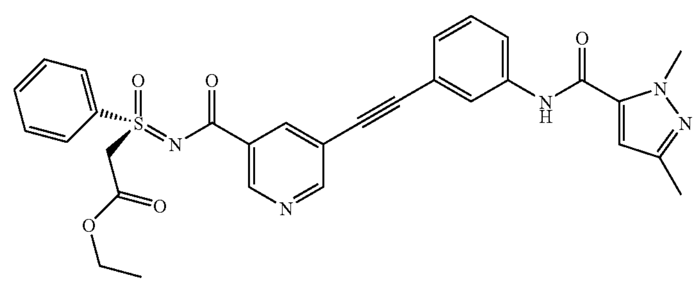 |
| 541 | 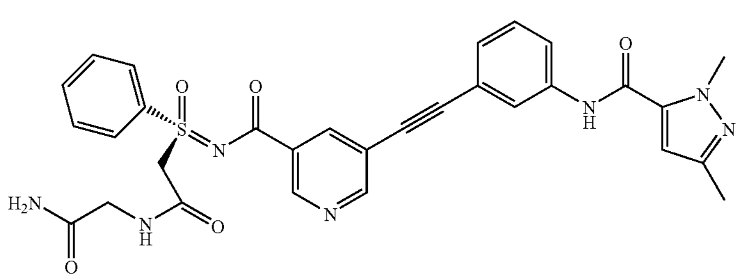 |

US 7,915,443 B2
TABLE 2-1-continued
| Example # | Structure |
|---|---|
| 542 | 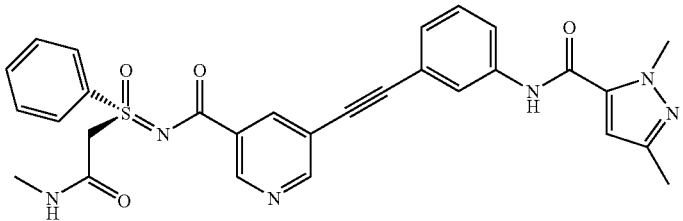 |
| 543 | 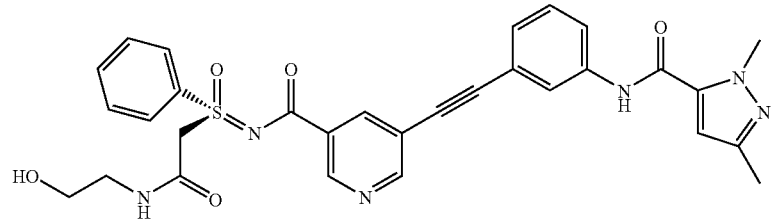 |
| 544 | 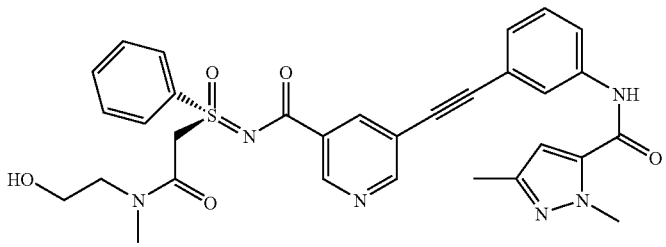 |
| 545 | 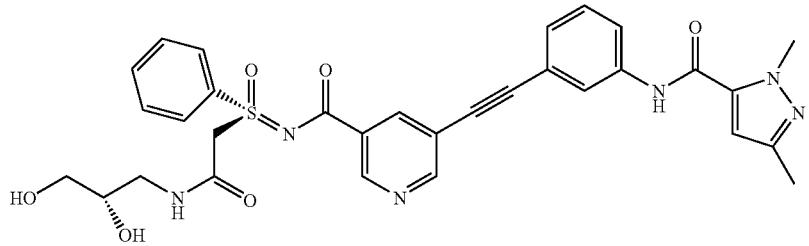 |
| 546 | 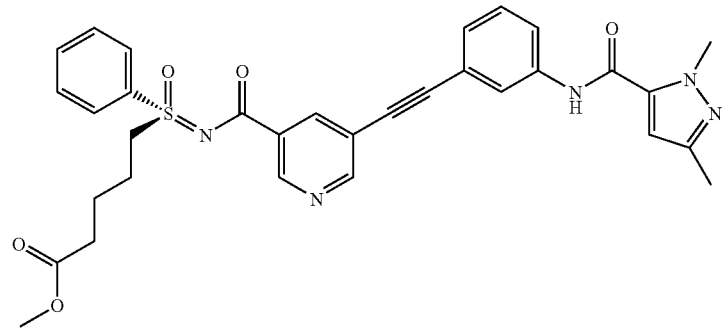 |

TABLE 2-1-continued
| Example # | Structure |
|---|---|
| 547 | 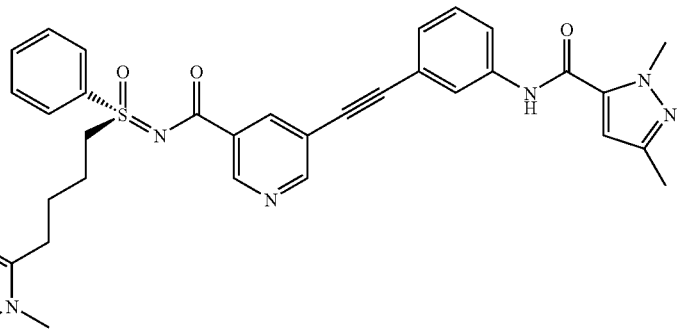 |
| 548 | 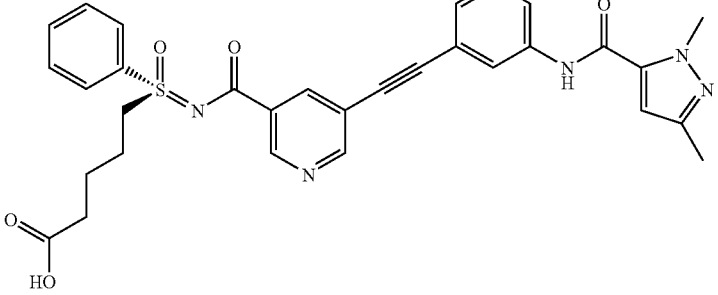 |
| 549 | 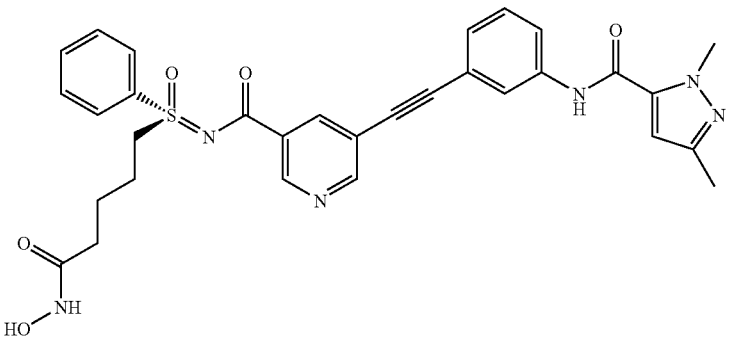 |
| 550 | 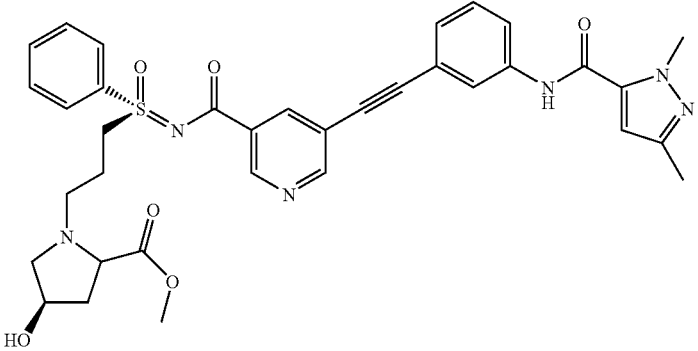 |

TABLE 2-1-continued
| Example # | Structure |
|---|---|
| 551 | 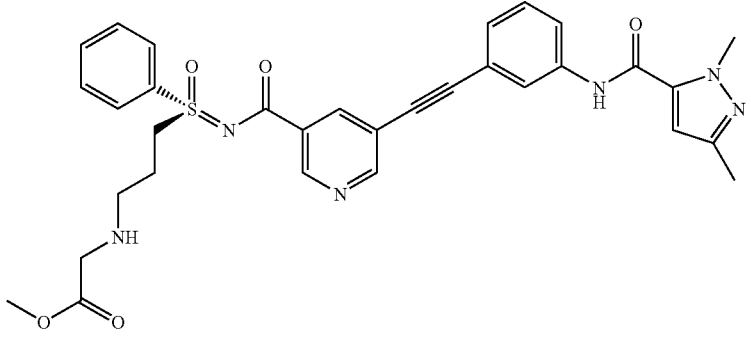 |
| 552 | 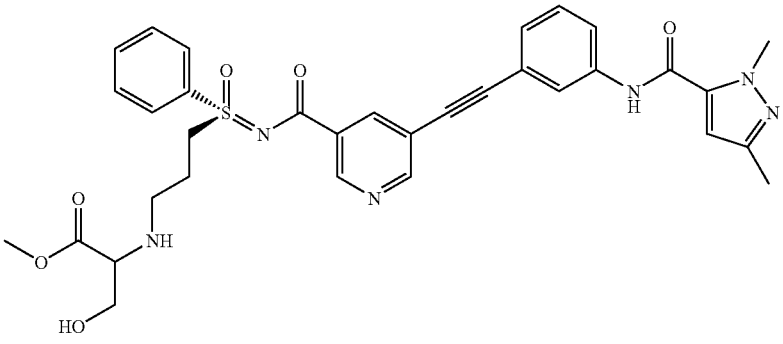 |
| 553 | 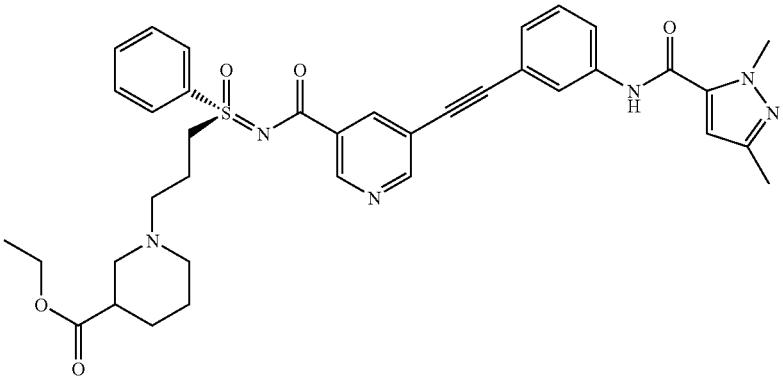 |
| 554 | 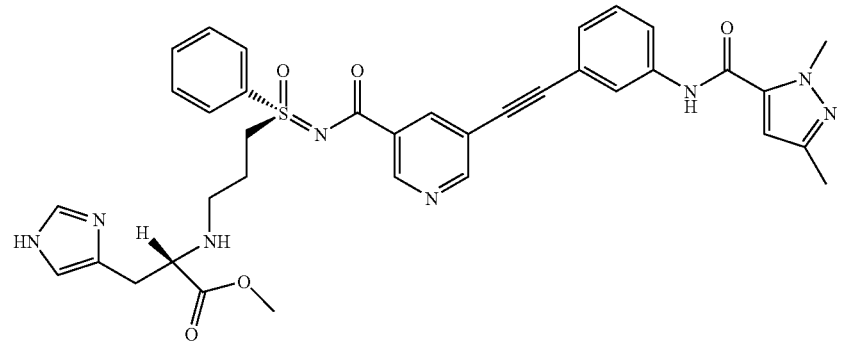 |

TABLE 2-1-continued

| Example # | Structure |
|---|---|
| 555 | 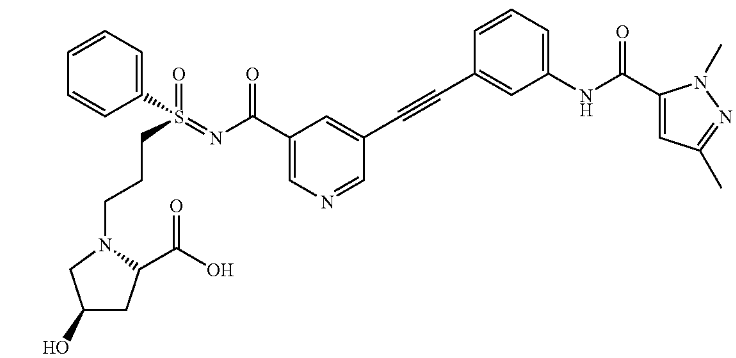 |
| 556 | 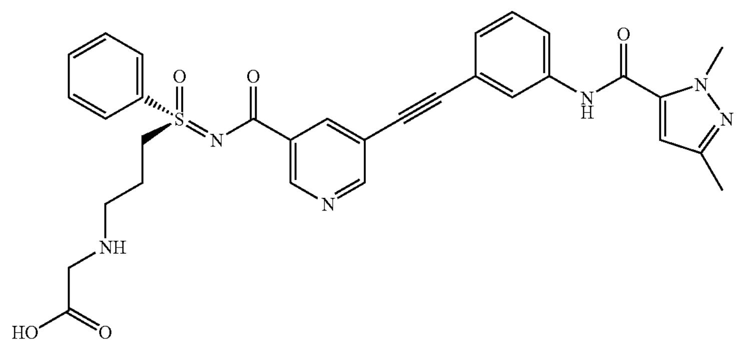 |
| 557 | 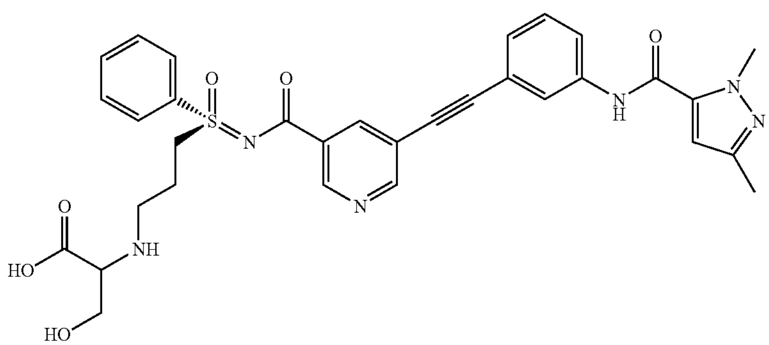 |
| 558 | 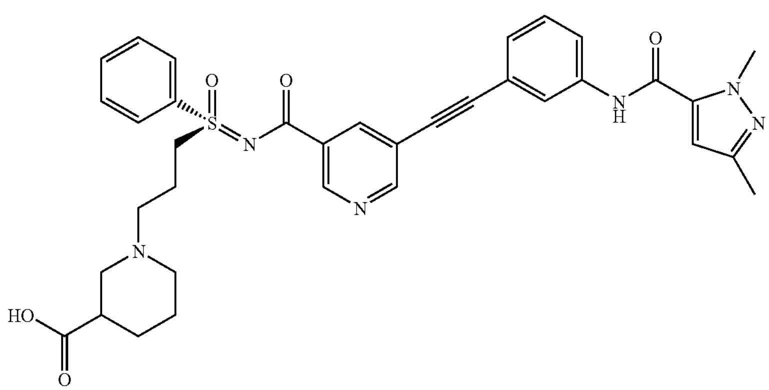 |

TABLE 2-1-continued
| Example # | Structure |
|---|---|
| 559 | 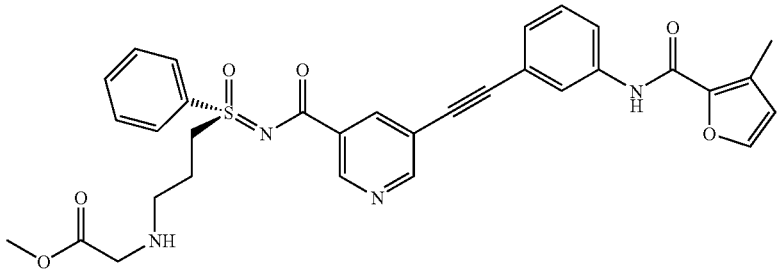 |
| 560 | 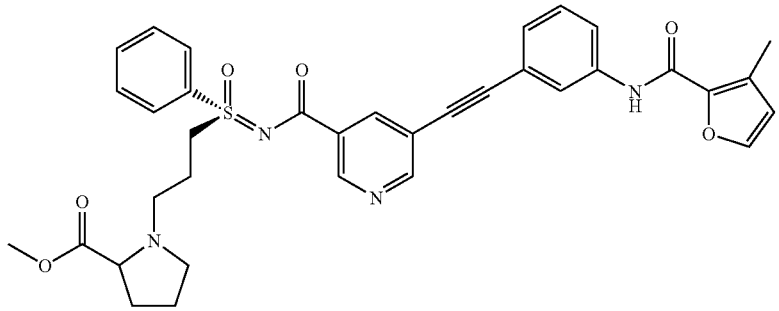 |
| 561 | 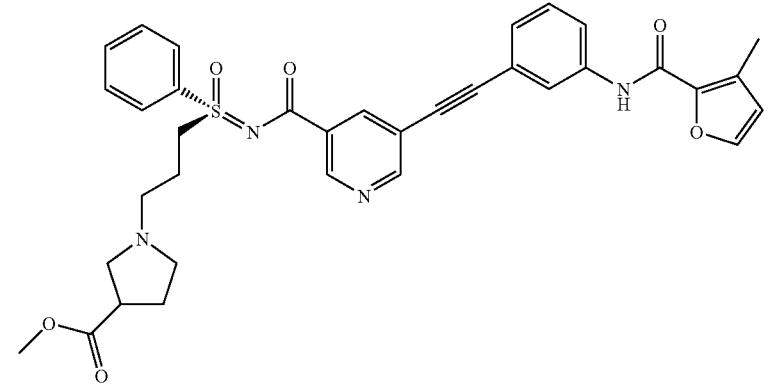 |
| 562 | 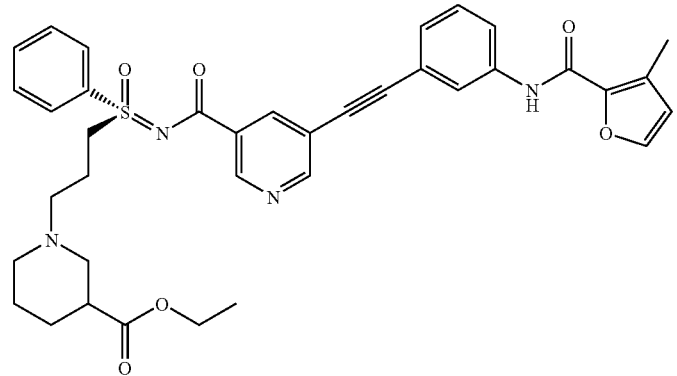 |

TABLE 2-1-continued

| Example # | Structure |
|---|---|
| 563 | 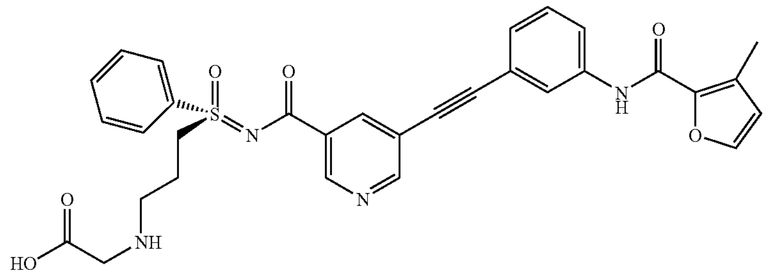 |
| 564 | 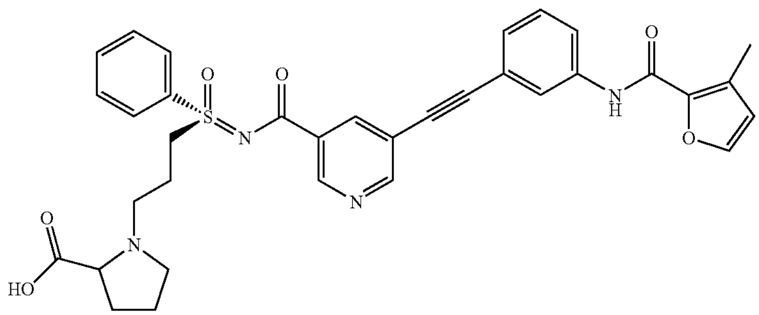 |
| 565 | 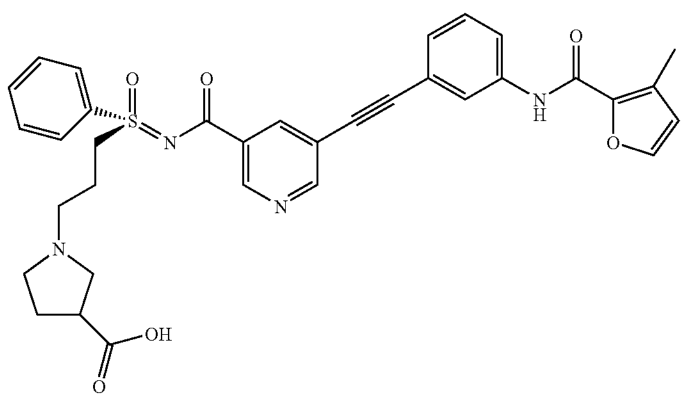 |
| 566 | 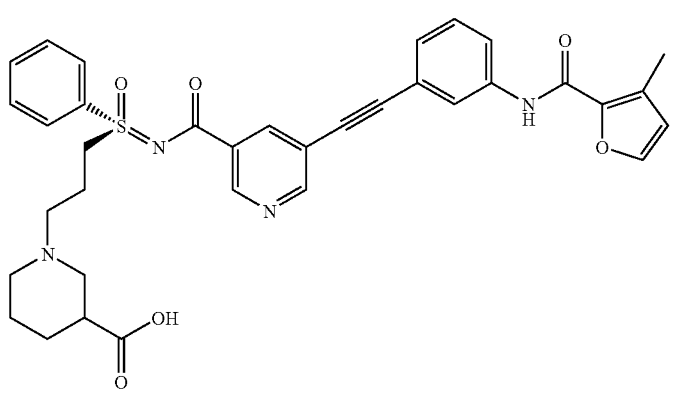 |

TABLE 2-1-continued

| Example # | Structure |
|---|---|
| 567 | (structure image) |

The present invention relates to compounds capable of regulating and/or modulating tyrosine kinase signal transduction and more particularly receptor and non-receptor tyrosine kinase signal transduction.

Receptor tyrosine kinase mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic effects and responses to the extracellular microenvironment).

It has been shown that tyrosine phosphorylation sites in growth factor receptors function as high-affinity binding sites for SH2 (src homology) domains of signaling molecules. Several intracellular substrate proteins that associate with receptor tyrosine kinases have been identified. They may be divided into two principal groups: (1) substrates which have a catalytic domain; and (2) substrates which lack such domain but serve as adapters and associate with catalytically active molecules. The specificity of the interactions between receptors and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

Tyrosine kinase signal transduction results in, among other responses, cell proliferation, differentiation and metabolism. Abnormal cell proliferation may result in a wide array of disorders and diseases, including the development of neoplasia such as carcinoma, sarcoma, leukemia, glioblastoma, hemangioma, psoriasis, arteriosclerosis, arthritis and diabetic retinopathy (or other disorders related to uncontrolled angiogenesis and/or vasculogenesis, e.g. macular degeneration).

This invention is therefore directed to compounds which regulate, modulate and/or inhibit tyrosine kinase signal transduction by affecting the enzymatic activity of the RTKs and/or the non-receptor tyrosine kinases and interfering with the signal transduced such proteins. More particularly, the present invention is directed to compounds which regulate, modulate and/or inhibit the RTK and/or non-receptor tyrosine kinase mediated signal transduction pathways as a therapeutic approach to cure many kinds of solid tumors, including but not limited to carcinoma, sarcoma, leukemia, erythroblastoma, glioblastoma, meningioma, astrocytoma, melanoma and myoblastoma. Indications may include, but are not limited to brain cancers, bladder cancers, ovarian cancers, gastric cancers, pancreas cancers, colon cancers, blood cancers, lung cancers and bone cancers.

Biological data for the compounds of the present invention was generated by use of the following assays.

VEGF Stimulated $Ca^{++}$ Signal in vitro

Automated FLIPR (Fluorometric Imaging Plate Reader) technology was used to screen for inhibitors of VEGF induced increases in intracellular calcium levels in fluorescent dye loaded endothelial cells. HUVEC (human umbilical vein endothelial cells) (Clonetics) were seeded in 96-well fibronectin coated black-walled plates overnight @37° C./5% CO2. Cells were loaded with calcium indicator Fluo-4 for 45 minutes at 37° C. Cells were washed 4 times (Original Cell Wash, Labsystems) to remove extracellular dye. For screening, cells were pre-incubated with test agents for 30 minutes, at a single concentration (10 uM) or at concentrations ranging from 0.01 to 10.0 uM followed by VEGF stimulation (5 ng/mL). Changes in fluorescence at 516 nm were measured simultaneously in all 96 wells using a cooled CCD camera. Data were generated by determining max-min fluorescence levels for unstimulated, stimulated, and drug treated samples. $IC_{50}$ values for test compounds were calculated from % inhibition of VEGF stimulated responses in the absence of inhibitor.

Protocol for KDR Assay:

The cytoplasmic domain of the human VEGF receptor (VEGFR-2) was expressed as a Histidine-tagged fusion protein following infection of insect cells using an engineered baculovirus. His-VEGFR-2 was purified to homogeneity, as determined by SDS-PAGE, using nickel resin chromatography. Kinase assays were performed in 96 well microtiter plates that were coated overnight with 30 μg of poly-Glu-Tyr (4:1) in 10 mM Phosphate Buffered Saline (PBS), pH 7.2-7.4. The plates were incubated with 1% BSA and then washed four times with PBS prior to starting the reaction. Reactions were carried out in 120 μL reaction volumes containing 3.6 μM ATP in kinase buffer (50 mM Hepes buffer pH 7.4, 20 mM $MgCl_2$, 0.1 mM $MnCl_2$ and 0.2 mM $Na_3VO_4$). Test compounds were reconstituted in 100% DMSO and added to the reaction to give a final DMSO concentration of 5%. Reactions were initiated by the addition 0.5 ng of purified protein. Following a ten minute incubation at 25° C., the reactions were washed four times with PBS containing 0.05% Tween-20. 100 μl of a monoclonal anti-phosphotyrosine antibody-peroxidase conjugate was diluted 1:10000 in PBS-Tween-20 and added to the wells for 30 minutes. Following four washes with PBS-Tween-20, 100 μl of O-Phenylenediamine Dihydrochloride in Phosphate-citrate buffer, containing urea hydrogen peroxide, was added to the wells for 7 minutes as a colorimetric substrate for the peroxidase. The reaction was terminated by the addition of 100 μl of 2.5NH$_2$SO$_4$ to each well and read using a microplate ELISA reader set at 492 nm. IC$_{50}$ values for compound inhibition were calculated directly from graphs of optical density (arbitrary units) versus compound concentration following subtraction of blank values.

The invention is further illustrated by the following non-limiting examples.

EXAMPLE 1

N-[(4-methoxyphenyl)(methyl)oxo-λ$^6$-sulfanylidene]-5-(phenylethynyl)nicotinamide Step 1—Representative Procedure for the Preparation of Sulfoxides Methyl phenyl sulfoxide

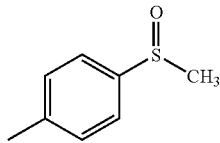

To a stirred suspension of iodoxybenzoic acid (3.7 g, 13.2 mmol, 1.1 eq) in 100:1 CHCl$_3$/H$_2$O (25 mL) was added tetraethylammonium bromide (TEAB) (126 mg, 5 mol %), followed by the addition of p-tolyl sulfide (1.66 g, 12 mmol) in one portion. The mixture was stirred at room temperature for approximately 30 minutes until consumption of sulfide was observed (TLC, hexanes/EtOAc 1/1). The residual solids were removed by filtration and washed with CHCl$_3$ (40 mL). The combined filtrate was washed successively with saturated aq. NaHCO$_3$ (30 mL), saturated aq. NaCl (30 mL), dried over sodium sulfate, and concentrated to provide the crude product. Purification by silica gel column chromatography (50% hexanes/EtOAc elution) afforded the title compound (1.68 g, yield 91%). $^1$H NMR (300 MHz, CDCl$_3$) δ 7.52 (d, J=8.4 Hz, 2H), 7.32 (d, J=8.4 Hz, 2H), 2.71 (s, 3H), 2.42 (s, 3H); ESI-MS m/z 154.7 (M+H)$^+$.

Step 2—Representative Procedure for the Preparation of Substituted Sulfoximines

S-methyl-S-(4-methoxyphenyl)-N-[[2-(trimethylsilyl)ethyl]sulfonyl]sulfoximine

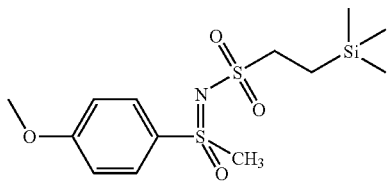

To a solution of 1-methanesulfinyl-4-methoxy-benzene (1.51 g, 8.88 mmol) in dry acetonitrile (35 mL), was added CuPF$_6$(CH$_3$CN)$_4$ (165 mg, 0.44 mmol, 0.05 eq.). The mixture was cooled to 0° C. and [N-(2-(trimethylsilyl)ethanesulfonyl)imino]phenyl-iodinate (3.75 g, 9.8 mmol, 1.1 eq.) (prepared by the method described in J. Org. Chem. 1999, 64, 5304-5307) was added. The reaction mixture was allowed to warm to room temperature, stirred for 20 h and the solvent then evaporated. The residue was dissolved in EtOAc (50 mL) and filtered through a pad of silica gel. The ethyl acetate solution was evaporated and the residue was triturated with hexanes to provide the title compound as a white solid (3.0 g, recovery 96%, purity >95% by HPLC). If required, the compound can be further purified by silica gel column chromatography (50% hexanes/EtOAc). $^1$H NMR (300 MHz, CDCl$_3$) δ 7.95 (d, J=9.0 Hz, 2H), 7.05 (d, J=9.0 Hz, 2H), 3.89 (s, 3H), 3.41 (s, 3H), 3.16-3.10 (m, 2H), 1.18-1.12 (m, 2H), 0.04 (s, 9H); ESI-MS m/z 349.9 (M+H)$^+$.

Step 3—Representative Procedure for the Deprotection of (trimethylsilyl)ethyl]sulfonyl Substituted Sulfoximines S-(4-methoxyphenyl)-S-methyl-sulfoximine

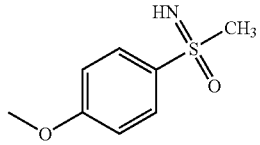

A mixture of S-methyl-S-(4-methoxyphenyl)-N-[[2-(trimethylsilyl)ethyl]sulfonyl]-sulfoximine (2.9 g, 8.3 mmol) and 1.0 M of TBAF (12.5 mL, 12.5 mmol, 1.5 eq.) was heated in a microwave at 120° C. for 20 minutes. After cooling to room temperature, the solvent was evaporated and the resulting mixture was purified by silica gel column chromatography (elution with 100% EtOAc) to provide the title compound (1.46 g, yield 96%). $^1$H NMR (300 MHz, CDCl$_3$) δ 7.92 (d, J=9.0 Hz, 2H), 6.99 (d, J=9 Hz, 2H), 3.87 (s, 3H), 3.08 (s, 3H); ESI-MS m/z 186.1 (M+H)$^+$.

Step 4—Representative Procedure for the Sonagashira Reaction of ethyl 5-bromonicotinate with acetylenes 5-Phenylethynyl-nicotinic acid ethyl ester

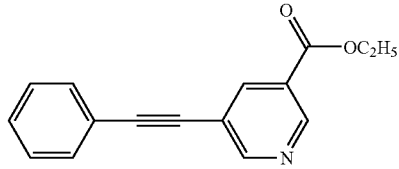

To a solution of ethyl 5-bromonicotinate (1.15 g, 5 mmol) in ethyl acetate (20 mL) under an N$_2$ atmosphere, was added triethylamine (1.1 mL, 7.5 mmol, 1.5 eq.), phenyl acetylene (0.766 g, 7.5 mmol, 1.5 eq.), dichloro-bis(triphenylphosphine)-palladium(II) (176 mg, 0.25 mmol, 0.05 eq.), and copper iodide (10 mg, 0.05 mmol, 0.01 eq). The reaction mixture was heated at 50° C. for 20 h before being cooled to room temperature, filtered through a pad of celite, and solvent evaporated to provide a dark brown oil. Silica gel column chromatography (9/1-4/1 hexanes/EtOAc elution) provided the title compound as a pale yellow oil (1.26 g, yield 100%). $^1$H NMR (300 MHz, CDCl$_3$) δ 9.11 (d, J=1.8 Hz, 1H), 8.87 (d, J=2.1 Hz, 1H), 8.39 (dd, J=1.8, 2.1 Hz, 1H), 7.56-7.53 (m, 2H), 7.40-7.30 (m, 3H), 4.42 (q, J=7.2 Hz, 2H), 1.43 (t, J=7.2 Hz, 3H); ESI-MS m/z 251.9 (M+H)$^+$.

Step 5—Representative Procedure for Nicotinic Acid Ester Hydrolysis

5-Phenylethynyl-nicotinic acid

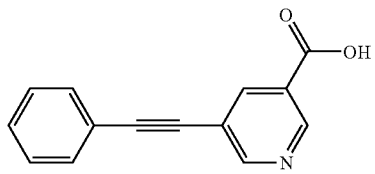

To a solution of 5-phenylethynyl-nicotinic acid ethyl ester (1.17 g, 4.64 mmol) in methanol (10 mL) was added 5 N aqueous sodium hydroxide (2 mL, 10 mmol). The mixture was stirred at room temperature for approximately 20 h, before the reaction mixture was diluted with water (3 mL) and extracted with hexanes/EtOAc (95/5) (10 mL). The aqueous solution was acidified with 1 N HCl to pH 4. The white precipitate that formed was collected by filtration, washed with water (2 mL), and dried under vacuum to provide the title compound as a white solid (987 mg, yield 95%). $^1$H NMR (300 MHz, d$_6$-DMSO) δ 9.02 (d, J=1.8 Hz, 1H), 8.94 (d, J=2.4 Hz, 1H), 8.34 (dd, J=1.8, 2.4 Hz, 1H), 7.63-7.60 (m, 2H), 7.48-7.44 (m, 3H); ESI-MS m/z 223.9 (M+H)$^+$.

Step 6—Representative Procedure for Coupling of Substituted Sulfoximine's to Substituted Nicotinic Acids N-[1-(4-Methoxy-phenyl)-methylsulfoximine]-5-phenylethynyl-nicotinamide A solution of 5-phenylethynyl-nicotinic acid (0.1 mmol) and S-(4-methoxyphenyl)-S-methyl-sulfoximine (0.1 mmol), 1-hydroxybenzotriazole (0.15 mmol) in dimethylformamide (1.5 mL) was treated with 1-ethyl-3-(3-dimethylaminopropyl)-carbodiimide (0.15 mmol) in dimethylformamide (1.5 mL). The reaction mixture was shaken at room temperature for 20 hours and concentrated. The residue was purified by high pressure liquid chromatography (phenomenex Luna C18 5 μm column, gradient elution, acetonitrile/10 mM aqueous ammonium carbonate) and concentrated to give the title compound.

EXAMPLES 2-422

Examples 2 through 422 (table 5) were prepared by the methods described in Example 1 by employing appropriate combinations of the aryl sulfides illustrated in table 3 and the acetylenes illustrated in table 4.

TABLE 3

Aryl Sulfide Reagents

| CAS Number | Reagent | CAS Number | Reagent |
|---|---|---|---|
| 623-13-2 | METHYL P-TOLYL SULFIDE | 68121-46-0 | 3,5-DICHLOROTHIOANISOLE |
| 1879-16-9 | 1-METHOXY-4-(METHYLTHIO)BENZENE | | 3-METHYLTHIOANISOLE |
| 701-57-5 | 4-NITROTHIOANISOLE | 2388-74-1 | 3-METHOXY THIOANISOLE |
| 123-09-1 | 4-CHLOROTHIOANISOLE | | 3,4-DIMETHYLTHIOANISOLE |
| 10352-44-0 | 4-ACETAMIDOTHIOANISOLE | | 3,5-DIMETHYLTHIOANISOLE |
| 2524-78-9 | 3-ACETAMIDOTHIOANISOLE | 100-68-5 | THIOANISOLE |
| 4867-37-2 | 3-CHLOROTHIOANISOLE | | 3,4-DIMETHOXYTHIOANISOLE |
| 2524-76-7 | 3-NITRO THIOANISOLE | | |

TABLE 4

Acetylene Reagents

| CAS # | Reagent | CAS # | Reagent |
|---|---|---|---|
| 126716-66-3 | PHENYLACETYLENE | 15727-65-8 | 1-ETHYNYLNAPHTHALENE |
| 766-97-2 | 4-ETHYNYLTOLUENE | 121697-66-3 | 3-ETHYNYLPYRIDINE |
| 627-41-8 | METHYL PROPARGYL ETHER | 927-74-2 | 3-BUTYN-1-OL |
| 917-92-0 | 3,3-DIMETHYL-1-BUTYNE | 2561-17-3 | 3-FLUOROPHENYLACETYLENE |
| 937-31-5 | 4-NITROPHENYLACETYLENE | 2510-22-7 | 4-ETHYNYLPYRIDINE |
| 351002-93-2 | 4-ETHYNYL-1-FLUORO-2-METHYLBENZENE | 766-47-2 | 2-ETHYNYLTOLUENE |
| 1945-84-2 | 2-ETHYNYLPYRIDINE | 766-81-4 | 1-BROMO-3-ETHYNYL-BENZENE |
| 10401- | 3- | 766-83-6 | 3'-CHLOROPHENYL ACETYLENE |

TABLE 4-continued

Acetylene Reagents

| CAS # | Reagent | CAS # | Reagent |
|---|---|---|---|
| 11-3 | HYDROXYPHENYLACETYLENE | | |
| 129113-00-4 | 2-ETHYNYL-6-METHOXYNAPHTHALENE | 171290-52-1 | 1-ETHYNYL-3,5-DIMETHOXYBENZENE |
| 768-70-7 | 1-ETHYNYL-3-METHOXYBENZENE | 4302-52-7 | 3',4'-DIMETHOXYPHENYL ACETYLENE |
| 768-60-5 | 1-ETH-1-YNYL-4-METHOXYBENZENE | 767-91-9 | 1-ETHYNYL-2-METHOXYBENZENE |
| 766-96-1 | 1-BROMO-4-ETHYNYLBENZENE | 41876-66-8 | 4'-N-PIPERIDINOPHENYL ACETYLENE |
| | 4,5-DICHLORO-1-PROP-2-YNYLIMIDAZOLE | 151361-87-4 | 1-ETHYNYL-3,5-DIFLUORO-BENZENE |
| 873-73-4 | 1-CHLORO-4-ETHYNYLBENZENE | | 5-ETHYNYL-1-METHYL-1H-IMIDAZOLE |
| 873-31-4 | 1-CHLORO-2-ETHYNYLBENZENE | 74331-69-4 | 1-ETHYNYL-4-METHOXY-2-METHYLBENZENE |
| 766-82-5 | M-TOLYLACETYLENE | 74-99-7 | PROPYNE |
| 705-31-7 | 4'-TRIFLUOROMETHYLPHENYL ACETYLENE | 922-67-8 | METHYL PROPIOLATE |
| 766-46-1 | 1-BROMO-2-ETHYNYLBENZENE | 930-51-8 | CYCLOPENTYLACETYLENE |
| 302912-34-1 | 1-ETHYNYL-2,4-DIFLUORO-BENZENE | | 1-ETHYNYL-2-(TRIFLUOROMETHOXY)BENZENE |

TABLE 5

| Example | Example Name |
|---|---|
| Example 2 | N-[(4-methoxyphenyl)(methyl)oxo-$\lambda^6$-sulfanylidene]-5-[(4-methylphenyl)ethynyl]nicotinamide |
| Example 3 | N-[(4-methoxyphenyl)(methyl)oxo-$\lambda^6$-sulfanylidene]-5-(3-methoxyprop-1-yn-1-yl)nicotinamide |
| Example 4 | 5-(3,3-dimethylbut-1-yn-1-yl)-N-[(4-methoxyphenyl)(methyl)oxo-$\lambda^6$-sulfanylidene]nicotinamide |
| Example 5 | N-[(4-methoxyphenyl)(methyl)oxo-$\lambda^6$-sulfanylidene]-5-prop-1-yn-1-ylnicotinamide |
| Example 6 | N-[(4-methoxyphenyl)(methyl)oxo-$\lambda^6$-sulfanylidene]-5-(pyridin-2-ylethynyl)nicotinamide |
| Example 7 | 5-[(3-hydroxyphenyl)ethynyl]-N-[(4-methoxyphenyl)(methyl)oxo-$\lambda^6$-sulfanylidene]nicotinamide |
| Example 8 | 5-[(6-methoxy-2-naphthyl)ethynyl]-N-[(4-methoxyphenyl)(methyl)oxo-$\lambda^6$-sulfanylidene]nicotinamide |
| Example 9 | 5-[(3-methoxyphenyl)ethynyl]-N-[(4-methoxyphenyl)(methyl)oxo-$\lambda^6$-sulfanylidene]nicotinamide |
| Example 10 | 5-[(4-methoxyphenyl)ethynyl]-N-[(4-methoxyphenyl)(methyl)oxo-$\lambda^6$-sulfanylidene]nicotinamide |
| Example 11 | 5-[(4-bromophenyl)ethynyl]-N-[(4-methoxyphenyl)(methyl)oxo-$\lambda^6$-sulfanylidene]nicotinamide |
| Example 12 | 5-[3-(4,5-dichloro-1H-imidazol-1-yl)prop-1-yn-1-yl]-N-[(4-methoxyphenyl)(methyl)oxo-$\lambda^6$-sulfanylidene]nicotinamide |
| Example 13 | 5-[(4-chlorophenyl)ethynyl]-N-[(4-methoxyphenyl)(methyl)oxo-$\lambda^6$-sulfanylidene]nicotinamide |
| Example 14 | 5-[(2-chlorophenyl)ethynyl]-N-[(4-methoxyphenyl)(methyl)oxo-$\lambda^6$-sulfanylidene]nicotinamide |
| Example 15 | N-[(4-methoxyphenyl)(methyl)oxo-$\lambda^6$-sulfanylidene]-5-[(3-methylphenyl)ethynyl]nicotinamide |
| Example 16 | N-[(4-methoxyphenyl)(methyl)oxo-$\lambda^6$-sulfanylidene]-5-{[4-(trifluoromethyl)phenyl]ethynyl}nicotinamide |
| Example 17 | 5-[(2,4-difluorophenyl)ethynyl]-N-[(4-methoxyphenyl)(methyl)oxo-$\lambda^6$-sulfanylidene]nicotinamide |
| Example 18 | N-[(4-methoxyphenyl)(methyl)oxo-$\lambda^6$-sulfanylidene]-5-(pyridin-3-ylethynyl)nicotinamide |
| Example 19 | 5-[(3-fluorophenyl)ethynyl]-N-[(4-methoxyphenyl)(methyl)oxo-$\lambda^6$-sulfanylidene]nicotinamide |
| Example 20 | N-[(4-methoxyphenyl)(methyl)oxo-$\lambda^6$-sulfanylidene]-5-(pyridin-4-ylethynyl)nicotinamide |
| Example 21 | N-[(4-methoxyphenyl)(methyl)oxo-$\lambda^6$-sulfanylidene]-5-[(2-methylphenyl)ethynyl]nicotinamide |
| Example 22 | 5-[(3-bromophenyl)ethynyl]-N-[(4-methoxyphenyl)(methyl)oxo-$\lambda^6$-sulfanylidene]nicotinamide |
| Example 23 | 5-[(3-chlorophenyl)ethynyl]-N-[(4-methoxyphenyl)(methyl)oxo-$\lambda^6$-sulfanylidene]nicotinamide |
| Example 24 | 5-[(3,5-dimethoxyphenyl)ethynyl]-N-[(4-methoxyphenyl)(methyl)oxo-$\lambda^6$-sulfanylidene]nicotinamide |

TABLE 5-continued

| Example | Example Name |
|---|---|
| Example 25 | 5-[(3,4-dimethoxyphenyl)ethynyl]-N-[(4-methoxyphenyl)(methyl)oxo-$\lambda^6$-sulfanylidene]nicotinamide |
| Example 26 | 5-[(2-methoxyphenyl)ethynyl]-N-[(4-methoxyphenyl)(methyl)oxo-$\lambda^6$-sulfanylidene]nicotinamide |
| Example 27 | N-[(4-methoxyphenyl)(methyl)oxo-$\lambda^6$-sulfanylidene]-5-[(4-piperidin-1-ylphenyl)ethynyl]nicotinamide |
| Example 28 | 5-[(3,5-difluorophenyl)ethynyl]-N-[(4-methoxyphenyl)(methyl)oxo-$\lambda^6$-sulfanylidene]nicotinamide |
| Example 29 | 5-[(4-methoxy-2-methylphenyl)ethynyl]-N-[(4-methoxyphenyl)(methyl)oxo-$\lambda^6$-sulfanylidene]nicotinamide |
| Example 30 | 5-[(4-fluoro-3-methylphenyl)ethynyl]-N-[(4-methoxyphenyl)(methyl)oxo-$\lambda^6$-sulfanylidene]nicotinamide |
| Example 31 | 5-(4-hydroxybut-1-yn-1-yl)-N-[methyl(oxo)phenyl-$\lambda^6$-sulfanylidene]nicotinamide |
| Example 32 | N-[methyl(oxo)phenyl-$\lambda^6$-sulfanylidene]-5-(phenylethynyl)nicotinamide |
| Example 33 | N-[methyl(oxo)phenyl-$\lambda^6$-sulfanylidene]-5-[(4-methylphenyl)ethynyl]nicotinamide |
| Example 34 | 5-(3-methoxyprop-1-yn-1-yl)-N-[methyl(oxo)phenyl-$\lambda^6$-sulfanylidene]nicotinamide |
| Example 35 | 5-(3,3-dimethylbut-1-yn-1-yl)-N-[methyl(oxo)phenyl-$\lambda^6$sulfanylidene]nicotinamide |
| Example 36 | N-[methyl(oxo)phenyl-$\lambda^6$-sulfanylidene]-5-[(4-nitrophenyl)ethynyl]nicotinamide |
| Example 37 | N-[methyl(oxo)phenyl-$\lambda^6$-sulfanylidene]-5-prop-1-yn-1-ylnicotinamide |
| Example 38 | N-[methyl(oxo)phenyl-$\lambda^6$-sulfanylidene]-5-(pyridin-2-ylethynyl)nicotinamide |
| Example 39 | 5-[(3-hydroxyphenyl)ethynyl]-N-[methyl(oxo)phenyl-$\lambda^6$-sulfanylidene]nicotinamide |
| Example 40 | 5-[(6-methoxy-2-naphthyl)ethynyl]-N-[methyl(oxo)phenyl-$\lambda^6$-sulfanylidene]nicotinamide |
| Example 41 | 5-[(3-methoxyphenyl)ethynyl]-N-[methyl(oxo)phenyl-$\lambda^6$-sulfanylidene]nicotinamide |
| Example 42 | 5-[(4-methoxyphenyl)ethynyl]-N-[methyl(oxo)phenyl-$\lambda^6$-sulfanylidene]nicotinamide |
| Example 43 | 5-[(4-bromophenyl)ethynyl]-N-[methyl(oxo)phenyl-$\lambda^6$-sulfanylidene]nicotinamide |
| Example 44 | 5-[3-(4,5-dichloro-1H-imidazol-1-yl)prop-1-yn-1-yl]-N-[methyl(oxo)phenyl-$\lambda^6$-sulfanylidene]nicotinamide |
| Example 45 | 5-[(4-chlorophenyl)ethynyl]-N-[methyl(oxo)phenyl-$\lambda^6$-sulfanylidene]nicotinamide |
| Example 46 | 5-[(2-chlorophenyl)ethynyl]-N-[methyl(oxo)phenyl-$\lambda^6$-sulfanylidene]nicotinamide |
| Example 47 | N-[methyl(oxo)phenyl-$\lambda^6$-sulfanylidene]-5-[(3-methylphenyl)ethynyl]nicotinamide |
| Example 48 | N-[methyl(oxo)phenyl-$\lambda^6$-sulfanylidene]-5-{[4-(trifluoromethyl)phenyl]ethynyl}nicotinamide |
| Example 49 | 5-[(2-bromophenyl)ethynyl]-N-[methyl(oxo)phenyl-$\lambda^6$-sulfanylidene]nicotinamide |
| Example 50 | 5-[(2,4-difluorophenyl)ethynyl]-N-[methyl(oxo)phenyl-$\lambda^6$-sulfanylidene]nicotinamide |
| Example 51 | N-[methyl(oxo)phenyl-$\lambda^6$-sulfanylidene]-5-(1-naphthylethynyl)nicotinamide |
| Example 52 | N-[methyl(oxo)phenyl-$\lambda^6$-sulfanylidene]-5-(pyridin-3-ylethynyl)nicotinamide |
| Example 53 | 5-[(3-fluorophenyl)ethynyl]-N-[methyl(oxo)phenyl-$\lambda^6$-sulfanylidene]nicotinamide |
| Example 54 | N-[methyl(oxo)phenyl-$\lambda^6$-sulfanylidene]-5-(pyridin-4-ylethynyl)nicotinamide |
| Example 55 | N-[methyl(oxo)phenyl-$\lambda^6$-sulfanylidene]-5-[(2-methylphenyl)ethynyl]nicotinamide |
| Example 56 | 5-[(3-bromophenyl)ethynyl]-N-[methyl(oxo)phenyl-$\lambda^6$-sulfanylidene]nicotinamide |
| Example 57 | 5-[(3-chlorophenyl)ethynyl]-N-[methyl(oxo)phenyl-$\lambda^6$-sulfanylidene]nicotinamide |
| Example 58 | 5-[(3,5-dimethoxyphenyl)ethynyl]-N-[methyl(oxo)phenyl-$\lambda^6$-sulfanylidene]nicotinamide |
| Example 59 | 5-[(3,4-dimethoxyphenyl)ethynyl]-N-[methyl(oxo)phenyl-$\lambda^6$-sulfanylidene]nicotinamide |
| Example 60 | 5-[(2-methoxyphenyl)ethynyl]-N-[methyl(oxo)phenyl-$\lambda^6$-sulfanylidene]nicotinamide |
| Example 61 | N-[methyl(oxo)phenyl-$\lambda^6$-sulfanylidene]-5-[(4-piperidin-1-ylphenyl)ethynyl]nicotinamide |
| Example 62 | 5-[(3,5-difluorophenyl)ethynyl]-N-[methyl(oxo)phenyl-$\lambda^6$-sulfanylidene]nicotinamide |
| Example 63 | 5-[(4-methoxy-2-methylphenyl)ethynyl]-N-[methyl(oxo)phenyl-$\lambda^6$-sulfanylidene]nicotinamide |
| Example 64 | 5-[(4-fluoro-3-methylphenyl)ethynyl]-N-[methyl(oxo)phenyl-$\lambda^6$-sulfanylidene]nicotinamide |

TABLE 5-continued

| Example | Example Name |
|---|---|
| Example 65 | 5-(4-hydroxybut-1-yn-1-yl)-N-[methyl(4-methylphenyl)oxo-$\lambda^6$-sulfanylidene]nicotinamide |
| Example 66 | N-[methyl(4-methylphenyl)oxo-$\lambda^6$-sulfanylidene]-5-[(4-methylphenyl)ethynyl]nicotinamide |
| Example 67 | 5-(3-methoxyprop-1-yn-1-yl)-N-[methyl(4-methylphenyl)oxo-$\lambda^6$-sulfanylidene]nicotinamide |
| Example 68 | 5-(3,3-dimethylbut-1-yn-1-yl)-N-[methyl(4-methylphenyl)oxo-$\lambda^6$-sulfanylidene]nicotinamide |
| Example 69 | N-[methyl(4-methylphenyl)oxo-$\lambda^6$-sulfanylidene]-5-[(4-nitrophenyl)ethynyl]nicotinamide |
| Example 70 | N-[methyl(4-methylphenyl)oxo-$\lambda^6$-sulfanylidene]-5-prop-1-yn-1-ylnicotinamide |
| Example 71 | N-[methyl(4-methylphenyl)oxo-$\lambda^6$-sulfanylidene]-5-(pyridin-2-ylethynyl)nicotinamide |
| Example 72 | 5-[(3-hydroxyphenyl)ethynyl]-N-[methyl(4-methylphenyl)oxo-$\lambda^6$-sulfanylidene]nicotinamide |
| Example 73 | 5-[(6-methoxy-2-naphthyl)ethynyl]-N-[methyl(4-methylphenyl)oxo-$\lambda^6$-sulfanylidene]nicotinamide |
| Example 74 | 5-[(3-methoxyphenyl)ethynyl]-N-[methyl(4-methylphenyl)oxo-$\lambda^6$-sulfanylidene]nicotinamide |
| Example 75 | 5-[(4-methoxyphenyl)ethynyl]-N-[methyl(4-methylphenyl)oxo-$\lambda^6$-sulfanylidene]nicotinamide |
| Example 76 | 5-[(4-bromophenyl)ethynyl]-N-[methyl(4-methylphenyl)oxo-$\lambda^6$-sulfanylidene]nicotinamide |
| Example 77 | 5-[3-(4,5-dichloro-1H-imidazol-1-yl)prop-1-yn-1-yl]-N-[methyl(4-methylphenyl)oxo-$\lambda^6$-sulfanylidene]nicotinamide |
| Example 78 | 5-[(4-chlorophenyl)ethynyl]-N-[methyl(4-methylphenyl)oxo-$\lambda^6$-sulfanylidene]nicotinamide |
| Example 79 | 5-[(2-chlorophenyl)ethynyl]-N-[methyl(4-methylphenyl)oxo-$\lambda^6$-sulfanylidene]nicotinamide |
| Example 80 | N-[methyl(4-methylphenyl)oxo-$\lambda^6$-sulfanylidene]-5-[(3-methylphenyl)ethynyl]nicotinamide |
| Example 81 | N-[methyl(4-methylphenyl)oxo-$\lambda^6$-sulfanylidene]-5-{[4-(trifluoromethyl)phenyl]ethynyl}nicotinamide |
| Example 82 | 5-[(2-bromophenyl)ethynyl]-N-[methyl(4-methylphenyl)oxo-$\lambda^6$-sulfanylidene]nicotinamide |
| Example 83 | N-[methyl(4-methylphenyl)oxo-$\lambda^6$-sulfanylidene]-5-(1-naphthylethynyl)nicotinamide |
| Example 84 | N-[methyl(4-methylphenyl)oxo-$\lambda^6$-sulfanylidene]-5-(pyridin-3-ylethynyl)nicotinamide |
| Example 85 | 5-[(3-fluorophenyl)ethynyl]-N-[methyl(4-methylphenyl)oxo-$\lambda^6$-sulfanylidene]nicotinamide |
| Example 86 | N-[methyl(4-methylphenyl)oxo-$\lambda^6$-sulfanylidene]-5-(pyridin-4-ylethynyl)nicotinamide |
| Example 87 | N-[methyl(4-methylphenyl)oxo-$\lambda^6$-sulfanylidene]-5-[(2-methylphenyl)ethynyl]nicotinamide |
| Example 88 | 5-[(3-bromophenyl)ethynyl]-N-[methyl(4-methylphenyl)oxo-$\lambda^6$-sulfanylidene]nicotinamide |
| Example 89 | 5-[(3-chlorophenyl)ethynyl]-N-[methyl(4-methylphenyl)oxo-$\lambda^6$-sulfanylidene]nicotinamide |
| Example 90 | 5-[(3,5-dimethoxyphenyl)ethynyl]-N-[methyl(4-methylphenyl)oxo-$\lambda^6$-sulfanylidene]nicotinamide |
| Example 91 | 5-[(3,4-dimethoxyphenyl)ethynyl]-N-[methyl(4-methylphenyl)oxo-$\lambda^6$-sulfanylidene]nicotinamide |
| Example 92 | 5-[(2-methoxyphenyl)ethynyl]-N-[methyl(4-methylphenyl)oxo-$\lambda^6$-sulfanylidene]nicotinamide |
| Example 93 | 5-[(3,5-difluorophenyl)ethynyl]-N-[methyl(4-methylphenyl)oxo-$\lambda^6$-sulfanylidene]nicotinamide |
| Example 94 | 5-[(1-methyl-1H-imidazol-5-yl)ethynyl]-N-[methyl(4-methylphenyl)oxo-$\lambda^6$-sulfanylidene]nicotinamide |
| Example 95 | 5-[(4-methoxy-2-methylphenyl)ethynyl]-N-[methyl(4-methylphenyl)oxo-$\lambda^6$-sulfanylidene]nicotinamide |
| Example 96 | 5-[(4-fluoro-3-methylphenyl)ethynyl]-N-[methyl(4-methylphenyl)oxo-$\lambda^6$-sulfanylidene]nicotinamide |
| Example 97 | 5-(4-hydroxybut-1-yn-1-yl)-N-[(4-methoxyphenyl)(methyl)oxo-$\lambda^6$-sulfanylidene]nicotinamide |
| Example 98 | N-[(4-chlorophenyl)(methyl)oxo-$\lambda^6$-sulfanylidene]-5-(4-hydroxybut-1-yn-1-yl)nicotinamide |
| Example 99 | N-[(4-chlorophenyl)(methyl)oxo-$\lambda^6$-sulfanylidene]-5-(phenylethynyl)nicotinamide |
| Example 100 | N-[(4-chlorophenyl)(methyl)oxo-$\lambda^6$-sulfanylidene]-5-[(4-methylphenyl)ethynyl]nicotinamide |
| Example 101 | N-[(4-chlorophenyl)(methyl)oxo-$\lambda^6$-sulfanylidene]-5-(3-methoxyprop-1-yn-1-yl)nicotinamide |
| Example 102 | N-[(4-chlorophenyl)(methyl)oxo-$\lambda^6$-sulfanylidene]-5-(3,3-dimethylbut-1-yn-1-yl)nicotinamide |
| Example 103 | N-[(4-chlorophenyl)(methyl)oxo-$\lambda^6$-sulfanylidene]-5-[(4-nitrophenyl)ethynyl]nicotinamide |

TABLE 5-continued

| Example | Example Name |
|---|---|
| Example 104 | N-[(4-chlorophenyl)(methyl)oxo-$\lambda^6$-sulfanylidene]-5-prop-1-yn-1-ylnicotinamide |
| Example 105 | N-[(4-chlorophenyl)(methyl)oxo-$\lambda^6$-sulfanylidene]-5-(pyridin-2-ylethynyl)nicotinamide |
| Example 106 | N-[(4-chlorophenyl)(methyl)oxo-$\lambda^6$-sulfanylidene]-5-[(3-hydroxyphenyl)ethynyl]nicotinamide |
| Example 107 | N-[(4-chlorophenyl)(methyl)oxo-$\lambda^6$-sulfanylidene]-5-[(3-methoxyphenyl)ethynyl]nicotinamide |
| Example 108 | N-[(4-chlorophenyl)(methyl)oxo-$\lambda^6$-sulfanylidene]-5-[(4-methoxyphenyl)ethynyl]nicotinamide |
| Example 109 | 5-[(4-bromophenyl)ethynyl]-N-[(4-chlorophenyl)(methyl)oxo-$\lambda^6$-sulfanylidene]nicotinamide |
| Example 110 | N-[(4-chlorophenyl)(methyl)oxo-$\lambda^6$-sulfanylidene]-5-[3-(4,5-dichloro-1H-imidazol-1-yl)prop-1-yn-1-yl]nicotinamide |
| Example 111 | 5-[(4-chlorophenyl)ethynyl]-N-[(4-chlorophenyl)(methyl)oxo-$\lambda^6$-sulfanylidene]nicotinamide |
| Example 112 | 5-[(2-bromophenyl)ethynyl]-N-[(4-chlorophenyl)(methyl)oxo-$\lambda^6$-sulfanylidene]nicotinamide |
| Example 113 | N-[(4-chlorophenyl)(methyl)oxo-$\lambda^6$-sulfanylidene]-5-[(2,4-difluorophenyl)ethynyl]nicotinamide |
| Example 114 | N-[(4-chlorophenyl)(methyl)oxo-$\lambda^6$-sulfanylidene]-5-(1-naphthylethynyl)nicotinamide |
| Example 115 | N-[(4-chlorophenyl)(methyl)oxo-$\lambda^6$-sulfanylidene]-5-(pyridin-3-ylethynyl)nicotinamide |
| Example 116 | N-[(4-chlorophenyl)(methyl)oxo-$\lambda^6$-sulfanylidene]-5-[(3-fluorophenyl)ethynyl]nicotinamide |
| Example 117 | N-[(4-chlorophenyl)(methyl)oxo-$\lambda^6$-sulfanylidene]-5-[(2-methylphenyl)ethynyl]nicotinamide |
| Example 118 | 5-[(3-bromophenyl)ethynyl]-N-[(4-chlorophenyl)(methyl)oxo-$\lambda^6$-sulfanylidene]nicotinamide |
| Example 119 | 5-[(3-chlorophenyl)ethynyl]-N-[(4-chlorophenyl)(methyl)oxo-$\lambda^6$-sulfanylidene]nicotinamide |
| Example 120 | N-[(4-chlorophenyl)(methyl)oxo-$\lambda^6$-sulfanylidene]-5-[(3,5-dimethoxyphenyl)ethynyl]nicotinamide |
| Example 121 | N-[(4-chlorophenyl)(methyl)oxo-$\lambda^6$-sulfanylidene]-5-[(3,4-dimethoxyphenyl)ethynyl]nicotinamide |
| Example 122 | N-[(4-chlorophenyl)(methyl)oxo-$\lambda^6$-sulfanylidene]-5-[(2-methoxyphenyl)ethynyl]nicotinamide |
| Example 123 | N-[(4-chlorophenyl)(methyl)oxo-$\lambda^6$-sulfanylidene]-5-[(3,5-difluorophenyl)ethynyl]nicotinamide |
| Example 124 | N-[(4-chlorophenyl)(methyl)oxo-$\lambda^6$-sulfanylidene]-5-[(1-methyl-1H-imidazol-5-yl)ethynyl]nicotinamide |
| Example 125 | N-[(4-chlorophenyl)(methyl)oxo-$\lambda^6$-sulfanylidene]-5-[(4-methoxy-2-methylphenyl)ethynyl]nicotinamide |
| Example 126 | N-[(4-chlorophenyl)(methyl)oxo-$\lambda^6$-sulfanylidene]-5-[(4-fluoro-3-methylphenyl)ethynyl]nicotinamide |
| Example 127 | N-{[4-(acetylamino)phenyl](methyl)oxo-$\lambda^6$-sulfanylidene}-5-(4-hydroxybut-1-yn-1-yl)nicotinamide |
| Example 128 | N-{[4-(acetylamino)phenyl](methyl)oxo-$\lambda^6$-sulfanylidene}-5-(phenylethynyl)nicotinamide |
| Example 129 | N-{[4-(acetylamino)phenyl](methyl)oxo-$\lambda^6$-sulfanylidene}-5-[(4-methylphenyl)ethynyl]nicotinamide |
| Example 130 | N-{[4-(acetylamino)phenyl](methyl)oxo-$\lambda^6$-sulfanylidene}-5-(3-methoxyprop-1-yn-1-yl)nicotinamide |
| Example 131 | N-{[4-(acetylamino)phenyl](methyl)oxo-$\lambda^6$-sulfanylidene}-5-(3,3-dimethylbut-1-yn-1-yl)nicotinamide |
| Example 132 | N-{[4-(acetylamino)phenyl](methyl)oxo-$\lambda^6$-sulfanylidene}-5-[(4-nitrophenyl)ethynyl]nicotinamide |
| Example 133 | N-{[4-(acetylamino)phenyl](methyl)oxo-$\lambda^6$-sulfanylidene}-5-prop-1-yn-1-ylnicotinamide |
| Example 134 | N-{[4-(acetylamino)phenyl](methyl)oxo-$\lambda^6$-sulfanylidene}-5-(pyridin-2-ylethynyl)nicotinamide |
| Example 135 | N-{[4-(acetylamino)phenyl](methyl)oxo-$\lambda^6$-sulfanylidene}-5-[(6-methoxy-2-naphthyl)ethynyl]nicotinamide |
| Example 136 | N-{[4-(acetylamino)phenyl](methyl)oxo-$\lambda^6$-sulfanylidene}-5-[(3-methoxyphenyl)ethynyl]nicotinamide |
| Example 137 | N-{[4-(acetylamino)phenyl](methyl)oxo-$\lambda^6$-sulfanylidene}-5-[(4-methoxyphenyl)ethynyl]nicotinamide |
| Example 138 | N-{[4-(acetylamino)phenyl](methyl)oxo-$\lambda^6$-sulfanylidene}-5-[(4-bromophenyl)ethynyl]nicotinamide |
| Example 139 | N-{[4-(acetylamino)phenyl](methyl)oxo-$\lambda^6$-sulfanylidene}-5-[(4-chlorophenyl)ethynyl]nicotinamide |
| Example 140 | N-{[4-(acetylamino)phenyl](methyl)oxo-$\lambda^6$-sulfanylidene}-5-[(2-chlorophenyl)ethynyl]nicotinamide |
| Example 141 | N-{[4-(acetylamino)phenyl](methyl)oxo-$\lambda^6$-sulfanylidene}-5-[(3-methylphenyl)ethynyl]nicotinamide |
| Example 142 | N-{[4-(acetylamino)phenyl](methyl)oxo-$\lambda^6$-sulfanylidene}-5-{[4-(trifluoromethyl)phenyl]ethynyl}nicotinamide |

TABLE 5-continued

| Example | Example Name |
|---|---|
| Example 143 | N-{[4-(acetylamino)phenyl](methyl)oxo-$\lambda^6$-sulfanylidene}-5-[(2-bromophenyl)ethynyl]nicotinamide |
| Example 144 | N-{[4-(acetylamino)phenyl](methyl)oxo-$\lambda^6$-sulfanylidene}-5-[(2,4-difluorophenyl)ethynyl]nicotinamide |
| Example 145 | N-{[4-(acetylamino)phenyl](methyl)oxo-$\lambda^6$-sulfanylidene}-5-(1-naphthylethynyl)nicotinamide |
| Example 146 | N-{[4-(acetylamino)phenyl](methyl)oxo-$\lambda^6$-sulfanylidene}-5-(pyridin-3-ylethynyl)nicotinamide |
| Example 147 | N-{[4-(acetylamino)phenyl](methyl)oxo-$\lambda^6$-sulfanylidene}-5-[(3-fluorophenyl)ethynyl]nicotinamide |
| Example 148 | N-{[4-(acetylamino)phenyl](methyl)oxo-$\lambda^6$-sulfanylidene}-5-(pyridin-4-ylethynyl)nicotinamide |
| Example 149 | N-{[4-(acetylamino)phenyl](methyl)oxo-$\lambda^6$-sulfanylidene}-5-[(2-methylphenyl)ethynyl]nicotinamide |
| Example 150 | N-{[4-(acetylamino)phenyl](methyl)oxo-$\lambda^6$-sulfanylidene}-5-[(3-bromophenyl)ethynyl]nicotinamide |
| Example 151 | N-{[4-(acetylamino)phenyl](methyl)oxo-$\lambda^6$-sulfanylidene}-5-[(3-chlorophenyl)ethynyl]nicotinamide |
| Example 152 | N-{[4-(acetylamino)phenyl](methyl)oxo-$\lambda^6$-sulfanylidene}-5-[(3,5-dimethoxyphenyl)ethynyl]nicotinamide |
| Example 153 | N-{[4-(acetylamino)phenyl](methyl)oxo-$\lambda^6$-sulfanylidene}-5-[(2-methoxyphenyl)ethynyl]nicotinamide |
| Example 154 | N-{[4-(acetylamino)phenyl](methyl)oxo-$\lambda^6$-sulfanylidene}-5-[(3,5-difluorophenyl)ethynyl]nicotinamide |
| Example 155 | N-{[4-(acetylamino)phenyl](methyl)oxo-$\lambda^6$-sulfanylidene}-5-[(1-methyl-1H-imidazol-5-yl)ethynyl]nicotinamide |
| Example 156 | N-{[4-(acetylamino)phenyl](methyl)oxo-$\lambda^6$-sulfanylidene}-5-[(4-methoxy-2-methylphenyl)ethynyl]nicotinamide |
| Example 157 | N-{[4-(acetylamino)phenyl](methyl)oxo-$\lambda^6$-sulfanylidene}-5-[(4-fluoro-3-methylphenyl)ethynyl]nicotinamide |
| Example 158 | N-{[3-(acetylamino)phenyl](methyl)oxo-$\lambda^6$-sulfanylidene}-5-(4-hydroxybut-1-yn-1-yl)nicotinamide |
| Example 159 | N-{[3-(acetylamino)phenyl](methyl)oxo-$\lambda^6$-sulfanylidene}-5-(phenylethynyl)nicotinamide |
| Example 160 | N-{[3-(acetylamino)phenyl](methyl)oxo-$\lambda^6$-sulfanylidene}-5-[(4-methylphenyl)ethynyl]nicotinamide |
| Example 161 | N-{[3-(acetylamino)phenyl](methyl)oxo-$\lambda^6$-sulfanylidene}-5-(3-methoxyprop-1-yn-1-yl)nicotinamide |
| Example 162 | N-{[3-(acetylamino)phenyl](methyl)oxo-$\lambda^6$-sulfanylidene}-5-(3,3-dimethylbut-1-yn-1-yl)nicotinamide |
| Example 163 | N-{[3-(acetylamino)phenyl](methyl)oxo-$\lambda^6$-sulfanylidene}-5-[(4-nitrophenyl)ethynyl]nicotinamide |
| Example 164 | N-{[3-(acetylamino)phenyl](methyl)oxo-$\lambda^6$-sulfanylidene}-5-prop-1-yn-1-ylnicotinamide |
| Example 165 | N-{[3-(acetylamino)phenyl](methyl)oxo-$\lambda^6$-sulfanylidene}-5-(pyridin-2-ylethynyl)nicotinamide |
| Example 166 | N-{[3-(acetylamino)phenyl](methyl)oxo-$\lambda^6$-sulfanylidene}-5-[(3-hydroxyphenyl)ethynyl]nicotinamide |
| Example 167 | N-{[3-(acetylamino)phenyl](methyl)oxo-$\lambda^6$-sulfanylidene}-5-[(6-methoxy-2-naphthyl)ethynyl]nicotinamide |
| Example 168 | N-{[3-(acetylamino)phenyl](methyl)oxo-$\lambda^6$-sulfanylidene}-5-[(3-methoxyphenyl)ethynyl]nicotinamide |
| Example 169 | N-{[3-(acetylamino)phenyl](methyl)oxo-$\lambda^6$-sulfanylidene}-5-[(4-methoxyphenyl)ethynyl]nicotinamide |
| Example 170 | N-{[3-(acetylamino)phenyl](methyl)oxo-$\lambda^6$-sulfanylidene}-5-[(4-bromophenyl)ethynyl]nicotinamide |
| Example 171 | N-{[3-(acetylamino)phenyl](methyl)oxo-$\lambda^6$-sulfanylidene}-5-[3-(4,5-dichloro-1H-imidazol-1-yl)prop-1-yn-1-yl]nicotinamide |
| Example 172 | N-{[3-(acetylamino)phenyl](methyl)oxo-$\lambda^6$-sulfanylidene}-5-[(4-chlorophenyl)ethynyl]nicotinamide |
| Example 173 | N-{[3-(acetylamino)phenyl](methyl)oxo-$\lambda^6$-sulfanylidene}-5-[(2-chlorophenyl)ethynyl]nicotinamide |
| Example 174 | N-{[3-(acetylamino)phenyl](methyl)oxo-$\lambda^6$-sulfanylidene}-5-[(3-methylphenyl)ethynyl]nicotinamide |
| Example 175 | N-{[3-(acetylamino)phenyl](methyl)oxo-$\lambda^6$-sulfanylidene}-5-{[4-(trifluoromethyl)phenyl]ethynyl}nicotinamide |
| Example 176 | N-{[3-(acetylamino)phenyl](methyl)oxo-$\lambda^6$-sulfanylidene}-5-[(2-bromophenyl)ethynyl]nicotinamide |
| Example 177 | N-{[3-(acetylamino)phenyl](methyl)oxo-$\lambda^6$-sulfanylidene}-5-[(2,4-difluorophenyl)ethynyl]nicotinamide |
| Example 178 | N-{[3-(acetylamino)phenyl](methyl)oxo-$\lambda^6$-sulfanylidene}-5-(1-naphthylethynyl)nicotinamide |
| Example 179 | N-{[3-(acetylamino)phenyl](methyl)oxo-$\lambda^6$-sulfanylidene}-5-(pyridin-3-ylethynyl)nicotinamide |
| Example 180 | N-{[3-(acetylamino)phenyl](methyl)oxo-$\lambda^6$-sulfanylidene}-5-[(3-fluorophenyl)ethynyl]nicotinamide |
| Example 181 | N-{[3-(acetylamino)phenyl](methyl)oxo-$\lambda^6$-sulfanylidene}-5-(pyridin-4-ylethynyl)nicotinamide |

TABLE 5-continued

| Example | Example Name |
| --- | --- |
| Example 182 | N-{[3-(acetylamino)phenyl](methyl)oxo-λ$^6$-sulfanylidene}-5-[(2-methylphenyl)ethynyl]nicotinamide |
| Example 183 | N-{[3-(acetylamino)phenyl](methyl)oxo-λ$^6$-sulfanylidene}-5-[(3-bromophenyl)ethynyl]nicotinamide |
| Example 184 | N-{[3-(acetylamino)phenyl](methyl)oxo-λ$^6$-sulfanylidene}-5-[(3-chlorophenyl)ethynyl]nicotinamide |
| Example 185 | N-{[3-(acetylamino)phenyl](methyl)oxo-λ$^6$-sulfanylidene}-5-[(3,5-dimethoxyphenyl)ethynyl]nicotinamide |
| Example 186 | N-{[3-(acetylamino)phenyl](methyl)oxo-λ$^6$-sulfanylidene}-5-[(3,4-dimethoxyphenyl)ethynyl]nicotinamide |
| Example 187 | N-{[3-(acetylamino)phenyl](methyl)oxo-λ$^6$-sulfanylidene}-5-[(2-methoxyphenyl)ethynyl]nicotinamide |
| Example 188 | N-{[3-(acetylamino)phenyl](methyl)oxo-λ$^6$-sulfanylidene}-5-[(4-piperidin-1-ylphenyl)ethynyl]nicotinamide |
| Example 189 | N-{[3-(acetylamino)phenyl](methyl)oxo-λ$^6$-sulfanylidene}-5-[(3,5-difluorophenyl)ethynyl]nicotinamide |
| Example 190 | N-{[3-(acetylamino)phenyl](methyl)oxo-λ$^6$-sulfanylidene}-5-[(1-methyl-1H-imidazol-5-yl)ethynyl]nicotinamide |
| Example 191 | N-{[3-(acetylamino)phenyl](methyl)oxo-λ$^6$-sulfanylidene}-5-[(4-methoxy-2-methylphenyl)ethynyl]nicotinamide |
| Example 192 | N-{[3-(acetylamino)phenyl](methyl)oxo-λ$^6$-sulfanylidene}-5-[(4-fluoro-3-methylphenyl)ethynyl]nicotinamide |
| Example 193 | N-[(3-chlorophenyl)(methyl)oxo-λ$^6$-sulfanylidene]-5-(4-hydroxybut-1-yn-1-yl)nicotinamide |
| Example 194 | N-[(3-chlorophenyl)(methyl)oxo-λ$^6$-sulfanylidene]-5-(phenylethynyl)nicotinamide |
| Example 195 | N-[(3-chlorophenyl)(methyl)oxo-λ$^6$-sulfanylidene]-5-[(4-methylphenyl)ethynyl]nicotinamide |
| Example 196 | N-[(3-chlorophenyl)(methyl)oxo-λ$^6$-sulfanylidene]-5-(3-methoxyprop-1-yn-1-yl)nicotinamide |
| Example 197 | N-[(3-chlorophenyl)(methyl)oxo-λ$^6$-sulfanylidene]-5-(3,3-dimethylbut-1-yn-1-yl)nicotinamide |
| Example 198 | N-[(3-chlorophenyl)(methyl)oxo-λ$^6$-sulfanylidene]-5-[(4-nitrophenyl)ethynyl]nicotinamide |
| Example 199 | N-[(3-chlorophenyl)(methyl)oxo-λ$^6$-sulfanylidene]-5-prop-1-yn-1-ylnicotinamide |
| Example 200 | N-[(3-chlorophenyl)(methyl)oxo-λ$^6$-sulfanylidene]-5-(pyridin-2-ylethynyl)nicotinamide |
| Example 201 | N-[(3-chlorophenyl)(methyl)oxo-λ$^6$-sulfanylidene]-5-[(3-hydroxyphenyl)ethynyl]nicotinamide |
| Example 202 | N-[(3-chlorophenyl)(methyl)oxo-λ$^6$-sulfanylidene]-5-[(6-methoxy-2-naphthyl)ethynyl]nicotinamide |
| Example 203 | N-[(3-chlorophenyl)(methyl)oxo-λ$^6$-sulfanylidene]-5-[(3-methoxyphenyl)ethynyl]nicotinamide |
| Example 204 | N-[(3-chlorophenyl)(methyl)oxo-λ$^6$-sulfanylidene]-5-[(4-methoxyphenyl)ethynyl]nicotinamide |
| Example 205 | 5-[(4-bromophenyl)ethynyl]-N-[(3-chlorophenyl)(methyl)oxo-λ$^6$-sulfanylidene]nicotinamide |
| Example 206 | N-[(3-chlorophenyl)(methyl)oxo-λ$^6$-sulfanylidene]-5-[3-(4,5-dichloro-1H-imidazol-1-yl)prop-1-yn-1-yl]nicotinamide |
| Example 207 | 5-[(4-chlorophenyl)ethynyl]-N-[(3-chlorophenyl)(methyl)oxo-λ$^6$-sulfanylidene]nicotinamide |
| Example 208 | 5-[(2-chlorophenyl)ethynyl]-N-[(3-chlorophenyl)(methyl)oxo-λ$^6$-sulfanylidene]nicotinamide |
| Example 209 | N-[(3-chlorophenyl)(methyl)oxo-λ$^6$-sulfanylidene]-5-[(3-methylphenyl)ethynyl]nicotinamide |
| Example 210 | N-[(3-chlorophenyl)(methyl)oxo-λ$^6$-sulfanylidene]-5-{[4-(trifluoromethyl)phenyl]ethynyl}nicotinamide |
| Example 211 | 5-[(2-bromophenyl)ethynyl]-N-[(3-chlorophenyl)(methyl)oxo-λ$^6$-sulfanylidene]nicotinamide |
| Example 212 | N-[(3-chlorophenyl)(methyl)oxo-λ$^6$-sulfanylidene]-5-[(2,4-difluorophenyl)ethynyl]nicotinamide |
| Example 213 | N-[(3-chlorophenyl)(methyl)oxo-λ$^6$-sulfanylidene]-5-(1-naphthylethynyl)nicotinamide |
| Example 214 | N-[(3-chlorophenyl)(methyl)oxo-λ$^6$-sulfanylidene]-5-(pyridin-3-ylethynyl)nicotinamide |
| Example 215 | N-[(3-chlorophenyl)(methyl)oxo-λ$^6$-sulfanylidene]-5-[(3-fluorophenyl)ethynyl]nicotinamide |
| Example 216 | N-[(3-chlorophenyl)(methyl)oxo-λ$^6$-sulfanylidene]-5-[(2-methylphenyl)ethynyl]nicotinamide |
| Example 217 | 5-[(3-bromophenyl)ethynyl]-N-[(3-chlorophenyl)(methyl)oxo-λ$^6$-sulfanylidene]nicotinamide |
| Example 218 | 5-[(3-chlorophenyl)ethynyl]-N-[(3-chlorophenyl)(methyl)oxo-λ$^6$-sulfanylidene]nicotinamide |
| Example 219 | N-[(3-chlorophenyl)(methyl)oxo-λ$^6$-sulfanylidene]-5-[(3,5-dimethoxyphenyl)ethynyl]nicotinamide |
| Example 220 | N-[(3-chlorophenyl)(methyl)oxo-λ$^6$-sulfanylidene]-5-[(3,4-dimethoxyphenyl)ethynyl]nicotinamide |

TABLE 5-continued

| Example | Example Name |
| --- | --- |
| Example 221 | N-[(3-chlorophenyl)(methyl)oxo-$\lambda^6$-sulfanylidene]-5-[(2-methoxyphenyl)ethynyl]nicotinamide |
| Example 222 | N-[(3-chlorophenyl)(methyl)oxo-$\lambda^6$-sulfanylidene]-5-[(4-piperidin-1-ylphenyl)ethynyl]nicotinamide |
| Example 223 | N-[(3-chlorophenyl)(methyl)oxo-$\lambda^6$-sulfanylidene]-5-[(3,5-difluorophenyl)ethynyl]nicotinamide |
| Example 224 | N-[(3-chlorophenyl)(methyl)oxo-$\lambda^6$-sulfanylidene]-5-[(1-methyl-1H-imidazol-5-yl)ethynyl]nicotinamide |
| Example 225 | N-[(3-chlorophenyl)(methyl)oxo-$\lambda^6$-sulfanylidene]-5-[(4-methoxy-2-methylphenyl)ethynyl]nicotinamide |
| Example 226 | N-[(3-chlorophenyl)(methyl)oxo-$\lambda^6$-sulfanylidene]-5-[(4-fluoro-3-methylphenyl)ethynyl]nicotinamide |
| Example 227 | N-[(3,5-dichlorophenyl)(methyl)oxo-$\lambda^6$-sulfanylidene]-5-(4-hydroxybut-1-yn-1-yl)nicotinamide |
| Example 228 | N-[(3,5-dichlorophenyl)(methyl)oxo-$\lambda^6$-sulfanylidene]-5-(phenylethynyl)nicotinamide |
| Example 229 | N-[(3,5-dichlorophenyl)(methyl)oxo-$\lambda^6$-sulfanylidene]-5-[(4-methylphenyl)ethynyl]nicotinamide |
| Example 230 | N-[(3,5-dichlorophenyl)(methyl)oxo-$\lambda^6$-sulfanylidene]-5-(3-methoxyprop-1-yn-1-yl)nicotinamide |
| Example 231 | N-[(3,5-dichlorophenyl)(methyl)oxo-$\lambda^6$-sulfanylidene]-5-(3,3-dimethylbut-1-yn-1-yl)nicotinamide |
| Example 232 | N-[(3,5-dichlorophenyl)(methyl)oxo-$\lambda^6$-sulfanylidene]-5-prop-1-yn-1-ylnicotinamide |
| Example 233 | N-[(3,5-dichlorophenyl)(methyl)oxo-$\lambda^6$-sulfanylidene]-5-(pyridin-2-ylethynyl)nicotinamide |
| Example 234 | N-[(3,5-dichlorophenyl)(methyl)oxo-$\lambda^6$-sulfanylidene]-5-[(3-hydroxyphenyl)ethynyl]nicotinamide |
| Example 235 | N-[(3,5-dichlorophenyl)(methyl)oxo-$\lambda^6$-sulfanylidene]-5-[(6-methoxy-2-naphthyl)ethynyl]nicotinamide |
| Example 236 | N-[(3,5-dichlorophenyl)(methyl)oxo-$\lambda^6$-sulfanylidene]-5-[(3-methoxyphenyl)ethynyl]nicotinamide |
| Example 237 | N-[(3,5-dichlorophenyl)(methyl)oxo-$\lambda^6$-sulfanylidene]-5-[(4-methoxyphenyl)ethynyl]nicotinamide |
| Example 238 | 5-[(4-bromophenyl)ethynyl]-N-[(3,5-dichlorophenyl)(methyl)oxo-$\lambda^6$-sulfanylidene]nicotinamide |
| Example 239 | 5-[(4-chlorophenyl)ethynyl]-N-[(3,5-dichlorophenyl)(methyl)oxo-$\lambda^6$-sulfanylidene]nicotinamide |
| Example 240 | 5-[(2-chlorophenyl)ethynyl]-N-[(3,5-dichlorophenyl)(methyl)oxo-$\lambda^6$-sulfanylidene]nicotinamide |
| Example 241 | N-[(3,5-dichlorophenyl)(methyl)oxo-$\lambda^6$-sulfanylidene]-5-[(3-methylphenyl)ethynyl]nicotinamide |
| Example 242 | N-[(3,5-dichlorophenyl)(methyl)oxo-$\lambda^6$-sulfanylidene]-5-{[4-(trifluoromethyl)phenyl]ethynyl}nicotinamide |
| Example 243 | 5-[(2-bromophenyl)ethynyl]-N-[(3,5-dichlorophenyl)(methyl)oxo-$\lambda^6$-sulfanylidene]nicotinamide |
| Example 244 | N-[(3,5-dichlorophenyl)(methyl)oxo-$\lambda^6$-sulfanylidene]-5-[(2,4-difluorophenyl)ethynyl]nicotinamide |
| Example 245 | N-[(3,5-dichlorophenyl)(methyl)oxo-$\lambda^6$-sulfanylidene]-5-(1-naphthylethynyl)nicotinamide |
| Example 246 | N-[(3,5-dichlorophenyl)(methyl)oxo-$\lambda^6$-sulfanylidene]-5-[(3-fluorophenyl)ethynyl]nicotinamide |
| Example 247 | N-[(3,5-dichlorophenyl)(methyl)oxo-$\lambda^6$-sulfanylidene]-5-[(2-methylphenyl)ethynyl]nicotinamide |
| Example 248 | 5-[(3-bromophenyl)ethynyl]-N-[(3,5-dichlorophenyl)(methyl)oxo-$\lambda^6$-sulfanylidene]nicotinamide |
| Example 249 | 5-[(3-chlorophenyl)ethynyl]-N-[(3,5-dichlorophenyl)(methyl)oxo-$\lambda^6$-sulfanylidene]nicotinamide |
| Example 250 | N-[(3,5-dichlorophenyl)(methyl)oxo-$\lambda^6$-sulfanylidene]-5-[(3,5-dimethoxyphenyl)ethynyl]nicotinamide |
| Example 251 | N-[(3,5-dichlorophenyl)(methyl)oxo-$\lambda^6$-sulfanylidene]-5-[(3,4-dimethoxyphenyl)ethynyl]nicotinamide |
| Example 252 | N-[(3,5-dichlorophenyl)(methyl)oxo-$\lambda^6$-sulfanylidene]-5-[(2-methoxyphenyl)ethynyl]nicotinamide |
| Example 253 | N-[(3,5-dichlorophenyl)(methyl)oxo-$\lambda^6$-sulfanylidene]-5-[(3,5-difluorophenyl)ethynyl]nicotinamide |
| Example 254 | N-[(3,5-dichlorophenyl)(methyl)oxo-$\lambda^6$-sulfanylidene]-5-[(1-methyl-1H-imidazol-5-yl)ethynyl]nicotinamide |
| Example 255 | N-[(3,5-dichlorophenyl)(methyl)oxo-$\lambda^6$-sulfanylidene]-5-[(4-methoxy-2-methylphenyl)ethynyl]nicotinamide |
| Example 256 | N-[(3,5-dichlorophenyl)(methyl)oxo-$\lambda^6$-sulfanylidene]-5-[(4-fluoro-3-methylphenyl)ethynyl]nicotinamide |
| Example 257 | 5-(4-hydroxybut-1-yn-1-yl)-N-[methyl(3-methylphenyl)oxo-$\lambda^6$-sulfanylidene]nicotinamide |
| Example 258 | N-[methyl(3-methylphenyl)oxo-$\lambda^6$-sulfanylidene]-5-(phenylethynyl)nicotinamide |
| Example 259 | N-[methyl(3-methylphenyl)oxo-$\lambda^6$-sulfanylidene]-5-[(4-methylphenyl)ethynyl]nicotinamide |

TABLE 5-continued

| Example | Example Name |
|---|---|
| Example 260 | 5-(3-methoxyprop-1-yn-1-yl)-N-[methyl(3-methylphenyl)oxo-$\lambda^6$-sulfanylidene]nicotinamide |
| Example 261 | 5-(3,3-dimethylbut-1-yn-1-yl)-N-[methyl(3-methylphenyl)oxo-$\lambda^6$-sulfanylidene]nicotinamide |
| Example 262 | N-[methyl(3-methylphenyl)oxo-$\lambda^6$-sulfanylidene]-5-[(4-nitrophenyl)ethynyl]nicotinamide |
| Example 263 | N-[methyl(3-methylphenyl)oxo-$\lambda^6$-sulfanylidene]-5-prop-1-yn-1-ylnicotinamide |
| Example 264 | N-[methyl(3-methylphenyl)oxo-$\lambda^6$-sulfanylidene]-5-(pyridin-2-ylethynyl)nicotinamide |
| Example 265 | 5-[(3-hydroxyphenyl)ethynyl]-N-[methyl(3-methylphenyl)oxo-$\lambda^6$-sulfanylidene]nicotinamide |
| Example 266 | 5-[(6-methoxy-2-naphthyl)ethynyl]-N-[methyl(3-methylphenyl)oxo-$\lambda^6$-sulfanylidene]nicotinamide |
| Example 267 | 5-[(3-methoxyphenyl)ethynyl]-N-[methyl(3-methylphenyl)oxo-$\lambda^6$-sulfanylidene]nicotinamide |
| Example 268 | 5-[(4-methoxyphenyl)ethynyl]-N-[methyl(3-methylphenyl)oxo-$\lambda^6$-sulfanylidene]nicotinamide |
| Example 269 | 5-[(4-bromophenyl)ethynyl]-N-[methyl(3-methylphenyl)oxo-$\lambda^6$-sulfanylidene]nicotinamide |
| Example 270 | 5-[3-(4,5-dichloro-1H-imidazol-1-yl)prop-1-yn-1-yl]-N-[methyl(3-methylphenyl)oxo-$\lambda^6$-sulfanylidene]nicotinamide |
| Example 271 | 5-[(4-chlorophenyl)ethynyl]-N-[methyl(3-methylphenyl)oxo-$\lambda^6$-sulfanylidene]nicotinamide |
| Example 272 | 5-[(2-chlorophenyl)ethynyl]-N-[methyl(3-methylphenyl)oxo-$\lambda^6$-sulfanylidene]nicotinamide |
| Example 273 | N-[methyl(3-methylphenyl)oxo-$\lambda^6$-sulfanylidene]-5-[(3-methylphenyl)ethynyl]nicotinamide |
| Example 274 | N-[methyl(3-methylphenyl)oxo-$\lambda^6$-sulfanylidene]-5-{[4-(trifluoromethyl)phenyl]ethynyl}nicotinamide |
| Example 275 | 5-[(2-bromophenyl)ethynyl]-N-[methyl(3-methylphenyl)oxo-$\lambda^6$-sulfanylidene]nicotinamide |
| Example 276 | 5-[(2,4-difluorophenyl)ethynyl]-N-[methyl(3-methylphenyl)oxo-$\lambda^6$-sulfanylidene]nicotinamide |
| Example 277 | N-[methyl(3-methylphenyl)oxo-$\lambda^6$-sulfanylidene]-5-(1-naphthylethynyl)nicotinamide |
| Example 278 | N-[methyl(3-methylphenyl)oxo-$\lambda^6$-sulfanylidene]-5-(pyridin-3-ylethynyl)nicotinamide |
| Example 279 | 5-[(3-fluorophenyl)ethynyl]-N-[methyl(3-methylphenyl)oxo-$\lambda^6$-sulfanylidene]nicotinamide |
| Example 280 | N-[methyl(3-methylphenyl)oxo-$\lambda^6$-sulfanylidene]-5-(pyridin-4-ylethynyl)nicotinamide |
| Example 281 | N-[methyl(3-methylphenyl)oxo-$\lambda^6$-sulfanylidene]-5-[(2-methylphenyl)ethynyl]nicotinamide |
| Example 282 | 5-[(3-bromophenyl)ethynyl]-N-[methyl(3-methylphenyl)oxo-$\lambda^6$-sulfanylidene]nicotinamide |
| Example 283 | 5-[(3-chlorophenyl)ethynyl]-N-[methyl(3-methylphenyl)oxo-$\lambda^6$-sulfanylidene]nicotinamide |
| Example 284 | 5-[(3,5-dimethoxyphenyl)ethynyl]-N-[methyl(3-methylphenyl)oxo-$\lambda^6$-sulfanylidene]nicotinamide |
| Example 285 | 5-[(3,4-dimethoxyphenyl)ethynyl]-N-[methyl(3-methylphenyl)oxo-$\lambda^6$-sulfanylidene]nicotinamide |
| Example 286 | 5-[(2-methoxyphenyl)ethynyl]-N-[methyl(3-methylphenyl)oxo-$\lambda^6$-sulfanylidene]nicotinamide |
| Example 287 | N-[methyl(3-methylphenyl)oxo-$\lambda^6$-sulfanylidene]-5-[(4-piperidin-1-ylphenyl)ethynyl]nicotinamide |
| Example 288 | 5-[(3,5-difluorophenyl)ethynyl]-N-[methyl(3-methylphenyl)oxo-$\lambda^6$-sulfanylidene]nicotinamide |
| Example 289 | 5-[(1-methyl-1H-imidazol-5-yl)ethynyl]-N-[methyl(3-methylphenyl)oxo-$\lambda^6$-sulfanylidene]nicotinamide |
| Example 290 | 5-[(4-methoxy-2-methylphenyl)ethynyl]-N-[methyl(3-methylphenyl)oxo-$\lambda^6$-sulfanylidene]nicotinamide |
| Example 291 | 5-[(4-fluoro-3-methylphenyl)ethynyl]-N-[methyl(3-methylphenyl)oxo-$\lambda^6$-sulfanylidene]nicotinamide |
| Example 292 | 5-(4-hydroxybut-1-yn-1-yl)-N-[(3-methoxyphenyl)(methyl)oxo-$\lambda^6$-sulfanylidene]nicotinamide |
| Example 293 | N-[(3-methoxyphenyl)(methyl)oxo-$\lambda^6$-sulfanylidene]-5-(phenylethynyl)nicotinamide |
| Example 294 | N-[(3-methoxyphenyl)(methyl)oxo-$\lambda^6$-sulfanylidene]-5-[(4-methylphenyl)ethynyl]nicotinamide |
| Example 295 | N-[(3-methoxyphenyl)(methyl)oxo-$\lambda^6$-sulfanylidene]-5-(3-methoxyprop-1-yn-1-yl)nicotinamide |
| Example 296 | 5-(3,3-dimethylbut-1-yn-1-yl)-N-[(3-methoxyphenyl)(methyl)oxo-$\lambda^6$-sulfanylidene]nicotinamide |
| Example 297 | N-[(3-methoxyphenyl)(methyl)oxo-$\lambda^6$-sulfanylidene]-5-prop-1-yn-1-ylnicotinamide |
| Example 298 | N-[(3-methoxyphenyl)(methyl)oxo-$\lambda^6$-sulfanylidene]-5-(pyridin-2-ylethynyl)nicotinamide |

TABLE 5-continued

| Example | Example Name |
|---|---|
| Example 299 | 5-[(3-hydroxyphenyl)ethynyl]-N-[(3-methoxyphenyl)(methyl)oxo-$\lambda^6$-sulfanylidene]nicotinamide |
| Example 300 | 5-[(6-methoxy-2-naphthyl)ethynyl]-N-[(3-methoxyphenyl)(methyl)oxo-$\lambda^6$-sulfanylidene]nicotinamide |
| Example 301 | 5-[(3-methoxyphenyl)ethynyl]-N-[(3-methoxyphenyl)(methyl)oxo-$\lambda^6$-sulfanylidene]nicotinamide |
| Example 302 | 5-[(4-methoxyphenyl)ethynyl]-N-[(3-methoxyphenyl)(methyl)oxo-$\lambda^6$-sulfanylidene]nicotinamide |
| Example 303 | 5-[(4-bromophenyl)ethynyl]-N-[(3-methoxyphenyl)(methyl)oxo-$\lambda^6$-sulfanylidene]nicotinamide |
| Example 304 | 5-[3-(4,5-dichloro-1H-imidazol-1-yl)prop-1-yn-1-yl]-N-[(3-methoxyphenyl)(methyl)oxo-$\lambda^6$-sulfanylidene]nicotinamide |
| Example 305 | 5-[(4-chlorophenyl)ethynyl]-N-[(3-methoxyphenyl)(methyl)oxo-$\lambda^6$-sulfanylidene]nicotinamide |
| Example 306 | 5-[(2-chlorophenyl)ethynyl]-N-[(3-methoxyphenyl)(methyl)oxo-$\lambda^6$-sulfanylidene]nicotinamide |
| Example 307 | N-[(3-methoxyphenyl)(methyl)oxo-$\lambda^6$-sulfanylidene]-5-[(3-methylphenyl)ethynyl]nicotinamide |
| Example 308 | N-[(3-methoxyphenyl)(methyl)oxo-$\lambda^6$-sulfanylidene]-5-{[4-(trifluoromethyl)phenyl]ethynyl}nicotinamide |
| Example 309 | 5-[(2-bromophenyl)ethynyl]-N-[(3-methoxyphenyl)(methyl)oxo-$\lambda^6$-sulfanylidene]nicotinamide |
| Example 310 | 5-[(2,4-difluorophenyl)ethynyl]-N-[(3-methoxyphenyl)(methyl)oxo-$\lambda^6$-sulfanylidene]nicotinamide |
| Example 311 | N-[(3-methoxyphenyl)(methyl)oxo-$\lambda^6$-sulfanylidene]-5-(1-naphthylethynyl)nicotinamide |
| Example 312 | N-[(3-methoxyphenyl)(methyl)oxo-$\lambda^6$-sulfanylidene]-5-(pyridin-3-ylethynyl)nicotinamide |
| Example 313 | 5-[(3-fluorophenyl)ethynyl]-N-[(3-methoxyphenyl)(methyl)oxo-$\lambda^6$-sulfanylidene]nicotinamide |
| Example 314 | N-[(3-methoxyphenyl)(methyl)oxo-$\lambda^6$-sulfanylidene]-5-(pyridin-4-ylethynyl)nicotinamide |
| Example 315 | N-[(3-methoxyphenyl)(methyl)oxo-$\lambda^6$-sulfanylidene]-5-[(2-methylphenyl)ethynyl]nicotinamide |
| Example 316 | 5-[(3-bromophenyl)ethynyl]-N-[(3-methoxyphenyl)(methyl)oxo-$\lambda^6$-sulfanylidene]nicotinamide |
| Example 317 | 5-[(3-chlorophenyl)ethynyl]-N-[(3-methoxyphenyl)(methyl)oxo-$\lambda^6$-sulfanylidene]nicotinamide |
| Example 318 | 5-[(3,5-dimethoxyphenyl)ethynyl]-N-[(3-methoxyphenyl)(methyl)oxo-$\lambda^6$-sulfanylidene]nicotinamide |
| Example 319 | 5-[(3,4-dimethoxyphenyl)ethynyl]-N-[(3-methoxyphenyl)(methyl)oxo-$\lambda^6$-sulfanylidene]nicotinamide |
| Example 320 | 5-[(2-methoxyphenyl)ethynyl]-N-[(3-methoxyphenyl)(methyl)oxo-$\lambda^6$-sulfanylidene]nicotinamide |
| Example 321 | 5-[(3,5-difluorophenyl)ethynyl]-N-[(3-methoxyphenyl)(methyl)oxo-$\lambda^6$-sulfanylidene]nicotinamide |
| Example 322 | N-[(3-methoxyphenyl)(methyl)oxo-$\lambda^6$-sulfanylidene]-5-[(1-methyl-1H-imidazol-5-yl)ethynyl]nicotinamide |
| Example 323 | 5-[(4-methoxy-2-methylphenyl)ethynyl]-N-[(3-methoxyphenyl)(methyl)oxo-$\lambda^6$-sulfanylidene]nicotinamide |
| Example 324 | 5-[(4-fluoro-3-methylphenyl)ethynyl]-N-[(3-methoxyphenyl)(methyl)oxo-$\lambda^6$-sulfanylidene]nicotinamide |
| Example 325 | N-[(3,4-dimethylphenyl)(methyl)oxo-$\lambda^6$-sulfanylidene]-5-(4-hydroxybut-1-yn-1-yl)nicotinamide |
| Example 326 | N-[(3,4-dimethylphenyl)(methyl)oxo-$\lambda^6$-sulfanylidene]-5-(phenylethynyl)nicotinamide |
| Example 327 | N-[(3,4-dimethylphenyl)(methyl)oxo-$\lambda^6$-sulfanylidene]-5-[(4-methylphenyl)ethynyl]nicotinamide |
| Example 328 | N-[(3,4-dimethylphenyl)(methyl)oxo-$\lambda^6$-sulfanylidene]-5-(3-methoxyprop-1-yn-1-yl)nicotinamide |
| Example 329 | 5-(3,3-dimethylbut-1-yn-1-yl)-N-[(3,4-dimethylphenyl)(methyl)oxo-$\lambda^6$-sulfanylidene]nicotinamide |
| Example 330 | N-[(3,4-dimethylphenyl)(methyl)oxo-$\lambda^6$-sulfanylidene]-5-[(4-nitrophenyl)ethynyl]nicotinamide |
| Example 331 | N-[(3,4-dimethylphenyl)(methyl)oxo-$\lambda^6$-sulfanylidene]-5-prop-1-yn-1-ylnicotinamide |
| Example 332 | N-[(3,4-dimethylphenyl)(methyl)oxo-$\lambda^6$-sulfanylidene]-5-(pyridin-2-ylethynyl)nicotinamide |
| Example 333 | N-[(3,4-dimethylphenyl)(methyl)oxo-$\lambda^6$-sulfanylidene]-5-[(3-hydroxyphenyl)ethynyl]nicotinamide |
| Example 334 | N-[(3,4-dimethylphenyl)(methyl)oxo-$\lambda^6$-sulfanylidene]-5-[(6-methoxy-2-naphthyl)ethynyl]nicotinamide |
| Example 335 | N-[(3,4-dimethylphenyl)(methyl)oxo-$\lambda^6$-sulfanylidene]-5-[(3-methoxyphenyl)ethynyl]nicotinamide |
| Example 336 | N-[(3,4-dimethylphenyl)(methyl)oxo-$\lambda^6$-sulfanylidene]-5-[(4-methoxyphenyl)ethynyl]nicotinamide |
| Example 337 | 5-[(4-bromophenyl)ethynyl]-N-[(3,4-dimethylphenyl)(methyl)oxo-$\lambda^6$-sulfanylidene]nicotinamide |

TABLE 5-continued

| Example | Example Name |
|---|---|
| Example 338 | 5-[3-(4,5-dichloro-1H-imidazol-1-yl)prop-1-yn-1-yl]-N-[(3,4-dimethylphenyl)(methyl)oxo-$\lambda^6$-sulfanylidene]nicotinamide |
| Example 339 | 5-[(4-chlorophenyl)ethynyl]-N-[(3,4-dimethylphenyl)(methyl)oxo-$\lambda^6$-sulfanylidene]nicotinamide |
| Example 340 | 5-[(2-chlorophenyl)ethynyl]-N-[(3,4-dimethylphenyl)(methyl)oxo-$\lambda^6$-sulfanylidene]nicotinamide |
| Example 341 | N-[(3,4-dimethylphenyl)(methyl)oxo-$\lambda^6$-sulfanylidene]-5-[(3-methylphenyl)ethynyl]nicotinamide |
| Example 342 | N-[(3,4-dimethylphenyl)(methyl)oxo-$\lambda^6$-sulfanylidene]-5-{[4-(trifluoromethyl)phenyl]ethynyl}nicotinamide |
| Example 343 | 5-[(2-bromophenyl)ethynyl]-N-[(3,4-dimethylphenyl)(methyl)oxo-$\lambda^6$-sulfanylidene]nicotinamide |
| Example 344 | 5-[(2,4-difluorophenyl)ethynyl]-N-[(3,4-dimethylphenyl)(methyl)oxo-$\lambda^6$-sulfanylidene]nicotinamide |
| Example 345 | N-[(3,4-dimethylphenyl)(methyl)oxo-$\lambda^6$-sulfanylidene]-5-(1-naphthylethynyl)nicotinamide |
| Example 346 | N-[(3,4-dimethylphenyl)(methyl)oxo-$\lambda^6$-sulfanylidene]-5-(pyridin-3-ylethynyl)nicotinamide |
| Example 347 | N-[(3,4-dimethylphenyl)(methyl)oxo-$\lambda^6$-sulfanylidene]-5-[(3-fluorophenyl)ethynyl]nicotinamide |
| Example 348 | N-[(3,4-dimethylphenyl)(methyl)oxo-$\lambda^6$-sulfanylidene]-5-(pyridin-4-ylethynyl)nicotinamide |
| Example 349 | N-[(3,4-dimethylphenyl)(methyl)oxo-$\lambda^6$-sulfanylidene]-5-[(2-methylphenyl)ethynyl]nicotinamide |
| Example 350 | 5-[(3-bromophenyl)ethynyl]-N-[(3,4-dimethylphenyl)(methyl)oxo-$\lambda^6$-sulfanylidene]nicotinamide |
| Example 351 | 5-[(3-chlorophenyl)ethynyl]-N-[(3,4-dimethylphenyl)(methyl)oxo-$\lambda^6$-sulfanylidene]nicotinamide |
| Example 352 | 5-[(3,4-dimethoxyphenyl)ethynyl]-N-[(3,4-dimethylphenyl)(methyl)oxo-$\lambda^6$-sulfanylidene]nicotinamide |
| Example 353 | N-[(3,4-dimethylphenyl)(methyl)oxo-$\lambda^6$-sulfanylidene]-5-[(2-methoxyphenyl)ethynyl]nicotinamide |
| Example 354 | 5-[(3,5-difluorophenyl)ethynyl]-N-[(3,4-dimethylphenyl)(methyl)oxo-$\lambda^6$-sulfanylidene]nicotinamide |
| Example 355 | N-[(3,4-dimethylphenyl)(methyl)oxo-$\lambda^6$-sulfanylidene]-5-[(1-methyl-1H-imidazol-5-yl)ethynyl]nicotinamide |
| Example 356 | N-[(3,4-dimethylphenyl)(methyl)oxo-$\lambda^6$-sulfanylidene]-5-[(4-methoxy-2-methylphenyl)ethynyl]nicotinamide |
| Example 357 | N-[(3,4-dimethylphenyl)(methyl)oxo-$\lambda^6$-sulfanylidene]-5-[(4-fluoro-3-methylphenyl)ethynyl]nicotinamide |
| Example 358 | N-[(3,5-dimethylphenyl)(methyl)oxo-$\lambda^6$-sulfanylidene]-5-(4-hydroxybut-1-yn-1-yl)nicotinamide |
| Example 359 | N-[(3,5-dimethylphenyl)(methyl)oxo-$\lambda^6$-sulfanylidene]-5-(phenylethynyl)nicotinamide |
| Example 360 | N-[(3,5-dimethylphenyl)(methyl)oxo-$\lambda^6$-sulfanylidene]-5-[(4-methylphenyl)ethynyl]nicotinamide |
| Example 361 | N-[(3,5-dimethylphenyl)(methyl)oxo-$\lambda^6$-sulfanylidene]-5-(3-methoxyprop-1-yn-1-yl)nicotinamide |
| Example 362 | 5-(3,3-dimethylbut-1-yn-1-yl)-N-[(3,5-dimethylphenyl)(methyl)oxo-$\lambda^6$-sulfanylidene]nicotinamide |
| Example 363 | N-[(3,5-dimethylphenyl)(methyl)oxo-$\lambda^6$-sulfanylidene]-5-[(4-nitrophenyl)ethynyl]nicotinamide |
| Example 364 | N-[(3,5-dimethylphenyl)(methyl)oxo-$\lambda^6$-sulfanylidene]-5-prop-1-yn-1-ylnicotinamide |
| Example 365 | N-[(3,5-dimethylphenyl)(methyl)oxo-$\lambda^6$-sulfanylidene]-5-(pyridin-2-ylethynyl)nicotinamide |
| Example 366 | N-[(3,5-dimethylphenyl)(methyl)oxo-$\lambda^6$-sulfanylidene]-5-[(6-methoxy-2-naphthyl)ethynyl]nicotinamide |
| Example 367 | N-[(3,5-dimethylphenyl)(methyl)oxo-$\lambda^6$-sulfanylidene]-5-[(3-methoxyphenyl)ethynyl]nicotinamide |
| Example 368 | N-[(3,5-dimethylphenyl)(methyl)oxo-$\lambda^6$-sulfanylidene]-5-[(4-methoxyphenyl)ethynyl]nicotinamide |
| Example 369 | 5-[(4-bromophenyl)ethynyl]-N-[(3,5-dimethylphenyl)(methyl)oxo-$\lambda^6$-sulfanylidene]nicotinamide |
| Example 370 | 5-[3-(4,5-dichloro-1H-imidazol-1-yl)prop-1-yn-1-yl]-N-[(3,5-dimethylphenyl)(methyl)oxo-$\lambda^6$-sulfanylidene]nicotinamide |
| Example 371 | 5-[(4-chlorophenyl)ethynyl]-N-[(3,5-dimethylphenyl)(methyl)oxo-$\lambda^6$-sulfanylidene]nicotinamide |
| Example 372 | 5-[(2-chlorophenyl)ethynyl]-N-[(3,5-dimethylphenyl)(methyl)oxo-$\lambda^6$-sulfanylidene]nicotinamide |
| Example 373 | N-[(3,5-dimethylphenyl)(methyl)oxo-$\lambda^6$-sulfanylidene]-5-[(3-methylphenyl)ethynyl]nicotinamide |
| Example 374 | N-[(3,5-dimethylphenyl)(methyl)oxo-$\lambda^6$-sulfanylidene]-5-{[4-(trifluoromethyl)phenyl]ethynyl}nicotinamide |
| Example 375 | 5-[(2-bromophenyl)ethynyl]-N-[(3,5-dimethylphenyl)(methyl)oxo-$\lambda^6$-sulfanylidene]nicotinamide |
| Example 376 | 5-[(2,4-difluorophenyl)ethynyl]-N-[(3,5-dimethylphenyl)(methyl)oxo-$\lambda^6$-sulfanylidene]nicotinamide |

TABLE 5-continued

| Example | Example Name |
| --- | --- |
| Example 377 | N-[(3,5-dimethylphenyl)(methyl)oxo-λ⁶-sulfanylidene]-5-(1-naphthylethynyl)nicotinamide |
| Example 378 | N-[(3,5-dimethylphenyl)(methyl)oxo-λ⁶-sulfanylidene]-5-(pyridin-3-ylethynyl)nicotinamide |
| Example 379 | N-[(3,5-dimethylphenyl)(methyl)oxo-λ⁶-sulfanylidene]-5-[(3-fluorophenyl)ethynyl]nicotinamide |
| Example 380 | N-[(3,5-dimethylphenyl)(methyl)oxo-λ⁶-sulfanylidene]-5-(pyridin-4-ylethynyl)nicotinamide |
| Example 381 | N-[(3,5-dimethylphenyl)(methyl)oxo-λ⁶-sulfanylidene]-5-[(2-methylphenyl)ethynyl]nicotinamide |
| Example 382 | 5-[(3-bromophenyl)ethynyl]-N-[(3,5-dimethylphenyl)(methyl)oxo-λ⁶-sulfanylidene]nicotinamide |
| Example 383 | 5-[(3-chlorophenyl)ethynyl]-N-[(3,5-dimethylphenyl)(methyl)oxo-λ⁶-sulfanylidene]nicotinamide |
| Example 384 | 5-[(3,5-dimethoxyphenyl)ethynyl]-N-[(3,5-dimethylphenyl)(methyl)oxo-λ⁶-sulfanylidene]nicotinamide |
| Example 385 | 5-[(3,4-dimethoxyphenyl)ethynyl]-N-[(3,5-dimethylphenyl)(methyl)oxo-λ⁶-sulfanylidene]nicotinamide |
| Example 386 | N-[(3,5-dimethylphenyl)(methyl)oxo-λ⁶-sulfanylidene]-5-[(2-methoxyphenyl)ethynyl]nicotinamide |
| Example 387 | N-[(3,5-dimethylphenyl)(methyl)oxo-λ⁶-sulfanylidene]-5-[(4-piperidin-1-ylphenyl)ethynyl]nicotinamide |
| Example 388 | 5-[(3,5-difluorophenyl)ethynyl]-N-[(3,5-dimethylphenyl)(methyl)oxo-λ⁶-sulfanylidene]nicotinamide |
| Example 389 | N-[(3,5-dimethylphenyl)(methyl)oxo-λ⁶-sulfanylidene]-5-[(1-methyl-1H-imidazol-5-yl)ethynyl]nicotinamide |
| Example 390 | N-[(3,5-dimethylphenyl)(methyl)oxo-λ⁶-sulfanylidene]-5-[(4-methoxy-2-methylphenyl)ethynyl]nicotinamide |
| Example 391 | N-[(3,5-dimethylphenyl)(methyl)oxo-λ⁶-sulfanylidene]-5-[(4-fluoro-3-methylphenyl)ethynyl]nicotinamide |
| Example 392 | N-[(3,4-dimethoxyphenyl)(methyl)oxo-λ⁶-sulfanylidene]-5-(4-hydroxybut-1-yn-1-yl)nicotinamide |
| Example 393 | N-[(3,4-dimethoxyphenyl)(methyl)oxo-λ⁶-sulfanylidene]-5-(phenylethynyl)nicotinamide |
| Example 394 | N-[(3,4-dimethoxyphenyl)(methyl)oxo-λ⁶-sulfanylidene]-5-[(4-methylphenyl)ethynyl]nicotinamide |
| Example 395 | N-[(3,4-dimethoxyphenyl)(methyl)oxo-λ⁶-sulfanylidene]-5-(3-methoxyprop-1-yn-1-yl)nicotinamide |
| Example 396 | N-[(3,4-dimethoxyphenyl)(methyl)oxo-λ⁶-sulfanylidene]-5-(3,3-dimethylbut-1-yn-1-yl)nicotinamide |
| Example 397 | N-[(3,4-dimethoxyphenyl)(methyl)oxo-λ⁶-sulfanylidene]-5-[(4-nitrophenyl)ethynyl]nicotinamide |
| Example 398 | N-[(3,4-dimethoxyphenyl)(methyl)oxo-λ⁶-sulfanylidene]-5-prop-1-yn-1-ylnicotinamide |
| Example 399 | N-[(3,4-dimethoxyphenyl)(methyl)oxo-λ⁶-sulfanylidene]-5-(pyridin-2-ylethynyl)nicotinamide |
| Example 400 | N-[(3,4-dimethoxyphenyl)(methyl)oxo-λ⁶-sulfanylidene]-5-[(3-hydroxyphenyl)ethynyl]nicotinamide |
| Example 401 | N-[(3,4-dimethoxyphenyl)(methyl)oxo-λ⁶-sulfanylidene]-5-[(6-methoxy-2-naphthyl)ethynyl]nicotinamide |
| Example 402 | N-[(3,4-dimethoxyphenyl)(methyl)oxo-λ⁶-sulfanylidene]-5-[(3-methoxyphenyl)ethynyl]nicotinamide |
| Example 403 | N-[(3,4-dimethoxyphenyl)(methyl)oxo-λ⁶-sulfanylidene]-5-[(4-methoxyphenyl)ethynyl]nicotinamide |
| Example 404 | 5-[(4-bromophenyl)ethynyl]-N-[(3,4-dimethoxyphenyl)(methyl)oxo-λ⁶-sulfanylidene]nicotinamide |
| Example 405 | 5-[(4-chlorophenyl)ethynyl]-N-[(3,4-dimethoxyphenyl)(methyl)oxo-λ⁶-sulfanylidene]nicotinamide |
| Example 406 | 5-[(2-chlorophenyl)ethynyl]-N-[(3,4-dimethoxyphenyl)(methyl)oxo-λ⁶-sulfanylidene]nicotinamide |
| Example 407 | N-[(3,4-dimethoxyphenyl)(methyl)oxo-λ⁶-sulfanylidene]-5-[(3-methylphenyl)ethynyl]nicotinamide |
| Example 408 | N-[(3,4-dimethoxyphenyl)(methyl)oxo-λ⁶-sulfanylidene]-5-{[4-(trifluoromethyl)phenyl]ethynyl}nicotinamide |
| Example 409 | 5-[(2-bromophenyl)ethynyl]-N-[(3,4-dimethoxyphenyl)(methyl)oxo-λ⁶-sulfanylidene]nicotinamide |
| Example 410 | 5-[(2,4-difluorophenyl)ethynyl]-N-[(3,4-dimethoxyphenyl)(methyl)oxo-λ⁶-sulfanylidene]nicotinamide |
| Example 411 | N-[(3,4-dimethoxyphenyl)(methyl)oxo-λ⁶-sulfanylidene]-5-(1-naphthylethynyl)nicotinamide |
| Example 412 | N-[(3,4-dimethoxyphenyl)(methyl)oxo-λ⁶-sulfanylidene]-5-(pyridin-3-ylethynyl)nicotinamide |
| Example 413 | N-[(3,4-dimethoxyphenyl)(methyl)oxo-λ6-sulfanylidene]-5-[(3-fluorophenyl)ethynyl]nicotinamide |
| Example 414 | N-[(3,4-dimethoxyphenyl)(methyl)oxo-λ⁶-sulfanylidene]-5-(pyridin-4-ylethynyl)nicotinamide |
| Example 415 | N-[(3,4-dimethoxyphenyl)(methyl)oxo-λ⁶-sulfanylidene]-5-[(2-methylphenyl)ethynyl]nicotinamide |

TABLE 5-continued

| Example | Example Name |
|---|---|
| Example 416 | 5-[(3-bromophenyl)ethynyl]-N-[(3,4-dimethoxyphenyl)(methyl)oxo-$\lambda^6$-sulfanylidene]nicotinamide |
| Example 417 | 5-[(3-chlorophenyl)ethynyl]-N-[(3,4-dimethoxyphenyl)(methyl)oxo-$\lambda^6$-sulfanylidene]nicotinamide |
| Example 418 | 5-[(3,5-dimethoxyphenyl)ethynyl]-N-[(3,4-dimethoxyphenyl)(methyl)oxo-$\lambda^6$-sulfanylidene]nicotinamide |
| Example 419 | 5-[(3,4-dimethoxyphenyl)ethynyl]-N-[(3,4-dimethoxyphenyl)(methyl)oxo-$\lambda^6$-sulfanylidene]nicotinamide |
| Example 420 | N-[(3,4-dimethoxyphenyl)(methyl)oxo-$\lambda^6$-sulfanylidene]-5-[(4-piperidin-1-ylphenyl)ethynyl]nicotinamide |
| Example 421 | N-[(3,4-dimethoxyphenyl)(methyl)oxo-$\lambda^6$-sulfanylidene]-5-[(4-methoxy-2-methylphenyl)ethynyl]nicotinamide |
| Example 422 | N-[(3,4-dimethoxyphenyl)(methyl)oxo-$\lambda^6$-sulfanylidene]-5-[(4-fluoro-3-methylphenyl)ethynyl]nicotinamide |

EXAMPLE 423

(S)-N-[methyl(oxo)phenyl-$\lambda^6$-sulfanylidene]-5-(phenylethynyl)nicotinamide

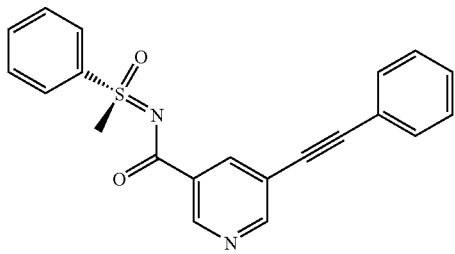

To a slurry of 5-(2-phenyleth-1-ynyl)nicotinic acid (339 mg, 1.5 mmol) in 6.0 mL THF at room temperature was added 1,1'-carbonyldiimidazole (271 mg, 1.7 mmol). After stirring 1.25 hour, a solution of (S)-(+)-S-methyl-5-phenylsulfoximine (260 mg, 1.7 mmol) in 1.5 mL THF was added and the mixture heated at 50° C. for 22 hours. Then an additional 50 mg (0.32 mmol) (S)-(+)-S-methyl-S-phenylsulfoximine was added and heating continued at 60° C. for 3.5 hours. The reaction was quenched with NaHCO$_3$ solution and then extracted into EtOAc. The EtOAc layer was washed with NaHCO$_3$ solution, H$_2$O, brine, dried with anhydrous Na$_2$SO$_4$ and concentrated. The yellow oil obtained was chromatographed eluting with hexane/EtOAc to give N-[methyl(oxo)phenyl-$\lambda^6$-sulfanylidene]-5-(phenylethynyl)nicotinamide as a white foam (303 mg, 55%).

EXAMPLE 424

(R)-N-[methyl(oxo)phenyl-$\lambda^6$-sulfanylidene]-5-(phenylethynyl)nicotinamide

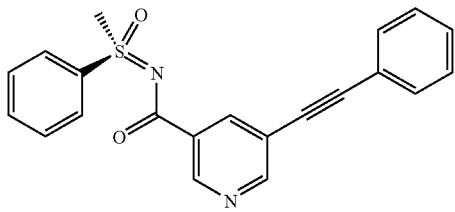

In a manner similar to that described in Example 423, 5-(2-phenyleth-1-ynyl)nicotinic acid and (R)-(−)-S-methyl-5-phenylsulfoximine were reacted to give the title compound as a white foam (54 mg, 25%).

EXAMPLE 425

5-[(2-fluorophenyl)ethynyl]-N-[methyl(oxo)phenyl-$\lambda^6$-sulfanylidene]nicotinamide Step 1

(S)-5-bromo-N-[methyl(oxo)phenyl-$\lambda^6$-sulfanylidene]nicotinamide

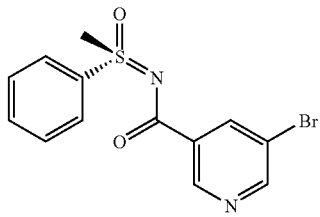

To a solution of 5-bromonicotinic acid (1.21 g, 6.0 mmol), N,N-diisopropylethylamine (2.1 mL, 12.0 mmol), and (S)-(+)-S-methyl-5-phenylsulfoximine (931 mg, 6.0 mmol) in DMF (11.0 mL) cooled to 0° C. was treated with 1-benzotriazolyloxytripyrrolidinylphosphonium hexafluorophosphate (PyBOP) (3.43 g, 6.6 mmol). The reaction mixture was stirred 10 minutes, the ice bath removed, and the reaction continued at room temperature for 2 hours. The mixture was taken up in EtOAc and washed with H$_2$O, Na$_2$CO$_3$ solution, brine, AcOH solution, H$_2$O, Na$_2$CO$_3$ solution, brine, dried with anhydrous Na$_2$SO$_4$ and concentrated. The residual brown oil was purified by chromatography (silica gel, hexane/EtOAc). The product containing eluent was concentrated and then triturated with hexane to give the title compound as an off-white solid (1.88 g, 92%).

Step 2

(S)-5-[(2-fluorophenyl)ethynyl]-N-[methyl(oxo)phenyl-λ⁶-sulfanylidene]nicotinamide

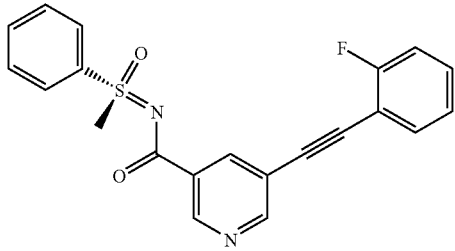

A mixture of (S)-5-bromo-N-[methyl(oxo)phenyl-λ⁶-sulfanylidene]nicotinamide (105 mg, 0.31mmol) and 1-ethynyl-2-fluorobenzene (75 mg, 0.62 mmol) in 2.0 mL EtOAc was degassed with argon at 70° C. Upon cooling to room temperature the reaction mixture was treated with triethylamine (0.16 mL, 1.1 mmol), dichlorobis(triphenylphosphine)palladium (II) (22 mg, 0.031 mmol) and copper(I) iodide (2 mg, 0.012 mmol). The reaction was heated at 70° C. for 20 hours then partitioned between EtOAc and H₂O. The EtOAc layer was washed with acetic acid solution, saturated NaHCO₃, brine, dried with anhydrous Na₂SO₄ and concentrated. The dark film obtained was purified by chromatography (silica gel, hexane/EtOAc) to give the title compound as a tan foam (110 mg, 94%).

EXAMPLE 426

(S)-5-[(4-chlorophenyl)ethynyl]-N-[methyl(oxo)phenyl-λ⁶-sulfanylidene]nicotinamide

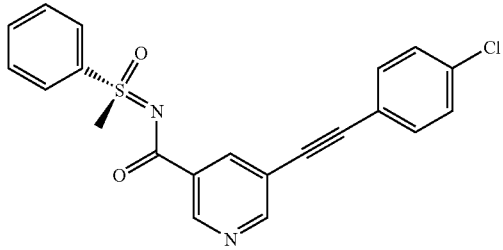

In a manner similar to that describe in Example 425 a mixture of (S)-5-bromo-N-[methyl(oxo)phenyl-λ⁶-sulfanylidene]nicotinamide and 4-chloro-1-ethynylbenzene were reacted to give the title compound as white needles (60 mg, 49%).

EXAMPLE 427

(S)-5-[(3-hydroxyphenyl)ethynyl]-N-[methyl(oxo)phenyl-λ⁶-sulfanylidene]nicotinamide

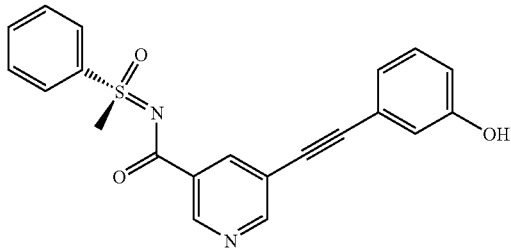

In a manner similar to that describe in Example 425, a mixture of (S)-5-bromo-N-[methyl(oxo)phenyl-λ⁶-sulfanylidene]nicotinamide and 3-hydroxy-1-ethynylbenzene were reacted to give the title compound as an off-white solid (19 mg, 17%).

EXAMPLE 428

(S)-5-[(4-phenoxyphenyl)ethynyl]-N-[methyl(oxo)phenyl-λ⁶-sulfanylidene]nicotinamide

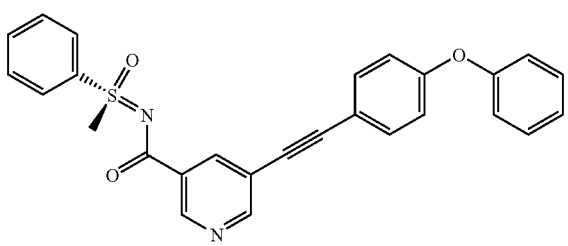

In a manner similar to that describe in Example 425 a mixture of (S)-5-bromo-N-[methyl(oxo)phenyl-λ⁶-sulfanylidene]nicotinamide and 1-ethynyl-4-phenoxybenzene were reacted to give the title compound as an off-white solid (95 mg, 68%).

EXAMPLE 429

(S)-N-[methyl(oxo)phenyl-λ⁶-sulfanylidene]-5-[(trimethylsilyl)ethynyl]nicotinamide

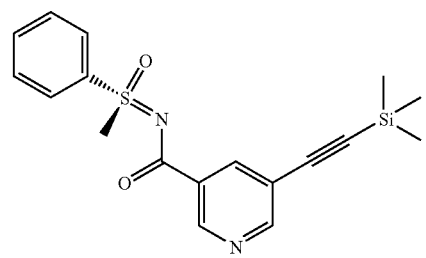

To a degassed solution of 10.0 mL DMF at room temperature was added (S)-5-bromo-N-[methyl(oxo)phenyl-λ⁶-sulfanylidene]nicotinamide (1.02 g, 3.0 mmol), triethylamine (1.3 mL, 9.0 mmol), trimethylsilylacetylene (0.83 mL, 6.0 mmol), and dichlorobis(triphenylphosphine)palladium(II) (211 mg, 0.3 mmol). After 15 minutes added copper(I) iodide (29 mg, 0.15 mmol) and continued reaction for 4 hours. The reaction was then partitioned between EtOAc and H₂O. The EtOAc layer was washed with saturated NaHCO₃, brine, dried with anhydrous Na₂SO₄ and rotary evaporated to 20 ml volume. The solution was placed overnight in the refrigerator and the resulting solid filtered and rinsed with 40% EtOAc/hexane to give the title compound (674 mg) as a tan solid. The filtrate was evaporated and purified by chromatography (silica gel, eluting with hexane/EtOAc) to give an additional 301 mg of the title compound. The product lots were combined and purified by chromatography (silica gel, eluting with hexane/EtOAc) to give the title compound as a tan solid (959 mg, 90%).

EXAMPLE 430

(S)-5-ethynyl-N-[methyl(oxo)phenyl-λ⁶-sulfanylidene]nicotinamide

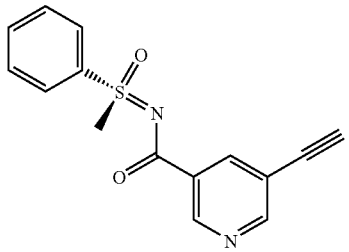

A solution of (S)-N-[methyl(oxo)phenyl-λ⁶-sulfanylidene]-5-[(trimethylsilyl)ethynyl]nicotinamide (806 mg, 2.3 mmol) in 70 mL THF/methanol (1:1 ratio) at room temperature was degassed with argon. The solution was cooled to 0° C. and K₂CO₃ (937 mg, 6.8 mmol) added. After 5 minutes the solution was decanted from the solids and partitioned between EtOAc and H₂O. The EtOAc layer was washed with brine, dried with anhydrous Na₂SO₄ and concentrated. The brown oil was purified by chromatography (silica gel, CHCl₃/EtOAc) to the title compound as a thick pale orange oil (630 mg, 98%).

EXAMPLE 431

(S)-5-[(4-hydroxyphenyl)ethynyl]-N-[methyl(oxo)phenyl-λ⁶-sulfanylidene]nicotinamide

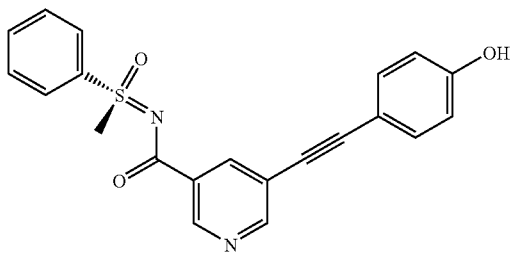

To a degassed solution of 1.3 mL DMF at room temperature containing (S)-5-ethynyl-N-[methyl(oxo)phenyl-λ⁶-sulfanylidene]nicotinamide (63 mg, 0.22 mmol), 4-iodophenol (121 mg, 0.55 mmol), and triethylamine (0.09 mL, 0.66 mmol) was added dichlorobis(triphenylphosphine)palladium (II) (15 mg, 0.022 mmol) and copper(I) iodide (4 mg, 0.022 mmol). After proceeding for 1 hour the reaction was partitioned between EtOAc and H₂O. The mixture was filtered to remove an insoluble brown precipitate and the EtOAc layer was washed with H₂O, brine, dried with anhydrous Na₂SO₄ and rotary evaporated. The brown film was chromatographed eluting with CHCl₃/EtOAc to give a yellow solid which was recrystallized from CHCl₃/hexane to give the title compound as an off-white solid (38 mg, 45%).

EXAMPLE 432

(S)-5-[(2-hydroxyphenyl)ethynyl]-N-[methyl(oxo)phenyl-λ⁶-sulfanylidene]nicotinamide

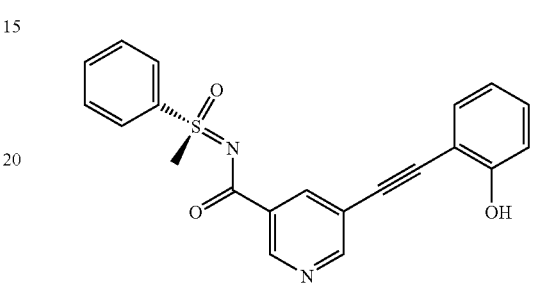

In a manner similar to that describe in Example 431 a mixture of (S)-5-ethynyl-N-[methyl(oxo)phenyl-λ⁶-sulfanylidene]nicotinamide and 1-ethynyl-2-hydroxybenzene were reacted to give the title compound as a white solid (6 mg, 7%).

EXAMPLE 433

Step 1

(R)-5-bromo-N-[methyl(oxo)phenyl-λ⁶-sulfanylidene]nicotinamide

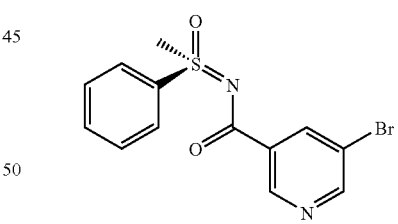

To a solution of 5-bromonicotinic acid (303 mg, 1.5 mmol), N,N-diisopropylethylamine (0.523 mL, 3.0 mmol), and (R)-(−)-S-methyl-5-phenylsulfoximine (233 mg, 1.5 mmol) in DMF (3.0 mL) cooled to 0° C. was added 1-benzotriazolyloxytripyrrolidinylphosphonium hexafluorophosphate (PyBOP) (859 mg, 1.65 mmol). The solution was stirred 10 minutes, the ice bath removed, and the reaction continued at room temperature for 2.5 hours. The mixture was taken up in EtOAc and washed with H₂O, Na₂CO₃ solution, brine, AcOH solution, H₂O, Na₂CO₃ solution, brine, dried with anhydrous Na₂SO₄ and rotary evaporated. The brown oil was chromatographed eluting with hexane/EtOAc to give the title compound as a yellow solid (478 mg, 94%).

Step 2

(R)-5-[(3-hydroxyphenyl)ethynyl]-N-[methyl(oxo)phenyl-λ⁶-sulfanylidene]nicotinamide

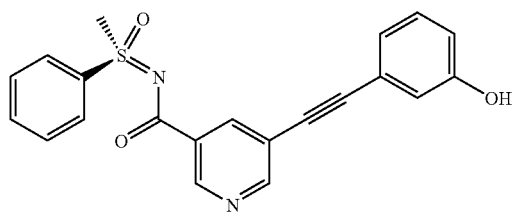

To a degassed solution of 2.0 mL DMF at room temperature containing (R)-5-bromo-N-[methyl(oxo)phenyl-λ⁶-sulfanylidene]nicotinamide (105 mg, 0.31 mmol), 3-hydroxyphenylacetylene (73 mg, 0.62 mmol) and triethylamine (0.13 mL, 0.93 mmol) was added dichlorobis(triphenylphosphine)palladium(II) (22 mg, 0.031 mmol) and copper(I) iodide (3 mg, 0.016 mmol). The reaction was stirred at room temperature for 1.5 hours. Additional 3-hydroxyphenylacetylene was added (30 mg, 0.25 mmol) and the reaction was stirred at room temperature for an additional 3.5 hours. After proceeding for 5 hours the reaction was partitioned between EtOAc and H₂O and the EtOAc layer washed with H₂O, brine, dried with anhydrous Na₂SO₄ and concentrated. The residual dark oil was purified by chromatography (silica gel, CHCl₃/EtOAc) and the product containing fractions were concentrated. The resulting solid was triturated with EtOAc/hexane to give the title compound as an off-white solid (37 mg, 32%).

EXAMPLE 434

(S)-3-{5-({[methyl(oxo)phenyl-λ⁶-sulfanylidene]amino}carbonyl)pyridin-3-yl]ethynyl}benzoic acid

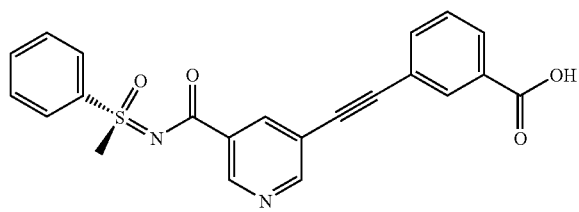

A mixture of (S)-N-[methyl(oxo)phenyl-λ⁶-sulfanylidene]-5-[(trimethylsilyl)ethynyl]nicotinamide (54 mg, 0.15 mmol), 3-iodobenzoic acid (56 mg, 0.23 mmol), dichlorobis(triphenylphosphine)palladium(II) (11 mg, 0.02 mmol), triphenylphosphine (1.0 mg, 0.004 mmol) and triethylamine (0.073 mL, 0.53 mmol) in 1.5 mL DMF at room temperature was degassed using vacuum and a H₂/N₂ (1:1) mixture and then copper(I) iodide (2 mg, 0.01 mmol) added. The reaction was heated to 60° C. then tetrabutylammonium fluoride (1.0 M in THF, 0.15 ml) added over 3.5 minutes. After 25 minutes the reaction was partitioned between EtOAc and dilute AcOH. The EtOAc layer was collected and washed with H₂O, brine, dried with anhydrous Na₂SO₄ and concentrated to a yellow solid. The solid was triturated with EtOAc at room temperature to give the title compound as a yellow solid (45 mg, 74%).

EXAMPLE 435

(S)-5-[(4-acetylphenyl)ethynyl]-N-[methyl(oxo)phenyl-λ⁶-sulfanylidene]nicotinamide

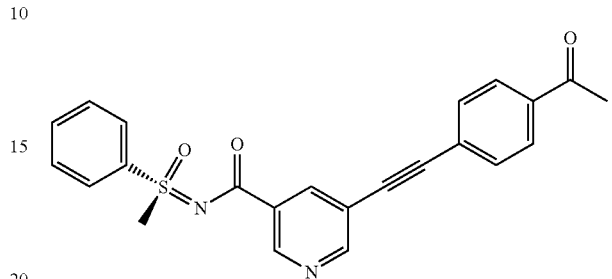

In a manner similar to that describe in Example 434 a mixture of (S)-5-ethynyl-N-[methyl(oxo)phenyl-λ⁶-sulfanylidene]nicotinamide and 4-iodoacetophenone were reacted to give the title compound as a light yellow foam (52 mg, 86%).

EXAMPLE 436

(S)-5-[(4-hydroxy-3-methylphenyl)ethynyl]-N-[methyl(oxo)phenyl-λ⁶-sulfanylidene]nicotinamide

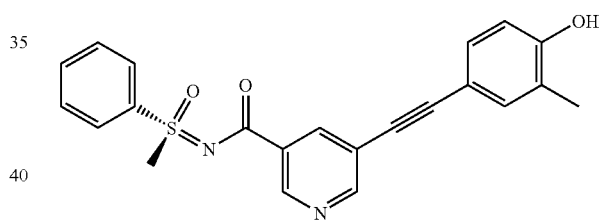

In a manner similar to that describe in Example 434, a mixture of (S)-5-ethynyl-N-[methyl(oxo)phenyl-λ⁶-sulfanylidene]nicotinamide and 4-iodo-2-methylphenol were reacted to give the title compound as a light yellow solid (43 mg, 73%).

EXAMPLE 437

(S)-2-hydroxy-5-{[5-({[methyl(oxo)phenyl-λ⁶-sulfanylidene]amino}carbonyl)pyridin-3-yl]ethynyl}benzoic acid

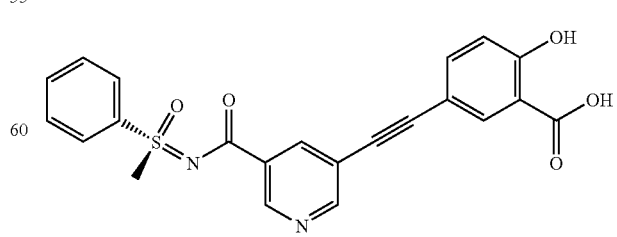

In a manner similar to that describe in Example 434, a mixture of (S)-5-ethynyl-N-[methyl(oxo)phenyl-λ⁶-sulfanylidene]nicotinamide and 5-iodosalicyclic acid were reacted to give the title compound as a light tan solid (28 mg, 45%).

EXAMPLE 438

(S)-4-{[5-({[methyl(oxo)phenyl-λ⁶-sulfanylidene]amino}carbonyl)pyridin-3-yl]ethynyl}benzoic acid

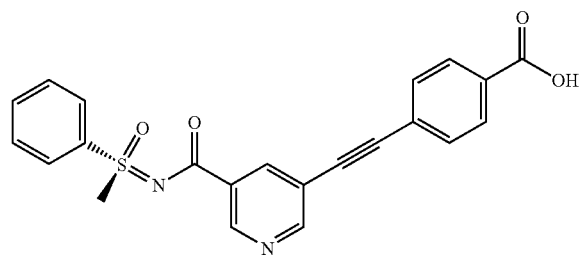

In a manner similar to that describe in Example 434, a mixture of (S)-5-ethynyl-N-[methyl(oxo)phenyl-λ⁶-sulfanylidene]nicotinamide and 4-iodobenzoic acid were reacted to give the title compound as a light yellow solid (30 mg, 49%).

EXAMPLE 439

(S)-5-(1H-imidazol-5-ylethynyl)-N-[methyl(oxo)phenyl-λ⁶-sulfanylidene]nicotinamide

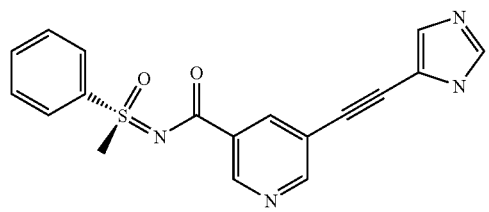

In a manner similar to that describe in Example 434, a mixture of (S)-5-ethynyl-N-[methyl(oxo)phenyl-λ⁶-sulfanylidene]nicotinamide and 5-iodo-1H-imidazole were reacted to give the title compound as a white foam (24 mg, 46%).

EXAMPLE 440

(S)-5-(1H-imidazol-2-ylethynyl)-N-[methyl(oxo)phenyl-λ⁶-sulfanylidene]nicotinamide

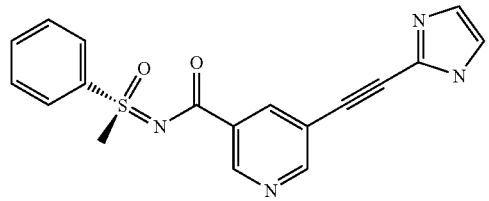

In a manner similar to that describe in Example 434, a mixture of (S)-5-ethynyl-N-[methyl(oxo)phenyl-λ⁶-sulfanylidene]nicotinamide and 2-iodo-1H-imidazole were reacted to give the title compound as a white solid (15 mg, 29%).

EXAMPLE 441

(S)-5-[(2-methyl-1H-imidazol-5-yl)ethynyl]-N-[methyl(oxo)phenyl-λ⁶-sulfanylidene]nicotinamide

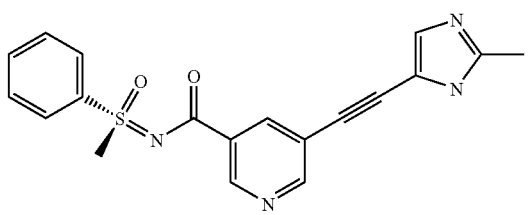

In a manner similar to that describe in Example 434, a mixture of (S)-5-ethynyl-N-[methyl(oxo)phenyl-λ⁶-sulfanylidene]nicotinamide and 5-iodo-2-methyl-1H-imidazole were reacted to give the title compound as an off-white foam (28 mg, 51%).

EXAMPLE 442

(S)-N-[methyl(oxo)phenyl-λ⁶-sulfanylidene]-5-(1H-pyrazol-4-ylethynyl)nicotinamide

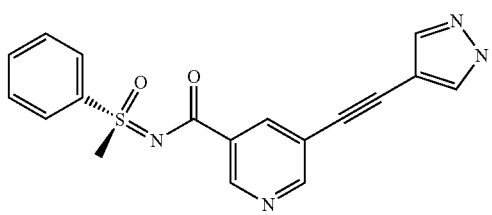

In a manner similar to that describe in Example 431 a mixture of (S)-5-ethynyl-N-[methyl(oxo)phenyl-λ⁶-sulfanylidene]nicotinamide and 4-iodopyrazole were reacted to give the title compound as a white film (15 mg, 17%).

EXAMPLE 443

(S)-5-[(6-hydroxypyridin-3-yl)ethynyl]-N-[methyl(oxo)phenyl-λ⁶-sulfanylidene]nicotinamide

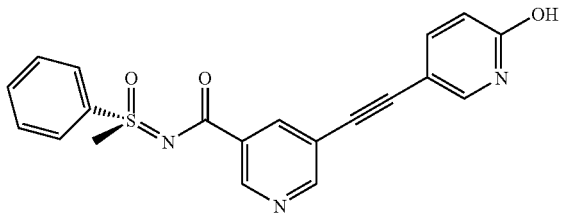

A solution of (S)-N-[methyl(oxo)phenyl-λ⁶-sulfanylidene]-5-[(trimethylsilyl)ethynyl]-nicotinamide (150 mg, 0.42 mmol) and 2-hydroxy-5-iodopyridine (105.4 mg, 0.46 mmol) in DMF (2.1 mL) was degassed (vacuum and argon). The resulting solution was treated tetrakis(triphenylphosphine)palladium(0) (24 mg, 0.021 mmol), triethylamine (0.08 mL, 0.55 mmol), and CuI (8 mg, 0.042 mmol). The reaction mixture was then heated to 85° C. and tetrabutylammonium fluoride (1.0 M solution in THF, 0.46 mL, 0.46 mmol) was added dropwise over 10 min. The reaction was allowed to be stirred at 85° C. for 2 hours. The reaction mixture was partitioned between EtOAc and H₂O. The organic extracts and associated solid were collected and concentrated. The residue was purified by chromatography (silica gel, gradient elution MeOH—CHCl₃: 1:100-1:4). The product containing fractions were collected, concentrated, and the brown solid residue was triturated with a combination of MeOH and EtOAc. The resulting mixture was filtered and the filtrate allowed to stand at room temperature. The solid which precipitated from solution was collected and dried to give the title compound as a white solid (11 mg).

EXAMPLE 444

(S)-5-(1H-indol-6-ylethynyl)-N-[methyl(oxo)phenyl-λ⁶-sulfanylidene]nicotinamide

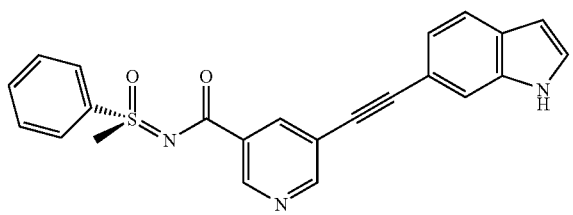

In a manner similar to that described in Example 443, (S)-N-[methyl(oxo)phenyl-λ⁶-sulfanylidene]-5-[(trimethylsilyl)ethynyl]nicotinamide (150 mg, 0.42 mmol) and 6-bromoindole (90.7 mg, 0.46 mmol) were reacted to give the title compound (30 mg).

EXAMPLE 445

(S)-5-[(2,3-dioxo-2,3-dihydro-1H-indol-5-yl)ethynyl]-N-[methyl(oxo)phenyl-λ⁶-sulfanylidene]nicotinamide

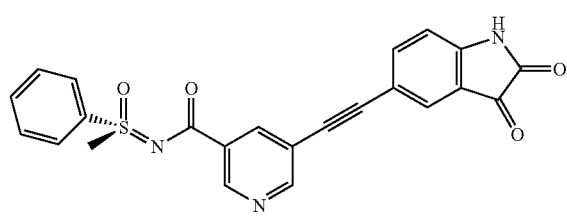

In a manner similar to that described in Example 443, (S)-N-[methyl(oxo)phenyl-λ⁶-sulfanylidene]-5-[(trimethylsilyl)ethynyl]nicotinamide (150 mg, 0.42 mmol) and 5-bromoisatin (116 mg, 0.46 mmol) were reacted to give the title compound as a reddish oil (40 mg).

EXAMPLE 446

(S)-5-[(6-chloropyridin-3-yl)ethynyl]-N-[methyl(oxo)phenyl-λ⁶-sulfanylidene]nicotinamide

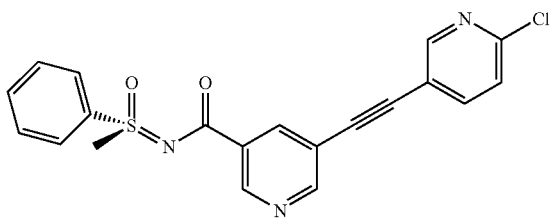

In a manner similar to that described in Example 443, (S)-N-[methyl(oxo)phenyl-λ⁶-sulfanylidene]-5-[(trimethylsilyl)ethynyl]nicotinamide (250 mg, 0.70 mmol) and 2-chloro-5-iodopyridine (173 mg, 0.70 mmol) were reacted to give the title compound as white solid (250 mg).

EXAMPLE 447

(S)-5-[(6-aminopyridin-3-yl)ethynyl]-N-[methyl(oxo)phenyl-λ⁶-sulfanylidene]nicotinamide

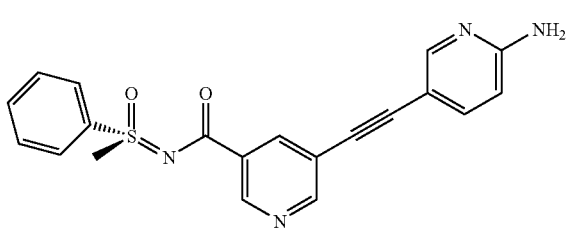

In a manner similar to that described in Example 443, (S)-N-[methyl(oxo)phenyl-λ⁶-sulfanylidene]-5-[(trimethylsilyl)ethynyl]nicotinamide (100 mg, 0.28 mmol) and 2-amino-5-iodopyridine (69.3 mg, 0.31 mmol) were reacted to give the title compound as light yellow solid (89 mg).

EXAMPLE 448

(S)-N-[methyl(oxo)phenyl-λ⁶-sulfanylidene]-5-[(2-oxo-2,3-dihydro-1,3-benzoxazol-5-yl)ethynyl]nicotinamide

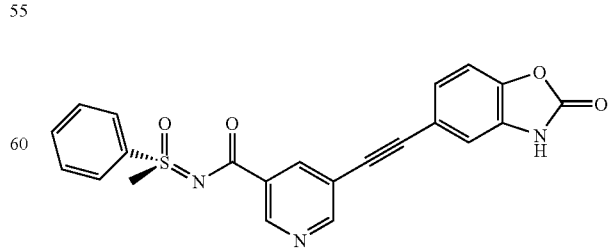

In a manner similar to that described in Example 443, (S)-N-[methyl(oxo)phenyl-λ⁶-sulfanylidene]-5-[(trimethylsilyl)ethynyl]nicotinamide (150 mg, 0.42 mmol) and 5-bromo-2-benzoxazolinone (102 mg, 0.46 mmol) were reacted to give the title compound as light yellow solid (71 mg).

EXAMPLE 449

(S)-N-[methyl(oxo)phenyl-λ$^6$-sulfanylidene]-5-({4-[(2-thienylcarbonyl)amino]phenyl}ethynyl)nicotinamide

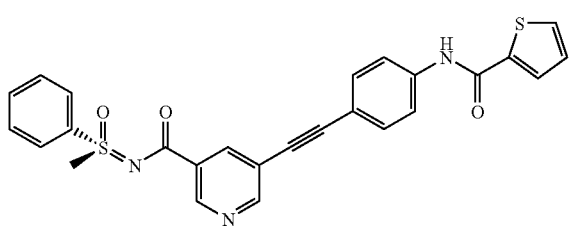

In a 4 mL vial, thiophene-2-carboxylic acid (4-ethynyl-phenyl)-amide (0.100 g, 0.443 mmol) and (S)-5-bromo-N-[methyl(oxo)phenyl-λ$^6$-sulfanylidene]nicotinamide (100 mg, 0.295 mmol) were added and dissolved into EtOAc (2 mL). The mixture was then degassed for ~20 min after which NEt$_3$ (0.141 mL, 1.035 mmol) was added followed by Pd(PPh$_3$)$_2$Cl$_2$ (20.7 mg, 0.0295 mmol) and CuI (2.8 mg, 0.148 mmol). The reaction mixture was allowed to stir at 50° C. for 3 hours after which the reaction mixture was extracted twice with EtOAc (~5 mL) and of water (~5 mL). The organic extracts were combined and dried over anhydrous Na$_2$SO$_4$(s) and then concentrated in vacuo. The crude residue was then purified by chromatography (silica gel, gradient elution, 25% EtOAc/hexanes to 100% EtOAc/hexanes). The product containing fractions were concentrated to give the title compound as a tan solid (87 mg, 0.18 mmol, 61%).

EXAMPLE 450

(S)-5-{[3-(acetylamino)phenyl]ethynyl}-N-[methyl(oxo)phenyl-λ$^6$-sulfanylidene]nicotinamide

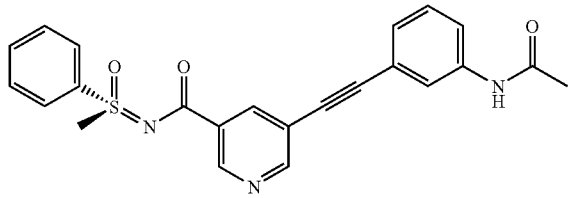

In a manner similar to that described in Example 449, N-(3-ethynyl-phenyl)-acetamide (0.0469 g, 0.443 mmol) and (S)-5-bromo-N-[methyl(oxo)phenyl-λ$^6$-sulfanylidene]nicotinamide (100 mg, 0.295 mmol) were reacted to give the title compound as a solid (83 mg, 0.20 mmol, 67%).

EXAMPLE 451

(S)-5-({4-[(2,6-difluorobenzoyl)amino]phenyl}ethynyl)-N-[methyl(oxo)phenyl-λ$^6$-sulfanylidene]nicotinamide

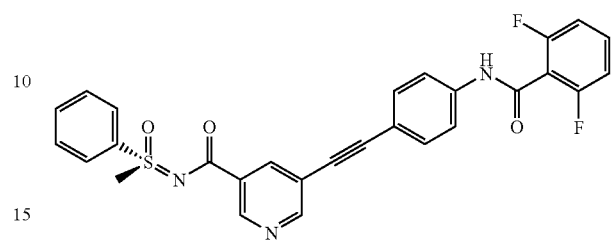

In a manner similar to that described in Example 449, N-(4-ethynyl-phenyl)-2,6-difluoro-benzamide (0.114 g, 0.443 mmol) and (S)-5-bromo-N-[methyl(oxo)phenyl-λ$^6$-sulfanylidene]nicotinamide (100 mg, 0.295 mmol) were reacted to give the title compound as a solid (113 mg, 74%)

EXAMPLE 452

(S)-5-({4-[(4-fluorobenzoyl)amino]phenyl}ethynyl)-N-[methyl(oxo)phenyl-λ$^6$-sulfanylidene]nicotinamide

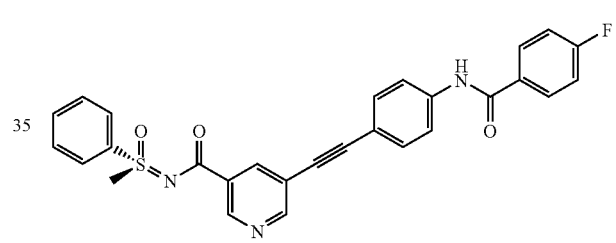

In a manner similar to that described in Example 449, N-(4-ethynyl-phenyl)-4-fluoro-benzamide (0.106 g, 0.443 mmol) and 5-bromo-N-[methyl(oxo)phenyl-λ$^6$-sulfanylidene]nicotinamide (100 mg, 0.295 mmol) were reacted to give the title compound as a solid (106 mg, 72%).

EXAMPLE 453

(S)-5-({4-[(4-methylbenzoyl)amino]phenyl}ethynyl)-N-[methyl(oxo)phenyl-λ$^6$-sulfanylidene]nicotinamide

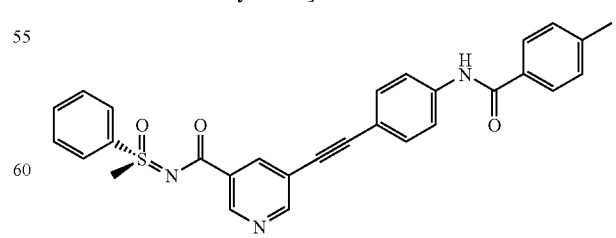

In a manner similar to that described in Example 449, N-(4-ethynyl-phenyl)-4-methyl-benzamide (0.104 g, 0.443 mmol) and (S)-5-bromo-N-[methyl(oxo)phenyl-λ$^6$-sulfanylidene]nicotinamide (100 mg, 0.295 mmol) were reacted to give the title compound as a solid (118 mg, 81%).

EXAMPLE 454

(S)-5-({4-[(2-methylbenzoyl)amino]phenyl}ethynyl)-N-[methyl(oxo)phenyl-$\lambda^6$-sulfanylidene]nicotinamide

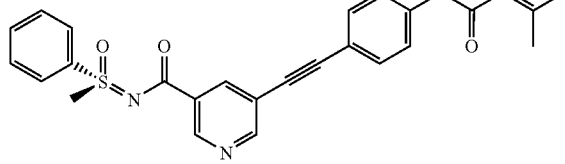

In a manner similar to that described in Example 449, N-(4-ethynyl-phenyl)-2-methyl-benzamide (0.104 g, 0.443 mmol) and (S)-5-bromo-N-[methyl(oxo)phenyl-$\lambda^6$-sulfanylidene]nicotinamide (100 mg, 0.295 mmol) were reacted to give the title compound (109 mg, 75%).

EXAMPLE 455 tert-butyl (4-{[5-({[methyl(oxo)phenyl-$\lambda^6$-sulfanylidene]amino}carbonyl)pyridin-3-yl]ethynyl}phenyl)carbamate

Step 1 tert-butyl 4-ethynylphenylcarbamate

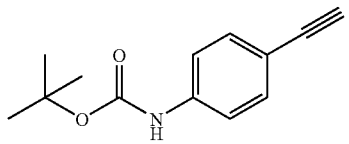

A dry 25 mL flask was charged with 3-ethynyl-phenylamine (0.100 g, 0.855 mmol) and then THF (5 mL) was added. Di-tert-butyl dicarbonate (0.242 g, 1.11 mmol) was added to the THF solution followed by NEt$_3$ (0.231 mL, 1.71 mL). The mixture was allowed to stir at 55° C. after which it was cooled to room temperature and extracted twice with EtOAc (~10 mL), water (~10 mL) and saturated aqueous NaHCO$_3$. The combined organic extracts were dried over anhydrous Na$_2$SO$_4$(s) and then concentrated to give the title compound (0.15 g, 0.67 mmol, 78%).

Step 2

(S)-tert-butyl (4-{[5-({[methyl(oxo)phenyl-$\lambda^6$-sulfanylidene]amino}carbonyl)pyridin-3-yl]ethynyl}phenyl)carbamate

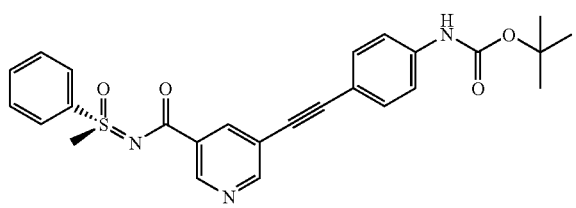

In a manner similar to that described in Example 449, tert-butyl 4-ethynylphenylcarbamate (0.096 g, 0.443 mmol) and 5-bromo-N-[methyl(oxo)phenyl-$\lambda^6$-sulfanylidene]nicotinamide (100 mg, 0.295 mmol) were reacted to give the title compound as a solid (63 mg, 0.13 mmol, 45%).

EXAMPLE 456

(S)-N-[methyl(oxo)phenyl-$\lambda^6$-sulfanylidene]-5-({3-[(2-thienylcarbonyl)amino]phenyl}ethynyl)nicotinamide

Step 1

N-(3-ethynylphenyl)thiophene-2-carboxamide

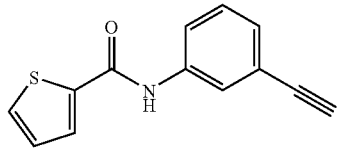

A dry 25 mL flask was charged with thiophene-2-carbonyl chloride and THF (5 mL) was added. 3-Ethynyl-phenylamine (0.905 g, 3.59 mmol) was added to the THF solution of the acid chloride followed by NEt$_3$, and the mixture was allowed to stir at 55° C. The reaction mixture was then allowed to cool to room temperature and extracted with EtOAc (~10 mL), 1M HCl (~10 mL), followed by brine (~10 mL). The combined organic extracts were combined and dried over anhydrous Na$_2$SO$_4$(s) and the concentrated. The crude residue was purified by chromatography (silica gel, gradient elution EtOAc/

Hexanes 0 to 50%). The product containing fractions were concentrated to give the title compound as a tan solid (0.33 mg, 1.45 mmol, 85%).

Step 2

(S)-N-[methyl(oxo)phenyl-λ$^6$-sulfanylidene]-5-({3-[(2-thienylcarbonyl)amino]phenyl}ethynyl)nicotinamide

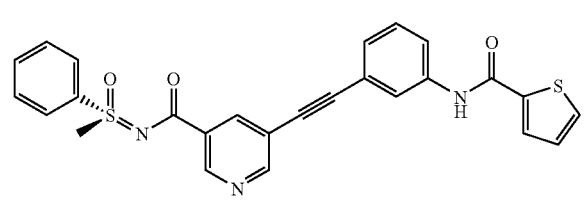

In a manner similar to that described in Example 449, thiophene-2-carboxylic acid (3-ethynyl-phenyl)-amide (0.100 g, 0.443 mmol) and (S)-5-bromo-N-[methyl(oxo)phenyl-λ$^6$-sulfanylidene]nicotinamide (100 mg, 0.295 mmol) were reacted to give the title compound as a solid (44 mg, 0.092 mmol, 31%).

EXAMPLE 457

(S)-5-[(3-{[(1,3-dimethyl-1H-pyrazol-5-yl)carbonyl]amino}phenyl)ethynyl]-N-[methyl(oxo)phenyl-λ$^6$-sulfanylidene]nicotinamide Step 1

2,5-Dimethyl-2H-pyrazole-3-carboxylic acid (3-ethynyl-phenyl)-amide

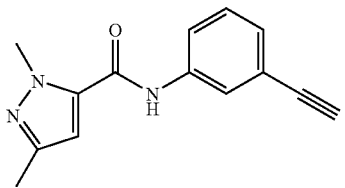

A dry 25 mL flask was charged with 2,5-dimethyl-2H-pyrazole-3-carbonyl chloride (0.135 g, 0.854 mmol) and THF (5 mL) was added. 3-Ethynyl-phenylamine (0.100 g, 0.854 mmol) was added to the THF solution of the acid chloride followed by NEt$_3$, and the mixture was allowed to stir at 55° C. The reaction mixture was then allowed to cool to room temperature. The reaction was extracted twice with EtOAc (5 mL) and water (10 mL) followed by saturated aqueous NaHCO$_3$ (~10 mL). The combined organic layers were dried over anhydrous Na$_2$SO$_4$ (s) and then concentrated. The crude residue was purified by chromatography (silica gel, gradient elution EtOAc/Hexanes 0 to 60%). The product containing fractions were concentrated to give the title compound as a tan solid (147 mg. 72%).

Step 2

(S)-5-[(3-{[(1,3-dimethyl-1H-pyrazol-5-yl)carbonyl]amino}phenyl)ethynyl]-N-[methyl(oxo)phenyl-λ$^6$-sulfanylidene]nicotinamide In a manner similar to that described in Example 449, 2,5-Dimethyl-2H-pyrazole-3-carboxylic acid (3-ethynyl-phenyl)-amide (0.0354 g, 0.222 mmol) and (S)-5-bromo-N-[methyl(oxo)phenyl-λ$^6$-sulfanylidene]nicotinamide (0.050 g, 0.148 mmol) were reacted to give the title compound as a white solid (47 mg, 64%).

EXAMPLE 458

N-[methyl(oxo)phenyl-λ$^6$-sulfanylidene]-5-({3-[(3-methylthienyl-2-carbonyl)amino]phenyl}ethynyl)nicotinamide Step 1

N-(3-ethynylphenyl)-3-methylthiophene-2-carboxamide

A dry 25 mL flask was charged with 3-methylthiophene-2-carboxylic acid (0.201 g, 1.41 mmol) followed by thionyl chloride (10 mL). The reaction was heated to 50° C. for 2 h after which the reaction was cooled to room temperature and concentrated to afford the crude acid chloride. The crude acid chloride was dissolved into 10 mL of THF and 3-ethynyl-phenylamine (0.165 g, 1.41 mmol) was added to the solution followed by NEt$_3$, and the mixture was allowed to stir at 55° C. for 4 hours. The reaction mixture was allowed to cool to room temperature and then partitioned between EtOAc and water. The organic layer was then washed once with of 1M HCl (~10 mL) and then twice with of saturated aqueous-NaHCO$_3$ (~10 mL). The organic extracts were combined, dried over anhydrous Na₂SO₄(s) and then concentrated to give the title compound as a tan solid (265 mg, 1.10 mmol, 78%).

Step 2

(S)-N-[methyl(oxo)phenyl-λ⁶-sulfanylidene]-5-({3-[(3-methylthienyl-2-carbonyl)amino]phenyl}ethynyl)nicotinamide

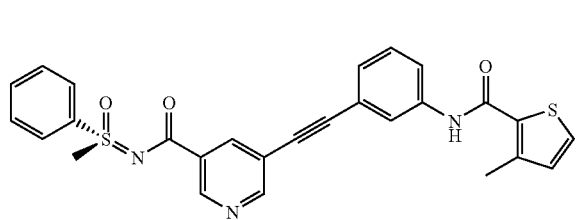

In a manner similar to that described in Example 449, N-(3-ethynylphenyl)-3-methylthiophene-2-carboxamide (0.213 g, 0.885 mmol) and (S)-5-bromo-N-[methyl(oxo)phenyl-λ⁶-sulfanylidene]nicotinamide (0.200 g, 0.590 mmol) were reacted to give the title compound as a solid (274 mg, 93%).

EXAMPLE 459

(S)-tert-butyl (3-{[5-({[methyl(oxo)phenyl-λ⁶-sulfanylidene]amino}carbonyl)pyridin-3-yl]ethynyl}phenyl)carbamate Step 1 tert-butyl 3-ethynylphenylcarbamate

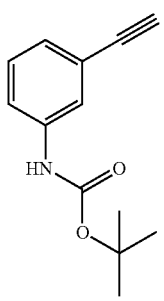

A dry 25 mL flask was charged with 3-ethynyl-phenylamine (0.100 g, 0.855 mmol) and THF (5 mL) was added. Di-tert-butyl dicarbonate (0.242 g, 1.11 mmol) was added to the THF solution followed by NEt₃ (0.23 mL, 1.71 mmol). The mixture was allowed to stir at 55° C. after which it was cooled to room temperature and extracted twice with EtOAc (~10 mL), water (~10 mL) and saturated aqueous NaHCO₃.

The combined organic extracts were dried over anhydrous Na₂SO₄(s) and then concentrated to give the title compound (0.13 g, 0.67 mmol, 72%).

Step 2

(S)-tert-butyl (3-{[5-({[methyl(oxo)phenyl-λ⁶-sulfanylidene]amino}carbonyl)pyridin-3-yl]ethynyl}phenyl)carbamate

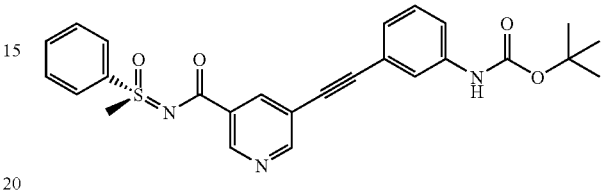

In a manner similar to that described in Example 449, tert-butyl 3-ethynylphenylcarbamate (0.098 g, 0.443 mmol) and (S)-5-bromo-N-[methyl(oxo)phenyl-λ⁶-sulfanylidene]nicotinamide (0.100 g, 0.295 mmol) reacted to give the title compounds as a white solid (32 mg, 23%).

EXAMPLE 460

(S)-5-({3-[(2-methylbenzoyl)amino]phenyl}ethynyl)-N-[methyl(oxo)phenyl-λ⁶-sulfanylidene]nicotinamide Step 1

N-(3-ethynylphenyl)-2-methylbenzamide

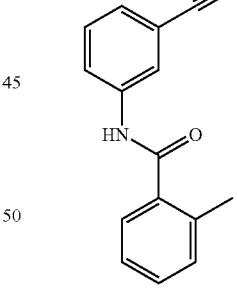

A dry 25 mL flask was charged with 2-methylbenzoyl chloride (0.155 g, 1.00 mmol) was cooled to room temperature, and THF (10 mL) was added. 3-Ethynyl-phenylamine (0.117 g, 1.00 mmol) was added to the THF solution of the acid chloride followed by NEt₃ (0.272 mL, 2.00 mmol), and the mixture was allowed to stir at 55° C. The reaction mixture was then allowed to cool to room temperature and partitioned between EtOAc (10 mL) and H₂O (15 mL). The organic layer was washed with then washed once with 1M HCl (20 mL) followed by of saturated aqueous NaHCO₃ (~20 mL) and of brine (~20 mL). The organic extracts were concentrated and the crude residue was purified by chromatography (silica gel, gradient elution EtOAc/hexanes 10 to 70%). The product containing fractions were concentrated to give the title compound as a tan solid (434 mg, 0.88 mmol, 88%).

Step 2

(S)-5-({3-[(2-methylbenzoyl)amino]phenyl}ethynyl)-N-[methyl(oxo)phenyl-λ⁶-sulfanylidene]nicotinamide

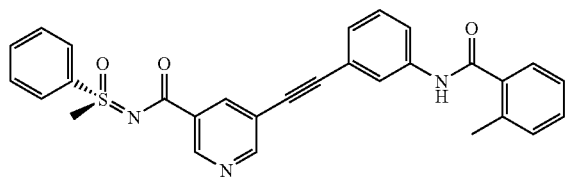

In a 4 mL vial, N-(3-ethynylphenyl)-2-methylbenzamide (0.104 g, 0.443 mmol) and (S)-5-bromo-N-[methyl(oxo)phenyl-λ⁶-sulfanylidene]nicotinamide (0.100 g, 0.295 mmol) were added and dissolved into EtOAc (2 mL) The mixture was then degassed for ~20 min after which NEt₃ (0.141 mL, 1.035 mmol) was added followed by Pd(PPh₃)₂Cl₂ (21.0 mg, 0.030 mmol) and CuI (2.9 mg, 0.016 mmol). The reaction mixture was allowed to stir at 50° C. for 4 hours after which the reaction mixture was partitioned between EtOAc (4 mL) and water (4 mL). The organic extracts were combined, dried over anhydrous Na₂SO₄ and concentrated. The residue as purified by chromatography (silica gel, gradient elution 25% EtOAc/Hexanes EtOAc). The product containing fractions were concentrated to give the title compound as a solid (121 mg, 83%).

EXAMPLE 461

(S)-N-[methyl(oxo)phenyl-λ⁶-sulfanylidene]-5-({3-[(3-methylfuryl-2-carbonyl)amino]phenyl}ethynyl)nicotinamide

Step 1

N-(3-ethynylphenyl)-3-methylfuran-2-carboxamide

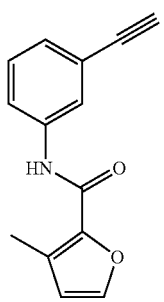

A dry 25 mL flask was charged with 3-methylfuran-2-carboxylic acid (0.500 g, 3.46 mmol) and thionyl chloride (10 mL). The reaction was heated to 50° C. and allowed to react for 2 h. The reaction was then cooled to room temperature and concentrated affording the crude acid chloride. The acid chloride was then dissolved in THF (5 mL) and 3-ethynyl-phenylamine (0.41 g, 3.47 mmol) was added followed by NEt₃ (0.95 mL, 7 mmol). The mixture was allowed to stir at 55° C. for 3 hours and the cooled to room temperature. The reaction was then partitioned between EtOAc and water. The organic layer was then washed once with 1M HCl (5 mL) and then once with saturated aqueous NaHCO₃ (5 mL). The organic extracts were then concentrated to give the title compound as a light brown solid (631 mg, 2.80 mmol, 81%).

Step 2

(S)-N-[methyl(oxo)phenyl-λ⁶-sulfanylidene]-5-({3-[(3-methylfuryl-2-carbonyl)amino]phenyl}ethynyl)nicotinamide

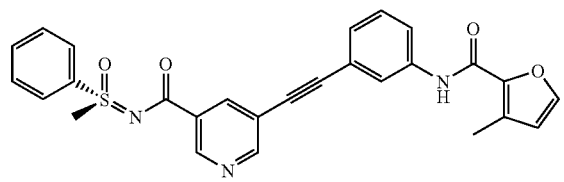

In a manner similar to that described in Example 460, N-(3-ethynylphenyl)-3-methylfuran-2-carboxamide (0.199 g, 0.885 mmol) and (S)-5-bromo-N-[methyl(oxo)phenyl-λ⁶-sulfanylidene]nicotinamide (0.200 g, 0.590 mmol) were reacted to give the title compound as a solid (243 mg, 87%).

EXAMPLE 462

(S)-tert-butyl (5-{[5-({[methyl(oxo)phenyl-λ⁶-sulfanylidene]amino}carbonyl)pyridin-3-yl]ethynyl}-1,3-thiazol-2-yl)carbamate

Step 1 tert-butyl (5-bromo-1,3-thiazol-2-yl)carbamate

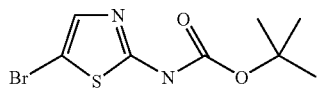

The title compound was prepared by a modification of the procedure described in J. Med. Chem. 2005, 48, 1886-1900. A mixture of 2-amino-6-bromothiazole monohydrobromide (390 mg, 1.5 mmol) and NaHCO₃ (441 mg, 5.3 mmol) in 6.0 mL tert-butyl alcohol was heated for 1 minute at near reflux, then cooled to room temperature. To this mixture was added DMAP (18 mg, 0.15 mmol) and di-tert-butyl dicarbonate (1.0 M in THF, 1.65 mL) and the reaction stirred at room temperature for 16 hours. In order to drive reaction to completion, additional di-tert-butyl dicarbonate (1.0 M in THF, 0.5 mL) was added, the reaction heated at 50° C. for 2 hours, then di-tert-butyl dicarbonate (1.0 M in THF, 1.0 mL) and 100 mg NaHCO₃ added and continued heating at 50° C. an additional 2 hours. The mixture was filtered and rinsed with EtOAc, then the EtOAc filtrate washed with H₂O, dilute aqueous HCl, saturated NaHCO₃ solution, brine, dried with anhydrous anhydrous Na₂SO₄ and rotary evaporated. The brown solid was chromatographed eluting with hexane/EtOAc and the product triturated with hexane to give the title compound as a cream solid (204 mg, 49%).

Step 2

(S)-tert-butyl (5-{[5-({[methyl(oxo)phenyl-λ⁶-sulfanylidene]amino}carbonyl)pyridin-3-yl]ethynyl}-1,3-thiazol-2-yl)carbamate

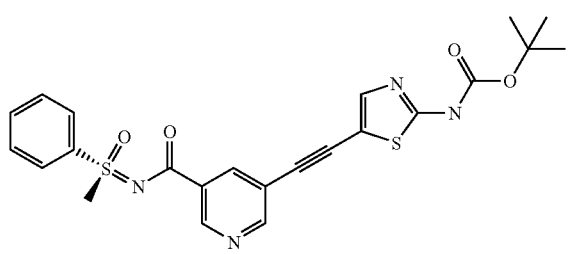

A mixture of N-[methyl(oxo)phenyl-λ⁶-sulfanylidene]-5-[(trimethylsilyl)ethynyl]nicotinamide (73 mg, 0.21 mmol), tert-butyl (5-bromo-1,3-thiazol-2-yl)carbamate (74 mg, 0.27 mmol), dichlorobis(triphenylphosphine)palladium(II) (14 mg, 0.02 mmol), triphenylphosphine (2.7 mg, 0.004 mmol) and triethylamine (0.071 mL, 0.51 mmol) in 1.8 mL DMF at room temperature was degassed using vacuum and a H₂/N₂ (1:1) mixture and then copper(I) iodide (2 mg, 0.01 mmol) added. While stirring the mixture at room temperature, tetrabutylammonium fluoride (1.0 M in THF, 0.21 mL) was added over 2.5 minutes. After 5 minutes the reaction was heated at 60° C. for 2 hours. The reaction was partitioned between EtOAc and H₂O and the EtOAc layer washed with H₂O, aqueous HCl, saturated NaHCO₃ solution, brine, dried with anhydrous Na₂SO₄ and concentrated. The brown oil was chromatographed eluting with hexane/acetone and the product containing fractions were concentrated to give the title compound as a light yellow solid (17 mg, 18%).

EXAMPLE 463

(S)-5-[(2-amino-1,3-thiazol-5-yl)ethynyl]-N-[methyl(oxo)phenyl-λ⁶-sulfanylidene]nicotinamide

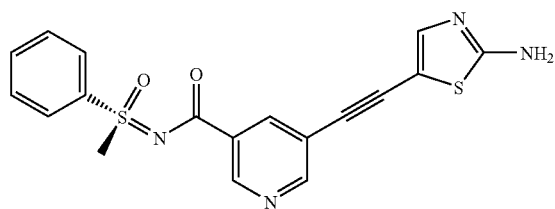

To a solution containing tert-butyl (5-{[5-({[methyl(oxo)phenyl-λ⁶-sulfanylidene]amino}carbonyl)pyridin-3-yl]ethynyl}-1,3-thiazol-2-yl)carbamate (16 mg, 0.032 mmol) in 2.0 mL dichloromethane at room temperature was added trifluoroacetic acid (0.099 mL, 1.3 mmol). The reaction was stirred at room temperature for 17 hours, then partitioned between EtOAc and saturated NaHCO₃ solution. The EtOAc layer was washed with H₂O, brine, dried with anhydrous Na₂SO₄ and rotary evaporated. The resulting solid film was purified by chromatography (silica gel, CHCl₃/EtOAc) to give the title compound as a tan solid (9 mg, 74%).

EXAMPLE 464

(S)-5-{[2-(benzoylamino)-1,3-thiazol-5-yl]ethynyl}-N-[methyl(oxo)phenyl-lambda~4~-sulfanylidene]nicotinamide

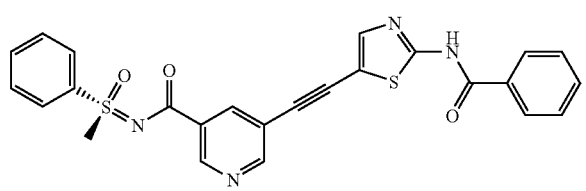

Step 1

N-(5-bromo-1,3-thiazol-2-yl)benzamide

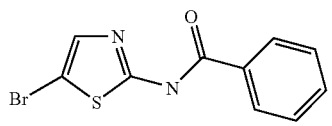

A mixture of 2-amino-6-bromothiazole monohydrobromide (156 mg, 0.6 mmol) in 2.0 mL pyridine (degassed) at room temperature was added benzoyl chloride (0.058 mL, 0.5 mmol) over 1 minute. After stirring at room temperature for 20 minutes the reaction was quenched with H₂O, and then extracted into EtOAc. The EtOAc layer was washed with H₂O, saturated NaHCO₃ solution, brine, dried with anhydrous Na₂SO₄ and rotary evaporated. The solid was triturated with hot 10% EtOAc/hexane to give a quantitative yield (142 mg) of the title compound as a light tan solid.

Step 2

5-{[2-(benzoylamino)-1,3-thiazol-5-yl]ethynyl}-N-[methyl(oxo)phenyl-λ⁶-sulfanylidene]nicotinamide In a manner similar to that described in Example 462, 5-ethynyl-N-[methyl(oxo)phenyl-λ⁶-sulfanylidene]nicotinamide (74 mg, 0.26 mmol), N-(5-bromo-1,3-thiazol-2-yl)

benzamide (74 mg, 0.26 mmol) were reacted to give the title compound as a cream solid (33 mg, 26%).

EXAMPLE 465

(S)-6-amino-N-[methyl(oxo)phenyl-$\lambda^6$-sulfanylidene]-5-[(trimethylsilyl)ethynyl]nicotinamide Step 1 methyl 6-amino-5-iodonicotinate

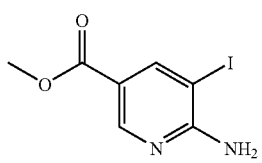

To a solution of iodine (3.55 g, 14.0 mmol) in 100 mL absolute ethanol at room temperature was added silver sulfate (4.37 g, 14.0 mmol) and methyl 6-aminonicotinate (1.52 g, 10.0 mmol). After 42 hours the reaction was filtered to isolate a tan precipitate. The solid was heated with 20% MeOH/CHCl$_3$ then cooled to room temperature, filtered, and rinsed with MeOH and CHCl$_3$. The filtrate was evaporated, dissolved in hot MeOH, filtered to remove brownish impurities, and then crystallized from MeOH to give the title compound as a light tan solid (1.73 g, 62%).

Step 2

6-amino-5-iodonicotinic acid

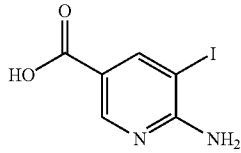

A solution of methyl 6-amino-5-iodonicotinate (723 mg, 2.6 mmol) and potassium hydroxide (729 mg, 13.0 mmol) in 40 mL methanol/H$_2$O (3:1 ratio) was heated at 50° C. After 4 hours 10 mL THF was added and the reaction continued until 22 hours. The reaction was cooled to room temperature and concentrated HCl added until the solution was pH 4. The solution was concentrated to a volume of 15 mL and the resulting precipitate filtered, rinsed with H$_2$O and 40% EtOAc/hexane to give the title compound as a white solid (443 mg, 65%).

Step 3

(S)-6-amino-5-iodo-N-[methyl(oxo)phenyl-$\lambda^6$-sulfanylidene]nicotinamide

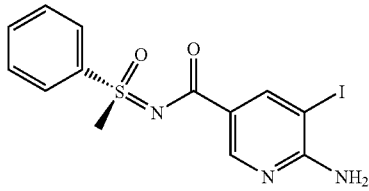

To a solution of 6-amino-5-iodonicotinic acid (330 mg, 1.3 mmol), N,N-diisopropylethylamine (0.44 mL, 2.5 mmol), and (S)-(+)-S-methyl-5-phenylsulfoximine (291 mg, 1.9 mmol) in 7.0 mL DMF at room temperature was added BOP (608 mg, 1.4 mmol). The solution was stirred 10 minutes and then heated at 60° C. for 5 hours. The mixture was dissolved in EtOAc, washed with Na$_2$CO$_3$ solution, H$_2$O, brine, dried with anhydrous Na$_2$SO$_4$ and rotary evaporated. The brown oil was purified by chromatography (silica gel, hexane/acetone). The product containing fractions were purified by chromatography one additional time (silica gel, EtOAc/MeOH). To give the title compound as a white foam (354 mg, 71%).

Step 4

(S)-6-amino-N-[methyl(oxo)phenyl-$\lambda^6$-sulfanylidene]-5-[(trimethylsilyl)ethynyl]nicotinamide

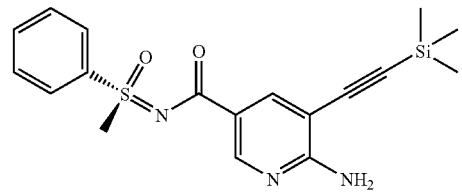

To a degassed solution containing (S)-6-amino-5-iodo-N-[methyl(oxo)phenyl-$\lambda^6$-sulfanylidene]nicotinamide (345 mg, 0.86 mmol) in 6.0 mL DMF at room temperature was added triethylamine (0.36 mL, 2.6 mmol), trimethylsilylacetylene (0.24 mL, 1.7 mmol), dichlorobis(triphenylphosphine)palladium(II) (60 mg, 0.09 mmol), and copper(I) iodide (16 mg, 0.09 mmol). After stirring at room temperature for 1 hour, the reaction was partitioned between EtOAc and H$_2$O. The EtOAc layer was washed with saturated NaHCO$_3$, brine, dried with anhydrous Na$_2$SO$_4$ and rotary evaporated. Then added 30 mL ethyl ether to the dark oil, filtered to remove the dark precipitate. The organic extracts were concentrated and the residue was purified by chromatography (silica gel, ethyl ether/EtOAc) to the title compound as a tan foam (317 mg, 99%).

EXAMPLE 466

(S)-6-amino-5-ethynyl-N-[methyl(oxo)phenyl-$\lambda^6$-sulfanylidene]nicotinamide

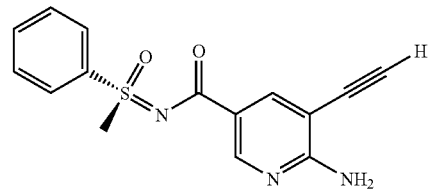

To a solution of (S)-6-amino-N-[methyl(oxo)phenyl-$\lambda^6$-sulfanylidene]-5-[(trimethylsilyl)ethynyl]nicotinamide (308 mg, 0.83 mmol) in 20 mL THF/methanol (1:1 ratio) at 0° C. was added K$_2$CO$_3$ (344 mg, 2.5 mmol) added. After 7 minutes the solution was decanted from the solids and partitioned between EtOAc and H$_2$O. The EtOAc layer was washed with brine, dried with anhydrous Na$_2$SO$_4$ and rotary evaporated.

The brown oil was purified by chromatography (silica gel, CHCl₃/EtOAc) to give the title compound as a white solid (193 mg, 78%).

EXAMPLE 467

6-amino-5-[(3-hydroxyphenyl)ethynyl]-N-[methyl(oxo)phenyl-λ⁶-sulfanylidene]nicotinamide

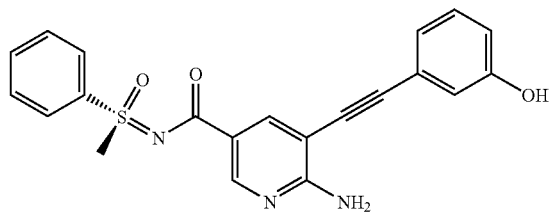

A mixture of (S)-6-amino-5-ethynyl-N-[methyl(oxo)phenyl-λ⁶-sulfanylidene]nicotinamide (60 mg, 0.2 mmol), 3-iodophenol (66 mg, 0.3 mmol), triethylamine (0.07 mL, 0.5 mmol), dichlorobis(triphenylphosphine)palladium(II) (14 mg, 0.02 mmol), triphenylphosphine (1.3 mg, 0.005 mmol) in 1.8 mL DMF at room temperature was degassed using a H₂/N₂ (1:1) mixture and then copper(I) iodide (2 mg, 0.01 mmol) added. The reaction was heated at 60° C. for 15 minutes and then partitioned between EtOAc and saturated NaHCO₃. The EtOAc layer was washed with brine, dried with anhydrous Na₂SO₄ and rotary evaporated to a brown oil. Before chromatography a different lot of product (23 mg) was added and the combined lots were purified by chromatography (silica gel, EtOAc/EtOH) to the title compound as an off-white solid (91 mg, 89%).

EXAMPLE 468

(S)-6-amino-5-[(4-hydroxyphenyl)ethynyl]-N-[methyl(oxo)phenyl-λ⁶-sulfanylidene]nicotinamide

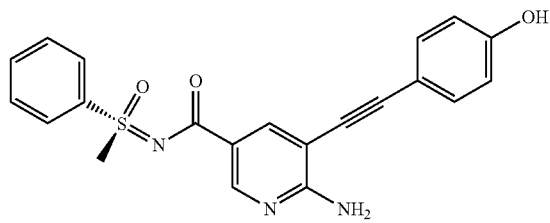

In a manner similar to that describe in Example 467, (S)-6-amino-5-ethynyl-N-[methyl(oxo)phenyl-λ⁶-sulfanylidene]nicotinamide and 4-iodophenol are converted to the title compound (41 mg, 62%).

EXAMPLE 469

(S)-2-amino-5-[(3-hydroxyphenyl)ethynyl]-N-[methyl(oxo)phenyl-λ⁶-sulfanylidene]nicotinamide Step 1

(S)-2-amino-5-bromo-N-[methyl(oxo)phenyl-λ⁶-sulfanylidene]nicotinamide

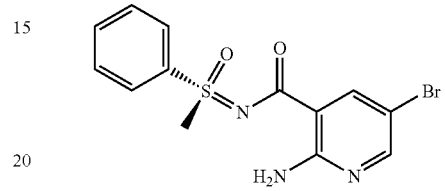

To a solution of 2-amino-5-bromonicotinic acid (189 mg, 0.87 mmol), N,N-diisopropylethylamine (0.30 mL, 1.7 mmol), and (S)-(+)-S-methyl-S-phenylsulfoximine (162 mg, 1.0 mmol) in 4.0 mL DMF at room temperature was added BOP (423 mg, 0.96 mmol). The solution was stirred 30 minutes, then heated at 60° C. for 30 minutes, and then cooled back to room temperature. After 19 hours, the mixture was dissolved in EtOAc, washed with Na₂CO₃ solution, H₂O, brine, dried with anhydrous Na₂SO₄ and rotary evaporated. The yellow foam was purified by chromatography (silica gel, CHCl₃/EtOAc) to give the title compound as a light yellow solid (260 mg, 84%).

Step 2

(S)-2-amino-5-[(3-hydroxyphenyl)ethynyl]-N-[methyl(oxo)phenyl-λ⁶-sulfanylidene]nicotinamide

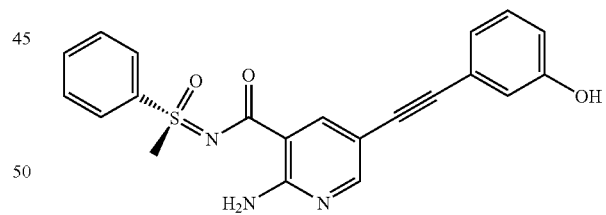

To a degassed solution containing (S)-2-amino-5-bromo-N-[methyl(oxo)phenyl-λ⁶-sulfanylidene]nicotinamide (106 mg, 0.3 mmol) and 3-hydroxyphenylacetylene (50 mg, 0.42 mmol) in 2.0 mL EtOAc at room temperature was added triethylamine (0.13 mL, 0.9 mmol), dichlorobis(triphenylphosphine)palladium(II) (21 mg, 0.03 mmol), and copper(I) iodide (6 mg, 0.03 mmol). The reaction was stirred at 70° C. for 3.3 hours. Additional 3-hydroxyphenylacetylene was added (50 mg, 0.42 mmol) and then again at 5.3 hours (75 mg, 0.63 mmol). The reaction was cooled to room temperature, and after 23 hours additional dichlorobis(triphenylphosphine)palladium(II) (20 mg, 0.03 mmol) was added. The reaction was heated to 60° C. and 3-hydroxyphenylacetylene (120 mg, 1.0 mmol) in 0.7 mL EtOAc (degassed) added dropwise over 7 minutes. The heat was removed after 1 hour and the reaction stirred an additional 22 hours at room temperature. The reaction was dissolved in EtOAc and washed with H₂O. The EtOAc layer was extracted with 2% aqueous HCl. The combined acidic aqueous layers were washed with 30% EtOAc/hexane and then made basic with Na₂CO₃. The basic aqueous layer was extracted with EtOAc. Then the combined organic layers washed with brine, dried with anhydrous Na₂SO₄ and concentrated. The yellow oil was purified by chromatography (silica gel, CHCl₃/EtOAc) to give the title compound as a white solid (5 mg, 4%).

EXAMPLE 470

Step 1

(S)-trimethyl{[methyl(oxo)phenyl-λ⁶-sulfanylidene]amino}silane

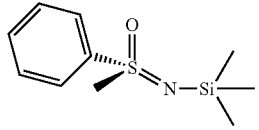

To a stirred pre-warmed solution of (S)-(+)-S-methyl-5-phenylsulphoximine (3 g, 18.7 mmol) in acetonitrile (2 mL) at 65° C. was added (trimethylsilyl)diethylamine (4.12 g, 21.1 mmol) dropwise via a syringe. The reaction was maintained at 65° C. and stirred for 3 hours. Additional amount of (trimethylsilyl)diethylamine (2 mL, 10.2 mmol) was added and the reaction mixture was stirred at 65° C. overnight. The reaction was then concentrated under reduced pressure and dried under vacuum to give the title compound. This material was used directly in next step of the synthesis without further purification.

Step 2

(S)-Ethyl[S-phenyl-N-(trimethylsilyl)sulfonimidoyl]acetate

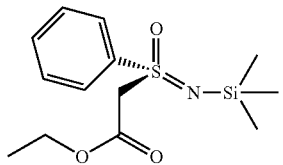

To a 100 mL round bottom flask equipped with a magnetic stir-bar and a rubber septum was added a solution of 2,2,6,6-tetra-methylpiperidine (8.91 mL, 52.5 mmol) in anhydrous THF (22 mL). The solution was cooled to 0° C. and was treated with n-BuLi (18 mL, 45 mmol) (2.5 M in hexanes) via a syringe. The resulting solution was stirred for 10 min at 0° C., cooled to −78° C., and treated dropwise with a solution of (S)-trimethyl{[methyl(oxo)phenyl-λ⁶-sulfanylidene]amino}silane (18.7 mmol) in THF (10 mL). The reaction mixture was stirred at −78° C. for 30 min and then was treated with ethyl chloroformate (5.16 mL, 52.5 mmol) dropwise.

The reaction mixture was stirred for an hour and warmed to room temperature. The reaction mixture was treated with saturated aqueous NH₄Cl (2.5 mL). The white solid which formed was collected by filtration and discarded. The filtrate was treated with additional saturated aqueous NH₄Cl solution and the resulting mixture was stored in a −20° C. fridge for 15 hours. The organic layer was collected and concentrated to give the title compound. This material was used directly in the next step of the synthesis.

Step 3

(S)-Ethyl(S-phenylsulfonimidoyl)acetate

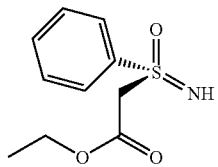

A solution of Ethyl[S-phenyl-N-(trimethylsilyl)sulfonimidoyl]acetate (18.7 mmol, obtained as crude oil from step 2) in MeOH—H₂O (10:1, 7.5 mL) was treated with cesium fluoride (0.25 g, 1.65 mmol) in one portion. The reaction mixture was heated to 50° C. and stirred for 2 hours. The reaction mixture was concentrated, the residue absorbed to silica gel and purified by chromatography (silica gel, EtOAc-Hexane, Et₃N 0.1%). The product containing fractions were concentrated to give the title compound as a pale yellow oil (1.65 g, 39% for steps 1-3).

Step 4

(S)-Ethyl {N-[(5-bromopyridin-3-yl)carbonyl]-S-phenylsulfonimidoyl}acetate

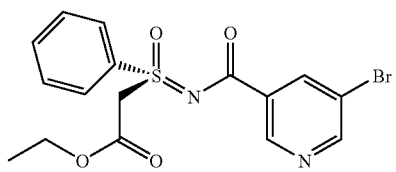

To a solution of 5-bromonicotinic acid (343 mg, 1.66 mmol) in anhydrous DMF (5.5 mL) was added N,N-diisopropylethylamine (0.58 mL, 3.32 mmol) and ethyl(S-phenylsulfonimidoyl)acetate (415 mg, 1.83 mmol) followed by the final addition of (benzotriazol-1-yloxy)-tris(dimethylamino)-phosphonium hexafluorophosphate (0.81 g, 1.83 mmol). The reaction mixture was stirred at room temperature for 20 min, and then partitioned between saturated aqueous NaHCO₃ and EtOAc. The organic layer was separated and washed once with brine and dried over anhydrous Na₂SO₄. The organic layer was concentrated and the residue purified by chromatography (silica gel, gradient elution (5:1 Hexane/

EtOAc to 3:1 Hexane/EtOAc). The product containing fractions were concentrated to give the title compound as a white solid (230 mg, 34%).

Step 5

(S)-Ethyl[N-({5-[(3-hydroxyphenyl)ethynyl]pyridin-3-yl}carbonyl)-S-phenylsulfonimidoyl]acetate

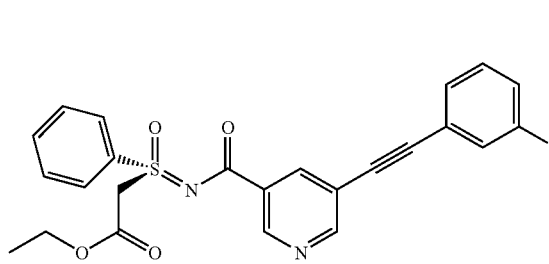

A solution ethyl {N-[(5-bromopyridin-3-yl)carbonyl]-S-phenylsulfonimidoyl}acetate (216 mg, 0.52 mmol) and 3-hydroxyphenylacetylene (0.052 mL, 0.79 mmol) in anhydrous DMF (3 mL) was treated with triethylamine (0.22 mL, 1.58 mmol). The reaction mixture was degassed (alternating vacuum and argon) and PdCl$_2$(Ph$_3$P)$_2$ (36.9 mg, 0.052 mmol) and triphenylphosphine (3.4 mg, 0.013 mmol) were added. The reaction mixture was degassed (alternating vacuum and argon) and placed under an atmosphere of 1:3 Argon/hydrogen atmosphere. Copper(1$^+$) iodide was added and the reaction mixture was heated at 60° C. for 50 min. The brown reaction mixture was partitioned between saturated aqueous NaHCO$_3$ and EtOAc. The organic layer was collected and washed further with saturated aqueous NaHCO$_3$ (1×), brine (1×), and dried over anhydrous Na$_2$SO$_4$. The residue was purified by chromatography (silica gel, 50:1 CHCl$_3$:MeOH). The product containing fractions were concentrated to give the title compound as a light yellow solid (220 mg, 94%).

EXAMPLE 471

(S)-N-[(2-{[2-(diethylamino)ethyl]amino}-2-oxoethyl)(oxo)phenyl-λ$^6$-sulfanylidene]-5-[(3-hydroxyphenyl)ethynyl]nicotinamide

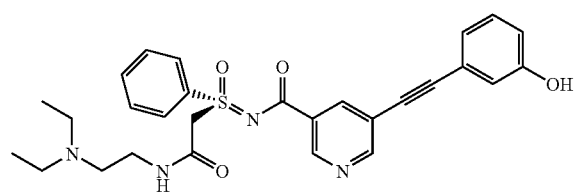

(S)-Ethyl[N-({5-[(3-hydroxyphenyl)ethynyl]pyridin-3-yl}carbonyl)-S-phenylsulfonimidoyl]acetate (73 mg, 0.16 mmol) in anhydrous MeOH (1.5 mL) was added N,N-diethylethylenediamine (0.12 mL, 0.84 mmol) dropwise. The reaction mixture was heated at 30° C. for 4 hours. The reaction mixture was evaporated and the residue was partitioned between EtOAc and saturated aqueous NaHCO$_3$. The organic layer was washed once with brine, dried (anhydrous Na$_2$SO$_4$), concentrated. The residue was purified by chromatography (silica gel, 50:1 CHCl$_3$:MeOH to 10:1 CHCl$_3$:MeOH). The product containing fractions were concentrated to give the title compound as a foamy solid (50 mg, 59%).

EXAMPLE 472

(S)-N-[{2-[(2-hydroxyethyl)(methyl)amino]-2-oxoethyl}(oxo)phenyl-λ$^6$-sulfanylidene]-5-[(3-hydroxyphenyl)ethynyl]nicotinamide

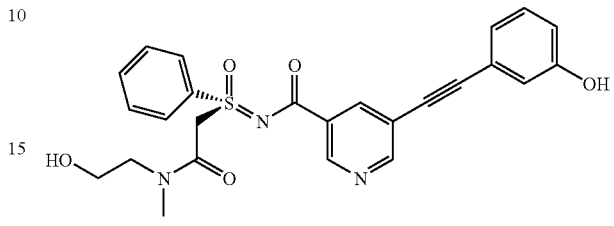

In a manner similar to that described for Example 471, (S)-Ethyl[N-({5-[(3-hydroxyphenyl)ethynyl]pyridin-3-yl}carbonyl)-S-phenylsulfonimidoyl]acetate (65 mg, 0.14 mmol) and 2-(methylamino)ethanol (0.1 mL, 1.2 mmol) were reacted to give the title as clear oil (42 mg, 61%).

EXAMPLE 473

5-[(3-hydroxyphenyl)ethynyl]-N-{[2-(methylamino)-2-oxoethyl] (oxo)phenyl-λ$^6$-sulfanylidene}nicotinamide

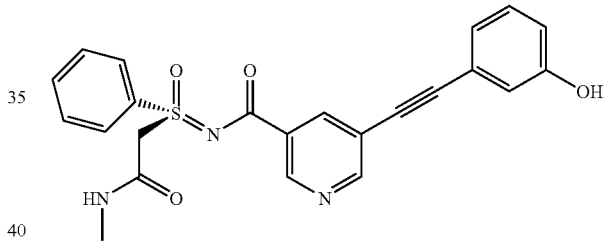

In a manner similar to that described for Example 471, (S)-Ethyl[N-({5-[(3-hydroxyphenyl)ethynyl]pyridin-3-yl}carbonyl)-S-phenylsulfonimidoyl]acetate (50 mg, 0.11 mmol) and methylamine (2.0 M solution in MeOH, 0.5 mL, 1.0 mmol) were reacted to give the title compound as colorless oil (43 mg, 90%).

EXAMPLE 474

N-[{2-[(2-hydroxyethyl)amino]-2-oxoethyl}(oxo)phenyl-λ$^6$-sulfanylidene]-5-[(3-hydroxyphenyl)ethynyl]nicotinamide

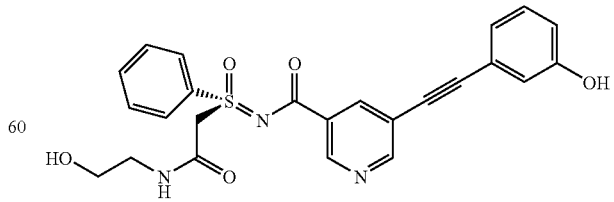

In a manner similar to that described for Example 471, (S)-Ethyl[N-({5-[(3-hydroxyphenyl)ethynyl]pyridin-3-yl}carbonyl)-S-phenylsulfonimidoyl]acetate (75 mg, 0.17 mmol) and ethanolamine (0.05 mL, 0.84 mmol) were reacted to give the title compound as colorless oil (63 mg, 81

EXAMPLE 475

N-[{2-[(2-amino-2-oxoethyl)amino]-2-oxoethyl}(oxo)phenyl-λ⁶-sulfanylidene]-5-[(3-hydroxyphenyl)ethynyl]nicotinamide

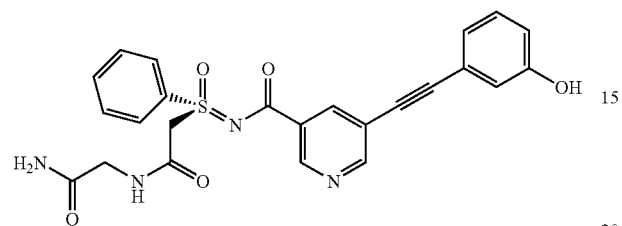

In a manner similar to that described for Example 471, (S)-Ethyl[N-({5-[(3-hydroxyphenyl)ethynyl]pyridin-3-yl}carbonyl)-S-phenylsulfonimidoyl]acetate (75 mg, 0.17 mmol) and glycinamide hydrochloride (95 mg, 0.84 mmol) were reacted to give the title compound as colorless oil (40 mg, 50%).

EXAMPLE 476

(S)-5-[(2-{[(1,3-dimethyl-1H-pyrazol-5-yl)carbonyl]amino}phenyl)ethynyl]-N-[methyl(oxido)phenyl-□⁴-sulfanylidene]nicotinamide Step 1

N-(3-ethynylphenyl)-1,3-dimethyl-1H-pyrazole-5-carboxamide

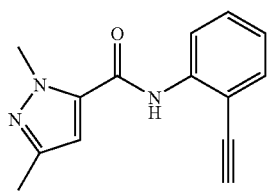

In a manner similar to that described in Example 457, 2,5-dimethyl-2H-pyrazole-3-carbonyl chloride (0.135 g, 0.854 mmol) was and 2-ethynyl-phenylamine (0.100 g, 0.854 mmol) were reacted to give the title compound as a tan solid (0.101 mg, 53%).

Step 2

(S)-5-[(2-{[(1,3-dimethyl-1H-pyrazol-5-yl)carbonyl]amino}phenyl)ethynyl]-N-[methyl(oxido)phenyl-□⁴-sulfanylidene]nicotinamide

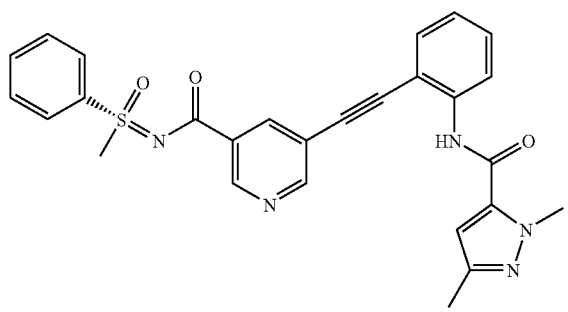

In a manner similar to that described in Example 460 (step 2) N-(3-ethynylphenyl)-1,3-dimethyl-1H-pyrazole-5-carboxamide (0.0354 g, 0.222) and (S)-5-bromo-N-[methyl(oxido)phenyl-∟⁴-sulfanylidene]nicotinamide (0.050 g, 0.148 mmol) reacted to give the title compound as a white solid (0.025 g, 34%).

EXAMPLE 477

(S)-5-({2-[(3-methyl-2-furoyl)amino]phenyl}ethynyl)-N-[methyl(oxido)phenyl-∟⁴-sulfanylidene]nicotinamide

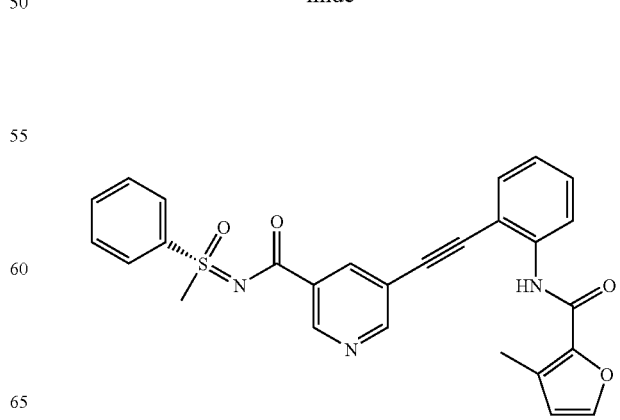

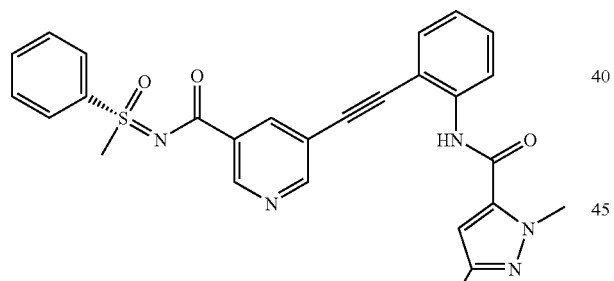

Step 1

3-Methyl-furan-2-carboxylic acid (2-ethynyl-phenyl)-amide

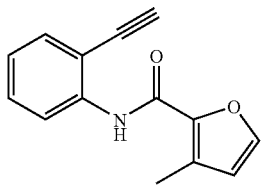

In a manner similar to that described in Example 458 (step 1), 3-methylthiophene-2-carboxylic acid (0.100 g, 0.794 mmol) and 2-ethynyl-phenylamine (0.093 g, 0.794 mmol) were reacted to give the title compound as a tan solid (0.110 g, 56%).

Step 2

(S)-5-({2-[(3-methyl-2-furoyl)amino]phenyl}ethynyl)-N-[methyl(oxido)phenyl-$\lambda^4$-sulfanylidene]nicotinamide

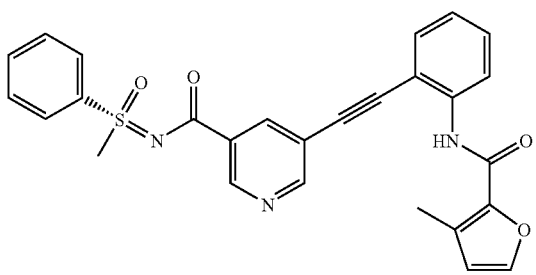

In a manner similar to that described for Example 460 (step 2), (S)-5-bromo-N-[methyl(oxido)phenyl-$\lambda^4$-sulfanylidene]nicotinamide (0.050 g, 0.148 mmol) and 3-methyl-furan-2-carboxylic acid (2-ethynyl-phenyl)-amide (0.050 g, 0.222 mmol) were reacted to give the title compound (0.031 g, 43%).

EXAMPLE 478

(S)-5-[(3-{[(1,3-dimethyl-1H-pyrazol-5-yl)amino]carbonyl}phenyl)ethynyl]-N-[methyl(oxido)phenyl-$\lambda^4$-sulfanylidene]nicotinamide

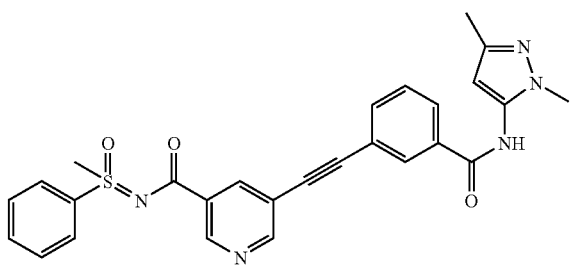

Step 1

N-(2,5-Dimethyl-2H-pyrazol-3-yl)-3-ethynyl-benzamide

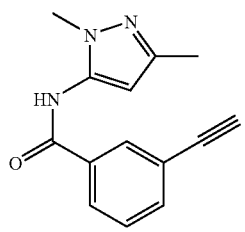

3-Ethynylbenzoic acid (0.1 g, 0.685 mmol) was added to a dry 50 mL round bottom flask and dissolved in DMF (6.85 mL). To the resulting solution was added 1,3-dimethyl-1H-pyrazol-5-amine (0.076 g, 0.685 mmol), followed by BOP (0.393 g, 0.890 mmol), and 0.238 mL of DIPEA (1.37 mmol). This reaction mixture was heated to 50° C. for 3 h. After allowing the reaction to cool to room temperature it was taken up in EtOAc (15 mL) and extracted with brine (3×15 mL). The EtOAc layer was then washed with saturated aqueous NaHCO$_3$ (2×15 mL). The organics were dried over anhydrous Na$_2$SO$_{4(s)}$, filtered and concentrated in vacuo. The crude residue was purified via column chromatography (silica gel, gradient eluant mixture of EtOAc in Hexanes: 0% to 100% EtOAc) affording N-(1,3-dimethyl-1H-pyrazol-5-yl)-3-ethynylbenzamide (0.128 g, 78%).

Step 2

(S)-5-[(3-{[(1,3-dimethyl-1H-pyrazol-5-yl)amino]carbonyl}phenyl)ethynyl]-N-[methyl(oxido)phenyl-$\lambda^4$-sulfanylidene]nicotinamide

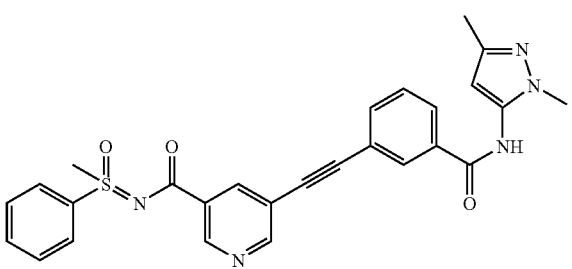

In a manner similar to that described in Example 460 (step 2), (S)-5-bromo-N-[methyl(oxido)phenyl-$\lambda^4$-sulfanylidene]nicotinamide (0.141 g, 0.418 mmol) and N-(1,3-dimethyl-1H-pyrazol-5-yl)-3-ethynylbenzamide (0.1 g, 0.418 mmol) were reacted to give the title compound (0.126 g, 61%).

EXAMPLE 479

(S)-5-({3-[(methoxyamino)carbonyl]phenyl}ethynyl)-
N-[methyl(oxido)phenyl-□⁴-sulfanylidene]nicotinamide

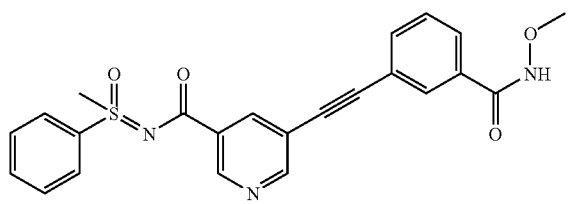

Step 1

3-Ethynyl-N-methoxy-benzamide

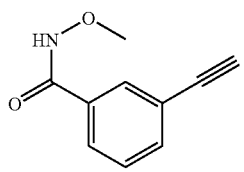

In a manner similar to that described for Example 478 (step 1), 3-ethynylbenzoic acid (0.1 g, 0.685 mmol) and O-methylhydroxylamine hydrogen chloride (0.057 g, 0.685 mmol) were reacted to give the title compound (0.128 g, 61%).

Step 2

(S)-5-({3-[(methoxyamino)carbonyl]phenyl}ethynyl)-
N-[methyl(oxido)phenyl-□⁴-sulfanylidene]nicotinamide

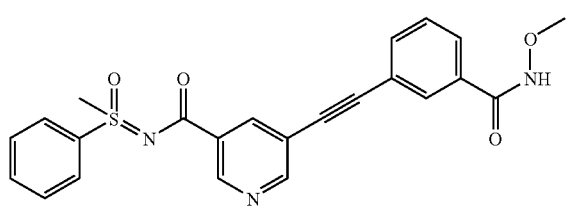

In a manner similar to that described in Example 460 (step 2), (S)-5-bromo-N-[methyl(oxido)phenyl-□⁴-sulfanylidene]nicotinamide (0.100 g, 0.295 mmol) and 3-Ethynyl-N-methoxy-benzamide (0.106 g, 0.442 mmol) were reacted to give the title compound yield (0.126 g, 86%).

EXAMPLE 480

Methyl 3-{4-[N-({5-[(3-{[(1,3-dimethyl-1H-pyrazol-5-yl)carbonyl]-amino}phenyl)ethynyl]pyridin-3-yl}carbonyl)-S-methylsulfonimidoyl]phenyl}-propanoate

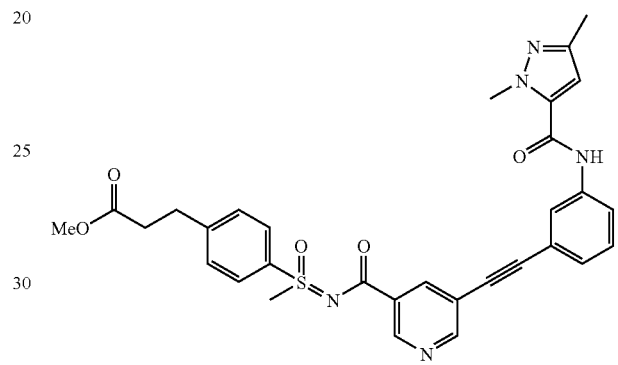

Step 1

5-[(3-{[(1,3-dimethyl-1H-pyrazol-5-yl)carbonyl]amino}phenyl)-ethynyl]nicotinic acid

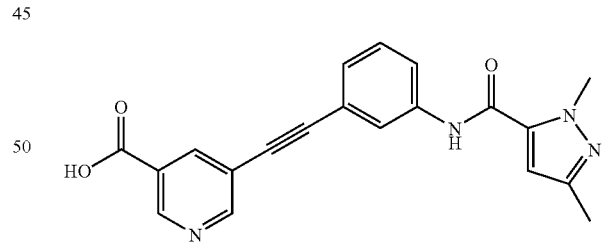

In a 50 mL round bottom flask, N-(3-ethynylphenyl)-1,3-dimethyl-1H-pyrazole-5-carboxamide (0.888 g, 3.71 mmol) and 5-bromo nicotinic acid (0.50 g, 2.47 mmol) were dissolved in DMF (15 mL) The mixture was then degassed by bubbling $N_{2(g)}$ through it for ~20 min. The mixture was then treated sequentially with $NEt_3$ (1.37 mL, 9.90 mmol), $Pd(PPh_3)_2Cl_2$ (0.173 g, 0.247 mmol) and CuI (0.094 g, 4.95 mmol). The reaction mixture was allowed to stir at 50° C. for 4 h. The reaction mixture was diluted with EtOAc (25 mL) causing a pale yellow precipitate to form. The white precipitate was filtered off giving the title compound (0.105 g, 12%).

Step 2

Methyl 3-[4-(methylthio)phenyl]propanoate

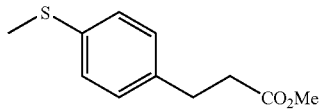

In a 100 mL round bottom flask, 3-(4-(methylthio)phenyl)propanoic acid (1.00 g, 5.10 mmol) was dissolved in DMF (17 mL) under $N_{2(g)}$. CDI (1.24 g, 7.65 mmol) was then added to the reaction mixture and the resulting mixture was allowed to stir at room temperature for ~45 min. MeOH (6 mL) was then added in dropwise fashion to the reaction. The reaction was allowed to stir for an additional 1 h, after which time it was extracted with EtOAc (3×50 mL) and brine (3×50 mL). The combined organic extracts were dried over anhydrous $Na_2SO_{4(s)}$, filtered and concentrated. The crude product was purified by column chromatography (silica gel, gradient elution mixture: 10% EtOAc in Hexanes to 0100% EtOAc) to give the title compound (0.771 g, 72%).

Step 3

Methyl 3-[4-(methylsulfinyl)phenyl]propanoate

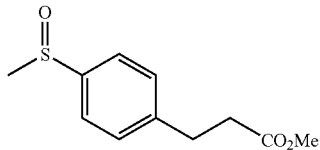

In a 250 mL round bottom flask, methyl 3-(4-(methylthio)phenyl)propanoate (0.50 g, 2.38 mmol) was dissolved in MeOH under a $N_{2(g)}$. The resulting solution was cooled to 0° C., then 0.5 M $NaIO_4$ (4.76 mL, 2.38 mmol) was added dropwise to the cooled solution causing the formation of a white precipitate. The reaction was allowed to warm to room temperature. When HPLC indicated complete consumption of starting thioether, the reaction was filtered and the filtrate was concentrated. The resulting residue was taken up in $CHCl_3$ (25 mL) then extracted with brine. The brine layer was subsequently extracted with $CHCl_3$ (2×25 mL). The combined organic extracts were then dried over anhydrous $Na_2SO_{4(s)}$, filtered and concentrated. The resulting sulfoxide was then purified by passing through a plug of silica using EtOAc/Hexanes as eluant affording methyl 3-(4-(methylsulfinyl)phenyl)propanoate (0.436 g, 81%).

Step 4

Methyl 3-{4-[S-methyl-N-(trifluoroacetyl)sulfonimidoyl]phenyl}-propanoate

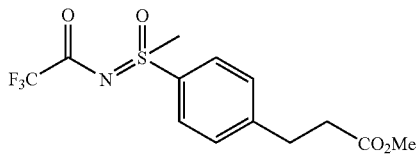

In a 100 mL round bottom flask, methyl 3-(4-(methylsulfinyl)phenyl)propanoate (0.4 g, 1.77 mmol) was added to $CH_2Cl_2$ (18 mL). Subsequently the reaction was treated with MgO (0.285 g, 7.08 mmol), trifluoroacetamide (0.400 g, 3.54 mmol), $PhI(OAc)_4$ (0.884 g, 2.66 mmol), and $Rh_2(OAc)_4$ (19.55 mg, 0.0443 mmol). The suspension was stirred overnight then filtered through celite. The filtrate was the concentrated. The resulting residue was purified via column chromatography (silica gel, gradient eluant mixture: 20% EtOAc in hexanes to 100% EtOAc) to give the title compound (0.294 g, 69%).

Step 5

Methyl 3-[4-(S-methylsulfonimidoyl)phenyl]propanoate

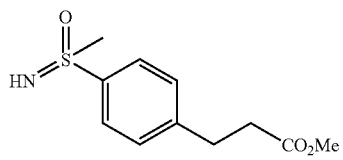

Methyl 3-{4-[S-methyl-N-(trifluoroacetyl)sulfonimidoyl]phenyl}propanoate (0.200 g, 0.653 mmol) was dissolved in MeOH (3 mL). $K_2CO_3$ (0.450 g, 3.27 mmol) was added to the solution, and the resulting suspension was allowed to stir for 5 minutes. The suspension was filtered and the filtrate was concentrated. The residue was dissolved in EtOAc and dried over anhydrous anhydrous $Na_2SO_{4(s)}$ to give the title compound (0.147 g, 93%).

Step 6

Methyl 3-{4-[N-({5-[(3-{[(1,3-dimethyl-1H-pyrazol-5-yl)carbonyl]-amino}phenyl)ethynyl]pyridin-3-yl}carbonyl)-S-methylsulfonimidoyl]phenyl}-propanoate

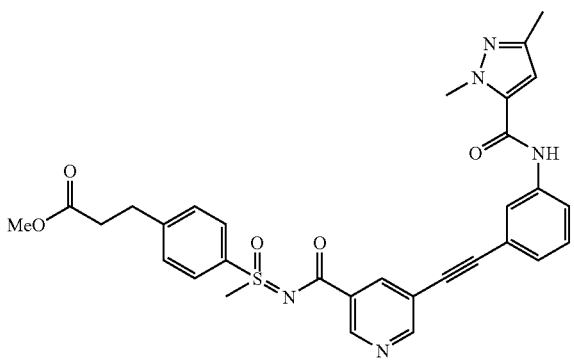

A solution of 5-[(3-{[(1,3-dimethyl-1H-pyrazol-5-yl)carbonyl]amino}phenyl)-ethynyl]nicotinic acid (0.149 g, 0.414 mmol) in DMF (4 mL) was treated with methyl 3-(4-(S-methylsulfonimidoyl)phenyl)propanoate (0.100 g, 0.414 mmol), followed by BOP (0.238 g, 0.539 mmol) and DIPEA (0.144 mL, 0.830 mmol). The reaction mixture was heated to 50° C. for 3 h. After allowing the reaction to cool to room temperature it was taken up in EtOAc (10 mL) and extracted with brine (3×10 mL). The EtOAc layer was then washed with saturated aqueous $Na_2CO_3$ (2×10 mL). The organic layer was dried over anhydrous $Na_2SO_{4(s)}$, filtered and concentrated. The crude residue was purified via column chromatography (silica gel, gradient elution, EtOAc in Hexanes: 0% to 100% EtOAc) affording the title compound (0.108 g, 45%).

EXAMPLE 481

3-{4-[N-({5-[(3-{[(1,3-dimethyl-1H-pyrazol-5-yl)carbonyl]amino}-phenyl)ethynyl]pyridin-3-yl}carbonyl)-S-methylsulfonimidoyl]phenyl}propanoic acid

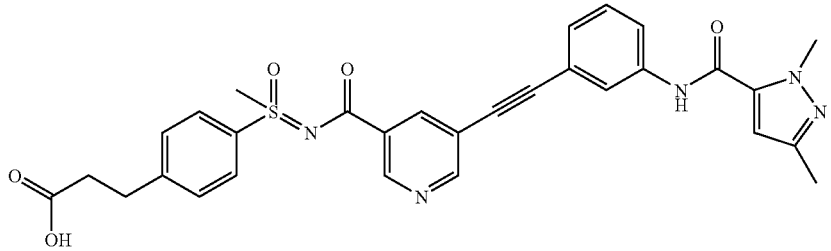

A solution of Methyl 3-{4-[N-({5-[(3-{[(1,3-dimethyl-1H-pyrazol-5-yl)carbonyl]amino}-phenyl)ethynyl]pyridin-3-yl}carbonyl)-S-methylsulfonimidoyl]phenyl}propanoate (0.075 g, 0.129 mmol) in THF (3 mL) was cooled to 0° C. and slowly treated with 0.5M NaOH (1.29 mL, 0.643 mmol). The reaction mixture was allowed to slowly come to room temperature. Once the reaction was done by TLC, the reaction was acidified with acetic acid and then extracted with EtOAc (20 mL) and H$_2$O (20 mL). The organic layer was dried over anhydrous Na$_2$SO$_{4(s)}$, filtered, and concentrated to give the title compound (0.052 g, 71%).

EXAMPLE 482

N-[(4-{[3-(dimethylamino)propyl]amino}phenyl)(methyl)oxido-□$^4$-sulfanylidene]-5-[(3-{[(1,3-dimethyl-1H-pyrazol-5-yl)carbonyl]amino}phenyl)ethynyl]nicotinamide

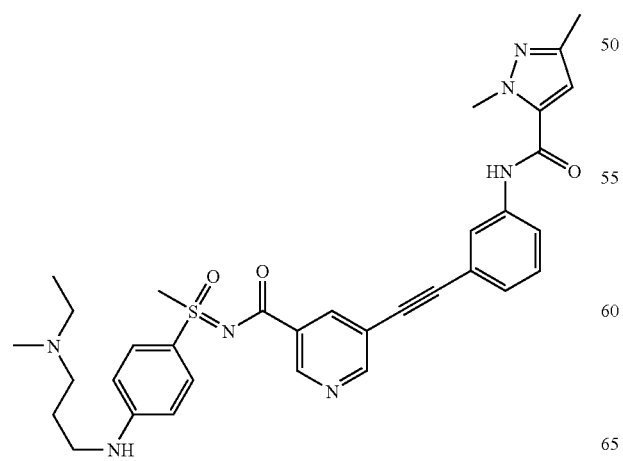

Step 1 tert-Butyl[4-(methylthio)phenyl]carbamate

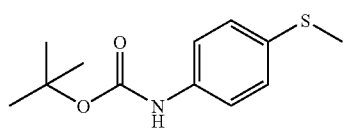

4-Methylsulfanyl-phenylamine (0.5 g, 3.59 mmol) was dissolved in THF (12 mL) The resulting solution was treated with di-tert butyl dicarbonate (1.02 g, 4.67 mmol) and then with TEA (1.5 mL, 10.78 mmol). The reaction was heated at 50° C. for 3 h and then allowed to cool to room temperature. The cool reaction mixture was taken up in EtOAc (20 mL) and extracted with H$_2$O (20 mL). The organic layer was further washed with a saturated aqueous solution of NaHCO$_3$ (20 mL). The organic layer was dried over anhydrous Na$_2$SO$_{4(s)}$, filtered and concentrated in vacuo. The crude mixture was purified via column chromatography (gradient eluant mixture of EtOAc in Hexanes: 0% to 100% EtOAc) to the title compound (0.652 g, 76%).

Step 2 tert-Butyl[4-(methylsulfinyl)phenyl]carbamate

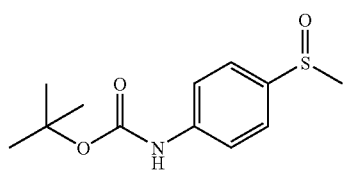

In a manner similar to that described in Example 480 (step 3), tert-Butyl[4-(methylthio)phenyl]carbamate (0.650 g, 2.72 mmol) was converted to the title compound (0.347 g, 50%).

Step 3 tert-butyl {4-[S-methyl-N-(trifluoroacetyl)sulfonimidoyl]phenyl}-carbamate

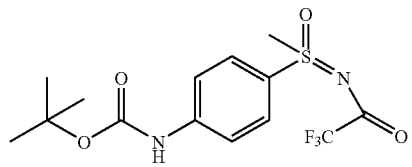

In a manner similar to that described in Example 480 (step 4), tert-Butyl[4-(methylsulfinyl)phenyl]carbamate (0.300 g, 1.18 mmol) was converted to the title compound (0.224 g, 52%).

Step 4 tert-Butyl[4-(S-methylsulfonimidoyl)phenyl]carbamate

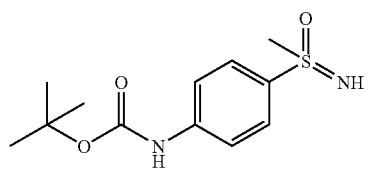

In a manner similar to that described in Example 480 (step 5), tert-butyl {4-[S-methyl-N-(trifluoroacetyl)sulfonimidoyl]phenyl}-carbamate (0.224 g, 0.612 mmol) was converted to the title compound (0.150 g, 91%).

Step 5 tert-butyl (4-{N-[(5-bromopyridin-3-yl)carbonyl]-S-methylsulfonimidoyl}phenyl)carbamate

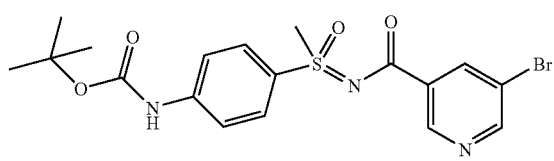

In a manner similar to that described in Example 480 (step 6), tert-Butyl[4-(S-methylsulfonimidoyl)phenyl]carbamate (0.141 g, 0.522 mmol) and 5-bromonicotinic acid (0.104 g, 0.522 mmol), were converted to the title compound (0.177 g, 75%).

Step 6

N-[(4-{[tertbutyloxycarbonyl]amino}phenyl)(methyl)oxido-□⁴-sulfanylidene]-5-[(3-{[(1,3-dimethyl-1H-pyrazol-5-yl)carbonyl]amino}phenyl)ethynyl]nicotinamide

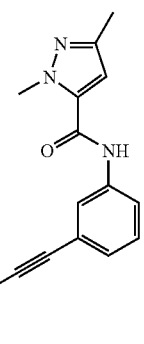

In a manner similar to that described in Example 460, tert-butyl (4-{N-[(5-bromopyridin-3-yl)carbonyl]-S-methylsulfonimidoyl}phenyl)carbamate (0.158 g, 0.349 mmol) and 2,5-dimethyl-2H-pyrazole-3-carboxylic acid (3-ethynyl-phenyl)-amide (0.125 g, 0.0524 mmol) were reacted to give the title compound (0.108 g, 51%).

Step 7

N-[(4-{amino}phenyl)(methyl)oxido-□⁴-sulfanylidene]-5-[(3-{[(1,3-dimethyl-1H-pyrazol-5-yl)carbonyl]amino}phenyl)ethynyl]nicotinamide

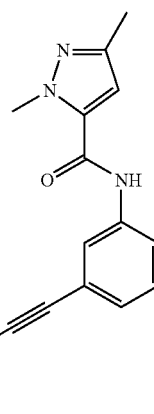

The BOC protected N-[(4-{amino}phenyl)(methyl)oxido-□⁴-sulfanylidene]-5-[(3-{[(1,3-dimethyl-1H-pyrazol-5-yl)carbonyl]amino}phenyl)ethynyl]nicotinamide (0.108 g, 0.177 mmol) was dissolved in CHCl₃ (3.5 mL) and the resulting solution was cooled to 0° C. The resulting reaction mixture was then treated slowly with CF₃COOH (1 mL) and allowed to stir while warming to rt. The reaction mixture was stirred at room temperature for 4 hours and then was diluted with CHCl₃ (5 mL). The organic mixture was extracted with H₂O (5 mL), then with a saturated aqueous solution of NaHCO₃ (2×5 mL) and then with brine (5 mL). The organic layer was then dried over anhydrous Na₂SO$_{4(s)}$, filtered and concentrated in vacuo give the title compound (0.086 g, 95%).

Step 8

N-[(4-{[3-(dimethylamino)propyl]amino}phenyl)(methyl)oxido-□⁴-sulfanylidene]-5-[(3-{[(1,3-dimethyl-1H-pyrazol-5-yl)carbonyl]amino}phenyl)ethynyl]nicotinamide

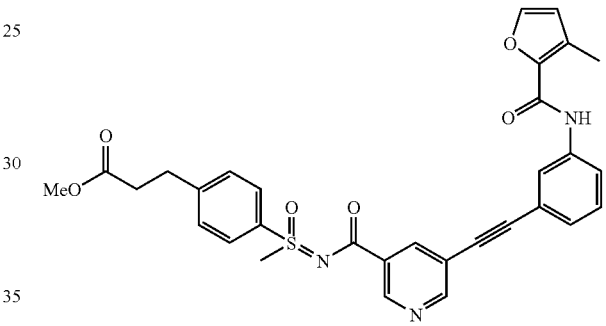

N-[(4-{amino}phenyl)(methyl)oxido-□⁴-sulfanylidene]-5-[(3-{[(1,3-dimethyl-1H-pyrazol-5-yl)carbonyl]amino}phenyl)ethynyl]nicotinamide (0.085 g, 0.168 mmol) was dissolved in dioxane (1.7 mL) then treated with (3-Chloro-propyl)-diethyl-amine (0.047 g, 0.252 mmol) and TEA (0.070 mL, 0.504 mmol). The reaction mixture was then heated to 100° C. for 48 h then cooled to room temperature. The cooled mixture was dissolved in EtOAc (5 mL) and then extracted with water (3×5 mL) and with brine (5 mL). The organic layer was dried over anhydrous Na₂SO$_{4(s)}$, filtered and concentrated in vacuo. The crude mixture was purified via column chromatography (gradient eluant mixture of MeOH in EtOAc: 0% to 20% MeOH) to give the title compound (4 mg, 3.5%).

EXAMPLE 483

Methyl 3-[4-(S-methyl-N-{[5-({3-[(3-methyl-2-furoyl)amino]phenyl}ethynyl)pyridin-3-yl]carbonyl}sulfonimidoyl)phenyl]propanoate

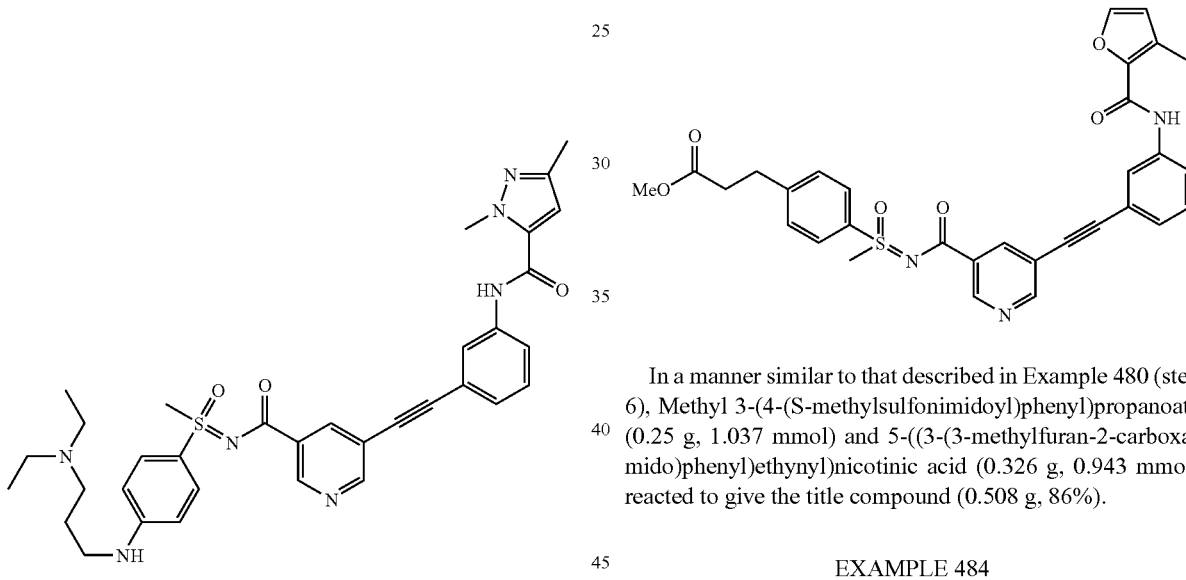

In a manner similar to that described in Example 480 (step 6), Methyl 3-(4-(S-methylsulfonimidoyl)phenyl)propanoate (0.25 g, 1.037 mmol) and 5-((3-(3-methylfuran-2-carboxamido)phenyl)ethynyl)nicotinic acid (0.326 g, 0.943 mmol) reacted to give the title compound (0.508 g, 86%).

EXAMPLE 484

3-[4-(S-methyl-N-{[5-({3-[(3-methyl-2-furoyl)amino]phenyl}-ethynyl)pyridin-3-yl]carbonyl}sulfonimidoyl)phenyl]propanoic acid

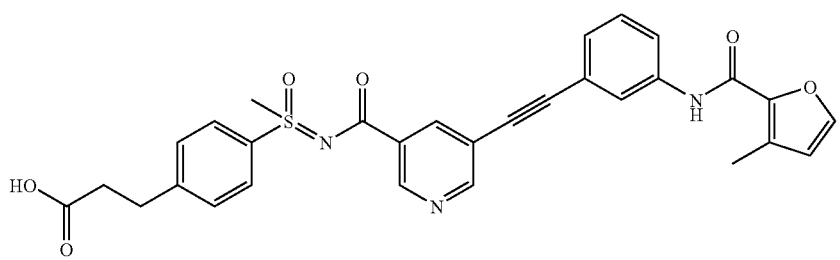

In a manner similar to that described in Example 481, Methyl 3-(4-(S-methyl-N-(5-((3-(3-methylfuran-2-carboxamido)phenyl)ethynyl)-nicotinoyl)-sulfonimidoyl)phenyl) propanoate (0.4 g, 0.703 mmol) was converted to the title compound (0.350 g, 89%).

EXAMPLE 485

5-({3-[(3-methyl-2-furoyl)amino]phenyl} ethynyl)-N-{methyl[4-(3-morpholin-4-yl-3-oxopropyl)phenyl] oxido-$\lambda^4$-sulfanylidene}nicotinamide

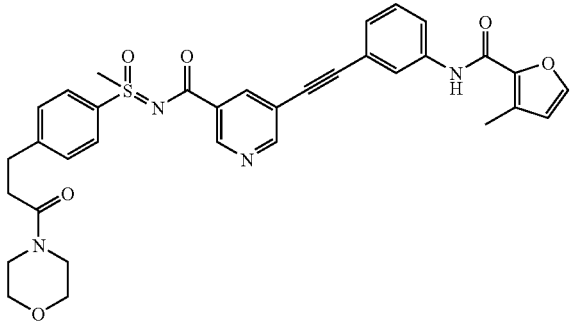

3-[4-(S-methyl-N-{[5-({3-[(3-methyl-2-furoyl)amino] phenyl}-ethynyl)pyridin-3-yl]carbonyl}sulfonimidoyl)phenyl]propanoic acid (0.050 g, 0.090 mmol) was dissolved in DMF (1 mL) then treated with BOP (0.051 g, 0.117 mmol) and TEA (0.050 mL, 0.360 mmol) and allowed to stir for 20 min. Morpholine (0.015 mL, 0.180 mmol) was then added and the reaction was allowed to stir for an additional 4 h. The resulting reaction mixture was dissolved in EtOAc (5 mL) and then extracted with brine (2×5 mL). The organic layer was then dried over anhydrous $Na_2SO_{4(s)}$, filtered and concentrated in vacuo. The crude mixture was then purified via column chromatography (silica gel, gradient eluant mixture of MeOH in EtOAc: 0% to 0% MeOH) give the title compound (0.023 g, 41%).

EXAMPLE 486

N-[(4-{3-[(2,3-dihydroxypropyl)(methyl)amino]-3-oxopropyl}phenyl)-(methyl)oxido-$\lambda^4$-sulfanylidene]-5-({3-[(3-methyl-2-furoyl)amino]phenyl}-ethynyl)nicotinamide

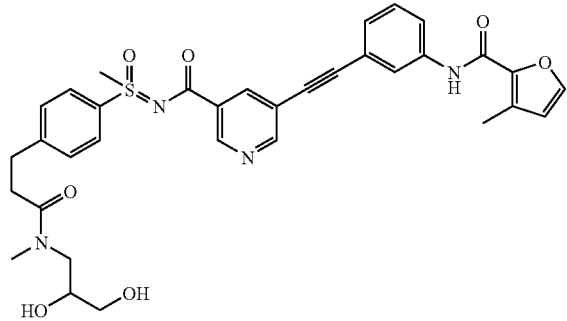

In a manner similar to that described in Example 485, 3-[4-(S-methyl-N-{[5-({3-[(3-methyl-2-furoyl)amino]phenyl}-ethynyl)pyridin-3-yl]carbonyl}sulfonimidoyl)-phenyl] propanoic acid (0.050 g, 0.090 mmol) and 3-methylamino-propane-1,2-diol (0.050 mL, 0.520 mmol) were reacted to give the title compound (0.020 g, 35%).

EXAMPLE 487

N-[{4-[3-(3-hydroxypyrrolidin-1-yl)-3-oxopropyl] phenyl}(methyl)oxido-$\lambda^4$-sulfanylidene]-5-({3-[(3-methyl-2-furoyl)amino]phenyl}-ethynyl)nicotinamide

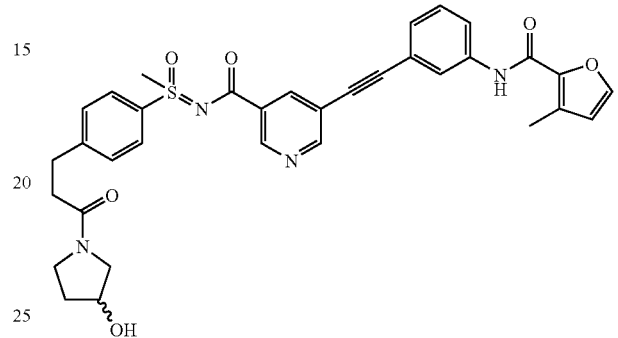

In a manner similar to that described in Example 485, 3-[4-(S-methyl-N-{[5-({3-[(3-methyl-2-furoyl)amino]phenyl}-ethynyl)pyridin-3-yl]carbonyl}sulfonimidoyl)-phenyl] propanoic acid (0.050 g, 0.090 mmol) and pyrrolidin-3-ol (0.016 g, 0.180 mmol) were reacted to give the title compound (0.015 g, 27%).

EXAMPLE 488

N-{[4-(3-{4-[2-(2-hydroxyethoxy)ethyl]piperazin-1-yl}-3-oxopropyl)phenyl] (methyl)oxido-$\lambda^4$-sulfanylidene]-5-({3-[(3-methyl-2-furoyl)amino] phenyl}ethynyl)nicotinamide

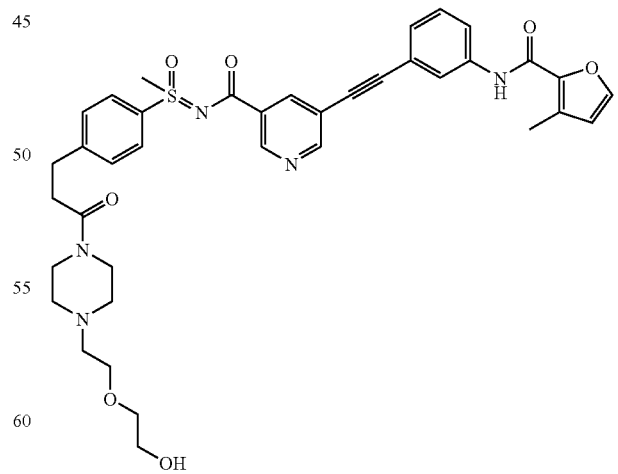

In a manner similar to that described in Example 485, 3-[4-(S-methyl-N-{[5-({3-[(3-methyl-2-furoyl)amino]phenyl}-ethynyl)pyridin-3-yl]carbonyl}sulfonimidoyl)-phenyl] propanoic acid (0.050 g, 0.090 mmol) and 2-(2-piperazin-1- yl-ethoxy)-ethanol (0.030 mL, 0.180 mmol) were reacted to give the title compound (0.030 g, 47%).

EXAMPLE 489

2-hydroxyethyl 3-[4-(S-methyl-N-{[5-({3-[(3-methyl-2-furoyl)amino]phenyl}ethynyl)pyridin-3-yl]carbonyl}sulfonimidoyl)phenyl]propanoate

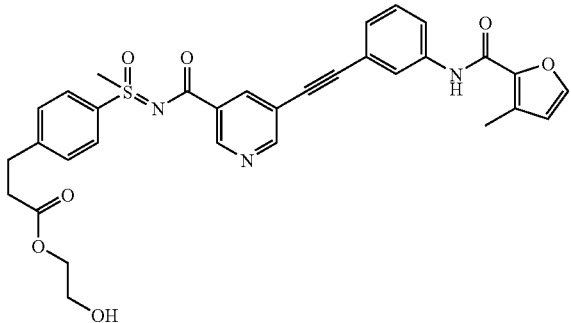

3-[4-(S-methyl-N-{[5-({3-[(3-methyl-2-furoyl)amino]phenyl}-ethynyl)pyridin-3-yl]carbonyl}sulfonimidoyl)phenyl]propanoic acid (0.150 g, 0.270 mmol) was dissolved in DMF (2.7 mL) then treated with EDCI (0.062 g, 0.324 mmol) and DMAP (0.003 g, 0.027 mmol) and allowed to stir at 60° C. for 30 min. Ethylene glycol (3 mL) was then added and the reaction was allowed to stir for 4 hours. The reaction mixture was then cooled to room temperature and dissolved in EtOAc (10 mL) and extracted with brine (3×10 mL). The organic layer was dried over anhydrous $Na_2SO_{4(s)}$, filtered and concentrated in vacuo. The crude mixture was then redissolved in EtOAc (1 mL) and triturated with Hexanes (20 mL) causing the product to precipitate out. The resulting white solid to give the title compound (0.125 g, 77%).

EXAMPLE 490

N-{[4-(hydroxymethyl)phenyl] (methyl) oxido-$\square^4$-sulfanylidene}-5-({3-[(3-methyl-2-furoyl)amino]phenyl}-ethynyl)nicotinamide

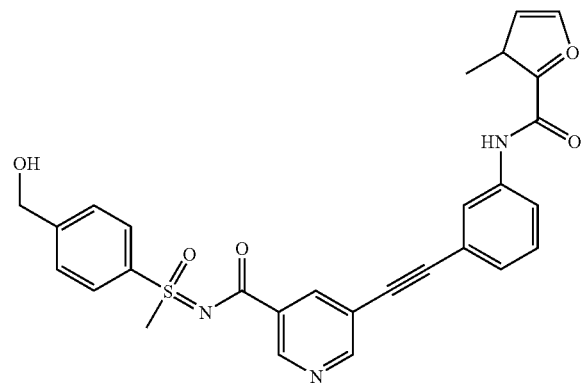

Step 1 tert-butyl(dimethyl){[4-(methylthio)benzyl]oxy}silane

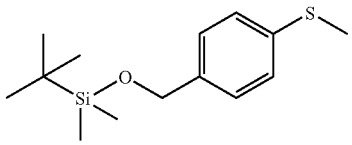

t-Butyldimethylsilyl chloride (2.45 g, 16.2 mmol) was dissolved in DMF (3.25 mL) then treated with imidazole (2.21 g, 32.4 mmol). The reaction mixture was allowed to stir for 20 minutes before 4-Methylsulfanyl-phenyl)-methanol (0.5 g, 3.25 mmol) was added. The reaction was stirred overnight and then dissolved in EtOAc (20 mL). The organic mixture was extracted with $H_2O$ (3×10 mL). The organic organic layer was dried over anhydrous $Na_2SO_{4(s)}$, filtered and concentrated in vacuo. The crude residue was then purified via column chromatography (gradient eluant mixture of EtOAc in Hexanes: 0% to 100% EtOAc to give the title compound (0.828 g, 95%).

Step 2 tert-butyl(dimethyl){[4-(methylsulfinyl)benzyl]oxy}silane

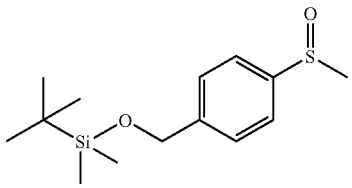

In a manner similar to that described in Example 480 (step 3), tert-Butyl-dimethyl-(4-methylsulfanyl-benzyloxy)-silane (0.828 g, 3.08 mmol), was converted to the title compound in 82% yield (0.716 g, 82%).

Step 3 tert-Butyl(dimethyl) {[4-(S-methyl-N-(trifluoroacetyl)-sulfonimidoyl)benzyl]oxy}silane

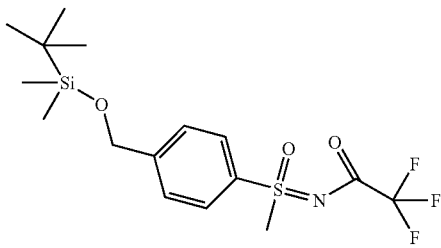

In a manner similar to that described in Example 480 (step 4), tert-butyl(dimethyl) {[4-(methylsulfinyl)benzyl]oxy}silane (0.716 g, 2.52 mmol) was converted to the title compound (0.524 g, 52%).

Step 4 tert-Butyl(dimethyl) {[4-(S-methylsulfonimidoyl)benzyl]oxy}silane

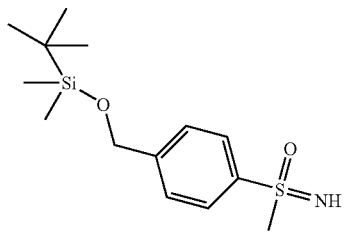

In a manner similar to that described in Example 480 (step 5), tert-Butyl(dimethyl) {[4-(S-methyl-N-(trifluoroacetyl)-sulfonimidoyl)benzyl]oxy}silane (0.524 g, 1.32 mmol) was converted to the title compound (0.385 g, 97%).

Step 5

N-{[4-({[tert-butyl(dimethyl)silyl]oxy}methyl)phenyl](methyl)oxido-$\square^4$-sulfanylidene}-5-({3-[(3-methyl-2-furoyl)amino]phenyl}-ethynyl)nicotinamide

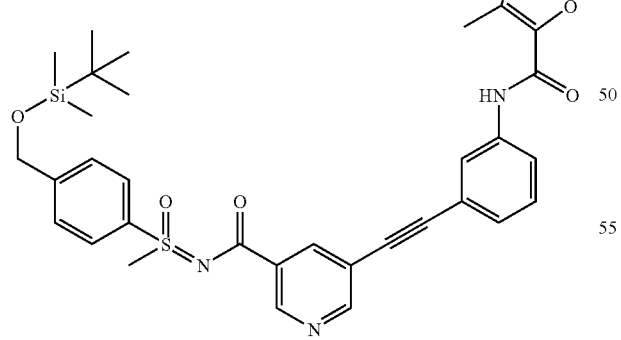

In a manner similar to that described in Example 480 (step 6), tert-Butyl(dimethyl) {[4-(S-methylsulfonimidoyl)benzyl]oxy}silane (0.485 g, 1.62 mmol) and 5-((3-(3-methylfuran-2-carboxamido)phenyl)ethynyl)nicotinic acid (0.561 g, 1.62 mmol) were reacted to give the title compound (0.722 g, 71%).

Step 6

N-{[4-(hydroxymethyl)phenyl] (methyl)oxido-$\square^4$-sulfanylidene}-5-({3-[(3-methyl-2-furoyl)amino]phenyl}-ethynyl)nicotinamide

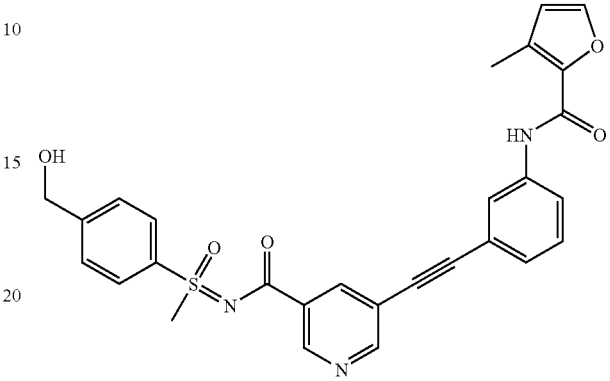

N-{[4-({[tert-butyl(dimethyl)silyl]oxy}methyl)phenyl](methyl)oxido-$\square^4$-sulfanylidene}-5-({3-[(3-methyl-2-furoyl)amino]phenyl}-ethynyl)nicotinamide (0.722 g, 1.15 mmol) was dissolved in THF (2.3 mL). The resulting solution was treated with 1M solution of TBAF in THF (2.3 mL, 2.30 mmol) causing the mixture to turn black in color. The mixture was allowed to stir for 1 h, subsequently dissolved in EtOAc (10 mL) and extracted with H$_2$O (3×15 mL). The organic layer was dried over anhydrous Na$_2$SO$_{4(s)}$, filtered and concentrated in vacuo. The crude product was purified via column chromatography (gradient eluant mixture of EtOAc in Hexanes: 0% to 100% EtOAc) to afford the title compound in 94% yield (0.350 g, 0.682 mmol).

EXAMPLE 491

N-{[4-({4-[2-(2-hydroxyethoxy)ethyl]piperazin-1-yl}methyl)phenyl] (methyl)oxido-$\square^4$-sulfanylidene}-5-({3-[(3-methyl-2-furoyl)amino]phenyl}ethynyl)nicotinamide

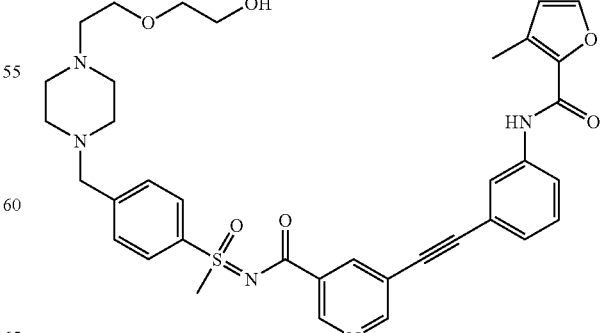

Step 1

N-{[4-(Bromomethyl)phenyl](methyl)oxido-$\square^4$-sulfanylidene}-5-({3-[(3-methyl-2-furoyl)amino]phenyl}ethynyl)nicotinamide Step 2

N-{[4-({4-[2-(2-hydroxyethoxy)ethyl]piperazin-1-yl}methyl)phenyl] (methyl)-oxido-$\square^4$-sulfanylidene}-5-({3-[(3-methyl-2-furoyl)amino]phenyl}ethynyl)nicotinamide

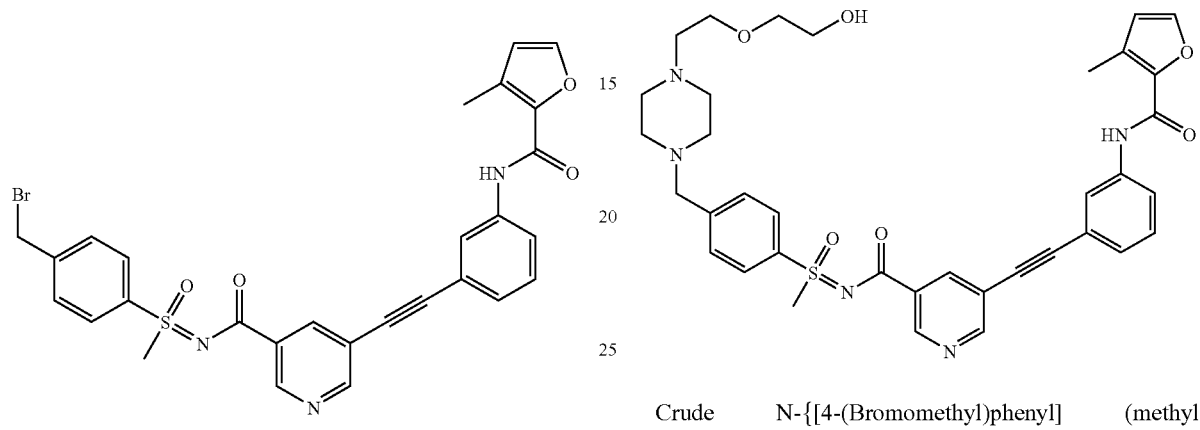

N-{[4-(hydroxymethyl)phenyl] (methyl)oxido-$\square^4$-sulfanylidene}-5-({3-[(3-methyl-2-furoyl)amino]phenyl}ethynyl)nicotinamide (0.1 g, 0.195 mmol) and CBr$_4$ (0.097 g, 0.293 mmol) were dissolved in CH$_2$Cl$_2$ (0.485 mL) and the resulting solution was cooled to 0° C. PPh$_3$ (0.858 g, 0.293 mmol) was dissolved in CH$_2$Cl$_2$ (0.250 mL) and then added dropwise to the 0° C. reaction mixture. Subsequently the reaction was allowed to warm to room temperature and stir for ~1.5 h. The reaction was then diluted with CH$_2$Cl$_2$ (5 mL) and the resulting organic mixture was washed with a saturated aqueous solution of NaHCO$_3$ (5 mL), then with brine (5 mL). The organic layer was dried anhydrous Na$_2$SO$_{4(s)}$, filtered and concentrated in vacuo. The crude product was then taken on without further purification.

Crude N-{[4-(Bromomethyl)phenyl] (methyl)oxido-$\square^4$-sulfanylidene}-5-({3-[(3-methyl-2-furoyl)amino]phenyl}ethynyl)nicotinamide was dissolved in THF (2 mL). 2-(2-piperazin-1-yl-ethoxy)-ethanol (0.064 g, 0.390 mmol) and TEA (0.054 mL, 0.390 mmol) were then added to the solution and the resulting reaction mixture was allowed to stir for 1 h at rt. The reaction mixture, subsequently, was dissolved in EtOAc and then extracted with H$_2$O (2× mL). The organic layer was dried over anhydrous Na$_2$SO$_{4(s)}$, filtered and concentrated in vacuo. The crude product was purified via column chromatography (gradient eluant mixture of MeOH in EtOAc: 0% to 20% MeOH) to afford the title compound (0.064 g, 49% overall for step 1 and 2).

EXAMPLE 492

Methyl 3-{4-[N-({6-amino-5-[(3-{[(1,3-dimethyl-1H-pyrazol-5-yl)carbonyl]amino}phenyl)ethynyl]pyridin-3-yl}carbonyl)-S-methylsulfonimidoyl]phenyl}propanoate

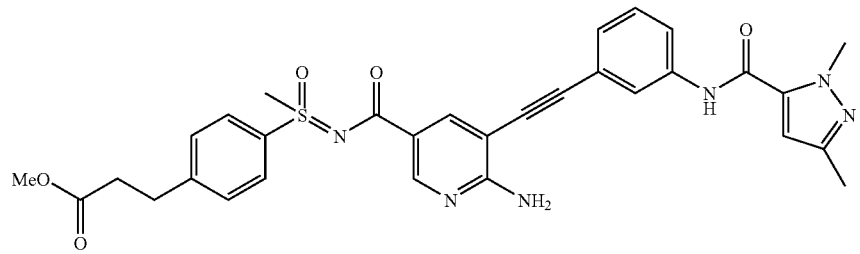

In a manner similar to that described in Example 480 (step 6), 6-Amino-5-{3-[(2,5-dimethyl-2H-pyrazole-3-carbonyl)-amino]-phenylethynyl}-nicotinic acid (0.250 g, 0.666 mmol) and methyl 3-(4-(S-methylsulfonimidoyl)-phenyl)propanoate (0.160 g, 0.666 mmol) were reacted to give the title compound (0.167 g, 42%).

EXAMPLE 493

3-{4-[N-({6-amino-5-[(3-{[(1,3-dimethyl-1H-pyrazol-5-yl)carbonyl]-amino}phenyl)ethynyl]pyridin-3-yl}carbonyl)-S-methylsulfonimidoyl]phenyl}propanoic acid

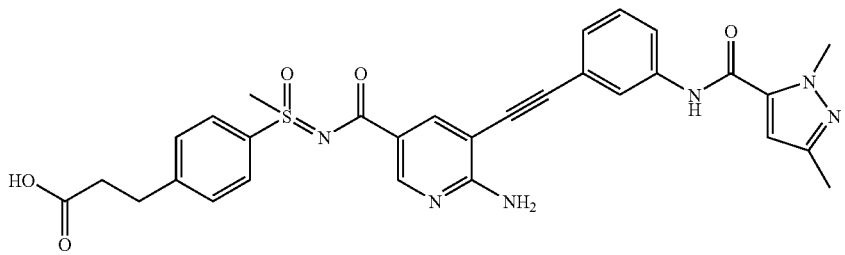

In a manner similar to that described for Example 481, methyl 3-{4-[N-({6-amino-5-[(3-{[(1,3-dimethyl-1H-pyrazol-5-yl)carbonyl]amino}-phenyl)ethynyl]pyridin-3-yl}carbonyl)-S-methylsulfonimidoyl]-phenyl}propanoate (0.167 g, 0.280 mmol) was converted to the title compound (0.150 g, 89%).

EXAMPLE 494

3-[4-(N-{[6-amino-5-({3-[(3-methyl-2-furoyl)amino]phenyl}ethynyl)-pyridin-3-yl]carbonyl}-S-methylsulfonimidoyl)phenyl]propanoic acid

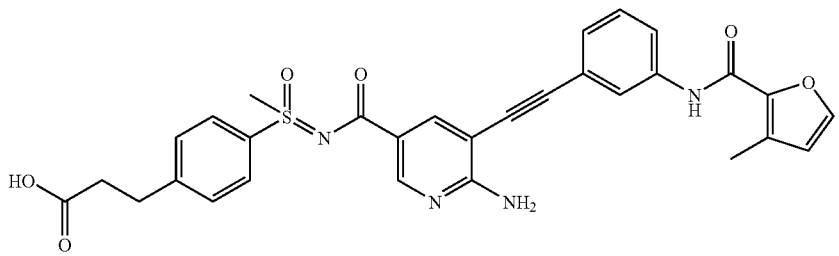

Step 1

6-Amino-5-{3-[(3-methyl-furan-2-carbonyl)-amino]-phenylethynyl}-nicotinic acid methyl ester

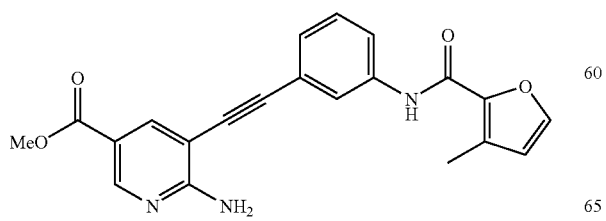

In a 4 mL vial, N-(3-ethynylphenyl)-3-methylfuran-2-carboxamide (0.607 g, 2.70 mmol) and methyl 6-amino-5-iodonicotinate (0.5 g, 1.80 mmol) were dissolved in DMF (6 mL). The solution was degassed by bubbling $N_{2(g)}$ through it for ~30 min. To the degassed solution was added DIPEA (1.25 mL, 7.19 mmol), followed by $Pd(PPh_3)_2Cl_2$ (0.126 g, 0.18 mmol) and CuI (0.068 g, 0.360 mmol). The reaction mixture was allowed to stir at 50° C. for 3 h. The reaction mixture then was taken up in EtOAc (10 mL) and was extracted with brine (3×10 mL). The organic layers were combined and concentrated in vacuo. The crude mixture was purified via column chromatography (gradient eluant mixture of EtOAc in Hexanes: 25% to 100% EtOAc) to give the title compound as a white solid (0.554 g, 82%).

Step 2

6-Amino-5-{3-[(3-methyl-furan-2-carbonyl)-amino]-phenylethynyl}-nicotinic acid

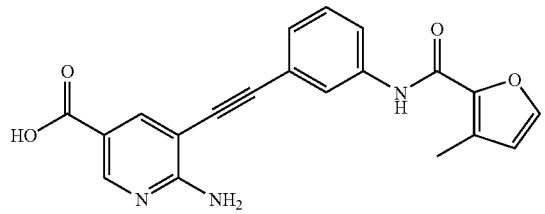

Methyl 6-amino-5-((3-(3-methylfuran-2-carboxamido)phenyl)ethynyl)nicotinate (0.550 g, 1.47 mmol) was dissolved in THF (15 mL) and then treated with 1.0 M NaOH (7.33 mL, 7.33 mmol). The reaction mixture was heated to 50° C. Once the reaction was done by TLC, the reaction was cooled to room temperature and then acidified with acetic acid. The reaction mixture was taken up in of EtOAc (~15 mL) then extracted with $H_2O$ (2×15 mL). The water layer then was re-washed with EtOAc (~15 mL) and the combined organic layers were dried over anhydrous $Na_2SO_{4(s)}$. The mixture was then filtered and concentrated in vacuo to give the title compound (0.495 g, 1.37 mmol).

Step 3

Methyl 3-[4-(N-{[6-amino-5-({3-[(3-methyl-2-furoyl)amino]phenyl}-ethynyl)pyridin-3-yl]carbonyl}-S-methylsulfonimidoyl)phenyl]propanoate

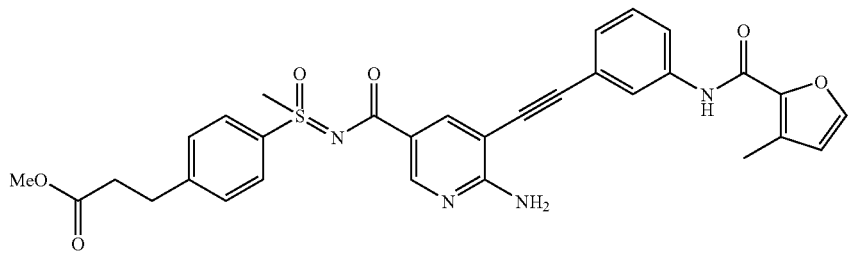

6-Amino-5-((3-(3-methylfuran-2-carboxamido)phenyl)ethynyl)nicotinic acid (0.1 g, 0.277 mmol) was dissolved in DMF (2.8 mL). EDCI (0.64 g, 0.332 mmol) and DMAP (3.42 mg, 0.028 mmol) were then added and the reaction mixture was stirred at 60° C. for 20 minutes. Methyl 3-(4-(S-methylsulfonimidoyl)-phenyl)propanoate (0.068 g, 0.277 mmol) was then added, and the reaction was allowed to stir for 3 hours at 60° C. The mixture was cooled to room temperature then taken up in EtOAc (10 mL) and extracted with brine (3×10 mL). The organic layer was dried over anhydrous $Na_2SO_{4(s)}$, filtered and concentrated in vacuo. The crude product was then purified over silica purified via column chromatography (gradient eluant mixture of MeOH in EtOAc: 0% to 10% MeOH) to give the title compound (0.060 g, 37%).

Step 4

3-[4-(N-{[6-amino-5-({3-[(3-methyl-2-furoyl)amino]phenyl}ethynyl)-pyridin-3-yl]carbonyl}-S-methylsulfonimidoyl)phenyl]propanoic acid

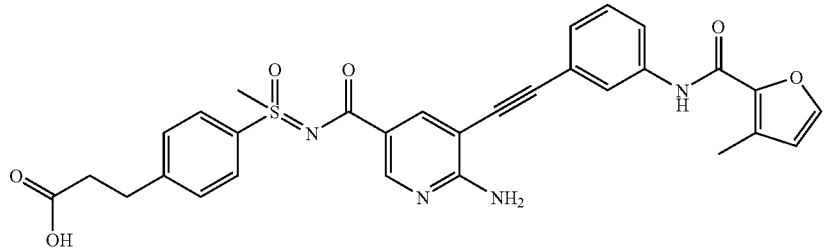

In a manner similar to that described in Example 481, methyl 3-(4-(N-(6-amino-5-((3-(3-methylfuran-2-carboxamido)phenyl)ethynyl)-nicotinoyl)-S-methylsulfonimidoyl)phenyl)propanoate (0.060 g, 0.103 mmol) was converted to the title compound in (0.040 g, 68%).

EXAMPLE 495

6-amino-5-[(3-{[(1,3-dimethyl-1H-pyrazol-5-yl)carbonyl]amino}phenyl)ethynyl]-N-[methyl(oxido)phenyl-□⁴-sulfanylidene]nicotinamide

Step 1

N-(3-iodophenyl)-1,3-dimethyl-1H-pyrazole-5-carboxamide

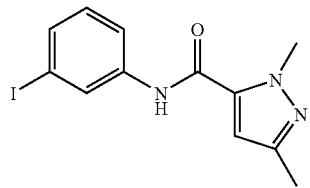

To a solution of 3-iodoaniline (131 mg, 0.60 mmol) in 1.5 ml pyridine at room temperature was added over 2 minutes a solution of 1,3-dimethylpyrazole-5-carbonyl chloride (79 mg, 0.50 mmol) in 0.3 ml 1,2-dichloroethane. The reaction was stirred at room temperature for 30 minutes, quenched into a NaHCO₃ solution, and extracted into EtOAc. The EtOAc solution was washed with NaHCO₃ solution, brine, dried with anhydrous Na₂SO₄ and rotary evaporated. The resultant gummy solid was recrystallized from hexane/EtOAc to give the title compound as solid white needles (135 mg, 80%).

Step 2

6-amino-5-[(3-{[(1,3-dimethyl-1H-pyrazol-5-yl)carbonyl]amino}phenyl)ethynyl]-N-[methyl(oxido)phenyl-□⁴-sulfanylidene]nicotinamide

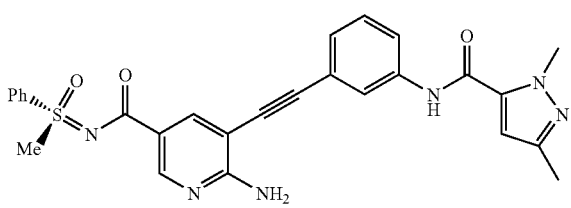

A mixture of 6-amino-5-ethynyl-N-[methyl(oxido)phenyl-□⁴-sulfanylidene]nicotinamide (42 mg, 0.14 mmol), N-(3-iodophenyl)-1,3-dimethyl-1H-pyrazole-5-carboxamide (57 mg, 0.17 mmol), triethylamine (0.049 ml, 0.35 mmol), dichlorobis(triphenylphosphine)palladium(II) (8 mg, 0.011 mmol), and triphenylphosphine (1.8 mg, 0.007 mmol) in 1.2 ml DMF at room temperature was degassed using a H₂/N₂ (1:1) mixture and then copper(I)iodide (1.3 mg, 0.007 mmol) added. The reaction was stirred at room temperature for 15 minutes and then partitioned between EtOAc and saturated NaHCO₃/brine mixture. The EtOAc layer was washed with NaHCO₃/brine mixture, brine, dried with anhydrous Na₂SO₄ and rotary evaporated. The orange oil was chromatographed eluting with hexane/acetone to give the title compound as a light tan solid (64 mg, 90%).

EXAMPLE 496

Step 1

[3-(methylsulfinyl)phenyl]acetic acid

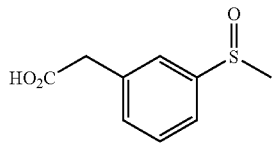

In a manner similar to that described in Example 480 (step 3), 3-(methylthio)phenylacetic acid (2.55 g, 14.0 mmol) was converted to give the title compound as a light tan solid (2.36 g, 85%).

Step 2

Methyl[3-(methylsulfinyl)phenyl]acetate

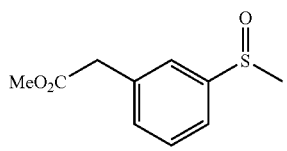

A solution of [3-(methylsulfinyl)phenyl]acetic acid (1.31 g, 6.60 mmol) and carbonyldiimidazole (1.18 g, 7.26 mmol) in 25.0 mL THF was stirred at room temperature for 15 minutes, then methanol (2.1 mL, 52.8 mmol) was added. After 10 minutes the reaction was briefly warmed to near reflux temperature, then allowed to cool to room temperature. After 20 minutes, the reaction was partitioned between EtOAc and NaHCO₃/brine mixture. The EtOAc layer was washed with dilute brine, dilute HCl solution, brine, dried with anhydrous Na₂SO₄ and rotary evaporated to give the title compound as a yellow-orange oil (1.14 g, 82%).

Step 3

Methyl{3-[S-methyl-N-(trifluoroacetyl)sulfonimidoyl]phenyl}acetate

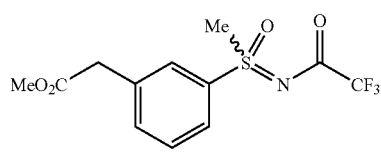

In a manner similar to that described in Example 480 (step 4), methyl[3-(methylsulfinyl)phenyl]acetate (1.18 g, 5.54 mmol), was converted to the title compound as a white solid (1.23 g, 68%).

Step 4

Methyl[3-(S-methylsulfonimidoyl)phenyl]acetate

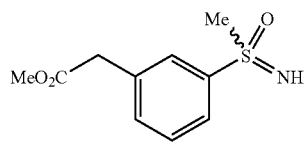

In a manner similar that described in Example 480 (step 5), methyl{3-[S-methyl-N-(trifluoroacetyl)sulfonimidoyl]phenyl}acetate (1.29 g, 3.98 mmol) was converted to the title compound as a cloudy white oil (849 mg, 94%).

Step 5

Methyl(3-{N-[(5-bromopyridin-3-yl)carbonyl]-S-methylsulfonimidoyl}phenyl)acetate

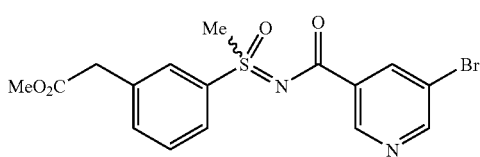

To a solution of 5-bromonicotinic acid (648 mg, 3.21 mmol), methyl[3-(S-methylsulfonimidoyl)phenyl]acetate (802 mg, 3.53 mmol), and catalytic DMAP in 15.0 ml DMF at room temperature was added 1-(3-dimethylaminopropyl)-3-ethylcarbodiimide hydrochloride (738 mg, 3.85 mmol). The reaction was stirred 1 hour at room temperature then added to EtOAc. The EtOAc solution was washed with dilute brine, NaHCO₃ solution, brine, dilute HCl/brine mixture, brine/NaHCO₃ solution, dried with anhydrous Na₂SO₄ and rotary evaporated. The oil was chromatographed eluting with CHCl₃/EtOAc to give viscous clear oil (994 mg, 75%).

Step 6 methyl{3-[N-({5-[(3-{[(1,3-dimethyl-1H-pyrazol-5-yl)carbonyl]amino}phenyl)ethynyl]pyridin-3-yl}carbonyl)-S-methylsulfonimidoyl]phenyl}acetate

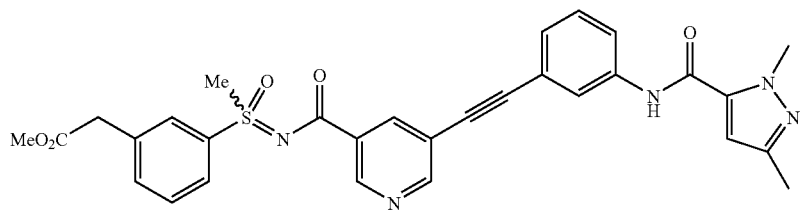

In a manner similar to that described in Example 460, methyl(3-{N-[(5-bromopyridin-3-yl)carbonyl]-S-methylsulfonimidoyl}phenyl)acetate (202 mg, 0.492 mmol) and N-(3-ethynylphenyl)-1,3-dimethyl-1H-pyrazole-5-carboxamide (153 mg, 0.64 mmol), were converted to the title compound as a light yellow solid foam (275 mg, 98%).

EXAMPLE 497

{3-[N-({5-[(3-{[(1,3-dimethyl-1H-pyrazol-5-yl)carbonyl]amino}phenyl)ethynyl]pyridin-3-yl}carbonyl)-S-methylsulfonimidoyl]phenyl}acetic acid

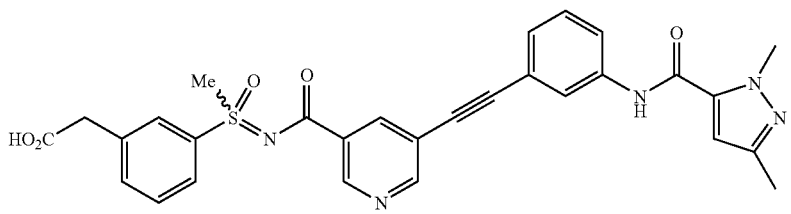

A 50 ml THF solution of methyl{3-[N-({5-[(3-{[(1,3-dimethyl-1H-pyrazol-5-yl)carbonyl]amino}phenyl)ethynyl]pyridin-3-yl}carbonyl)-S-methylsulfonimidoyl]phenyl}acetate (216 mg, 0.38 mmol) and 0.5M NaOH (6.1 ml, 3.04 mmol) was stirred at room temperature for 2 hours. The reaction was quenched with acetic acid (0.174 ml, 3.04 mmol) and rotary evaporated to remove the THF solvent. Additional impure lots of product (22 mg) were combined and the aqueous mixture partitioned between EtOAc and NaHCO$_3$ solution. The EtOAc layer was extracted with another portion of NaHCO$_3$ solution. The combined basic aqueous layers were adjusted to pH 4 using 10% HCl and extracted with EtOAc. The combined EtOAc layers were washed with brine, dried with anhydrous Na$_2$SO$_4$ and rotary evaporated. The off-white solid foam was chromatographed eluting with CHCl$_3$/MeOH and then recrystallized from a mixture of CHCl$_3$/EtOAc/MeCN to give white solid (144 mg, 62%).

EXAMPLE 498

Step 1

3-(methylsulfinyl)benzoic acid

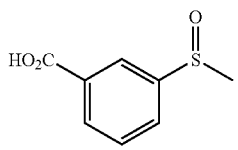

In a manner similar to that described in Example 480 (step 3), 3-(methylthio)benzoic acid (3.03 g, 18.0 mmol) to give the title compound as a white solid (3.11 g, 94%).

Step 2

Methyl 3-(methylsulfinyl)benzoate

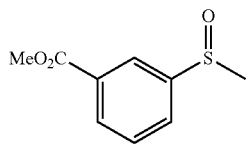

In a manner similar to that described in Example 496 (step 2), 3-(methylsulfinyl)benzoic acid was converted to the title compound.

Step 3

Methyl 3-(S-methylsulfonimidoyl)benzoate

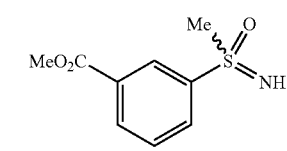

A solution of methyl 3-(methylsulfinyl)benzoate (3.23 g, 16.3 mmol), 2,2,2-trifluoroacetamide (3.69 g, 32.6 mmol), magnesium oxide (1.97 g, 48.9 mmol), rhodium(II) acetate dimer (0.18 g, 0.408 mmol), and iodobenzene diacetate (7.88 g, 24.5 mmol) in 150 ml dichloromethane was stirred at room temperature. After 16 hours, the mixture was filtered past filter agent (Celite), rinsed with chloroform, and rotary evaporated. The sample was dissolved in EtOAc, washed with brine/dilute HCl, brine, dried with anhydrous $Na_2SO_4$ and rotary evaporated. The yellow-orange oil was dissolved in 60 ml MeOH, $K_2CO_3$ (6.76 g, 48.9 mmol) added, and the mixture stirred at room temperature for 12 minutes. The MeOH filtrate was decanted from the solids, which were then rinsed with MeOH and EtOAc. The pH of the combined organic filtrates were adjusted to pH 2 using 4% HCl, then the aqueous layer diluted by adding $H_2O$. The aqueous layer was washed with 30% EtOAc in hexane, then the pH adjusted to pH 9 with saturated $Na_2CO_3$. The aqueous layer was extracted with $CHCl_3$, the combined $CHCl_3$ layers washed with brine, dried with anhydrous $Na_2SO_4$ and rotary evaporated to give the title compound as a light tan solid (2.58 g, 74%).

Step 4

Methyl 3-{N-[(5-bromopyridin-3-yl)carbonyl]-S-methylsulfonimidoyl}benzoate

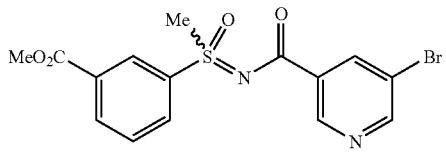

In a manner similar to that described in Example 480 (step 6), 5-bromonicotinic acid and methyl 3-(S-methylsulfonimidoyl)benzoate were reacted to give the title compound.

Step 5 methyl 3-[N-({5-[(3-{[(1,3-dimethyl-1H-pyrazol-5-yl)carbonyl]amino}phenyl)ethynyl]pyridin-3-yl}carbonyl)-S-methylsulfonimidoyl]benzoate In a manner similar to that described in Example 460, methyl 3-{N-[(5-bromopyridin-3-yl)carbonyl]-S-methylsulfonimidoyl}benzoate and N-(3-ethynylphenyl)-1,3-dimethyl-1H-pyrazole-5-carboxamide were reacted to give the title compound.

EXAMPLE 499

3-[N-({5-[(3-{[(1,3-dimethyl-1H-pyrazol-5-yl)carbonyl]amino}phenyl)ethynyl]pyridin-3-yl}carbonyl)-S-methylsulfonimidoyl]benzoic acid

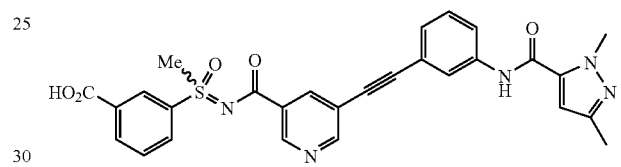

A 50 ml THF solution of methyl 3-[N-({5-[(3-{[(1,3-dimethyl-1H-pyrazol-5-yl)carbonyl]amino}phenyl)ethynyl]pyridin-3-yl}carbonyl)-S-methylsulfonimidoyl]benzoate (228 mg, 0.41 mmol) and 0.5M NaOH (6.6 ml, 3.28 mmol) was stirred at room temperature for 3 hours. The reaction was quenched with acetic acid (0.188 ml, 3.28 mmol) and rotary evaporated to remove the THF solvent. The aqueous solution was partitioned between EtOAc and dilute HCl/brine mixture, the EtOAc layer washed with brine, dried with anhydrous $Na_2SO_4$ and rotary evaporated to white solid foam. The solid was combined with impure product from another lot (14 mg) and recrystallized from EtOAc/hexane to give the title compound as a white solid (147 mg, 62%).

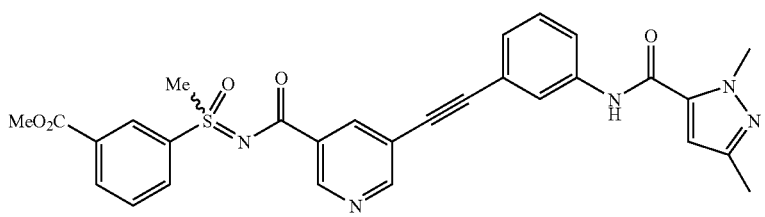

EXAMPLE 500

5-[(3-{[(1,3-dimethyl-1H-pyrazol-5-yl)carbonyl]amino}phenyl)ethynyl]-N-[methyl(3-{[(2-morpholin-4-ylethyl)amino]carbonyl}phenyl)oxido-λ⁴-sulfanylidene]nicotinamide

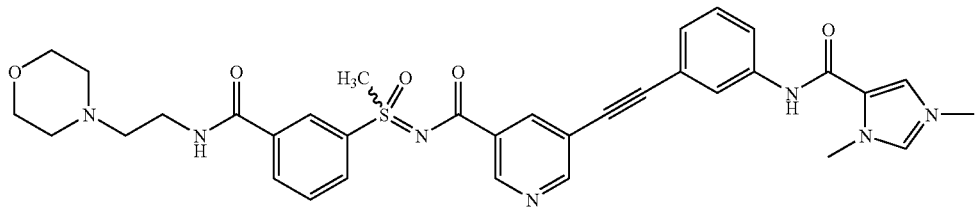

A solution of 3-[N-({5-[(3-{[(1,3-dimethyl-1H-pyrazol-5-yl)carbonyl]amino}phenyl)ethynyl]pyridin-3-yl}carbonyl)-S-methylsulfonimidoyl]benzoic acid (20 mg, 0.036 mmol) and 1,1'-carbonyldiimidazole (12 mg, 0.072 mmol) in 0.8 ml THF was stirred at room temperature for 35 minutes. Then 4-(2-aminoethyl)morpholine (0.009 ml, 0.072 mmol) was added, stirred 30 minutes at room temperature, and the mixture added to EtOAc. The EtOAc solution was washed with NaHCO₃ solution, brine, dried with anhydrous Na₂SO₄ and rotary evaporated. The clear film was chromatographed eluting with CHCl₃/MeOH and then chromatographed again using a preparative TLC plate (eluted with 8:2/CHCl₃: MeOH) to afford an off-white solid foam (19 mg, 81%).

EXAMPLE 501

5-[(3-{[(1,3-dimethyl-1H-pyrazol-5-yl)carbonyl]amino}phenyl)ethynyl]-N-[methyl(3-{2-[(2-morpholin-4-ylethyl)amino]-2-oxoethyl}phenyl)oxido-□⁴-sulfanylidene]nicotinamide

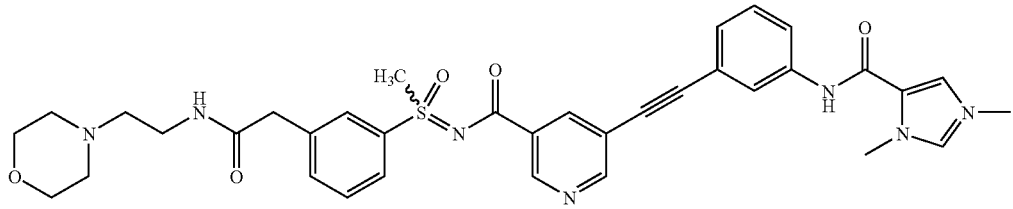

In a manner similar to that described in Example 500, {3-[N-({5-[(3-{[(1,3-dimethyl-1H-pyrazol-5-yl)carbonyl]amino}phenyl)ethynyl]pyridin-3-yl}carbonyl)-S-methylsulfonimidoyl]phenyl}acetic acid and 4-(2-aminoethyl)morpholine were reacted to give the title compound (54%).

EXAMPLE 502

N-{[3-({[2-(diethylamino)ethyl]amino}carbonyl)phenyl](methyl)oxido-□⁴-sulfanylidene}-5-[(3-{[(1,3-dimethyl-1H-pyrazol-5-yl)carbonyl]amino}phenyl)ethynyl]nicotinamide

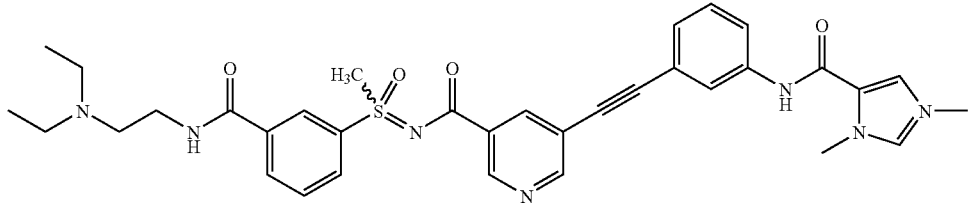

To a solution of 3-[N-({5-[(3-{[(1,3-dimethyl-1H-pyrazol-5-yl)carbonyl]amino}phenyl)ethynyl]pyridin-3-yl}carbonyl)-S-methylsulfonimidoyl]benzoic acid (52 mg, 0.096 mmol), 2-diethylaminoethylamine (0.016 ml, 0.115 mmol), and N,N-diisopropylethylamine (0.034 ml, 0.192 mmol) in 3.0 ml DMF at room temperature was added benzotriazole-1-yl-oxy-tris-(dimethylamino)-phosphonium-hexafluorophosphate (47 mg, 0.106 mmol). The reaction was stirred at room temperature for 1.5 hours, and then partitioned between EtOAc and dilute brine. The EtOAc layer was washed with saturated NaHCO₃ solution, dilute brine, dried with anhydrous Na₂SO₄ and rotary evaporated. The yellow oil (combined 7 mg impure product from another lot) was chromatographed eluting with EtOAc/MeOH, then rechromatographed using a preparative TLC plate (eluted with (1:1:

2.5) CHCl$_3$:EtOAc:MeOH plus NH$_4$OH) to give the title compound as a white solid foam (28 mg).

EXAMPLE 503

{3-[N-({6-amino-5-[(3-{[(1,3-dimethyl-1H-pyrazol-5-yl)carbonyl]amino}phenyl)ethynyl]pyridin-3-yl}carbonyl)-S-methylsulfonimidoyl]phenyl}acetic acid

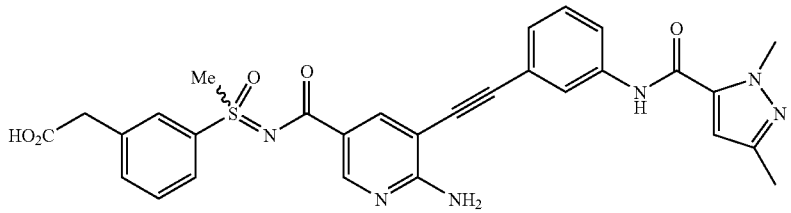

A solution of methyl{3-[N-({6-amino-5-[(3-{[(1,3-dimethyl-1H-pyrazol-5-yl)carbonyl]amino}phenyl)ethynyl]pyridin-3-yl}carbonyl)-S-methylsulfonimidoyl]phenyl}acetate (13 mg, 0.021 mmol) and 1.0M NaOH (0.171 ml, 0.171 mmol) in 2.0 ml MeOH and 0.1 ml H$_2$O was stirred at room temperature for 1 hour 10 minutes. The pH of the mixture was adjusted to pH 4 using 10% HCl, brine added, and the aqueous extracted with EtOAc. The combined EtOAc layers were washed with brine, dried with anhydrous Na$_2$SO$_4$ and rotary evaporated. The white solid was triturated with hot EtOAc to give white solid (11 mg, 92%).

EXAMPLE 504 methyl 3-[N-({6-amino-5-[(3-{[(1,3-dimethyl-1H-pyrazol-5-yl)carbonyl]amino}phenyl)ethynyl]pyridin-3-yl}carbonyl)-S-methylsulfonimidoyl]benzoate

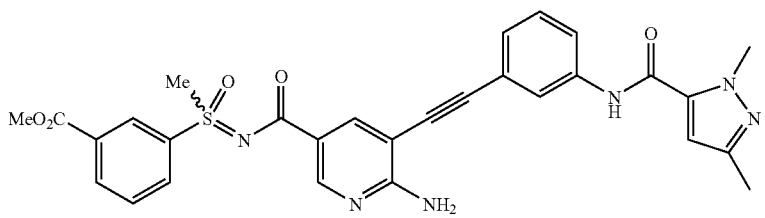

To a solution of 6-amino-5-[(3-{[(1,3-dimethyl-1H-pyrazol-5-yl)carbonyl]amino}phenyl)ethynyl]nicotinic acid (68 mg, 0.18 mmol), methyl 3-(S-methylsulfonimidoyl)benzoate (42 mg, 0.198 mmol), and N,N-diisopropylethylamine (0.063 ml, 0.36 mmol) in 1.5 ml DMF at room temperature was added benzotriazole-1-yl-oxy-tris-(dimethylamino)-phosphoniumhexafluorophosphate (88 mg, 0.198 mmol). The reaction was heated at 60° C. for 3.5 hours, then at 48° C. for 16.5 hours. The mixture was partitioned between EtOAc and dilute brine. The EtOAc layer was washed with NaHCO$_3$ solution, dilute HCl, NaHCO$_3$ solution, brine, dried with anhydrous Na$_2$SO$_4$ and rotary evaporated. The dark foam was chromatographed eluting with hexane/acetone yielding light pink solid (38 mg, 37%).

EXAMPLE 505

3-[N-({6-amino-5-[(3-{[(1,3-dimethyl-1H-pyrazol-5-yl)carbonyl]amino}phenyl)ethynyl]pyridin-3-yl}carbonyl)-S-methylsulfonimidoyl]benzoic acid

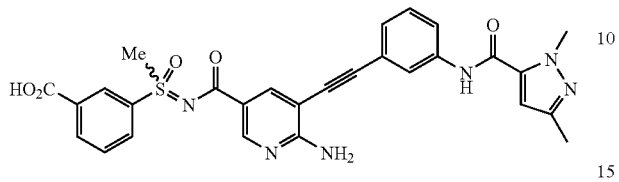

In a manner similar to that described in Example 503, methyl 3-[N-({6-amino-5-[(3-{[(1,3-dimethyl-1H-pyrazol-5-yl)carbonyl]amino}phenyl)ethynyl]pyridin-3-yl}carbonyl)-S-methylsulfonimidoyl]benzoate was converted to the title compound.

EXAMPLE 506

N-[(3-hydroxypropyl)(oxido)phenyl-$\lambda^4$-sulfanylidene]-5-({3-[(3-methyl-2-furoyl)amino]phenyl}ethynyl)nicotinamide

Step 1

(S)-tert-butyl(dimethyl)[3-(S-phenylsulfonimidoyl)propoxy]silane

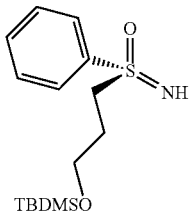

To the sulfoximine (6.46 g, 41.62 mmol) solution in anhydrous CH$_3$CN (5 mL) at 70° C. was added dropwise N,N-diethyl-trimethylsilylamine (1.2 eq ~1.5 eq). The reaction mixture was heated and stirred at this temperature for one hour. It was then concentrated under reduced pressure to yield slightly brown oil (9.26 g) which was dried in-vacuo. The brown oil was dissolved in anhydrous THF (40 mL) and the resulting solution was cooled to −78° C. followed by dropwise addition of nBuLi (17.1 mL, 2.5 M in hexanes). The reaction mixture was stirred 10 min at −78° C. and then 20 min at 0° C. After hexamethylphosphoramide (13.5 mL) was added, the reaction mixture was cooled back to −78° C. followed by dropwise addition of 2-bromoethoxy-tert-butyl-dimethylsilane over a few minutes. The reaction mixture was stirred at −78° C. for about an hour and allowed to warm-up to room temperature within 4 hours. The reaction mixture was then concentrated at room temperature under reduced pressure. The oily residue was taken up in ether (500 mL), which was subsequently washed with ice-water (2×300 mL), brine (1×), and dried with anhydrous Na$_2$SO$_4$ overnight. The ether layer was decanted and concentrated.

The crude oily residue was dissolved in MeOH—H$_2$O (16 mL, 10:1) followed by addition of CsF (1.24 g). The resulting reaction mixture was heated to 50° C. for one hour. It was then concentrated under reduced pressure and the yellow oily residue was partitioned between EtOAc (500 mL) and H$_2$O (300 mL). The organic layer was separated and washed subsequently with H$_2$O (2×), brine (1×), and dried (Anhydrous Na$_2$SO$_4$). The EtOAc layer was decanted and concentrated. The title compound was isolated as clear oil (6.65 g) upon gradient column chromatography (EtOAc-Hex:from 1:25 to 1:2). The overall yield is 51% for total of three steps.

Step 2

(S)-5-bromo-N-[(3-{[tert-butyl(dimethyl)silyl]oxy}propyl)(oxido)phenyl-$\lambda^4$-sulfanylidene]nicotinamide

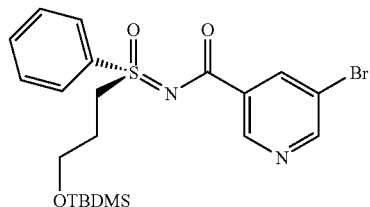

To the solution of (S)-tert-butyl(dimethyl)[3-(S-phenylsulfonimidoyl)propoxy]silane (1.55 g, 4.95 mmol) in DMF (15 mL) at room temperature was added N,N-diisopropylethylamine (1.72 mL), 3-bromonicotinic acid (1.07 g), and finally the coupling reagent, (benzotriazol-1-yloxy)-tris(dimethylamino)-phosphonium hexafluorophosphate (2.48 g). The reaction was stirred for 15 min and then poured into saturated aqueous NaHCO$_3$. The aqueous phase was extracted with EtOAC (1×), which was subsequently washed with aqueous NaHCO$_3$, brine (1×), and dried with anhydrous Na$_2$SO$_4$. The organic layer was decanted, concentrated, and the oily residue was subject to a gradient column chromatography (EtOAc-Hex:from 1:20 to 1:6) yielding the title compound as an amber oil (2.39 g, 97%).

Step 3

(S)-N-[(3-{[tert-butyl(dimethyl)silyl]oxy}propyl)(oxido)phenyl-$\lambda^4$-sulfanylidene]-5-({3-[(3-methyl-2-furoyl)amino]phenyl}ethynyl)nicotinamide

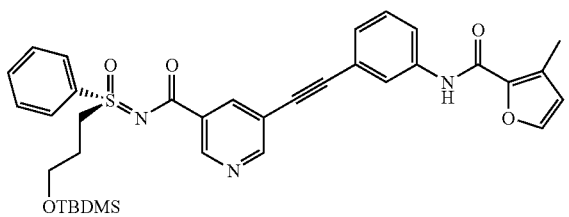

To the solution of (S)-5-bromo-N-[(3-{[tert-butyl(dimethyl)silyl]oxy}propyl)(oxido)phenyl-$\lambda^4$-sulfanylidene]nicotinamide (1.9 g, 3.82 mmol) in anhydrous DMF (19 mL) under nitrogen atmosphere was added sequentially 3-methyl-furan-2-carboxylic acid (3-ethynyl-phenyl)-amide (1.72 g), triethylamine (2.13 mL), bis(triphenylphosphine)palladium(II) dichloride (268 mg), and triphenylphosphine (25 mg). The reaction system was placed under a N₂—H₂ (1:1) atmosphere and CuI (145 mg) was added in one portion. After the reaction mixture was stirred and heated at 60° C. for 1.5 hours, it was poured into saturated aqueous NaHCO₃. The aqueous was extracted with EtOAc (1×), which was subsequently washed with aqueous NaHCO₃ (1×), brine (1×), and dried (anhydrous Na₂SO₄). The organic layer was decanted, evaporated and wrapped with silica gel. Two times column chromatography (EtOAc-Hex:from 1:4 to 1:2; and MeOH—CH₂Cl₂: 1:100) gave the title compound as yellow foam (2.2 g, 90%).

Step 4

(S)-N-[(3-hydroxypropyl)(oxido)phenyl-□⁴-sulfanylidene]-5-({3-[(3-methyl-2-furoyl)amino]phenyl}ethynyl)nicotinamide

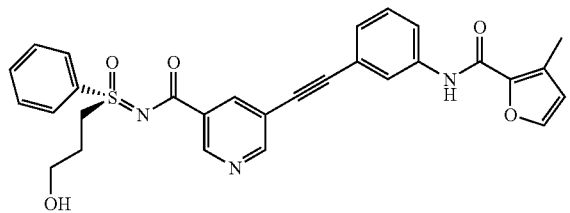

To the solution of (S)-N-[(3-{[tert-butyl(dimethyl)silyl]oxy}propyl)(oxido)phenyl-□⁴-sulfanylidene]-5-({3-[(3-methyl-2-furoyl)amino]phenyl}ethynyl)nicotinamide (2.2 g, 3.43 mmol) in anhydrous THF (60 mL) at 0° C. was added dropwise tert-butylammonium fluoride (7.2 mL, 1 M in THF) and the reaction was stirred at 0° C. for 1 hour. The yellow reaction solution was then concentrated at room temperature to give a red oil. The oily residue was diluted with EtOAc, which was washed with saturated aqueous NaHCO₃ (2×), brine (1×), and then dried (anhydrous Na₂SO₄). The organic layer was decanted, concentrated, and the resulting oily residue was chromatographed (MeOH—CH₂Cl₂: from 1:100 to 1:50) yielding the title compound as a clear oil which turned into white foam in-vacuo (1.72 g, 95%).

EXAMPLE 507

(S)-N-[(3-bromopropyl)(oxido)phenyl-∟⁴-sulfanylidene]-5-({3-[(3-methyl-2-furoyl)amino]phenyl}ethynyl)nicotinamide

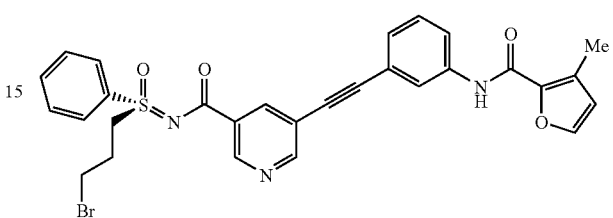

N-[(3-hydroxypropyl)(oxido)phenyl-□⁴-sulfanylidene]-5-({3-[(3-methyl-2-furoyl)amino]phenyl}ethynyl)nicotinamide (1.71 g, 3.24 mmol) was dissolved in anhydrous CH₂Cl₂ (5 mL) and the resulting solution was cooled to 0° C. A solution of carbon tetrabromide (1.565 g ) in CH₂Cl₂ (3 mL) was added dropwise followed by a dropwise addition of a solution of triphenylphosphine (1.24 g) in CH₂Cl₂ (3 mL). The reaction was stirred at room temperature for 1.5 hours and then partitioned between saturated aqueous NaHCO₃ and dichloromethane. The organic layer was separated, washed with brine (1×), dried with anhydrous Na₂SO₄, and concentrated with silica gel under reduced pressure. A gradient column chromatography (acetone-hex: from 1:10 to 1:4) rendered title compound as white solid in amount of 1.56 g (82%).

EXAMPLE 508

(S)-N-[(3-{4-[2-(2-hydroxyethoxy)ethyl]piperazin-1-yl}propyl)(oxido)phenyl-□⁴-sulfanylidene]-5-({3-[(3-methyl-2-furoyl)amino]phenyl}ethynyl)nicotinamide

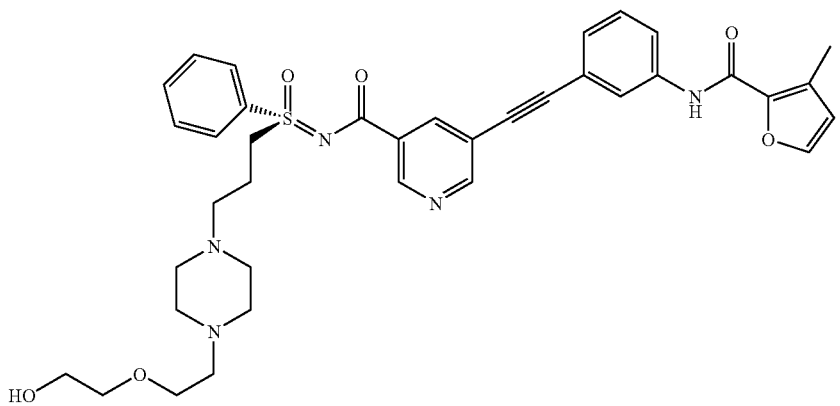

To the solution of N-[(3-bromopropyl)(oxido)phenyl-☐⁴-sulfanylidene]-5-({3-[(3-methyl-2-furoyl)amino]phenyl}ethynyl)nicotinamide (450 mg, 0.76 mmol) in anhydrous DMF (5 mL) was added dropwise 1-[2-(2-hydroxyethoxy)ethyl]piperazine. The resulting reaction solution was stirred and heated at 80° C. for 30 min. It was then partitioned between saturated aqueous NaHCO₃ and EtOAc. The EtOAc layer was separated and washed with brine (1×). The aqueous NaHCO₃ layer was extracted with CHCl₃ (1×) and the extract was washed with brine (1×). The organic layers were combined and dried over anhydrous sodium sulfate. The organic solution was decanted, concentrated, and wrapped with silica gel. Column chromatography (MeOH-EtOAc from 1:10 to 1:6) rendered the title compound as white foam in amount of 500 mg (96%).

EXAMPLE 509

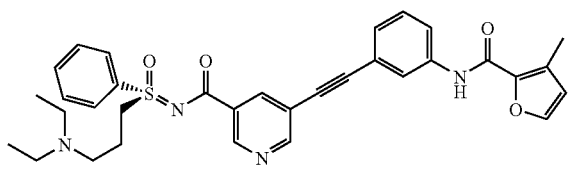

(S)-N-{[3-(diethylamino)propyl](oxido)phenyl-☐⁴-sulfanylidene}-5-({3-[(3-methyl-2-furoyl)amino]phenyl}ethynyl)nicotinamide In a manner similar to that described for Example 508, N-[(3-bromopropyl)(oxido)phenyl-∟⁴-sulfanylidene]-5-({3-[(3-methyl-2-furoyl)amino]phenyl}ethynyl)nicotinamide and diethylamine were converted to the title compound.

EXAMPLE 510

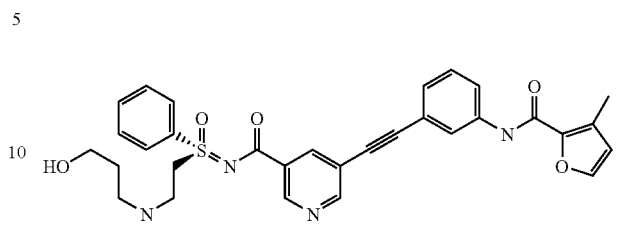

(S)-N-[{3-[(2-hydroxyethyl)amino]propyl}(oxido)phenyl-☐⁴-sulfanylidene]-5-({3-[(3-methyl-2-furoyl)amino]phenyl}ethynyl)nicotinamide In a manner similar to that described for Example 508, N-[(3-bromopropyl)(oxido)phenyl-☐⁴-sulfanylidene]-5-({3-[(3-methyl-2-furoyl)amino]phenyl}ethynyl)nicotinamide and 2-hydroxyethylamine were converted to the title compound.

EXAMPLE 511

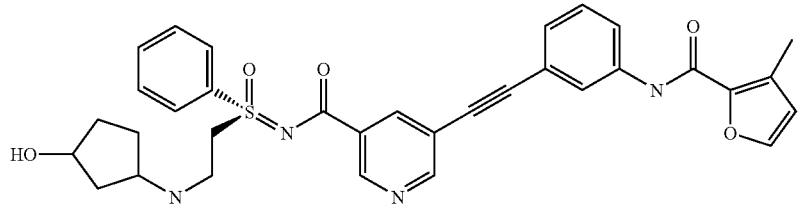

N-{[3-(3-hydroxypyrrolidin-1-yl)propyl](oxido)phenyl-☐⁴-sulfanylidene}-5-({3-[(3-methyl-2-furoyl)amino]phenyl}ethynyl)nicotinamide In a manner similar to that described for Example 508, N-[(3-bromopropyl)(oxido)phenyl-☐⁴-sulfanylidene]-5-({3-[(3-methyl-2-furoyl)amino]phenyl}ethynyl)nicotinamide and 3-hydroxypyrrolidine were converted to the title compound.

EXAMPLE 512

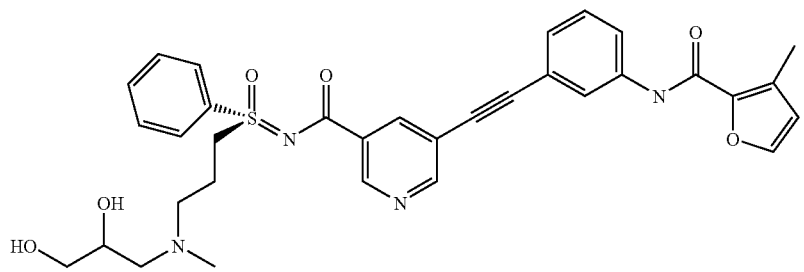

181

N-[{3-[(2,3-dihydroxypropyl)(methyl)amino]propyl}(oxido)phenyl-$\square^4$-sulfanylidene]-5-({3-[(3-methyl-2-furoyl)amino]phenyl}ethynyl)nicotinamide In a manner similar to that described for Example 508, N-[(3-bromopropyl)(oxido)phenyl-$\square^4$-sulfanylidene]-5-({3-[(3-methyl-2-furoyl)amino]phenyl}ethynyl)nicotinamide and 3-methylamino-1,2-propanediol were converted to the title compound.

EXAMPLE 513

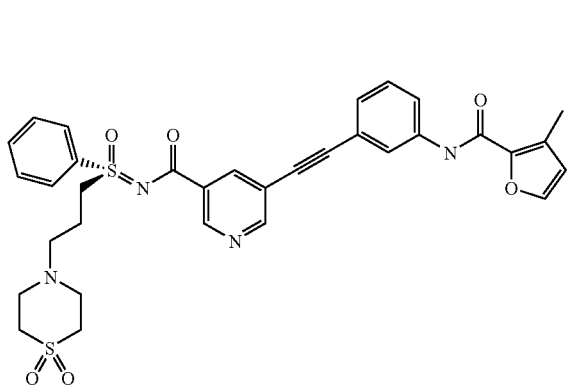

(S)-N-{[3-(1,1-dioxidothiomorpholin-4-yl)propyl](oxido)phenyl-$\square^4$-sulfanylidene}-5-({3-[(3-methyl-2-furoyl)amino]phenyl}ethynyl)nicotinamide In a manner similar to that described for Example 508, N-[(3-bromopropyl)(oxido)phenyl-$\square^4$-sulfanylidene]-5-({3-[(3-methyl-2-furoyl)amino]phenyl}ethynyl)nicotinamide and thiomorpholine-1,1-dioxide were converted to the title compound.

EXAMPLE 514

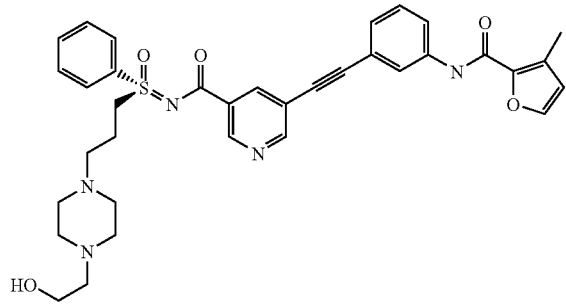

182

(S)-N-[{3-[4-(2-hydroxyethyl)piperazin-1-yl]propyl}(oxido)phenyl-$\square^4$-sulfanylidene]-5-({3-[(3-methyl-2-furoyl)amino]phenyl}ethynyl)nicotinamide In a manner similar to that described for Example 508, N-[(3-bromopropyl)(oxido)phenyl-$\square^4$-sulfanylidene]-5-({3-[(3-methyl-2-furoyl)amino]phenyl}ethynyl)nicotinamide and 1-piperazineethanol were converted to the title compound.

EXAMPLE 515

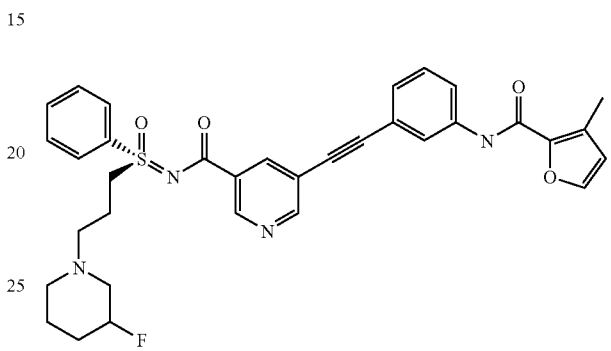

N-{[3-(3-fluoropiperidin-1-yl)propyl](oxido)phenyl-$\square^4$-sulfanylidene}-5-({3-[(3-methyl-2-furoyl)amino]phenyl}ethynyl)nicotinamide In a manner similar to that described for example 508, N-[(3-bromopropyl)(oxido)phenyl-$\square^4$-sulfanylidene]-5-({3-[(3-methyl-2-furoyl)amino]phenyl}ethynyl)nicotinamide and 3-fluoropiperidine were converted to the title compound.

EXAMPLE 516

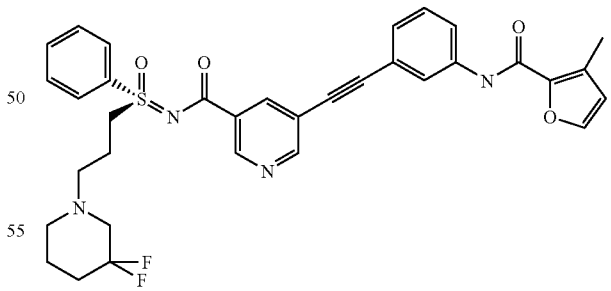

(S)-N-{[3-(3,3-difluoropiperidin-1-yl)propyl](oxido)phenyl-$\square^4$-sulfanylidene}-5-({3-[(3-methyl-2-furoyl)amino]phenyl}ethynyl)nicotinamide In a manner similar to that described for Example 508, N-[(3-bromopropyl)(oxido)phenyl-$\square^4$-sulfanylidene]-5-

({3-[(3-methyl-2-furoyl)amino]phenyl}ethynyl)nicotinamide and 3,3-difluoropiperidine were converted to the title compound.

EXAMPLE 517

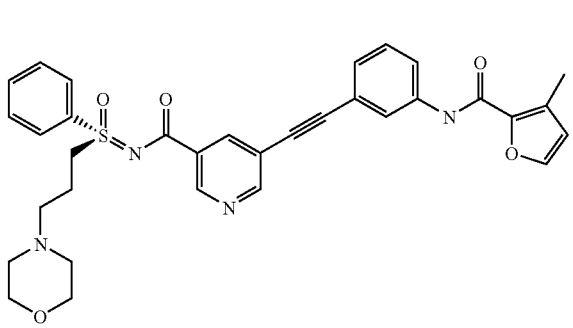

(S)-5-({3-[(3-methyl-2-furoyl)amino]phenyl}ethynyl)-N-[(3-morpholin-4-ylpropyl)(oxido)phenyl-$\square^4$-sulfanylidene]nicotinamide In a manner similar to that described for Example 508, N-[(3-bromopropyl)(oxido)phenyl-$\square^4$-sulfanylidene]-5-({3-[(3-methyl-2-furoyl)amino]phenyl}ethynyl)nicotinamide and morpholine were converted to the title compound.

EXAMPLE 518

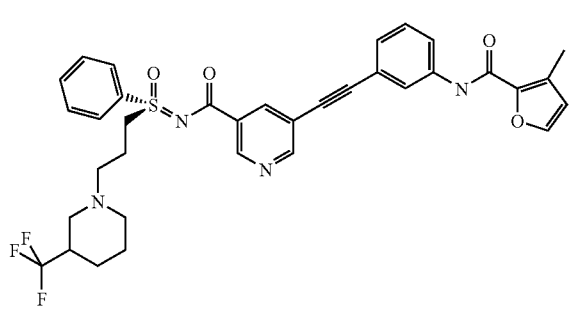

5-({3-[(3-methyl-2-furoyl)amino]phenyl}ethynyl)-N-[oxido(phenyl){3-[3-(trifluoromethyl)piperidin-1-yl]propyl}-$\square^4$-sulfanylidene]nicotinamide In a manner similar to that described for example 508, N-[(3-bromopropyl)(oxido)phenyl-$\square^4$-sulfanylidene]-5-({3-[(3-methyl-2-furoyl)amino]phenyl}ethynyl)nicotinamide and 3-(trifluoromethyl)piperidine were converted to the title compound.

EXAMPLE 519

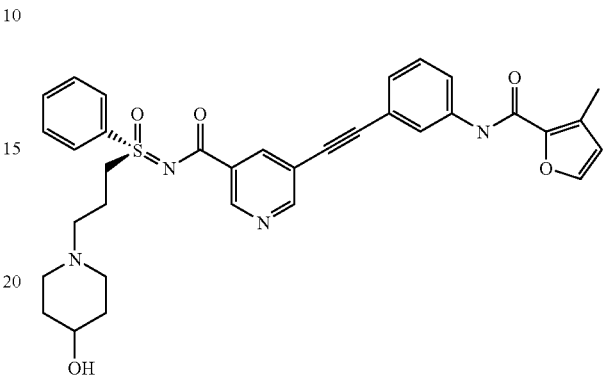

(S)-N-{[3-(4-hydroxypiperidin-1-yl)propyl](oxido)phenyl-$\square^4$-sulfanylidene}-5-({3-[(3-methyl-2-furoyl)amino]phenyl}ethynyl)nicotinamide In a manner similar to that described for Example 508, N-[(3-bromopropyl)(oxido)phenyl-$\square^4$-sulfanylidene]-5-({3-[(3-methyl-2-furoyl)amino]phenyl}ethynyl)nicotinamide and 4-hydroxypiperidine were converted to the title compound.

EXAMPLE 520

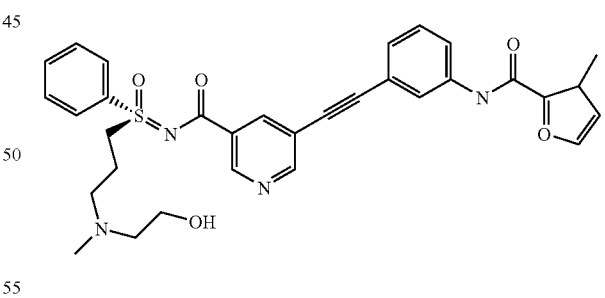

(S)-N-[{3-[(2-hydroxyethyl)(methyl)amino]propyl}(oxido)phenyl-$\square^4$-sulfanylidene]-5-({3-[(3-methyl-2-furoyl)amino]phenyl}ethynyl)nicotinamide In a manner similar to that described for Example 508, N-[(3-bromopropyl)(oxido)phenyl-$\square^4$-sulfanylidene]-5-({3-[(3-methyl-2-furoyl)amino]phenyl}ethynyl)nicotinamide and 2-methylaminoethanol were converted to the title compound.

EXAMPLE 521

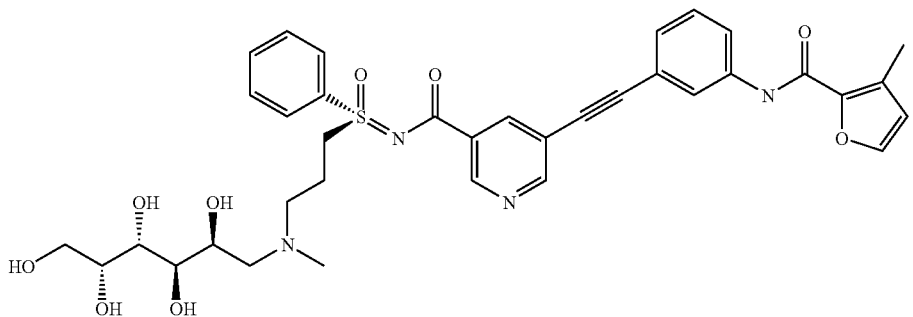

5-({3-[(3-methyl-2-furoyl)amino]phenyl}ethynyl)-N-[(3-{methyl[(2S,3R,4S,5R)-2,3,4,5,6-pentahydroxyhexyl]amino}propyl)(oxido)phenyl-$\square^4$-sulfanylidene]nicotinamide In a manner similar to that described for Example 508, N-[(3-bromopropyl)(oxido)phenyl-$\square^4$-sulfanylidene]-5-({3-[(3-methyl-2-furoyl)amino]phenyl}ethynyl)nicotinamide and 1-deoxy-1-(methylamino)-D-galactitol were converted to the title compound.

EXAMPLE 522

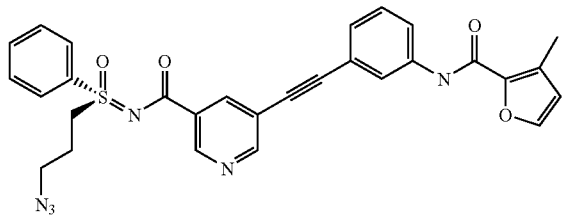

(S)-N-[(3-azidopropyl)(oxido)phenyl-$\square^4$-sulfanylidene]-5-({3-[(3-methyl-2-furoyl)amino]phenyl}ethynyl)nicotinamide In a manner similar to that described for Example 508, N-[(3-bromopropyl)(oxido)phenyl-$\square^4$-sulfanylidene]-5-({3-[(3-methyl-2-furoyl)amino]phenyl}ethynyl)nicotinamide and sodium azide were converted to the title compound.

EXAMPLE 523

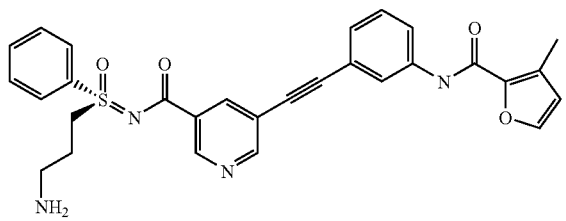

(S)-N-[(3-aminopropyl)(oxido)phenyl-$\square^4$-sulfanylidene]-5-({3-[(3-methyl-2-furoyl)amino]phenyl}ethynyl)nicotinamide In a manner similar to that described for example 508, (S)-N-[(3-bromopropyl)(oxido)phenyl-$\square^4$-sulfanylidene]-5-({3-[(3-methyl-2-furoyl)amino]phenyl}ethynyl)nicotinamide and ammonia were converted to the title compound.

EXAMPLE 524

(S)-N-[(3-{[tert-butyl(dimethyl)silyl]oxy}propyl)(oxido)phenyl-$\square^4$-sulfanylidene]-5-[(3-{[(1,3-dimethyl-1H-pyrazol-5-yl)carbonyl]amino}phenyl)ethynyl]nicotinamide

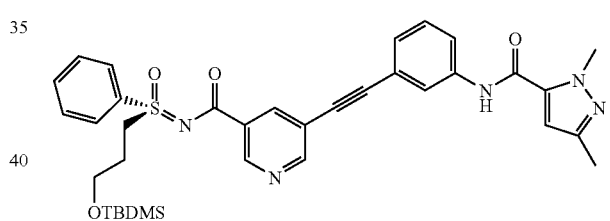

In a manner similar to that described in Example 506 (step 3), (S)-5-bromo-N-[(3-{[tert-butyl(dimethyl)silyl]oxy}propyl)(oxido)phenyl-$\square^4$-sulfanylidene]nicotinamide and N-(3-ethynylphenyl)-1,3-dimethyl-1H-pyrazole-5-carboxamide are converted to the title compound.

EXAMPLE 525

(S)-5-[(3-{[(1,3-dimethyl-1H-pyrazol-5-yl)carbonyl]amino}phenyl)ethynyl]-N-[(3-hydroxypropyl)(oxido)phenyl-lambda-$\square^4$-sulfanylidene]nicotinamide

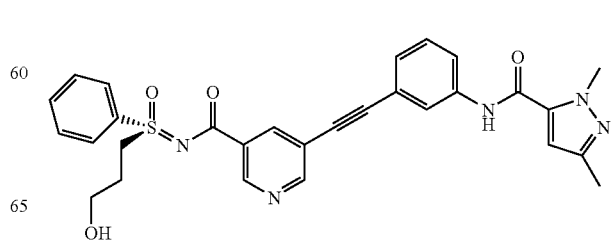

In a manner similar to that described in Example 506 (step 4), (S)-N-[(3-{[tert-butyl(dimethyl)silyl]oxy}propyl)(oxido)phenyl-г⁴-sulfanylidene]-5-[(3-{[(1,3-dimethyl-1H-pyrazol-5-yl)carbonyl]amino}phenyl)ethynyl]nicotinamide is converted to the title compound.

EXAMPLE 526

(S)-N-[(3-bromopropyl)(oxido)phenyl-4-sulfanylidene]-5-[(3-{[(1,3-dimethyl-1H-pyrazol-5-yl)carbonyl]amino}phenyl)ethynyl]nicotinamide

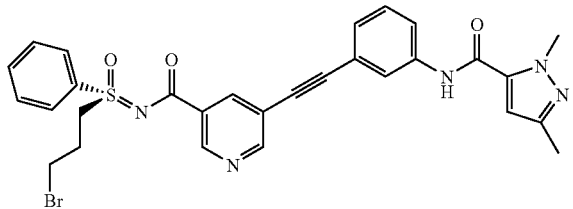

In a manner similar to that described in Example 507, (S)-5-[(3-{[(1,3-dimethyl-1H-pyrazol-5-yl)carbonyl]amino}phenyl)ethynyl]-N-[(3-hydroxypropyl)(oxido)phenyl-lambda-☐⁴-sulfanylidene]nicotinamide is converted to the title compound.

EXAMPLE 527

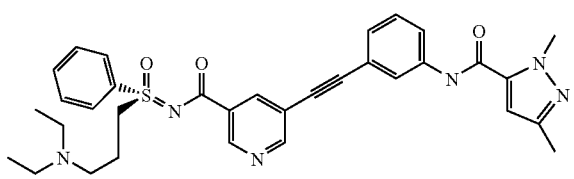

(S)-N-{[3-(diethylamino)propyl](oxido)phenyl-⊓⁴-sulfanylidene}-5-[(3-{[(1,3-dimethyl-1H-pyrazol-5-yl)carbonyl]amino}phenyl)ethynyl]nicotinamide In a manner similar to that described for example 508, (S)-N-[(3-bromopropyl)(oxido)phenyl-4-sulfanylidene]-5-[(3-{[(1,3-dimethyl-1H-pyrazol-5-yl)carbonyl]amino}phenyl)ethynyl]nicotinamide and diethylamine were converted to the title compound.

EXAMPLE 528

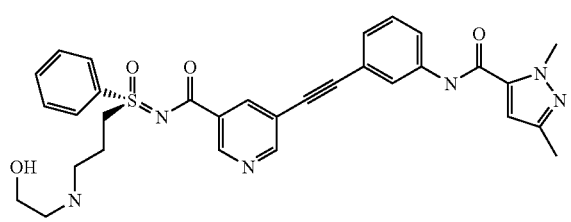

(S)-5-[(3-{[(1,3-dimethyl-1H-pyrazol-5-yl)carbonyl]amino}phenyl)ethynyl]-N-[{3-[(2-hydroxyethyl)amino]propyl}(oxido)phenyl-☐⁴-sulfanylidene]nicotinamide In a manner similar to that described for example 508, (S)-N-[(3-bromopropyl)(oxido)phenyl-4-sulfanylidene]-5-[(3-{[(1,3-dimethyl-1H-pyrazol-5-yl)carbonyl]amino}phenyl)ethynyl]nicotinamide and hydroxyethylamine were converted to the title compound.

EXAMPLE 529

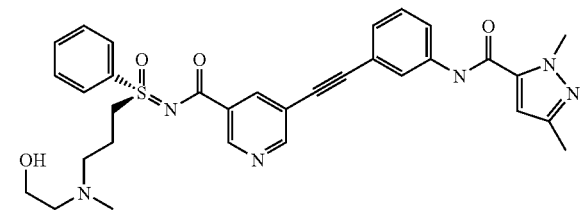

(S)-5-[(3-{[(1,3-dimethyl-1H-pyrazol-5-yl)carbonyl]amino}phenyl)ethynyl]-N-[{3-[(2-hydroxyethyl)(methyl)amino]propyl}(oxido)phenyl-☐⁴-sulfanylidene]nicotinamide In a manner similar to that described for example 508, (S)-N-[(3-bromopropyl)(oxido)phenyl-4-sulfanylidene]-5-[(3-{[(1,3-dimethyl-1H-pyrazol-5-yl)carbonyl]amino}phenyl)ethynyl]nicotinamide and 2-methylaminoethanol were converted to the title compound.

EXAMPLE 530

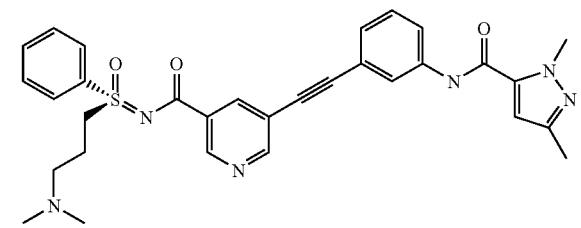

(S)-N-{[3-(dimethylamino)propyl](oxido)phenyl-г⁴-sulfanylidene}-5-[(3-{[(1,3-dimethyl-1H-pyrazol-5-yl)carbonyl]amino}phenyl)ethynyl]nicotinamide In a manner similar to that described for example 508, (S)-N-[(3-bromopropyl)(oxido)phenyl-∟⁴-sulfanylidene]-5-[(3-{[(1,3-dimethyl-1H-pyrazol-5-yl)carbonyl]amino}phenyl)ethynyl]nicotinamide and dimethylamine were converted to the title compound.

EXAMPLE 531

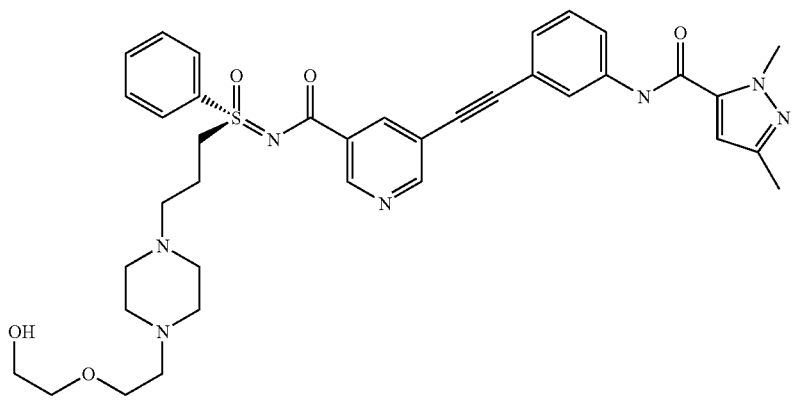

(S)-5-[(3-{[(1,3-dimethyl-1H-pyrazol-5-yl)carbonyl]
amino}phenyl)ethynyl]-N-[(3-{4-[2-(2-hydroxy-
ethoxy)
ethyl]piperazin-1-yl}propyl)(oxido)phenyl-$\square^4$-sulfa-
nylidene]nicotinamide In a manner similar to that described for example 508,
(S)-N-[(3-bromopropyl)(oxido)phenyl-4-sulfanylidene]-5-
[(3-{[(1,3-dimethyl-1H-pyrazol-5-yl)carbonyl]
amino}phenyl)ethynyl]nicotinamide and 1-[2-(2-hydroxy-
ethoxy)ethyl]piperazine were converted to the title
compound.

EXAMPLE 532

(S)-Ethyl(N-{[5-({3-[(3-methyl-2-furoyl)amino]
phenyl}ethynyl)pyridin-3-yl]carbonyl}-S-phenylsul-
fonimidoyl)acetate

Step 1

5-{3-[(3-Methyl-furan-2-carbonyl)-amino]-phenyl-
ethynyl}-nicotinic acid

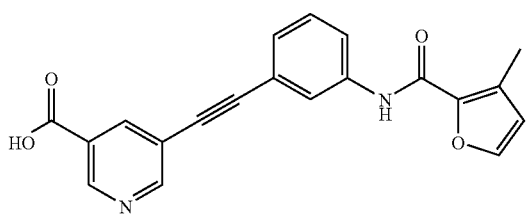

In a manner similar to that described for Example 480 (step
1), 3-methyl-furan-2-carboxylic acid (3-ethynyl-phenyl)-
amide and 5-bromo nicotinic acid were reacted to provide the
title compound.

Step 2

(S)-Ethyl(N-{[5-({3-[(3-methyl-2-furoyl)amino]
phenyl}ethynyl)pyridin-3-yl]carbonyl}-S-phenylsul-
fonimidoyl)acetate

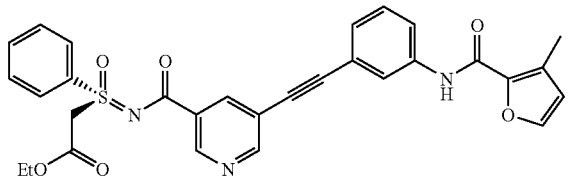

To a solution of ethyl(S)—(S-phenylsulfonimidoyl)acetate
(139 mg, 0.61 mmol) in anhydrous DMF (3 mL) at room
temperature was added 5-{3-[(3-Methyl-furan-2-carbonyl)-
amino]-phenylethynyl}-nicotinic acid (233 mg), catalytic
amount of 4-(dimethylamino)pyridine, and N-(3-dimethy-
laminopropyl)-N'-ethylcarbodiimide hydrochloride (141
mg). The reaction mixture was stirred at room temperature for
30 min. The reaction was then poured into aqueous HCl
(0.5%) and extracted with EtOAc. After the aqueous layer
was separated, solid sodium chloride was added and the
resulting aqueous mixture was extracted again with EtOAc.
The organic layers were combined, washed with brine (1×),
saturated aqueous NaHCO$_3$ (1×), then brine (1×), and finally
dried with sodium sulfate. The upper solution was decanted,
concentrated, and the yellow oily residue was subject to a
column chromatography (silica gel, gradient elution EtOAc-
Hex from 1:5 to 1:1.5) to give the title compound as a white
foam (147 mg, 43

EXAMPLE 533

N-{[2-(3-hydroxypyrrolidin-1-yl)-2-oxoethyl]
(oxido)phenyl-$\square^4$-sulfanylidene}-5-({3-[(3-methyl-2-furoyl)amino]phenyl}ethynyl)nicotinamide

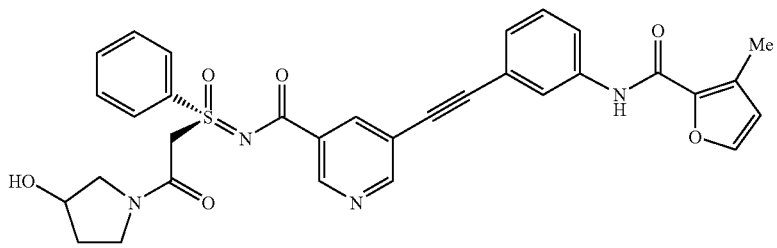

To the solution of (S)-ethyl(N-{[5-({3-[(3-methyl-2-furoyl)amino]phenyl}ethynyl)pyridin-3-yl]carbonyl}-S-phenylsulfonimidoyl)acetate (4.03 g, 7.26 mmol) in anhydrous THF (75 mL) was added dropwise 3-pyrrolidinol (6.0 mL) and the resulting reaction solution was heated at 65° C. for 5 hours. The reaction was then concentrated under reduced pressure and the yellow oily residue was partitioned between aqueous NH₄Cl and EtOAc. The organic layer was separated and washed sequentially with brine (1×), saturated aqueous NaHCO₃ (1×), brine (1×), and finally dried with anhydrous sodium sulfate overnight. The clear solution was decanted and concentrated. The oily residue was subject to multiple times of column chromatography (eg. from CH₂Cl₂ to MeOH—CH₂Cl₂ 1:25 or from EtOAc-Hex 3:1 to MeOH-EtOAc 1:100) the title compound as white foam (2.35 g, 54%).

EXAMPLE 534

N-[{2-[(2,3-dihydroxypropyl)(methyl)amino]-2-oxoethyl}(oxido)phenyl-$\square^4$-sulfanylidene]-5-({3-[(3-methyl-2-furoyl)amino]phenyl}ethynyl)nicotinamide

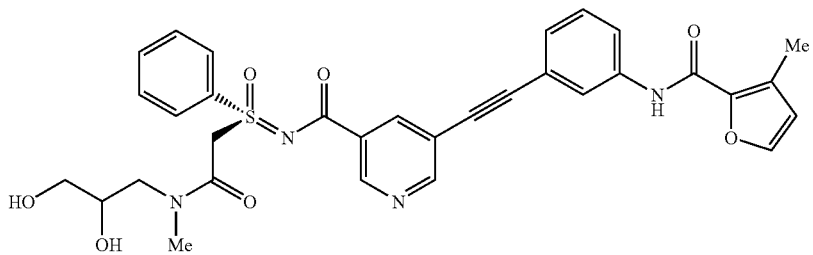

To the solution of (S)-ethyl(N-{[5-({3-[(3-methyl-2-furoyl)amino]phenyl}ethynyl)pyridin-3-yl]carbonyl}-S-phenylsulfonimidoyl)acetate (3.5 g, 6.3 mmol) in anhydrous THF (50 mL) was added dropwise 3-methylamino-1,2-propanediol (6.77 g) and the resulting reaction solution was heated at 75° C. for 8.5 hours. The reaction was then concentrated under reduced pressure and the yellow oily residue was partitioned between aqueous NH₄Cl and EtOAc. The organic layer was separated and washed with saturated aqueous NaHCO₃ (1×), brine (1×), and dried with sodium sulfate. The upper clear solution was decanted and evaporated, the resulting yellowish foamy residue was subjected to a gradient column chromatography (from EtOAc-Hex 6:1 to MeOH-EtOAc 1:50) yielding the title compound as white foam in amount of 2.56 g (66%).

EXAMPLE 535

(S)-N-{[2-(methylamino)-2-oxoethyl](oxido)phenyl-$\square^4$-sulfanylidene}-5-({3-[(3-methyl-2-furoyl)amino]phenyl}ethynyl)nicotinamide

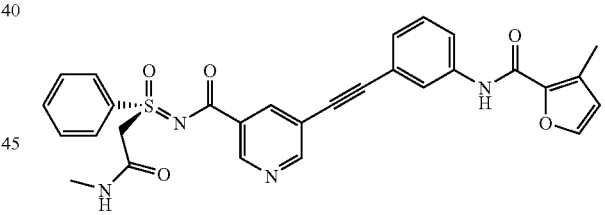

In a manner similar to that described in Example 534, (S)-Ethyl(N-{[5-({3-[(3-methyl-2-furoyl)amino]

phenyl}ethynyl)pyridin-3-yl]carbonyl}-S-phenylsulfonimi-doyl)acetate and methylamine were reacted to give the title compound.

EXAMPLE 536

(S)-N-{[2-(4-hydroxypiperidin-1-yl)-2-oxoethyl](oxido)phenyl-L⁴-sulfanylidene}-5-({3-[(3-methyl-2-furoyl)amino]phenyl}ethynyl)nicotinamide

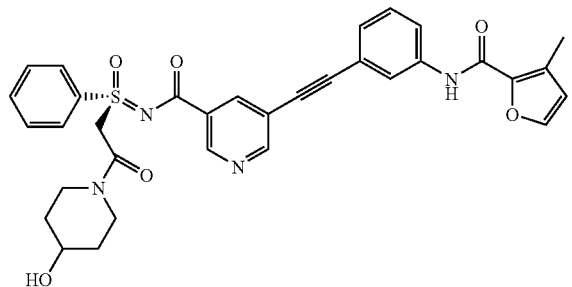

In a manner similar to that described in Example 534, (S)-Ethyl(N-{[5-({3-[(3-methyl-2-furoyl)amino]phenyl}ethynyl)pyridin-3-yl]carbonyl}-S-phenylsulfonimi-doyl)acetate and 4-hydroxypiperidine were reacted to give the title compound.

EXAMPLE 537

(S)-5-({3-[(3-methyl-2-furoyl)amino]phenyl}ethynyl)-N-[oxido(2-oxo-2-pyrrolidin-1-ylethyl)phenyl-⊔⁴-sulfanylidene]nicotinamide

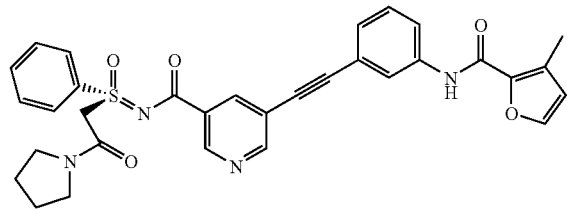

In a manner similar to that described in Example 534, (S)-Ethyl(N-{[5-({3-[(3-methyl-2-furoyl)amino]phenyl}ethynyl)pyridin-3-yl]carbonyl}-S-phenylsulfonimi-doyl)acetate and pyrrolidine were reacted to give the title compound.

EXAMPLE 538

N-{[2-(3-hydroxypiperidin-1-yl)-2-oxoethyl](oxido)phenyl-L⁴-sulfanylidene}-5-({3-[(3-methyl-2-furoyl)amino]phenyl}ethynyl)nicotinamide

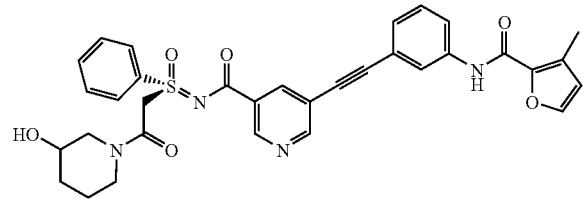

In a manner similar to that described in Example 534, (S)-Ethyl(N-{[5-({3-[(3-methyl-2-furoyl)amino]

phenyl}ethynyl)pyridin-3-yl]carbonyl}-S-phenylsulfonimi-doyl)acetate and 3-hydroxypiperidine were reacted to give the title compound.

EXAMPLE 539

(S)-Ethyl 1-[(N-{[5-({3-[(3-methyl-2-furoyl)amino]phenyl}ethynyl)pyridin-3-yl]carbonyl}-S-phenylsul-fonimidoyl)acetyl]piperidine-3-carboxylate

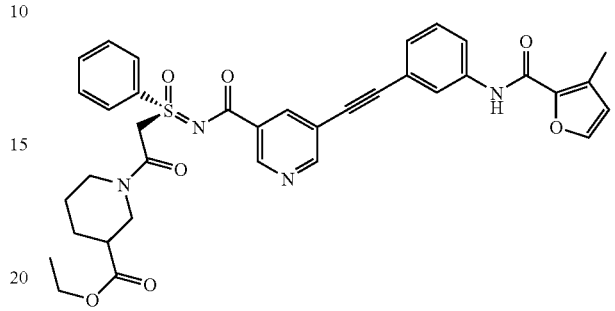

In a manner similar to that described in Example 534, (S)-Ethyl(N-{[5-({3-[(3-methyl-2-furoyl)amino]phenyl}ethynyl)pyridin-3-yl]carbonyl}-S-phenylsulfonimi-doyl)acetate and ethyl nipecotate were reacted to give the title compound.

EXAMPLE 540

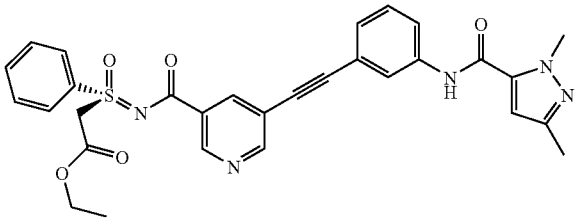

(S)-Ethyl[N-({5-[(3-{[(1,3-dimethyl-1H-pyrazol-5-yl)carbonyl]amino}phenyl)ethynyl]pyridin-3-yl}carbonyl)-S-phenylsulfonimidoyl]acetate In a manner similar to that described in Example 532 (step 2), (S)-Ethyl(S)—(S-phenylsulfonimidoyl)acetate and 5-[(3-{[(1,3-dimethyl-1H-pyrazol-5-yl)carbonyl]amino}phenyl)ethynyl]nicotinic acid were reacted to give the title compound.

EXAMPLE 541

(S)-N-[{2-[(2-amino-2-oxoethyl)amino]-2-oxoethyl}(oxido)phenyl-☐⁴-sulfanylidene]-5-[(3-{[(1,3-dim-ethyl-1H-pyrazol-5-yl)carbonyl]amino}phenyl)ethy-nyl]nicotinamide

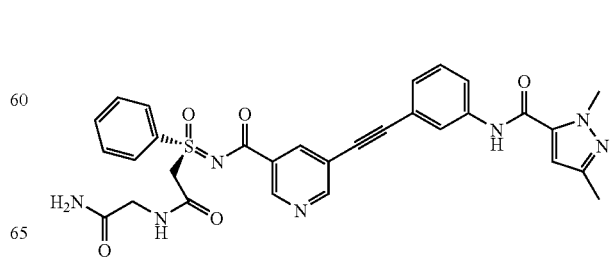

In a manner similar to that described in Example 534, (S)-Ethyl[N-({5-[(3-{[(1,3-dimethyl-1H-pyrazol-5-yl)carbonyl]amino}phenyl)ethynyl]pyridin-3-yl}carbonyl)-S-phenylsulfonimidoyl]acetate and glycineamide were reacted to give the title compound.

EXAMPLE 542

(S)-5-[(3-{[(1,3-dimethyl-1H-pyrazol-5-yl)carbonyl]amino}phenyl)ethynyl]-N-{[2-(methylamino)-2-oxoethyl](oxido)phenyl-$\lambda^4$-sulfanylidene}nicotinamide

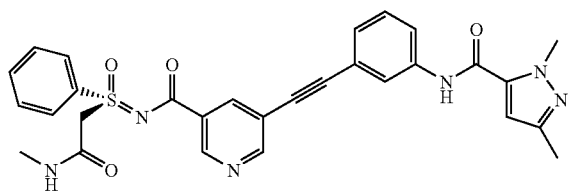

In a manner similar to that described in Example 534, (S)-Ethyl[N-({5-[(3-{[(1,3-dimethyl-1H-pyrazol-5-yl)carbonyl]amino}phenyl)ethynyl]pyridin-3-yl}carbonyl)-S-phenylsulfonimidoyl]acetate and methylamine were reacted to give the title compound.

EXAMPLE 543

(S)-5-[(3-{[(1,3-dimethyl-1H-pyrazol-5-yl)carbonyl]amino}phenyl)ethynyl]-N-[{2-[(2-hydroxyethyl)amino]-2-oxoethyl}(oxido)phenyl-$\lambda^4$-sulfanylidene]nicotinamide

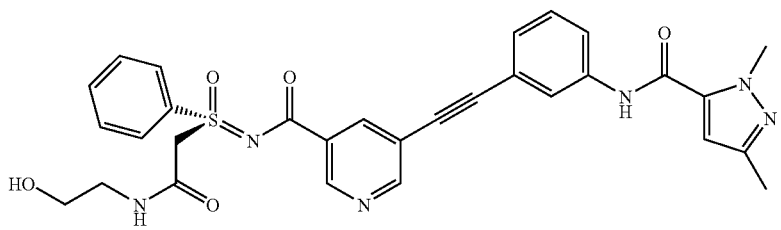

In a manner similar to that described in Example 534, (S)-Ethyl[N-({5-[(3-{[(1,3-dimethyl-1H-pyrazol-5-yl)carbonyl]amino}phenyl)ethynyl]pyridin-3-yl}carbonyl)-S-phenylsulfonimidoyl]acetate and 2-hydroxyethylamine were reacted to give the title compound.

EXAMPLE 544

(S)-5-[(3-{[(1,3-dimethyl-1H-pyrazol-5-yl)carbonyl]amino}phenyl)ethynyl]-N-[{2-[(2-hydroxyethyl)(methyl)amino]-2-oxoethyl}(oxido)phenyl-$\lambda^4$-sulfanylidene]nicotinamide

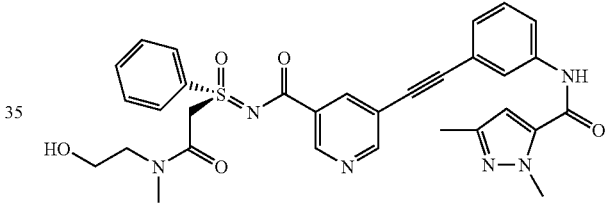

In a manner similar to that described in Example 534, (S)-Ethyl[N-({5-[(3-{[(1,3-dimethyl-1H-pyrazol-5-yl)carbonyl]amino}phenyl)ethynyl]pyridin-3-yl}carbonyl)-S-phenylsulfonimidoyl]acetate and 2-methylaminoethanol were reacted to give the title compound.

EXAMPLE 545

N-[{2-[(2,3-dihydroxypropyl)amino]-2-oxoethyl}(oxido)phenyl-$\lambda^4$-sulfanylidene]-5-[(3-{[(1,3-dimethyl-1H-pyrazol-5-yl)carbonyl]amino}phenyl)ethynyl]nicotinamide

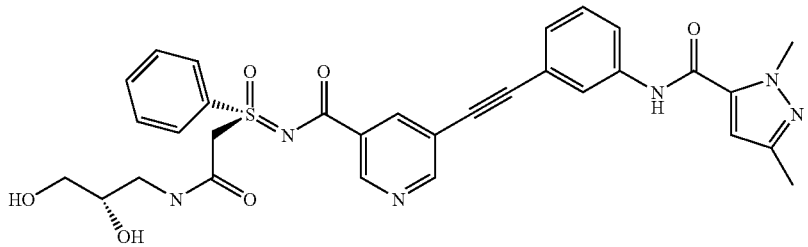

In a manner similar to that described in Example 534, (S)-Ethyl[N-({5-[(3-{[(1,3-dimethyl-1H-pyrazol-5-yl)carbonyl]amino}phenyl)ethynyl]pyridin-3-yl}carbonyl)-S-phenylsulfonimidoyl]acetate and 3-amino-1,2-propanediol were reacted to give the title compound.

EXAMPLE 546

(S)-Methyl 5-[N-({5-[(3-{[(1,3-dimethyl-1H-pyrazol-5-yl)carbonyl]amino}phenyl)ethynyl]pyridin-3-yl}carbonyl)-S-phenylsulfonimidoyl]pentanoate

Step 1

(S)-Trimethyl{[methyl(oxido)phenyl-$\lambda^4$-sulfanylidene]amino}silane

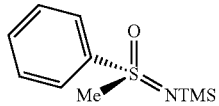

To a stirred solution of (S)-(+)-S-methyl-S-phenylsulphoximine (621 mg, 4.0 mmol) in anhydrous acetonitrile (1 mL) at 70° C. was added (trimethylsilyl)diethylamine (1.37 mL, 7.0 mmol) dropwise. The reaction was maintained at this temperature and stirred for 2 hours, at which time the TLC showed complete conversion of the starting material into a higher $R_f$ component. The reaction solution was concentrated under reduced pressure and dried in vacuo yielding brown oil, which was used directly in the next step without further purification.

Step 2

(S)-9,9-dimethoxy-2,2-dimethyl-4-phenyl-10-oxa-$\lambda^4$-thia-3-aza-2-silaundec-3-ene 4-oxide

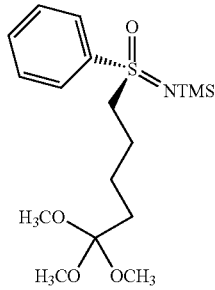

The brown oil, obtained from last step, was dissolved in 4 mL anhydrous THF. After the solution was cooled to −78° C., n-butyllithium (1.64 mL, 2.5 M solution in hexanes) was added dropwise. The resulting reaction mixture was stirred at −78° C. for 10 min, then at 0° C. for 20 min, followed by an addition of hexamethyl phosphoramide (1.32 mL). After the reaction was cooled back to −78° C., trimethyl 4-bromoorthobutyrate (1.1 mL) was added dropwise. The reaction was stirred and its temperature was allowed to rise to room temperature during 16 hours. The reaction mixture was then diluted with ethyl ether (250 mL) and washed with ice cold water (2×), brine (1×), and dried with anhydrous sodium sulfate. The solution was decanted and concentrated giving a brown oily residue which was used directly for next step.

Step 3

(S)-[S-(5,5,5-trimethoxypentyl)sulfonimidoyl]benzene

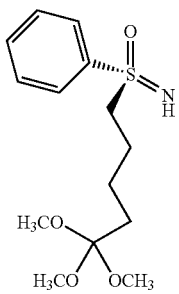

To the solution of the oily residue, obtained in last step, in MeOH—H$_2$O (10:1, 2 mL) was added cesium fluoride (91.2 mg) and the resulting reaction mixture was heated at 50° C. for 2 hours. The reaction was then concentrated and the oily residue was partitioned between cold water and EtOAc. The organic layer was separated and washed with brine (1×). After it was dried with anhydrous sodium sulfate, it was concentrated for a direct use in next step.

Step 4

(S)-Methyl 5-(S-phenylsulfonimidoyl)pentanoate

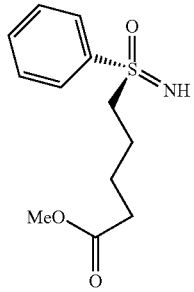

The crude oil, obtained in last step, was dissolved in MeOH—H₂O (4:0.1, 20 mL) and the resulting solution was cooled in an ice-bath. A catalytic amount of pyridinium toluene-4-sulfonate was added to the reaction and it was stirred at this temperature for 1 hour. The reaction was then concentrated at room temperature to remove most part of MeOH and the residue was diluted with EtOAc. The EtOAc was washed with saturated aqueous NaHCO₃ (2×), brine (1×), and dried with anhydrous sodium sulfate. The organic was decanted, concentrated under reduced pressure, and wrapped with silica gel. A gradient chromatography (Et₂O-Hex from 1:1 to Et₂O) rendered the title compound as clear oil in amount of 477 mg (47% for total of 4 steps).

Step 5

(S)-Methyl 5-{N-[(5-bromopyridin-3-yl)carbonyl]-S-phenylsulfonimidoyl}pentanoate

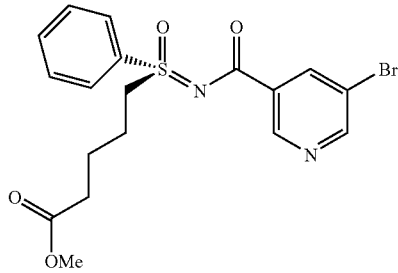

To the solution of (S)-Methyl 5-(S-phenylsulfonimidoyl)pentanoate (475 mg, 1.86 mmol) in anhydrous DMF (6 mL) at room temperature under nitrogen atmosphere was added diisopropylethylamine (0.65 mL), 5-bromonicotinic acid (0.38 g), and (benzotriazol-1-yloxy)-tris(dimethylamino)-phosphonium hexafluorophosphate (0.81 g). The resulting reaction mixture was stirred for about 15 min at room temperature and then poured into saturated aqueous NaHCO₃. The aqueous was extracted with EtOAc (1×), which was then washed with saturated aqueous NaHCO₃ and brine (v:v 1:1, 2×), brine (1×), and dried with anhydrous sodium sulfate. The solution was decanted and concentrated with silica gel. A column chromatography (EtOAc-Hex 1:2) rendered the title compound as slightly yellow colored solid in amount of (616 mg, 75%).

Step 6

(S)-Methyl 5-[N-({5-[(3-{[(1,3-dimethyl-1H-pyrazol-5-yl)carbonyl]amino}phenyl)ethynyl]pyridin-3-yl}carbonyl)-S-phenylsulfonimidoyl]pentanoate

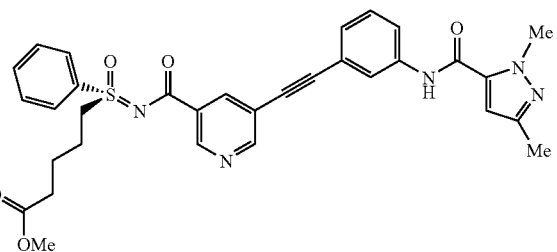

To the flame-dried 100 mL round bottom flask containing (S)-Methyl 5-{N-[(5-bromopyridin-3-yl)carbonyl]-S-phenylsulfonimidoyl}pentanoate (609 mg, 1.39 mmol), N-(3-ethynylphenyl)-1,3-dimethyl-1H-pyrazole-5-carboxamide (0.50 g), triethylamine (0.77 mL), bis(triphenylphosphine)palladium(II) dichloride (97.3 mg), and triphenylphosphine (9.1 mg) under nitrogen/hydrogen (1:1) atmosphere at room temperature was added copper(I) iodide (52.8 mg). The resulting reaction mixture was heated and stirred at 60° C. for 1 hour. It was then diluted with EtOAc, washed sequentially with saturated aqueous NaHCO₃ (2×), brine (1×), and finally dried with anhydrous sodium sulfate. The solution was decanted and concentrated with silica gel. Chromatography (EtOAc-Hex from 1:2 to 3:2) yielded the title compound as white foam in amount of (712 mg, 86%).

EXAMPLE 547

N-[{5-[(2,3-dihydroxypropyl)(methyl)amino]-5-oxopentyl}(oxido)phenyl-λ⁴-sulfanylidene]-5-[(3-{[(1,3-dimethyl-1H-pyrazol-5-yl)carbonyl]amino}phenyl)ethynyl]nicotinamide

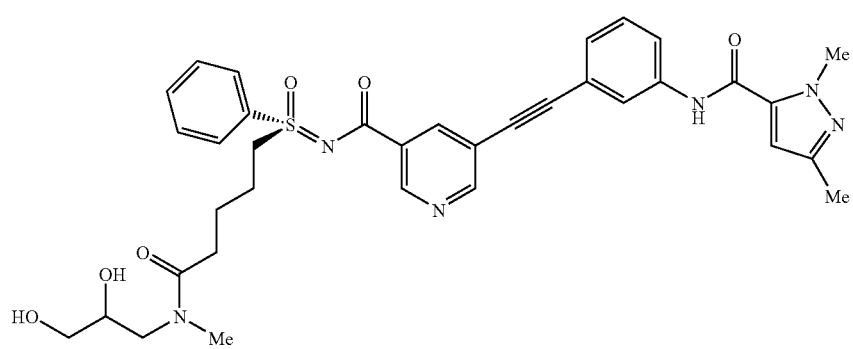

To the solution of 3-methylamino-1,2-propanediol (180 mg) in anhydrous THF was added (S)-Methyl 5-[N-({5-[(3-{[(1,3-dimethyl-1H-pyrazol-5-yl)carbonyl]amino}phenyl)ethynyl]pyridin-3-yl}carbonyl)-S-phenylsulfonimidoyl]pentanoate (100 mg, 0.17 mmol). The reaction solution was heated to 50° C. for 2 hours and then the temperature was raised to 70° C. for 17 hours. Further 3-methylamino-1,2-propanediol (100 mg) was added, and the reaction was stirred and heated at 85° C. for an additional 24 hours. The reaction mixture was then partitioned between saturated aqueous NaHCO$_3$ and EtOAc. The organic layer was isolated and washed with brine (1×), dried (anhydrous Na$_2$SO$_4$) and concentrated. Upon a gradient column chromatography (MeOH-EtOAc from 1:50 to 1:15) the title compound was obtained as a clear oil (74 mg, 66%) which gave a white foamy solid upon standing in vacuo.

EXAMPLE 548

(S)-5-[N-({5-[(3-{[(1,3-dimethyl-1H-pyrazol-5-yl)carbonyl]amino}phenyl)ethynyl]pyridin-3-yl}carbonyl)-S-phenylsulfonimidoyl]pentanoic acid

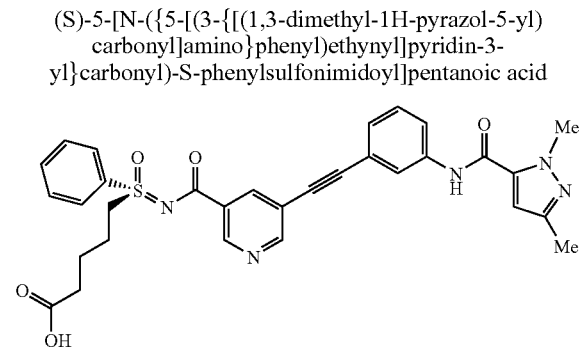

To the solution of (S)-Methyl 5-[N-({5-[(3-{[(1,3-dimethyl-1H-pyrazol-5-yl)carbonyl]amino}phenyl)ethynyl]pyridin-3-yl}carbonyl)-S-phenylsulfonimidoyl]pentanoate (120 mg, 0.2 mmol) in THF (4 mL) at 0° C. was added dropwise a solution of aqueous NaOH (0.5 N, 2.0 mL). After the reaction mixture was stirred at 0° C. for 2 hours, 2 N HCl was carefully added to adjust the pH~5 followed by a partition between aqueous NH$_4$Cl and EtOAc. The EtOAc layer was further washed with brine once and dried with anhydrous sodium sulfate. The organic layer was decanted, concentrated and subject to a gradient column chromatography (from EtOAc to MeOH-EtOAc 1:5) yielding the title compound as white foam in amount of (85 mg, 73%).

EXAMPLE 549

(S)-5-[(3-{[(1,3-dimethyl-1H-pyrazol-5-yl)carbonyl]amino}phenyl)ethynyl]-N-{5-(hydroxyamino)-5-oxopentyl](oxido)phenyl-λ$^4$-sulfanylidene}nicotinamide

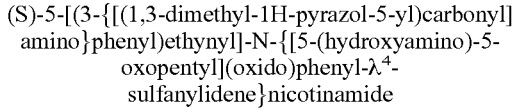
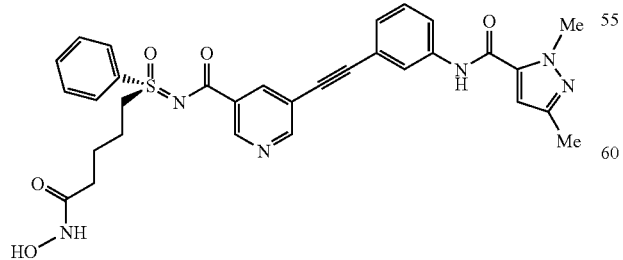

At 0° C. to the solution of 5-[N-({5-[(3-{[(1,3-dimethyl-1H-pyrazol-5-yl)carbonyl]amino}phenyl)ethynyl]pyridin-3-yl}carbonyl)-S-phenylsulfonimidoyl]pentanoic acid (50 mg, 0.086 mmol) in DMF (1 mL) was added hydroxylamine hydrochloride (30 mg), 1-hydroxybenzotriazole hydrate (20 mg), (benzotriazol-1-yloxy)-tris(dimethylamino)-phosphonium hexafluorophosphate (57 mg), and triethylamine (84 μL). The reaction mixture was stirred at this temperature for 30 min. The reaction was then poured into aqueous NH$_4$Cl and extracted with EtOAc. The organic layer was isolated, washed further with brine once, and dried (anhydrous Na$_2$SO$_4$). A gradient column chromatography (MeOH—CH$_2$Cl$_2$ from 1:100 to 1:5) gave the title compound as white foam (37 mg, 71%).

EXAMPLE 550

Methyl rel-(2R,4S)-1-{3-[N-({5-[(3-{[(1,3-dimethyl-1H-pyrazol-5-yl)carbonyl]amino}phenyl)ethynyl]pyridin-3-yl}carbonyl)-R-phenylsulfonimidoyl]propyl}-4-hydroxypyrrolidine-2-carboxylate

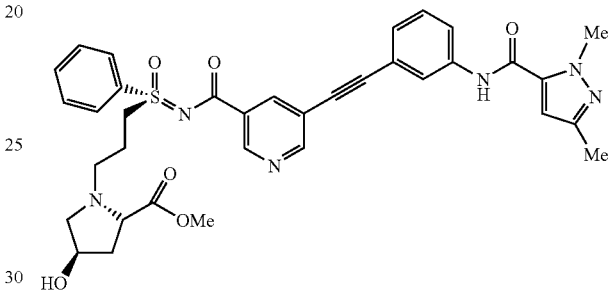

The mixture of N-[(3-bromopropyl)(oxido)phenyl-λ$^4$-sulfanylidene]-5-[(3-{[(1,3-dimethyl-1H-pyrazol-5-yl)carbonyl]amino}phenyl)ethynyl]nicotinamide (200 mg, 0.33 mmol), L-4-hydroxyproline methyl ester hydrochloride (126 mg), and sodium bicarbonate (167 mg) in anhydrous acetonitrile (2 mL) in a seal tube was stirred and heated at 90° C. for 5 hours. After it was cooled to room temperature, the reaction was diluted with EtOAc. The organic was washed with saturated aqueous NaHCO$_3$ (2×), brine (1×), and then dried with anhydrous sodium sulfate. The solution layer was decanted, concentrated, and the oily residual was chromatographed (EtOAc-Hex 1:1 to neat EtOAc) yielding the title compound as colorless oil in amount of 128 mg (58%).

EXAMPLE 551

(S)-Methyl({3-[N-({5-[(3-{[(1,3-dimethyl-1H-pyrazol-5-yl)carbonyl]amino}phenyl)ethynyl]pyridin-3-yl}carbonyl)-S-phenylsulfonimidoyl]propyl}amino)acetate

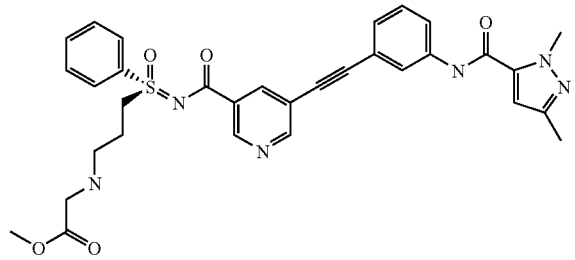

In a manner similar to that described in Example 550, N-[(3-bromopropyl)(oxido)phenyl-λ$^4$-sulfanylidene]-5-[(3-

{[(1,3-dimethyl-1H-pyrazol-5-yl)carbonyl]amino}phenyl)ethynyl]nicotinamide and glycine methyl ester were reacted to give the title compound.

EXAMPLE 552

Methyl 2-({3-[N-({5-[(3-{[(1,3-dimethyl-1H-pyrazol-5-yl)carbonyl]amino}phenyl)ethynyl]pyridin-3-yl}carbonyl)-S-phenylsulfonimidoyl]propyl}amino)-3-hydroxypropanoate

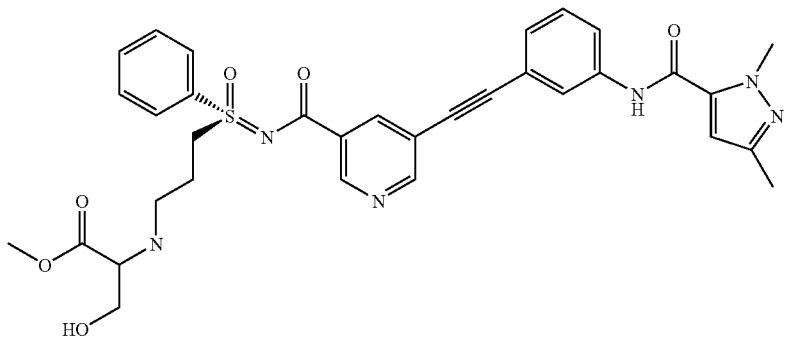

In a manner similar to that described in Example 550, N-[(3-bromopropyl)(oxido)phenyl-λ⁴-sulfanylidene]-5-[(3-{[(1,3-dimethyl-1H-pyrazol-5-yl)carbonyl]amino}phenyl)ethynyl]nicotinamide and 2-amino-3-hydroxypropionic acid methyl ester were reacted to give the title compound.

EXAMPLE 553

Ethyl 1-{3-[N-({5-[(3-{[(1,3-dimethyl-1H-pyrazol-5-yl)carbonyl]amino}phenyl)ethynyl]pyridin-3-yl}carbonyl)-S-phenylsulfonimidoyl]propyl}piperidine-3-carboxylate

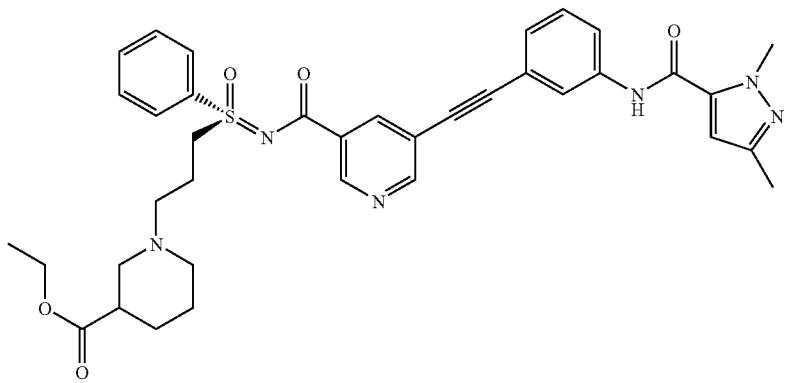

In a manner similar to that described in Example 550, N-[(3-bromopropyl)(oxido)phenyl-λ⁴-sulfanylidene]-5-[(3-{[(1,3-dimethyl-1H-pyrazol-5-yl)carbonyl]amino}phenyl)ethynyl]nicotinamide and ethyl nipecotate were reacted to give the title compound.

EXAMPLE 554

Methyl 2-({3-[N-({5-[(3-{[(1,3-dimethyl-1H-pyrazol-5-yl)carbonyl]amino}phenyl)ethynyl]pyridin-3-yl}carbonyl)-S-phenylsulfonimidoyl]propyl}amino)-3-(1H-imidazol-4-yl)propanoate

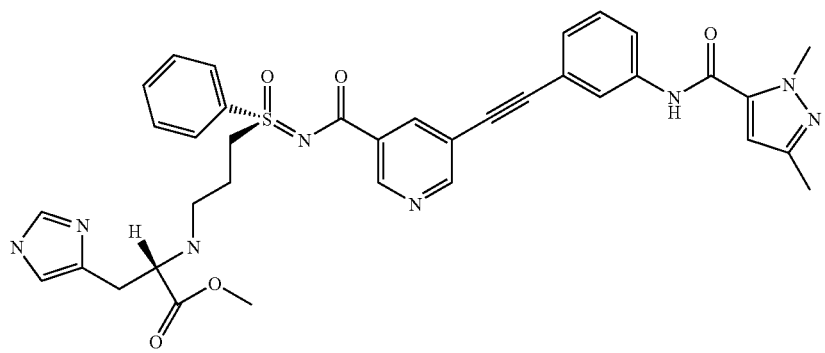

In a manner similar to that described in Example 550, N-[(3-bromopropyl)(oxido)phenyl-λ⁴-sulfanylidene]-5-[(3-{[(1,3-dimethyl-1H-pyrazol-5-yl)carbonyl]amino}phenyl)ethynyl]nicotinamide and histidine methyl ester were reacted to give the title compound.

EXAMPLE 555 rel-(2R,4S)-1-{3-[N-({5-[(3-{[(1,3-dimethyl-1H-pyrazol-5-yl)carbonyl]amino}phenyl)ethynyl]pyridin-3-yl}carbonyl)-R-phenylsulfonimidoyl]propyl}-4-hydroxypyrrolidine-2-carboxylic acid

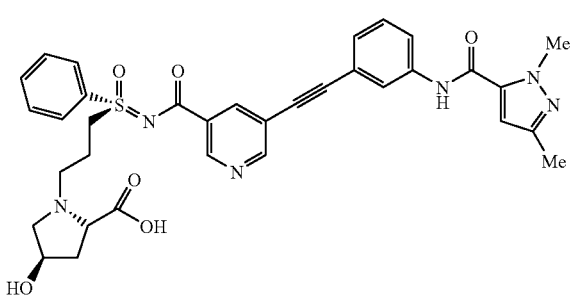

Methyl rel-(2R,4S)-1-{3-[N-({5-[(3-{[(1,3-dimethyl-1H-pyrazol-5-yl)carbonyl]amino}phenyl)ethynyl]pyridin-3-yl}carbonyl)-R-phenylsulfonimidoyl]propyl}-4-hydroxypyrrolidine-2-carboxylate (116 mg, 0.17 mmol) was dissolved in THF (3.5 mL) and the resulting solution was cooled in an ice-bath. After aqueous NaOH (0.5 N, 1.75 mL) was dropwise added, the reaction was stirred at 0° C. for 30 min. The reaction was then diluted with ice water followed by a pH adjustment to 3~4 with 2 N HCl. The reaction was further diluted with saturated brine, and then extracted with CHCl₃-iPrOH (5:1) (2×). The organic layers were combined, dried (anhydrous Na₂SO₄), and then filtered through a plug of cotton. The filtrate was concentrated and the residue was chromatographed (MeOH—CHCl₃ 1:10 to 1:4) yielding the title compound as white solid in amount of 108 mg (95%).

EXAMPLE 556

({3-[N-({5-[(3-{[(1,3-dimethyl-1H-pyrazol-5-yl)carbonyl]amino}phenyl)ethynyl]pyridin-3-yl}carbonyl)-S-phenylsulfonimidoyl]propyl}amino)acetic acid

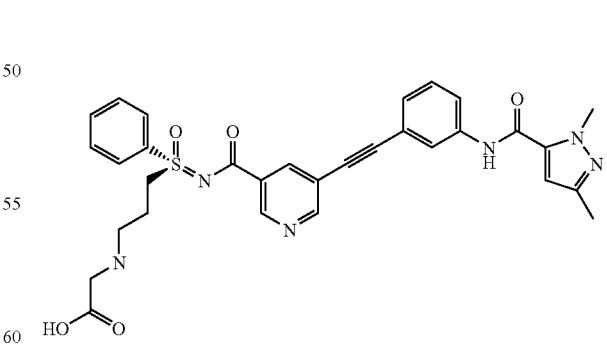

In a manner similar to that described in Example 555, methyl({3-[N-({5-[(3-{[(1,3-dimethyl-1H-pyrazol-5-yl)carbonyl]amino}phenyl)ethynyl]pyridin-3-yl}carbonyl)-S-phenylsulfonimidoyl]propyl}amino)acetate was converted to the title compound.

EXAMPLE 557

2-({3-[N-({5-[(3-{[(1,3-dimethyl-1H-pyrazol-5-yl)carbonyl]amino}phenyl)ethynyl]pyridin-3-yl}carbonyl)-S-phenylsulfonimidoyl]propyl}amino)-3-hydroxypropanoic acid

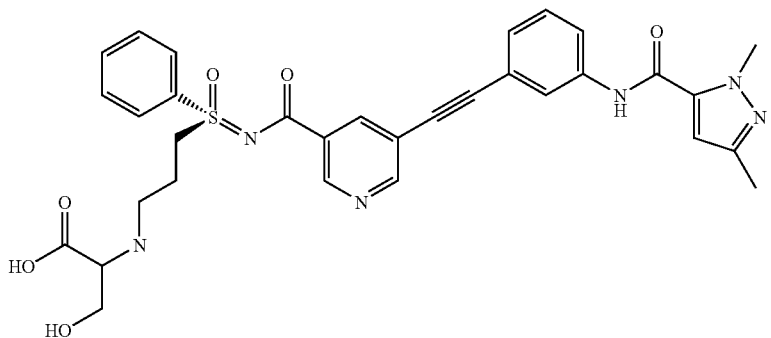

In a manner similar to that described in Example 555, methyl 2-({3-[N-({5-[(3-{[(1,3-dimethyl-1H-pyrazol-5-yl)carbonyl]amino}phenyl)ethynyl]pyridin-3-yl}carbonyl)-S-phenylsulfonimidoyl]propyl}amino)-3-hydroxypropanoate was converted to the title compound.

EXAMPLE 558

1-{3-[N-({5-[(3-{[(1,3-dimethyl-1H-pyrazol-5-yl)carbonyl]amino}phenyl)ethynyl]pyridin-3-yl}carbonyl)-S-phenylsulfonimidoyl]propyl}piperidine-3-carboxylic acid

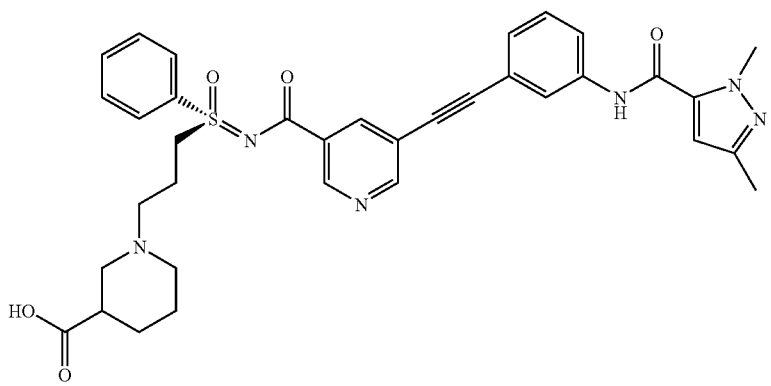

In a manner similar to that described in Example 555, ethyl 1-{3-[N-({5-[(3-{[(1,3-dimethyl-1H-pyrazol-5-yl)carbonyl]amino}phenyl)ethynyl]pyridin-3-yl}carbonyl)-S-phenylsulfonimidoyl]propyl}piperidine-3-carboxylate was converted to the title compound.

EXAMPLE 559

(S)-Methyl{[3-(N-{[5-({3-[(3-methyl-2-furoyl)amino]phenyl}ethynyl)pyridin-3-yl]carbonyl}-S-phenylsulfonimidoyl)propyl]amino}acetate

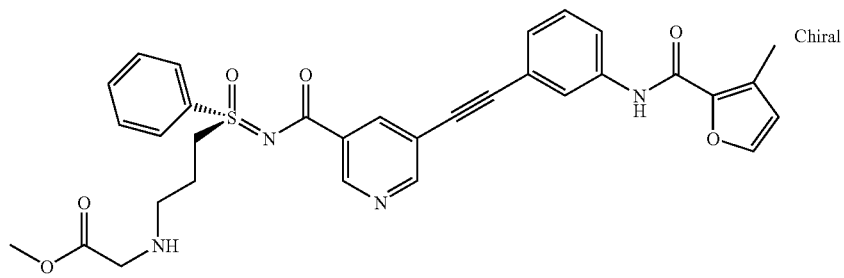

In a manner similar to that described in Example 550, N-[(3-bromopropyl)(oxido)phenyl-$\lambda^4$-sulfanylidene]-5-({3-[(3-methyl-2-furoyl)amino]phenyl}ethynyl)nicotinamide and glycine methyl ester are converted to the title compound.

EXAMPLE 560 methyl 1-[3-(N-{[5-({3-[(3-methyl-2-furoyl)amino]phenyl}ethynyl)pyridin-3-yl]carbonyl}-S-phenylsulfonimidoyl)propyl]pyrrolidine-2-carboxylate

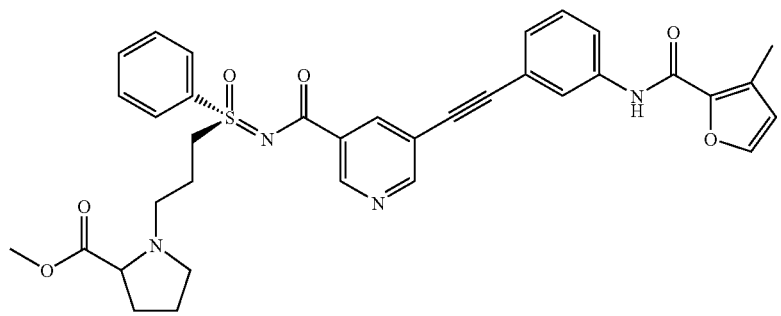

In a manner similar to that described in Example 550, N-[(3-bromopropyl)(oxido)phenyl-lambda~4~-sulfanylidene]-5-({3-[(3-methyl-2-furoyl)amino]phenyl}ethynyl)nicotinamide and 2-carboxymethyl pyrrolidine are converted to the title compound.

EXAMPLE 561 methyl 1-[3-(N-{[5-({3-[(3-methyl-2-furoyl)amino]phenyl}ethynyl)pyridin-3-yl]carbonyl}-S-phenylsulfonimidoyl)propyl]pyrrolidine-3-carboxylate

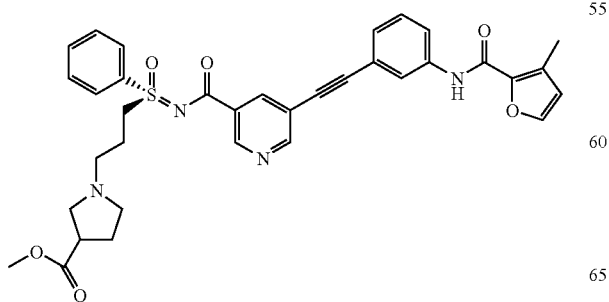

In a manner similar to that described in Example 550, N-[(3-bromopropyl)(oxido)phenyl-λ⁴-sulfanylidene]-5-({3-[(3-methyl-2-furoyl)amino]phenyl}ethynyl)nicotinamide and 3-carboxymethyl pyrrolidine are converted to the title compound.

EXAMPLE 562 ethyl 1-[3-(N-{[5-({3-[(3-methyl-2-furoyl)amino]phenyl}ethynyl)pyridin-3-yl]carbonyl}-S-phenylsulfonimidoyl)propyl]piperidine-3-carboxylate

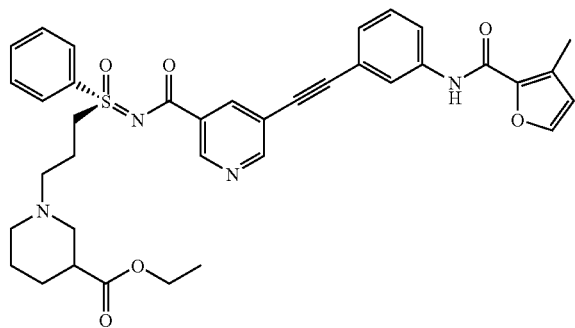

In a manner similar to that described in Example 550, N-[(3-bromopropyl)(oxido)phenyl-λ⁴-sulfanylidene]-5-({3-[(3-methyl-2-furoyl)amino]phenyl}ethynyl)nicotinamide and ethyl nipecotate are converted to the title compound.

EXAMPLE 563

(S)-{[3-(N-{[5-({3-[(3-methyl-2-furoyl)amino]phenyl}ethynyl)pyridin-3-yl]carbonyl}-S-phenylsulfonimidoyl)propyl]amino}acetic acid

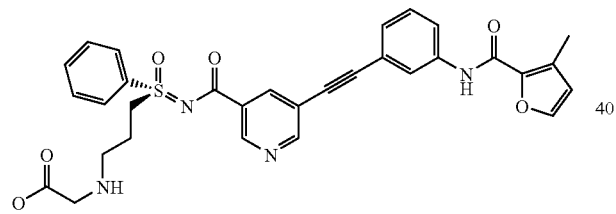

In a manner similar to that described in Example 555, methyl{[3-(N-{[5-({3-[(3-methyl-2-furoyl)amino]phenyl}ethynyl)pyridin-3-yl]carbonyl}-S-phenylsulfonimidoyl)propyl]amino}acetate is converted to the title compound.

EXAMPLE 564

1-[3-(N-{[5-({3-[(3-methyl-2-furoyl)amino]phenyl}ethynyl)pyridin-3-yl]carbonyl}-S-phenylsulfonimidoyl)propyl]pyrrolidine-2-carboxylic acid

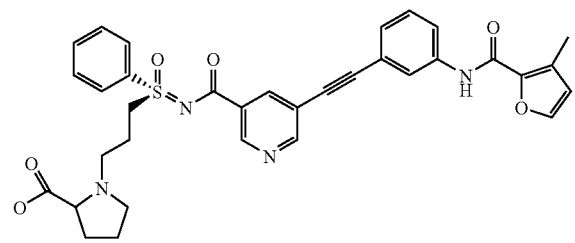

In a manner similar to that described in Example 555, methyl 1-[3-(N-{[5-({3-[(3-methyl-2-furoyl)amino]phenyl}ethynyl)pyridin-3-yl]carbonyl}-S-phenylsulfonimidoyl)propyl]pyrrolidine-2-carboxylate is converted to the title compound.

EXAMPLE 565

1-[3-(N-{[5-({3-[(3-methyl-2-furoyl)amino]phenyl}ethynyl)pyridin-3-yl]carbonyl}-S-phenylsulfonimidoyl)propyl]pyrrolidine-3-carboxylic acid

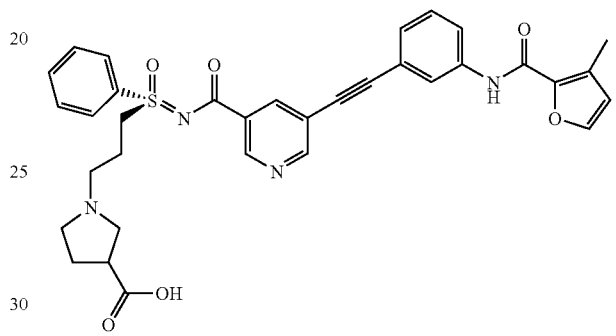

In a manner similar to that described in Example 555, methyl 1-[3-(N-{[5-({3-[(3-methyl-2-furoyl)amino]phenyl}ethynyl)pyridin-3-yl]carbonyl}-S-phenylsulfonimidoyl)propyl]pyrrolidine-3-carboxylate is converted to the title compound.

EXAMPLE 566

1-[3-(N-{[5-({3-[(3-methyl-2-furoyl)amino]phenyl}ethynyl)pyridin-3-yl]carbonyl}-S-phenylsulfonimidoyl)propyl]piperidine-3-carboxylic acid

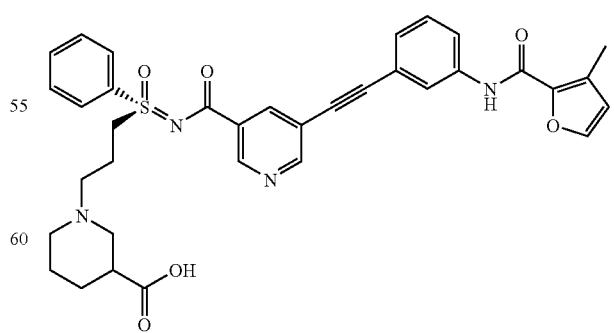

In a manner similar to that described in Example 555, ethyl 1-[3-(N-{[5-({3-[(3-methyl-2-furoyl)amino]

phenyl}ethynyl)pyridin-3-yl]carbonyl}-S-phenylsulfonimidoyl)propyl]piperidine-3-carboxylate is converted to the title compound.

EXAMPLE 567 methyl{3-[N-({6-amino-5-[(3-{[(1,3-dimethyl-1H-pyrazol-5-yl)carbonyl]amino}phenyl)ethynyl]pyridin-3-yl}carbonyl)-S-methylsulfonimidoyl]phenyl}acetate Step 1 methyl 6-amino-5-[(3-{[(1,3-dimethyl-1H-pyrazol-5-yl)carbonyl]amino}phenyl)ethynyl]nicotinate

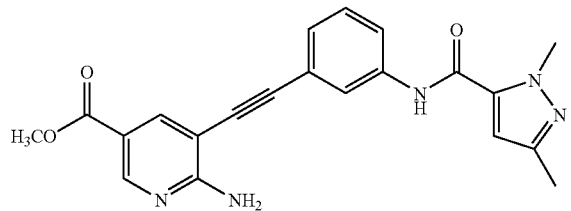

A mixture of methyl 6-amino-5-iodonicotinate (111 mg, 0.40 mmol), N-(3-ethynylphenyl)-1,3-dimethyl-1H-pyrazole-5-carboxamide (144 mg, 0.60 mmol), triethylamine (0.167 ml, 1.2 mmol), dichlorobis(triphenylphosphine)palladium(II) (23 mg, 0.032 mmol) and triphenylphosphine (5.2 mg, 0.020 mmol) in 3.2 ml DMF at room temperature was degassed using vacuum and a balloon of $H_2$, then copper(I) iodide (3.8 mg, 0.020 mmol) added. The reaction was heated at 60° C. for 1 hour 40 minutes, then partitioned between EtOAc and dilute brine. The EtOAc layer was dried with anhydrous $Na_2SO_4$ and rotary evaporated. The solid was recrystallized from EtOAc/hexane to give the title compound as a yellow-tan solid (122 mg, 78%).

Step 2

6-amino-5-[(3-{[(1,3-dimethyl-1H-pyrazol-5-yl)carbonyl]amino}phenyl)ethynyl]nicotinic acid

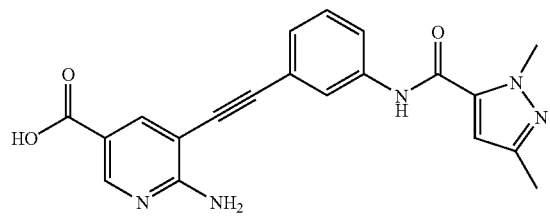

A solution of methyl 6-amino-5-[(3-{[(1,3-dimethyl-1H-pyrazol-5-yl)carbonyl]amino}phenyl)ethynyl]nicotinate (51 mg, 0.13 mmol) and KOH (37 mg, 0.65 mmol) in 4.0 ml MeOH:$H_2O$ (3:1) was heated at 65° C. for 1 hour 40 minutes. The pH of the mixture was adjusted to pH 4 using 10% HCl, brine added, and the aqueous extracted with EtOAc. The combined EtOAc layers were dried with anhydrous $Na_2SO_4$ and rotary evaporated. The light yellow solid was triturated with hot EtOAc to give the title compound as an off-white solid (41 mg, 84%).

Step 3 methyl{3-[N-({6-amino-5-[(3-{[(1,3-dimethyl-1H-pyrazol-5-yl)carbonyl]amino}phenyl)ethynyl]pyridin-3-yl}carbonyl)-S-methylsulfonimidoyl]phenyl}acetate

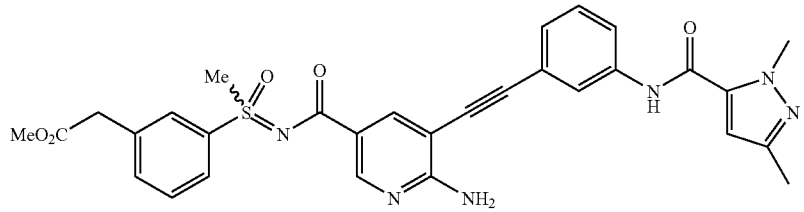

In a manner similar to that described in Example 496 (step 5), 6-amino-5-[(3-{[(1,3-dimethyl-1H-pyrazol-5-yl)carbonyl]amino}phenyl)ethynyl]nicotinic acid and methyl{3-[S-methyl-N-(trifluoroacetyl)sulfonimidoyl]phenyl}acetate were reacted to give the title compound.

The present invention is not to be limited in scope by the exemplified embodiments which are intended as illustrations of single aspects of the invention only. Indeed, various modifications of the invention in addition to those described herein will become apparent to those skilled in the art from the foregoing description.

For example, the novel compounds of this invention include any compound which is a substituted aroyl sulfoximine compound which binds to the tyrosine kinase receptor wherein said substituted aryl moiety may be represented by formula IV below:

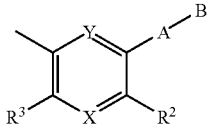

or said substituted aryl moiety may be represented by formula V below

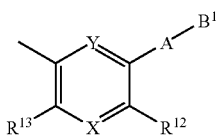

wherein $B^1$, $R^{12}$ and $R^{13}$ are selected from the group consisting of halogen, nitro, hydroxy, hydrocarbyl, substituted hydrocarbyl, amide, thioamide, amine, thioether and cyano or said novel sulfoximine may be represented by formula VI below

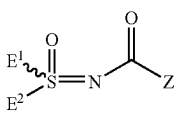

wherein Z is said substituted aroyl group and $E^1$ and $E^2$ are selected from the group consisting of halogen, nitro, hydroxy, hydrocarbyl, substituted hydrocarbyl, amide, thioamide, amine, thioether and cyano.

Such modifications are intended to fall within the scope of the appended claims.

All references cited herein are hereby incorporated by reference in their entirety.

In particular, the compounds of the present invention may be prepared by methods that are analogous to the methods disclosed in such references, with one of skill in the art varying the reactants to achieve the desired compounds. Also, the compounds of the present invention may be tested by the various in-vitro and in-vivo assays disclosed in such references to demonstrate the claimed utilities.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

The invention claimed is:

1. A compound represented by the general formula I:

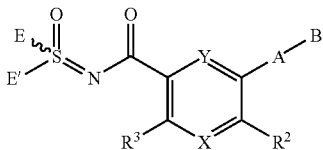

Wherein:
X is $CR^4$ or N;
Y is $CR^1$ or N;
$R^1$ is selected from the group consisting of hydrogen, alkyl, halogen, $OR^4$, CN, $NO_2$, $COR^4$, $(CH_2)_aOR^4$, $(CH_2)_aN(R^4)_2$, $C(O)N(R^4)_2$ and $N(R^4)_2$;

$R^2$ is selected from the group consisting of hydrogen, halogen, alkyl, $OR^4$, CN, $NO_2$, $SO_2N(R^4)_2$, $COR^4$, $(CH_2)_a OR^4$, $(CH_2)_aN(R^4)_2$, $C(O)N(R^4)_2$, $N(R^4)_2$ and $N(R^6)(CR^7R^8)_aR^{10}$;

$R^3$ is selected from the group consisting of hydrogen, halogen, alkyl, $OR^4$, CN, $NO_2$, $SO_2N(R^4)_2$, $COR^4$, $(CH_2)_a OR^4$, $(CH_2)_aN(R^4)_2$, $C(O)N(R^4)_2$, $N(R^4)_2$ and $N(R^6)(CR^7R^8)_aR^{10}$;

$R^4$ is hydrogen or $C_1$ to $C_4$ alkyl;

A is selected from the group consisting of C≡C, CH═CH, $CH_2CH_2$, $CH_2O$, $CF_2O$, $OCH_2$, $OCF_2$, $N(R^4)$, C(O), $S(O)_e$, $NR^7C(O)$, $C(O)NR^7$ and $N(R^7)C(O)NR^7$;

B is selected from the group consisting of hydrogen, alkyl and alkyloxyalkyl or B may be a 5 or 6 membered carbocyclic aryl or heterocyclic aryl group;

E is a 5 or 6 membered carbocyclic aryl or heterocyclic aryl group;

E' is selected from the group consisting of alkyl, $CF_3$, $(CR^7R^8)_aC(O)OR^{10}$, $(CR^7R^8)_aC(O)N(R^{10})_2$, $(CR^7R^8)_aC(O)N(OR^{10})(R^{10})$, $(CR^7R^8)_a(OR^{10})$, $(CR^7R^8)_aN(R^{10})_2$, and $(CR^7R^8)_aR^{10}$; wherein $R^7$ and $R^8$ are selected from the group consisting of H, halogen, hydroxyl, and alkyl or $CR^7R^8$ may represent a carbocyclic ring of from 3 to 6 carbons; and $R^{10}$ is selected from the group consisting of hydrogen, halogen, alkyl, hydroxyl, hydroxymethyl, carbocyclic aryl, heterocyclic aryl, $(CR^7R^8)_aC(O)OR^6$, $(CR^7R^8)_aC(O)R_6$, $(CR^7R^8)_aC(O)N(R^6)_2$, $(CR^7R^8)_aC(O)N(OR^6)(R^6)$, $(CR^7R^8)_a(OR^6)$, $(CR^7R^8)_aN(R^6)_2$ and $(CR^7R^8)_aR^6$, wherein $R^6$ is selected from the group consisting of hydrogen, carboalkyl, alkylamine, alkylhydroxy, and alkyloxyalkyl or $R^6$ is a 5 or 6 membered carbocyclic or heterocyclic group;

wherein $R^6$ is selected from the group consisting of hydrogen, alkyl, carboalkyl, alkylamine, alkylhydroxy and alkyloxyalkyl or $R^6$ is a 5 or 6 membered carbocyclic or heterocyclic group;

a is 0 or an integer of from 1 to 5;
b is an integer of from 2 to 5;
c is 0 or an integer of from 1 to 4;
d is 0 or an integer of from 1 to 5;
e is 0 or an integer of from 1 to 2 and further including prodrugs, pharmaceutically acceptable salts, racemic mixtures and enantiomers of said compound.

2. The compound of claim 1 wherein B is a carbocyclic aryl or heterocyclic aryl represented by formula II below:

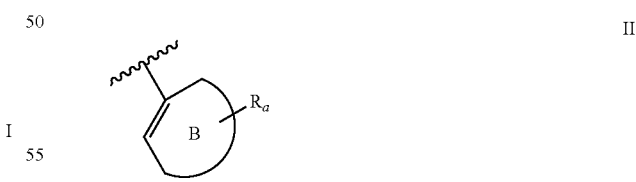

wherein said carbocyclic aryl and heterocyclic aryl groups are selected from the group consisting of:

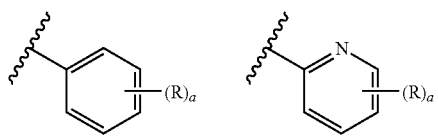

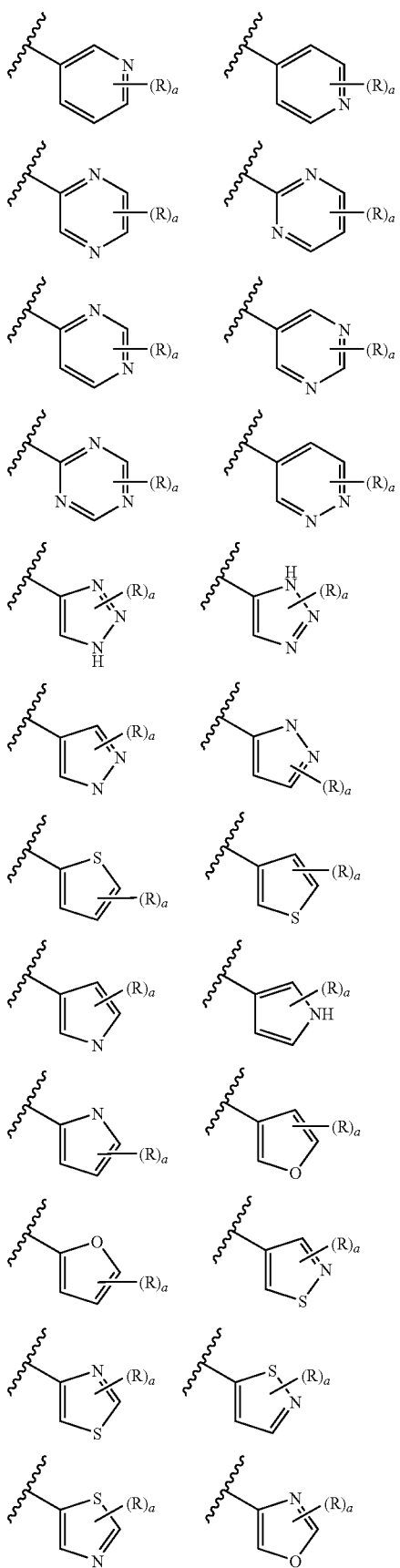
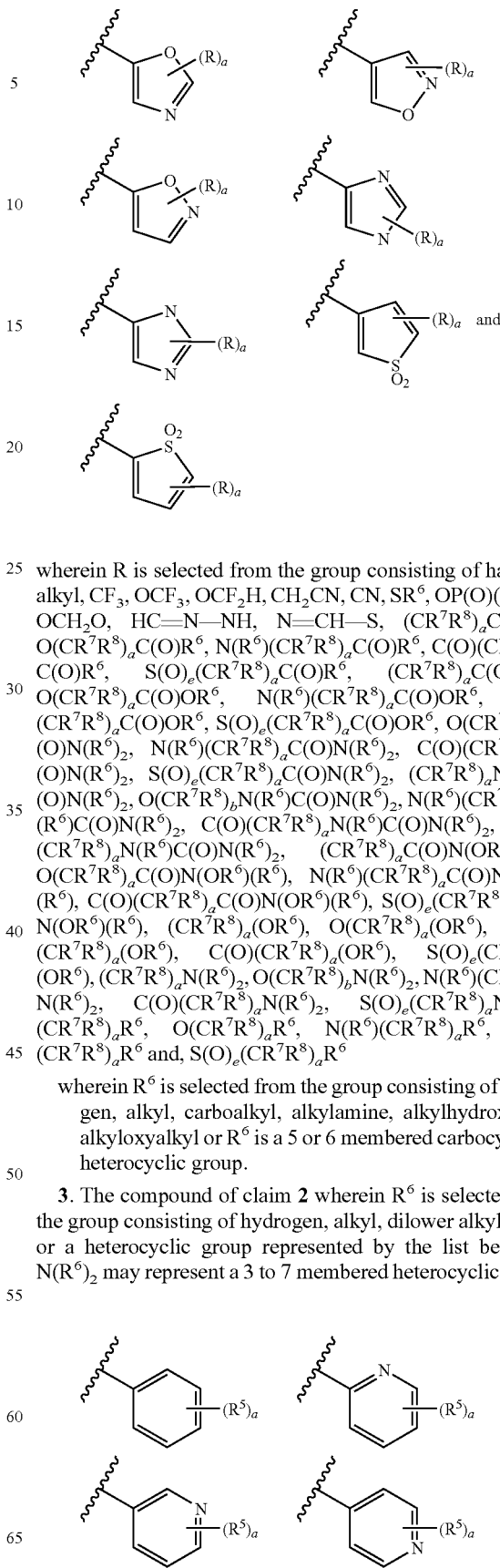

wherein R is selected from the group consisting of halogen, alkyl, $CF_3$, $OCF_3$, $OCF_2H$, $CH_2CN$, CN, $SR^6$, $OP(O)(OR^6)_2$, $OCH_2O$, HC=N—NH, N=CH—S, $(CR^7R^8)_aC(O)R^6$, $O(CR^7R^8)_aC(O)R^6$, $N(R^6)(CR^7R^8)_aC(O)R^6$, $C(O)(CR^7R^8)_aC(O)R^6$, $S(O)_e(CR^7R^8)_aC(O)R^6$, $(CR^7R^8)_aC(O)OR^6$, $O(CR^7R^8)_aC(O)OR^6$, $N(R^6)(CR^7R^8)_aC(O)OR^6$, $C(O)(CR^7R^8)_aC(O)OR^6$, $S(O)_e(CR^7R^8)_aC(O)OR^6$, $O(CR^7R^8)_aC(O)N(R^6)_2$, $N(R^6)(CR^7R^8)_aC(O)N(R^6)_2$, $C(O)(CR^7R^8)_aC(O)N(R^6)_2$, $S(O)_e(CR^7R^8)_aC(O)N(R^6)_2$, $(CR^7R^8)_aN(R^6)C(O)N(R^6)_2$, $O(CR^7R^8)_bN(R^6)C(O)N(R^6)_2$, $N(R^6)(CR^7R^8)_bN(R^6)C(O)N(R^6)_2$, $C(O)(CR^7R^8)_aN(R^6)C(O)N(R^6)_2$, $S(O)_e(CR^7R^8)_aN(R^6)C(O)N(R^6)_2$, $(CR^7R^8)_aC(O)N(OR^6)(R^6)$, $O(CR^7R^8)_aC(O)N(OR^6)(R^6)$, $N(R^6)(CR^7R^8)_aC(O)N(OR^6)(R^6)$, $C(O)(CR^7R^8)_aC(O)N(OR^6)(R^6)$, $S(O)_e(CR^7R^8)_aC(O)N(OR^6)(R^6)$, $(CR^7R^8)_a(OR^6)$, $O(CR^7R^8)_a(OR^6)$, $N(R^6)(CR^7R^8)_a(OR^6)$, $C(O)(CR^7R^8)_a(OR^6)$, $S(O)_e(CR^7R^8)_a(OR^6)$, $(CR^7R^8)_aN(R^6)_2$, $O(CR^7R^8)_bN(R^6)_2$, $N(R^6)(CR^7R^8)_bN(R^6)_2$, $C(O)(CR^7R^8)_aN(R^6)_2$, $S(O)_e(CR^7R^8)_aN(R^6)_2$, $(CR^7R^8)_aR^6$, $O(CR^7R^8)_aR^6$, $N(R^6)(CR^7R^8)_aR^6$, $C(O)(CR^7R^8)_aR^6$ and, $S(O)_e(CR^7R^8)_aR^6$ wherein $R^6$ is selected from the group consisting of hydrogen, alkyl, carboalkyl, alkylamine, alkylhydroxy and alkyloxyalkyl or $R^6$ is a 5 or 6 membered carbocyclic or heterocyclic group.

3. The compound of claim 2 wherein $R^6$ is selected from the group consisting of hydrogen, alkyl, dilower alkyl amine or a heterocyclic group represented by the list below or $N(R^6)_2$ may represent a 3 to 7 membered heterocyclic group,

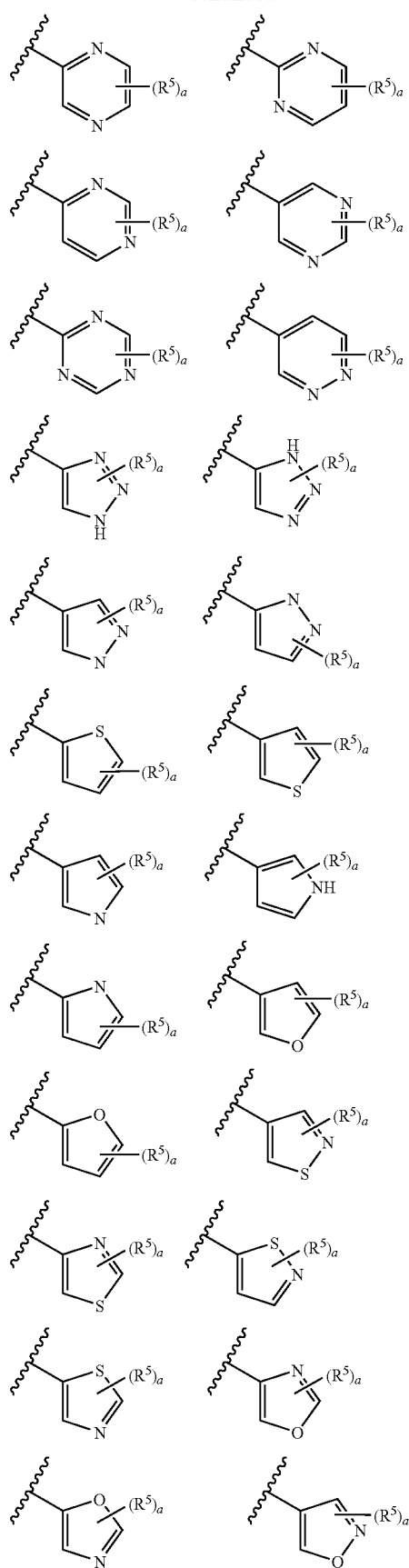
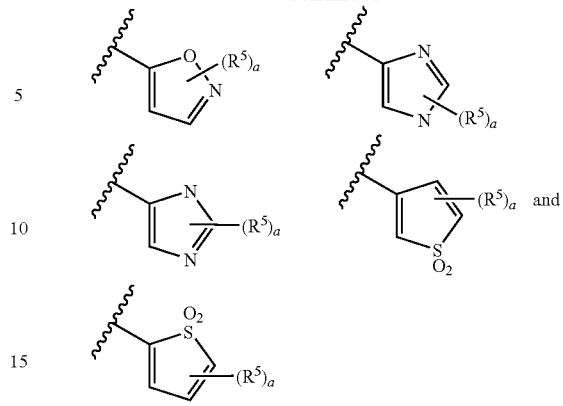
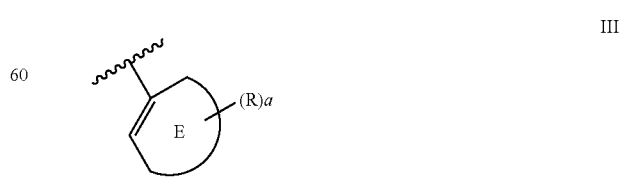

wherein $R^5$ is hydrogen, halogen, simple alkyl, $CF_3$, hydroxyl, $OR^7$, $N(R^7)_2$ or NO2.

4. The compound of claim 2 wherein $R^6$ is selected from the group consisting of hydrogen, alkyl, dilower alkyl amine, 3-fluoropyrrolidinyl, 3-fluoropiperidinyl, 2-pyridinyl, 3-pyridinyl, 4-pyridinyl, 3-pyrrolinyl, pyrrolidinyl, methyl isonipecotate, N-(2-methoxyethyl)-N-methylamyl, 1,2,3,6-tetrahydropyridinyl, morpholinyl, hexamethyleneiminyl, piperazinyl-2-one, piperazinyl, N-(2-methoxyethyl)ethylaminyl, thiomorpholinyl, heptamethyleneiminyl, 1-piperazinylcarboxaldehyde, 2,3,6,7-tetrahydro-(1H)-1,4-diazepinyl-5(4H)-one, N-methylhomopiperazinyl, (3-dimethylamino)pyrrolidinyl, N-(2-methoxyethyl)-N-propylaminyl, isoindolinyl, nipecotamidinyl, isonipecotamidinyl, 1-acetylpiperazinyl, 3-acetamidopyrrolidinyl, trans-decahydroisoquinolinyl, cis-decahydroisoquinolinyl, N-acetylhomopiperazinyl, 3-(diethylamino)pyrrolidinyl, 1,4-dioxa-8-azaspiro[4.5]decaninyl, 1-(2-methoxyethyl)-piperazinyl, 2-pyrrolidin-3-ylpyridinyl, 4-pyrrolidin-3-ylpyridinyl, 3-(methylsulfonyl)pyrrolidinyl, 3-picolylmethylaminyl, 2-(2-methylaminoethyl)pyridinyl, 1-(2-pyrimidyl)-piperazinyl, 1-(2-pyrazinyl)-piperazinyl, 2-methylaminomethyl-1,3-dioxolane, 2-(N-methyl-2-aminoethyl)-1,3-dioxolane, 3-(N-acetyl-N-methylamino)pyrrolidinyl, 2-methoxyethylaminyl, tetrahydrofurfurylaminyl, 4-aminotetrahydropyran, 2-amino-1-methoxybutane, 2-methoxyisopropylaminyl, 1-(3-aminopropyl)imidazole, histamyl, N,N-diisopropylethylenediaminyl, 1-benzyl-3-aminopyrrolidyl 2-(aminomethyl)-5-methylpyrazinyl, 2,2-dimethyl-1,3-dioxolane-4-methanaminyl, (R)-3-amino-1-N—BOC-pyrrolidinyl, 4-amino-1,2,2,6,6-pentamethylpiperidinyl, 4-aminomethyltetrahydropyran and ethanolamine.

5. The compound of claim 2 wherein E is a 5 or 6 membered carbocyclic aryl or heterocyclic aryl represented by formula III below:

III wherein said carbocyclic aryl and heterocyclic aryl is selected from the group consisting of:

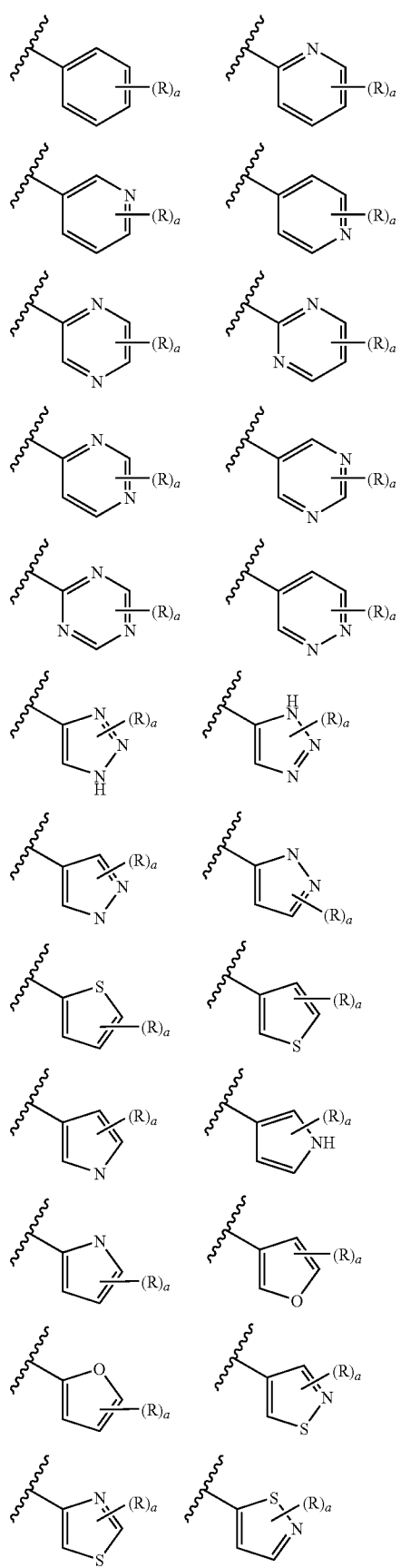
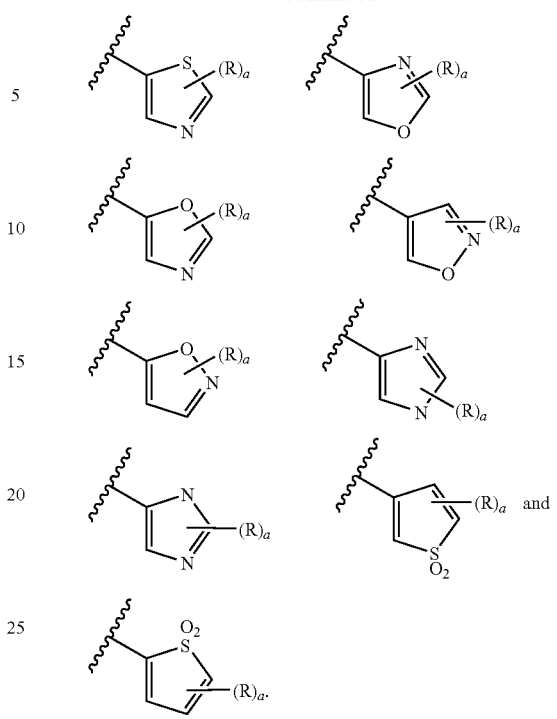
6. A compound of claim 3 wherein A is ≡.
7. A compound of claim 6 wherein
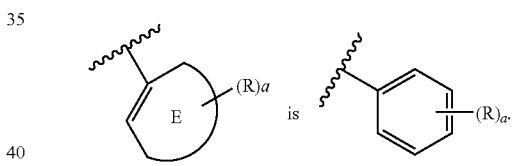
8. A compound of claim 6 wherein B is
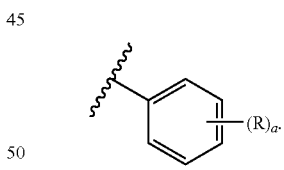
9. A compound of claim 6 wherein $R^2$ is $NH_2$.
10. A compound of claim 6 wherein $R^3$ is $NH_2$.
11. A compound of claim 8 wherein
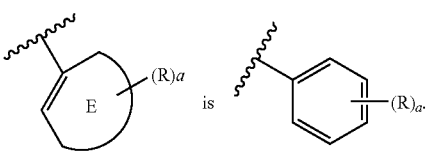

12. A compound of claim 6 wherein B is

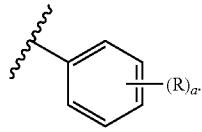

13. A compound of claim 6 wherein B is

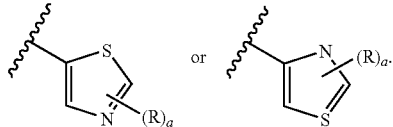

14. A compound of claim 12 wherein $R^2$ is $NH_2$.
15. A compound of claim 12 wherein $R^3$ is $NH_2$.
16. A compound of claim 13 wherein $R^2$ is $NH_2$.
17. A compound of claim 13 wherein $R^3$ is $NH_2$.
18. A compound of claim 12 wherein

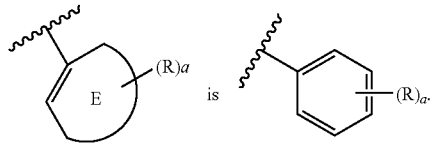

19. A compound of claim 13 wherein

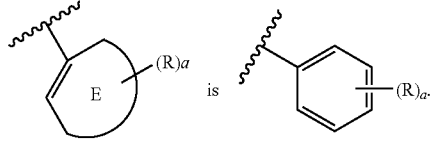

20. A compound of claim 14 wherein

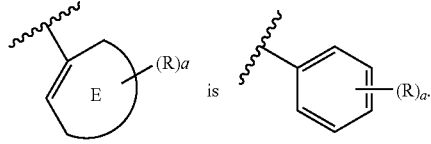

21. A compound of claim 15 wherein

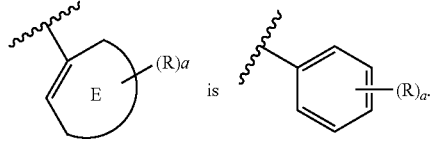

22. A compound of claim 16 wherein

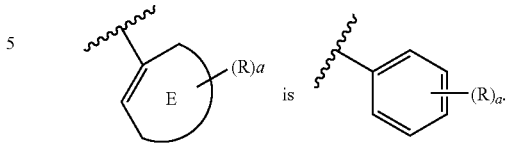

23. A compound of claim 17 wherein

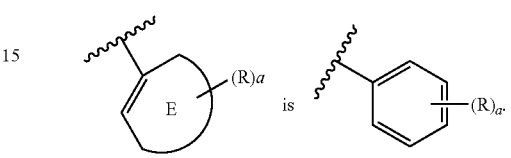

24. A compound of claim 18 wherein R selected from the group consisting of halogen, alkyl, $CF_3$, $OCF_3$, $OCF_2H$, $CH_2CN$, CN, $S(O)_eR^6$, $SO_2N(R^6)_2$, $OP(O)(OR^6)_2$, $OCH_2O$, HC=N—NH, N=CH—S, N=N—NH, $(CR^7R^8)_aC(O)R^6$, $O(CR^7R^8)_aC(O)R^6$, $N(R^6)(CR^7R^8)_aC(O)R^6$, $C(O)(CR^7R^8)_aC(O)R^6$, $S(O)_e(CR^7R^8)_aC(O)R^6$, $(CR^7R^8)_aC(O)OR^6$, $O(CR^7R^8)_aC(O)OR^6$, $N(R^6)(CR^7R^8)_aC(O)OR^6$, $C(O)(CR^7R^8)_aC(O)OR^6$, $S(O)_e(CR^7R^8)_aC(O)OR^6$, $(CR^7R^8)_aC(O)N(R^6)_2$, $O(CR^7R^8)_aC(O)N(R^6)_2$, $N(R^6)(CR^7R^8)_aC(O)N(R^6)_2$, $C(O)(CR^7R^8)_aC(O)N(R^6)_2$, $S(O)_e(CR^7R^8)_aC(O)N(R^6)_2$, $(CR^7R^8)_aN(R^6)C(O)N(R^6)_2$, $O(CR^7R^8)_bN(R^6)C(O)N(R^6)_2$, $N(R^6)(CR^7R^8)_bN(R^6)C(O)N(R^6)_2$, $C(O)(CR^7R^8)_aN(R^6)C(O)N(R^6)_2$, $S(O)_e(CR^7R^8)_aN(R^6)C(O)N(R^6)_2$, $(CR^7R^8)_aC(O)N(OR^6)(R^6)$, $O(CR^7R^8)_aC(O)N(OR^6)(R^6)$, $N(R^6)(CR^7R^8)_aC(O)N(OR^6)(R^6)$, $C(O)(CR^7R^8)_aC(O)N(OR^6)(R^6)$, $S(O)_e(CR^7R^8)_aC(O)N(OR^6)(R^6)$, $(CR^7R^8)_a(OR^6)$, $O(CR^7R^8)_a(OR^6)$, $N(R^6)(CR^7R^8)_a(OR^6)$, $C(O)(CR^7R^8)_a(OR^6)$, $S(O)_e(CR^7R^8)_a(OR^6)$, $(CR^7R^8)_aN(R^6)_2$, $O(CR^7R^8)_bN(R^6)_2$, $N(R^6)(CR^7R^8)_bN(R^6)_2$, $C(O)(CR^7R^8)_aN(R^6)_2$, $S(O)_e(CR^7R^8)_aN(R^6)_2$, $(CR^7R^8)_aR^6$, $O(CR^7R^8)_aR^6$, $N(R^6)(CR^7R^8)_aR^6$, $C(O)(CR^7R^8)_aR^6$ and $S(O)_e(CR^7R^8)_aR^6$.

25. A compound of claim 19 wherein R is selected from the group consisting of halogen, alkyl, $CF_3$, $OCF_3$, $OCF_2H$, $CH_2CN$, CN, $S(O)_eR^6$, $SO_2N(R^6)_2$, $OP(O)(OR^6)_2$, $OCH_2O$, HC=N—NH, N=CH—S, N=N—NH, $(CR^7R^8)_aC(O)R^6$, $O(CR^7R^8)_aC(O)R^6$, $N(R^6)(CR^7R^8)_aC(O)R^6$, $C(O)(CR^7R^8)_aC(O)R^6$, $S(O)_e(CR^7R^8)_aC(O)R^6$, $(CR^7R^8)_aC(O)OR^6$, $O(CR^7R^8)_aC(O)OR^6$, $N(R^6)(CR^7R^8)_aC(O)OR^6$, $C(O)(CR^7R^8)_aC(O)OR^6$, $S(O)_e(CR^7R^8)_aC(O)OR^6$, $(CR^7R^8)_aC(O)N(R^6)_2$, $O(CR^7R^8)_aC(O)N(R^6)_2$, $N(R^6)(CR^7R^8)_aC(O)N(R^6)_2$, $C(O)(CR^7R^8)_aC(O)N(R^6)_2$, $S(O)_e(CR^7R^8)_aC(O)N(R^6)_2$, $(CR^7R^8)_aN(R^6)C(O)N(R^6)_2$, $O(CR^7R^8)_bN(R^6)C(O)N(R^6)_2$, $N(R^6)(CR^7R^8)_bN(R^6)C(O)N(R^6)_2$, $C(O)(CR^7R^8)_aN(R^6)C(O)N(R^6)_2$, $S(O)_e(CR^7R^8)_aN(R^6)C(O)N(R^6)_2$, $(CR^7R^8)_aC(O)N(OR^6)(R^6)$, $O(CR^7R^8)_aC(O)N(OR^6)(R^6)$, $N(R^6)(CR^7R^8)_aC(O)N(OR^6)(R^6)$, $C(O)(CR^7R^8)_aC(O)N(OR^6)(R^6)$, $S(O)_e(CR^7R^8)_aC(O)N(OR^6)(R^6)$, $(CR^7R^8)_a(OR^6)$, $O(CR^7R^8)_a(OR^6)$, $N(R^6)(CR^7R^8)_a(OR^6)$, $C(O)(CR^7R^8)_a(OR^6)$, $S(O)_e(CR^7R^8)_a(OR^6)$, $(CR^7R^8)_aN(R^6)_2$, $O(CR^7R^8)_bN(R^6)_2$, $N(R^6)(CR^7R^8)_bN(R^6)_2$, $C(O)(CR^7R^8)_aN(R^6)_2$, $S(O)_e(CR^7R^8)_aN(R^6)_2$, $(CR^7R^8)_aR^6$, $O(CR^7R^8)_aR^6$, $N(R^6)(CR^7R^8)_aR^6$, $C(O)(CR^7R^8)_aR^6$ and $S(O)_e(CR^7R^8)_aR^6$.

26. A compound of claim 20 wherein R is selected from the group consisting of halogen, alkyl, $CF_3$, $OCF_3$, $OCF_2H$, $CH_2CN$, CN, $S(O)_eR^6$, $SO_2N(R^6)_2$, $OP(O)(OR^6)_2$, $OCH_2O$, HC=N—NH, N=CH—S, N=N—NH, $(CR^7R^8)_aC(O)R^6$, $O(CR^7R^8)_aC(O)R^6$, $N(R^6)(CR^7R^8)_aC(O)R^6$, $C(O)(CR^7R^8)_a$ C(O)R$^6$, S(O)$_e$(CR$^7$R$^8$)$_a$C(O)R$^6$, (CR$^7$R$^8$)$_a$C(O)OR$^6$, O(CR$^7$R$^8$)$_a$C(O)OR$^6$, N(R$^6$)(CR$^7$R$^8$)$_a$C(O)OR$^6$, C(O)(CR$^7$R$^8$)$_a$C(O)OR$^6$, S(O)$_e$(CR$^7$R$^8$)$_a$C(O)OR$^6$, (CR$^7$R$^8$)$_a$C(O)N(R$^6$)$_2$, O(CR$^7$R$^8$)$_a$C(O)N(R$^6$)$_2$, N(R$^6$)(CR$^7$R$^8$)$_a$C(O)N(R$^6$)$_2$, C(O)(CR$^7$R$^8$)$_a$C(O)N(R$^6$)$_2$, S(O)$_e$(CR$^7$R$^8$)$_a$C(O)N(R$^6$)$_2$, (CR$^7$R$^8$)$_a$N(R$^6$)C(O)N(R$^6$)$_2$, O(CR$^7$R$^8$)$_b$N(R$^6$)C(O)N(R$^6$)$_2$, N(R$^6$)(CR$^7$R$^8$)$_b$N(R$^6$)C(O)N(R$^6$)$_2$, C(O)(CR$^7$R$^8$)$_a$N(R$^6$)C(O)N(R$^6$)$_2$, S(O)$_e$(CR$^7$R$^8$)$_a$N(R$^6$)C(O)N(R$^6$)$_2$, (CR$^7$R$^8$)$_a$C(O)N(OR$^6$)(R$^6$), O(CR$^7$R$^8$)$_a$C(O)N(OR$^6$)(R$^6$), N(R$^6$)(CR$^7$R$^8$)$_a$C(O)N(OR$^6$)(R$^6$), C(O)(CR$^7$R$^8$)$_a$C(O)N(OR$^6$)(R$^6$), S(O)$_e$(CR$^7$R$^8$)$_a$C(O)N(OR$^6$)(R$^6$), (CR$^7$R$^8$)$_a$(OR$^6$), O(CR$^7$R$^8$)$_a$(OR$^6$), N(R$^6$)(CR$^7$R$^8$)$_a$(OR$^6$), C(O)(CR$^7$R$^8$)$_a$(OR$^6$), S(O)$_e$(CR$^7$R$^8$)$_a$(OR$^6$), (CR$^7$R$^8$)$_a$N(R$^6$)$_2$, O(CR$^7$R$^8$)$_b$N(R$^6$)$_2$, N(R$^6$)(CR$^7$R$^8$)$_b$N(R$^6$)$_2$, C(O)(CR$^7$R$^8$)$_a$N(R$^6$)$_2$, S(O)$_e$(CR$^7$R$^8$)$_a$N(R$^6$)$_2$, (CR$^7$R$^8$)$_a$R$^6$, O(CR$^7$R$^8$)$_a$R$^6$, N(R$^6$)(CR$^7$R$^8$)$_a$R$^6$, C(O)(CR$^7$R$^8$)$_a$R$^6$ and S(O)$_e$(CR$^7$R$^8$)$_a$R$^6$.

27. A compound of claim 21 wherein R is selected from the group consisting of halogen, alkyl, CF$_3$, OCF$_3$, OCF$_2$H, CH$_2$CN, CN, S(O)$_e$R$^6$, SO$_2$N(R$^6$)$_2$, OP(O)(OR$^6$)$_2$, OCH$_2$O, HC=N—NH, N=CH—S, N=N—NH, (CR$^7$R$^8$)$_a$C(O)R$^6$, O(CR$^7$R$^8$)$_a$C(O)R$^6$, N(R$^6$)(CR$^7$R$^8$)$_a$C(O)R$^6$, C(O)(CR$^7$R$^8$)$_a$C(O)R$^6$, S(O)$_e$(CR$^7$R$^8$)$_a$C(O)R$^6$, (CR$^7$R$^8$)$_a$C(O)OR$^6$, O(CR$^7$R$^8$)$_a$C(O)OR$^6$, N(R$^6$)(CR$^7$R$^8$)$_a$C(O)OR$^6$, C(O)(CR$^7$R$^8$)$_a$C(O)OR$^6$, S(O)$_e$(CR$^7$R$^8$)$_a$C(O)OR$^6$, (CR$^7$R$^8$)$_a$C(O)N(R$^6$)$_2$, O(CR$^7$R$^8$)$_a$C(O)N(R$^6$)$_2$, N(R$^6$)(CR$^7$R$^8$)$_a$C(O)N(R$^6$)$_2$, C(O)(CR$^7$R$^8$)$_a$C(O)N(R$^6$)$_2$, S(O)$_e$(CR$^7$R$^8$)$_a$C(O)N(R$^6$)$_2$, (CR$^7$R$^8$)$_a$N(R$^6$)C(O)N(R$^6$)$_2$, O(CR$^7$R$^8$)$_b$N(R$^6$)C(O)N(R$^6$)$_2$, N(R$^6$)(CR$^7$R$^8$)$_b$N(R$^6$)C(O)N(R$^6$)$_2$, C(O)(CR$^7$R$^8$)$_a$N(R$^6$)C(O)N(R$^6$)$_2$, S(O)$_e$(CR$^7$R$^8$)$_a$N(R$^6$)C(O)N(R$^6$)$_2$, (CR$^7$R$^8$)$_a$C(O)N(OR$^6$)(R$^6$), O(CR$^7$R$^8$)$_a$C(O)N(OR$^6$)(R$^6$), N(R$^6$)(CR$^7$R$^8$)$_a$C(O)N(OR$^6$)(R$^6$), C(O)(CR$^7$R$^8$)$_a$C(O)N(OR$^6$)(R$^6$), S(O)$_e$(CR$^7$R$^8$)$_a$C(O)N(OR$^6$)(R$^6$), (CR$^7$R$^8$)$_a$(OR$^6$), O(CR$^7$R$^8$)$_a$(OR$^6$), N(R$^6$)(CR$^7$R$^8$)$_a$(OR$^6$), C(O)(CR$^7$R$^8$)$_a$(OR$^6$), S(O)$_e$(CR$^7$R$^8$)$_a$(OR$^6$), (CR$^7$R$^8$)$_a$N(R$^6$)$_2$, O(CR$^7$R$^8$)$_b$N(R$^6$)$_2$, N(R$^6$)(CR$^7$R$^8$)$_b$N(R$^6$)$_2$, C(O)(CR$^7$R$^8$)$_a$N(R$^6$)$_2$, S(O)$_e$(CR$^7$R$^8$)$_a$N(R$^6$)$_2$, (CR$^7$R$^8$)$_a$R$^6$, O(CR$^7$R$^8$)$_a$R$^6$, N(R$^6$)(CR$^7$R$^8$)$_a$R$^6$, C(O)(CR$^7$R$^8$)$_a$R$^6$ and S(O)$_e$(CR$^7$R$^8$)$_a$R$^6$.

28. A compound of claim 22 wherein R is selected from the group consisting of halogen, alkyl, CF$_3$, OCF$_3$, OCF$_2$H, CH$_2$CN, CN, S(O)$_e$R$^6$, SO$_2$N(R$^6$)$_2$, OP(O)(OR$^6$)$_2$, OCH$_2$O, HC=N—NH, N=CH—S, N=N—NH, (CR$^7$R$^8$)$_a$C(O)R$^6$, O(CR$^7$R$^8$)$_a$C(O)R$^6$, N(R$^6$)(CR$^7$R$^8$)$_a$C(O)R$^6$, C(O)(CR$^7$R$^8$)$_a$C(O)R$^6$, S(O)$_e$(CR$^7$R$^8$)$_a$C(O)R$^6$, (CR$^7$R$^8$)$_a$C(O)OR$^6$, O(CR$^7$R$^8$)$_a$C(O)OR$^6$, N(R$^6$)(CR$^7$R$^8$)$_a$C(O)OR$^6$, C(O)(CR$^7$R$^8$)$_a$C(O)OR$^6$, S(O)$_e$(CR$^7$R$^8$)$_a$C(O)OR$^6$, (CR$^7$R$^8$)$_a$C(O)N(R$^6$)$_2$, O(CR$^7$R$^8$)$_a$C(O)N(R$^6$)$_2$, N(R$^6$)(CR$^7$R$^8$)$_a$C(O)N(R$^6$)$_2$, C(O)(CR$^7$R$^8$)$_a$C(O)N(R$^6$)$_2$, S(O)$_e$(CR$^7$R$^8$)$_a$C(O)N(R$^6$)$_2$, (CR$^7$R$^8$)$_a$N(R$^6$)C(O)N(R$^6$)$_2$, O(CR$^7$R$^8$)$_b$N(R$^6$)C(O)N(R$^6$)$_2$, N(R$^6$)(CR$^7$R$^8$)$_b$N(R$^6$)C(O)N(R$^6$)$_2$, C(O)(CR$^7$R$^8$)$_a$N(R$^6$)C(O)N(R$^6$)$_2$, S(O)$_e$(CR$^7$R$^8$)$_a$N(R$^6$)C(O)N(R$^6$)$_2$, (CR$^7$R$^8$)$_a$C(O)N(OR$^6$)(R$^6$), O(CR$^7$R$^8$)$_a$C(O)N(OR$^6$)(R$^6$), N(R$^6$)(CR$^7$R$^8$)$_a$C(O)N(OR$^6$)(R$^6$), C(O)(CR$^7$R$^8$)$_a$C(O)N(OR$^6$)(R$^6$), S(O)$_e$(CR$^7$R$^8$)$_a$C(O)N(OR$^6$)(R$^6$), (CR$^7$R$^8$)$_a$(OR$^6$), O(CR$^7$R$^8$)$_a$(OR$^6$), N(R$^6$)(CR$^7$R$^8$)$_a$(OR$^6$), C(O)(CR$^7$R$^8$)$_a$(OR$^6$), S(O)$_e$(CR$^7$R$^8$)$_a$(OR$^6$), (CR$^7$R$^8$)$_a$N(R$^6$)$_2$, O(CR$^7$R$^8$)$_b$N(R$^6$)$_2$, N(R$^6$)(CR$^7$R$^8$)$_b$N(R$^6$)$_2$, C(O)(CR$^7$R$^8$)$_a$N(R$^6$)$_2$, S(O)$_e$(CR$^7$R$^8$)$_a$N(R$^6$)$_2$, (CR$^7$R$^8$)$_a$R$^6$, O(CR$^7$R$^8$)$_a$R$^6$, N(R$^6$)(CR$^7$R$^8$)$_a$R$^6$, C(O)(CR$^7$R$^8$)$_a$R$^6$ and S(O)$_e$(CR$^7$R$^8$)$_a$R$^6$.

29. A compound of claim 23 wherein R is selected from the group consisting of halogen, alkyl, CF$_3$, OCF$_3$, OCF$_2$H, CH$_2$CN, CN, S(O)$_e$R$^6$, SO$_2$N(R$^6$)$_2$, OP(O)(OR$^6$)$_2$, OCH$_2$O, HC=N—NH, N=CH—S, N=N—NH, (CR$^7$R$^8$)$_a$C(O)R$^6$, O(CR$^7$R$^8$)$_a$C(O)R$^6$, N(R$^6$)(CR$^7$R$^8$)$_a$C(O)R$^6$, C(O)(CR$^7$R$^8$)$_a$C(O)R$^6$, S(O)$_e$(CR$^7$R$^8$)$_a$C(O)R$^6$, (CR$^7$R$^8$)$_a$C(O)OR$^6$, O(CR$^7$R$^8$)$_a$C(O)OR$^6$, N(R$^6$)(CR$^7$R$^8$)$_a$C(O)OR$^6$, C(O)(CR$^7$R$^8$)$_a$C(O)OR$^6$, S(O)$_e$(CR$^7$R$^8$)$_a$C(O)OR$^6$, (CR$^7$R$^8$)$_a$C(O)N(R$^6$)$_2$, O(CR$^7$R$^8$)$_a$C(O)N(R$^6$)$_2$, N(R$^6$)(CR$^7$R$^8$)$_a$C(O)N(R$^6$)$_2$, C(O)(CR$^7$R$^8$)$_a$C(O)N(R$^6$)$_2$, S(O)$_e$(CR$^7$R$^8$)$_a$C(O)N(R$^6$)$_2$, (CR$^7$R$^8$)$_a$N(R$^6$)C(O)N(R$^6$)$_2$, O(CR$^7$R$^8$)$_b$N(R$^6$)C(O)N(R$^6$)$_2$, N(R$^6$)(CR$^7$R$^8$)$_b$N(R$^6$)C(O)N(R$^6$)$_2$, C(O)(CR$^7$R$^8$)$_a$N(R$^6$)C(O)N(R$^6$)$_2$, S(O)$_e$(CR$^7$R$^8$)$_a$N(R$^6$)C(O)N(R$^6$)$_2$, (CR$^7$R$^8$)$_a$C(O)N(OR$^6$)(R$^6$), O(CR$^7$R$^8$)$_a$C(O)N(OR$^6$)(R$^6$), N(R$^6$)(CR$^7$R$^8$)$_a$C(O)N(OR$^6$)(R$^6$), C(O)(CR$^7$R$^8$)$_a$C(O)N(OR$^6$)(R$^6$), S(O)$_e$(CR$^7$R$^8$)$_a$C(O)N(OR$^6$)(R$^6$), (CR$^7$R$^8$)$_a$(OR$^6$), O(CR$^7$R$^8$)$_a$(OR$^6$), N(R$^6$)(CR$^7$R$^8$)$_a$(OR$^6$), C(O)(CR$^7$R$^8$)$_a$(OR$^6$), S(O)$_e$(CR$^7$R$^8$)$_a$(OR$^6$), (CR$^7$R$^8$)$_a$N(R$^6$)$_2$, O(CR$^7$R$^8$)$_b$N(R$^6$)$_2$, N(R$^6$)(CR$^7$R$^8$)$_b$N(R$^6$)$_2$, C(O)(CR$^7$R$^8$)$_a$N(R$^6$)$_2$, S(O)$_e$(CR$^7$R$^8$)$_a$N(R$^6$)$_2$, (CR$^7$R$^8$)$_a$R$^6$, O(CR$^7$R$^8$)$_a$R$^6$, N(R$^6$)(CR$^7$R$^8$)$_a$R$^6$, C(O)(CR$^7$R$^8$)$_a$R$^6$ and S(O)$_e$(CR$^7$R$^8$)$_a$R$^6$.

30. A compound of claim 24 wherein R is selected from the group consisting of N(R$^6$)(CR$^7$R$^8$)$_a$C(O)R$^6$, (CR$^7$R$^8$)$_a$C(O)N(R$^6$)$_2$, (CR$^7$R$^8$)$_a$C(O)N(OR$^6$)(R$^6$), (CR$^7$R$^8$)$_a$(OR$^6$), C(O)(CR$^7$R$^8$)$_a$N(R$^6$)$_2$ and N(R$^6$)(CR$^7$R$^8$)$_a$C(O)OR$^6$.

31. A compound of claim 25 wherein R is selected from the group consisting of N(R$^6$)(CR$^7$R$^8$)$_a$C(O)R$^6$, (CR$^7$R$^8$)$_a$C(O)N(R$^6$)$_2$, (CR$^7$R$^8$)$_a$C(O)N(OR$^6$)(R$^6$), (CR$^7$R$^8$)$_a$(OR$^6$), C(O)(CR$^7$R$^8$)$_a$N(R$^6$)$_2$ and N(R$^6$)(CR$^7$R$^8$)$_a$C(O)OR$^6$.

32. A compound of claim 26 wherein R is selected from the group consisting of N(R$^6$)(CR$^7$R$^8$)$_a$C(O)R$^6$, (CR$^7$R$^8$)$_a$C(O)N(R$^6$)$_2$, (CR$^7$R$^8$)$_a$C(O)N(OR$^6$)(R$^6$), (CR$^7$R$^8$)$_a$(OR$^6$), C(O)(CR$^7$R$^8$)$_a$N(R$^6$)$_2$ and N(R$^6$)(CR$^7$R$^8$)$_a$C(O)OR$^6$.

33. A compound of claim 27 wherein R is selected from the group consisting of N(R$^6$)(CR$^7$R$^8$)$_a$C(O)R$^6$, (CR$^7$R$^8$)$_a$C(O)N(R$^6$)$_2$, (CR$^7$R$^8$)$_a$C(O)N(OR$^6$)(R$^6$), (CR$^7$R$^8$)$_a$(OR$^6$), C(O)(CR$^7$R$^8$)$_a$N(R$^6$)$_2$ and N(R$^6$)(CR$^7$R$^8$)$_a$C(O)OR$^6$.

34. A compound of claim 28 wherein R is selected from the group consisting of N(R$^6$)(CR$^7$R$^8$)$_a$C(O)R$^6$, (CR$^7$R$^8$)$_a$C(O)N(R$^6$)$_2$, (CR$^7$R$^8$)$_a$C(O)N(OR$^6$)(R$^6$), (CR$^7$R$^8$)$_a$(OR$^6$), C(O)(CR$^7$R$^8$)$_a$N(R$^6$)$_2$ and N(R$^6$)(CR$^7$R$^8$)$_a$C(O)OR$^6$.

35. A compound of claim 29 wherein R is selected from the group consisting of N(R$^6$)(CR$^7$R$^8$)$_a$C(O)R$^6$, (CR$^7$R$^8$)$_a$C(O)N(R$^6$)$_2$, (CR$^7$R$^8$)$_a$C(O)N(OR$^6$)(R$^6$), (CR$^7$R$^8$)$_a$(OR$^6$), C(O)(CR$^7$R$^8$)$_a$N(R$^6$)$_2$ and N(R$^6$)(CR$^7$R$^8$)$_a$C(O)OR$^6$.

36. A compound of claim 24 selected from the group consisting of
- 5-[(3-hydroxyphenyl)ethynyl]-N-[(4-methoxyphenyl)(methyl)oxo-λ$^6$-sulfanylidene]nicotinamide,
- N-[methyl(oxo)phenyl-λ$^6$-sulfanylidene]-5-(phenylethynyl)nicotinamide,
- N-[methyl(oxo)phenyl-λ$^6$-sulfanylidene]-5-[(4-methylphenyl)ethynyl]nicotinamide,
- 5-[(3-hydroxyphenyl)ethynyl]-N-[methyl(oxo)phenyl-λ$^6$-sulfanylidene]nicotinamide,
- 5-[(3-methoxyphenyl)ethynyl]-N-[methyl(oxo)phenyl-λ$^6$-sulfanylidene]nicotinamide,
- 5-[(4-methoxyphenyl)ethynyl]-N-[methyl(oxo)phenyl-λ$^6$-sulfanylidene]nicotinamide,
- 5-[(4-bromophenyl)ethynyl]-N-[methyl(oxo)phenyl-λ$^6$-sulfanylidene]nicotinamide,
- 5-[(4-chlorophenyl)ethynyl]-N-[methyl(oxo)phenyl-λ$^6$-sulfanylidene]nicotinamide,
- 5-[(2-chlorophenyl)ethynyl]-N-[methyl(oxo)phenyl-λ$^6$-sulfanylidene]nicotinamide,
- N-[methyl(oxo)phenyl-λ$^6$-sulfanylidene]-5-{[4-(trifluoromethyl)phenyl]ethynyl}nicotinamide,
- 5-[(2-bromophenyl)ethynyl]-N-[methyl(oxo)phenyl-λ$^6$-sulfanylidene]nicotinamide,
- 5-[(2,4-difluorophenyl)ethynyl]-N-[methyl(oxo)phenyl-λ$^6$-sulfanylidene]nicotinamide,
- 5-[(3-fluorophenyl)ethynyl]-N-[methyl(oxo)phenyl-λ$^6$-sulfanylidene]nicotinamide,
- N-[methyl(oxo)phenyl-λ$^6$-sulfanylidene]-5-[(2-methylphenyl)ethynyl]nicotinamide, 5-[(3-bromophenyl)ethynyl]-N-[methyl(oxo)phenyl-λ⁶-sulfanylidene]nicotinamide,
5-[(3-chlorophenyl)ethynyl]-N-[methyl(oxo)phenyl-λ⁶-sulfanylidene]nicotinamide,
5-[(3,5-dimethoxyphenyl)ethynyl]-N-[methyl(oxo)phenyl-λ⁶-sulfanylidene]nicotinamide,
5-[(4-methoxy-2-methylphenyl)ethynyl]-N-[methyl(oxo)phenyl-λ⁶-sulfanylidene]nicotinamide,
5-[(4-fluoro-3-methylphenyl)ethynyl]-N-[methyl(oxo)phenyl-λ⁶-sulfanylidene]nicotinamide,
5-[(3-hydroxyphenyl)ethynyl]-N-[methyl(4-methylphenyl)oxo-λ⁶-sulfanylidene]nicotinamide,
5-[(3-methoxyphenyl)ethynyl]-N-[methyl(4-methylphenyl)oxo-λ⁶-sulfanylidene]nicotinamide,
5-[(4-methoxyphenyl)ethynyl]-N-[methyl(4-methylphenyl)oxo-λ⁶-sulfanylidene]nicotinamide,
N-[(4-chlorophenyl)(methyl)oxo-λ⁶-sulfanylidene]-5-(phenylethynyl)nicotinamide,
N-[(4-chlorophenyl)(methyl)oxo-λ⁶-sulfanylidene]-5-[(3-hydroxyphenyl)ethynyl]nicotinamide,
N-{[3-(acetylamino)phenyl](methyl)oxo-λ⁶-sulfanylidene}-5-[(3-hydroxyphenyl)ethynyl]nicotinamide,
N-[(3-chlorophenyl)(methyl)oxo-λ⁶-sulfanylidene]-5-(phenylethynyl)nicotinamide,
N-[(3-chlorophenyl)(methyl)oxo-λ⁶-sulfanylidene]-5-[(3-hydroxyphenyl)ethynyl]nicotinamide,
N-[(3,5-dichlorophenyl)(methyl)oxo-λ⁶-sulfanylidene]-5-(phenylethynyl)nicotinamide,
N-[(3,5-dichlorophenyl)(methyl)oxo-λ⁶-sulfanylidene]-5-[(3-hydroxyphenyl)ethynyl]nicotinamide,
5-[(3-hydroxyphenyl)ethynyl]-N-[methyl(3-methylphenyl)oxo-λ⁶-sulfanylidene]nicotinamide,
N-[(3-methoxyphenyl)(methyl)oxo-λ⁶-sulfanylidene]-5-(phenylethynyl)nicotinamide,
5-[(3-hydroxyphenyl)ethynyl]-N-[(3-methoxyphenyl)(methyl)oxo-λ⁶-sulfanylidene]nicotinamide,
N-[(3,4-dimethylphenyl)(methyl)oxo-λ⁶-sulfanylidene]-5-(phenylethynyl)nicotinamide,
N-[(3,4-dimethylphenyl)(methyl)oxo-λ⁶-sulfanylidene]-5-[(3-hydroxyphenyl)ethynyl]nicotinamide,
N-[(3,5-dimethylphenyl)(methyl)oxo-λ⁶-sulfanylidene]-5-(phenylethynyl)nicotinamide,
N-[(3,4-dimethoxyphenyl)(methyl)oxo-λ⁶-sulfanylidene]-5-[(3-hydroxyphenyl)ethynyl]nicotinamide,
(S)-N-[methyl(oxo)phenyl-λ⁶-sulfanylidene]-5-(phenylethynyl)nicotinamide,
(S)-5-[(2-fluorophenyl)ethynyl]-N-[methyl(oxo)phenyl-λ⁶-sulfanylidene]nicotinamide,
(S)-5-[(4-chlorophenyl)ethynyl]-N-[methyl(oxo)phenyl-λ⁶-sulfanylidene]nicotinamide,
(S)-5-[(3-hydroxyphenyl)ethynyl]-N-[methyl(oxo)phenyl-λ⁶-sulfanylidene]nicotinamide,
(S)-5-[(4-hydroxyphenyl)ethynyl]-N-[methyl(oxo)phenyl-λ⁶-sulfanylidene]nicotinamide,
(R)-5-[(3-hydroxyphenyl)ethynyl]-N-[methyl(oxo)phenyl-λ⁶-sulfanylidene]nicotinamide,
(S)-5-[(4-hydroxy-3-methylphenyl)ethynyl]-N-[methyl(oxo)phenyl-λ⁶-sulfanylidene]nicotinamide,
(S)-5-(1H-indol-6-ylethynyl)-N-[methyl(oxo)phenyl-λ⁶-sulfanylidene]nicotinamide,
(S)-N-[methyl(oxo)phenyl-λ⁶-sulfanylidene]-5-({4-[(2-thienylcarbonyl)amino]phenyl}ethynyl)nicotinamide,
(S)-5-{[3-(acetylamino)phenyl]ethynyl}-N-[methyl(oxo)phenyl-λ⁶-sulfanylidene]nicotinamide,
(S)-5-({4-[(2,6-difluorobenzoyl)amino]phenyl}ethynyl)-N-[methyl(oxo)phenyl-λ⁶-sulfanylidene]nicotinamide,
(S)-5-({4-[(4-fluorobenzoyl)amino]phenyl}ethynyl)-N-[methyl(oxo)phenyl-λ⁶-sulfanylidene]nicotinamide,
(S)-5-({4-[(4-methylbenzoyl)amino]phenyl}ethynyl)-N-[methyl(oxo)phenyl-λ⁶-sulfanylidene]nicotinamide,
(S)-5-({4-[(2-methylbenzoyl)amino]phenyl}ethynyl)-N-[methyl(oxo)phenyl-λ⁶-sulfanylidene]nicotinamide,
(S)-N-[methyl(oxo)phenyl-λ⁶-sulfanylidene]-5-({3-[(2-thienylcarbonyl)amino]phenyl}ethynyl)nicotinamide,
(S)-5-[(3-{[(1,3-dimethyl-1H-pyrazol-5-yl)carbonyl]amino}phenyl)ethynyl]-N-[methyl(oxo)phenyl-λ⁶-sulfanylidene]nicotinamide,
(S)-N-[methyl(oxo)phenyl-λ⁶-sulfanylidene]-5-({3-[(3-methylthienyl-2-carbonyl)amino]phenyl}ethynyl)nicotinamide,
(S)-tert-butyl (3-{[5-({[methyl(oxo)phenyl-λ⁶-sulfanylidene]amino}carbonyl)pyridin-3-yl]ethynyl}phenyl)carbamate and
(S)-5-({3-[(2-methylbenzoyl)amino]phenyl}ethynyl)-N-[methyl(oxo)phenyl-λ⁶-sulfanylidene]nicotinamide.

37. A compound of claim 30 selected from (S)-5-({4-[(2-methylbenzoyl)amino]phenyl}ethynyl)-N-[methyl(oxo)phenyl-λ⁶-sulfanylidene]nicotinamide,
(S)-N-[methyl(oxo)phenyl-λ⁶-sulfanylidene]-5-({3-[(2-thienylcarbonyl)amino]phenyl}ethynyl)nicotinamide,
(S)-5-[(3-{[(1,3-dimethyl-1H-pyrazol-5-yl)carbonyl]amino}phenyl)ethynyl]-N-[methyl(oxo)phenyl-λ⁶-sulfanylidene]nicotinamide,
(S)-N-[methyl(oxo)phenyl-λ⁶-sulfanylidene]-5-({3-[(3-methylthienyl-2-carbonyl)amino]phenyl}ethynyl)nicotinamide
(S)-tert-butyl (3-{[5-({[methyl(oxo)phenyl-λ⁶-sulfanylidene]amino}carbonyl)pyridin-3-yl]ethynyl}phenyl)carbamate,
(S)-5-({3-[(2-methylbenzoyl)amino]phenyl}ethynyl)-N-[methyl(oxo)phenyl-λ⁶-sulfanylidene]nicotinamide and
(S)-5-{[3-(acetylamino)phenyl]ethynyl}-N-[methyl(oxo)phenyl-λ⁶-sulfanylidene]nicotinamide.

38. A compound of claim 25 selected from the group consisting of (S)-tert-butyl (5-{[5-({[methyl(oxo)phenyl-λ⁶-sulfanylidene]amino}carbonyl)pyridin-3-yl]ethynyl}-1,3-thiazol-2-yl)carbamate,
(S)-5-[(2-amino-1,3-thiazol-5-yl)ethynyl]-N-[methyl(oxo)phenyl-λ⁶-sulfanylidene]nicotinamide and
(S)-5-{[2-(benzoylamino)-1,3-thiazol-5-yl]ethynyl}-N-[methyl(oxo)phenyl-λ⁶ sulfanylidene]nicotinamide.

39. A compound according to claim 31 that is (S)-5-{[2-(benzoylamino)-1,3-thiazol-5-yl]ethynyl}-N-[methyl(oxo)phenyl-λ⁶-sulfanylidene]nicotinamide.

40. A compound according to claim 26 selected from the group consisting of (S)-6-amino-5-[(3-hydroxyphenyl)ethynyl]-N-[methyl(oxo)phenyl-λ⁶-sulfanylidene]nicotinamide and
(S)-6-amino-5-[(4-hydroxyphenyl)ethynyl]-N-[methyl(oxo)phenyl-λ⁶-sulfanylidene]nicotinamide.

41. A compound according to claim 27 that is

S)-2-amino-5-[(3-hydroxyphenyl)ethynyl]-N-[methyl(oxo)phenyl-λ⁶-sulfanylidene]nicotinamide.

42. A compound which is a substituted aroyl sulfoximine compound which binds to the tyrosine kinase receptor.

43. The compound of claim 42 wherein the substituted aryl moiety is represented by formula IV below:

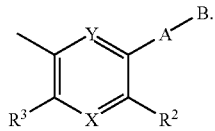

44. The compound of claim 41 wherein said substituted aryl moiety is represented by formula V below

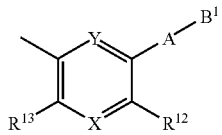

wherein $B^1$, $R^{12}$ and $R^{13}$ are selected from the group consisting of halogen, nitro, hydroxy, hydrocarbyl, substituted hydrocarbyl, amide, thioamide, amine, thioether and cyano.

* * * * *

UNITED STATES PATENT AND TRADEMARK OFFICE
CERTIFICATE OF CORRECTION

PATENT NO. : 7,915,443 B2
APPLICATION NO. : 11/941753
DATED : March 29, 2011
INVENTOR(S) : Julie A. Wurster et al.

Page 1 of 1

It is certified that error appears in the above-identified patent and that said Letters Patent is hereby corrected as shown below:

In column 184, line 50, delete " 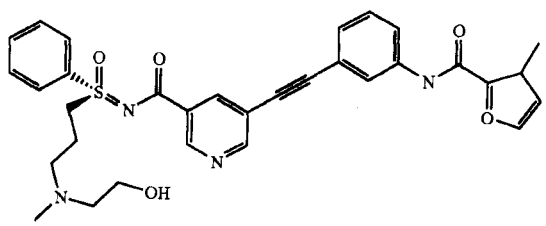 " and insert -- 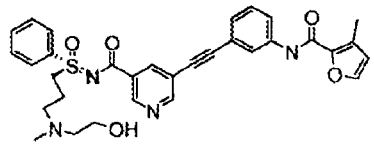 --, therefor.

Signed and Sealed this
Fifth Day of July, 2011

David J. Kappos
*Director of the United States Patent and Trademark Office*

UNITED STATES PATENT AND TRADEMARK OFFICE
CERTIFICATE OF CORRECTION

PATENT NO. : 7,915,443 B2
APPLICATION NO. : 11/941753
DATED : March 29, 2011
INVENTOR(S) : Julie A. Wurster et al.

It is certified that error appears in the above-identified patent and that said Letters Patent is hereby corrected as shown below:

In column 2, line 26, delete "fins" and insert -- fms --, therefor.

In column 3, line 29, delete "patents" and insert -- Patents --, therefor.

In column 4, line 2, delete "(CH$^2$)" and insert -- (CH2) --, therefor.

In column 6, line 41, delete "S(O)a(CR7R8)a(OR6)," and insert -- S(O)e(CR7R8)a(OR6), --, therefor.

In column 6, line 41, delete "(CR7R8)N(R6)2," and insert -- (CR7R8)aN(R6)2, --, therefor.

In column 79, line 6, delete "2.5NH2SO4" and insert -- 2.5N H2SO4 --, therefor.

In column 80, line 45, delete "Sonagashira" and insert -- Sonogashira --, therefor.

In column 85, line 22, delete "λ6sulfanylidene" and insert -- λ6-sulfanylidene --, therefor.

In column 97, line 76, delete "λ6" and insert -- $\lambda^6$ --, therefor.

In column 103, line 74, delete "λ6" and insert -- $\lambda^6$ --, therefor.

In column 105, line 39, delete "methyl-5-" and insert -- methyl-S- --, therefor.

In column 106, line 20, delete "5-" and insert -- S- --, therefor.

In column 106, line 53, delete "methyl-5-" and insert -- methyl-S- --, therefor.

In column 107, line 17, delete "0.31mmol)" and insert -- 0.31 mmol) --, therefor.

In column 110, line 57, delete "methyl-5-" and insert -- methyl-S- --, therefor.

In column 113, line 1, delete "5-iodosalicyclic" and insert -- 5-iodosalicylic --, therefor.

In column 118, line 23, delete "74%)" and insert -- 74%). --, therefor.

Signed and Sealed this
Twelfth Day of July, 2011

David J. Kappos
*Director of the United States Patent and Trademark Office*

CERTIFICATE OF CORRECTION (continued)
U.S. Pat. No. 7,915,443 B2

In column 121, line 63, delete "(5" and insert -- (~5 --, therefor.

In column 121, line 64, delete "(10" and insert -- (~10 --, therefor.

In column 124, line 1-3, delete "The combined organic extracts were dried over anhydrous Na2SO4(s) and then concentrated to give the title compound (0.13 g, 0.67 mmol, 72%)." and insert the same on Col. 123, Line 68, after "NaHCO3." as the continuation of the Paragraph.

In column 124, line 63, delete "(20" and insert -- (~20 --, therefor.

In column 128, line 15, delete "lambda~4~-" and insert -- S- --, therefor.

In column 130, line 1, delete "methyl-5-" and insert -- methyl-S- --, therefor.

In column 132, line 26, delete "methyl-5-" and insert -- methyl-S- --, therefor.

In column 133, line 29, delete "methyl-5-" and insert -- methyl-S- --, therefor.

In column 137, line 2, delete "81" and insert -- 81%). --, therefor.

In column 143, line 23, delete "0100%" and insert -- 100% --, therefor.

In column 171-172, line 8, delete

"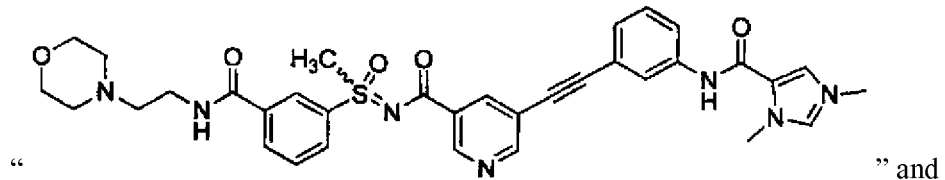" and insert -- 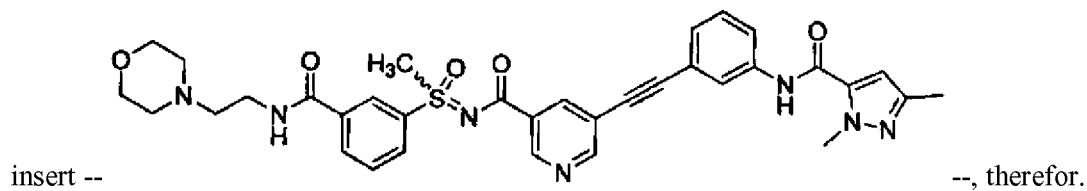 --, therefor.

In column 171-172, line 51, delete

"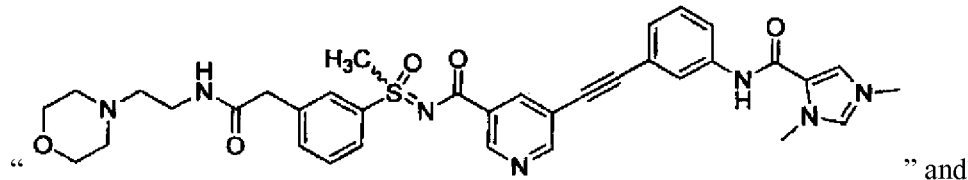" and insert -- 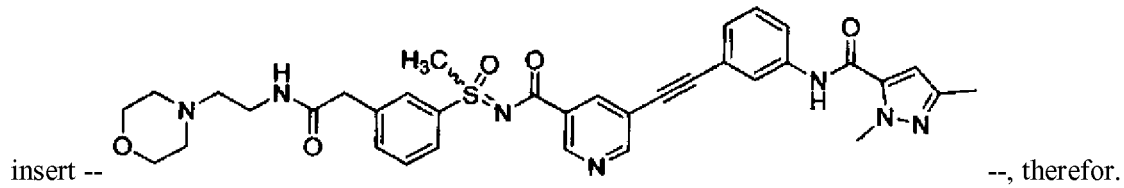 --, therefor.

CERTIFICATE OF CORRECTION (continued)

U.S. Pat. No. 7,915,443 B2

In column 171-172, line 39, delete

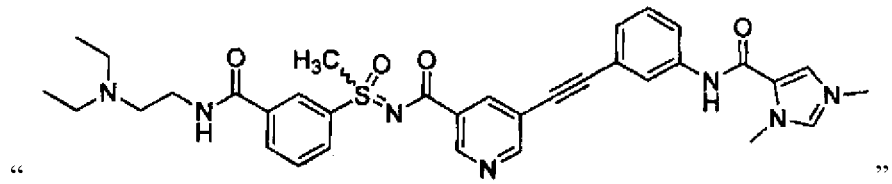

" " and

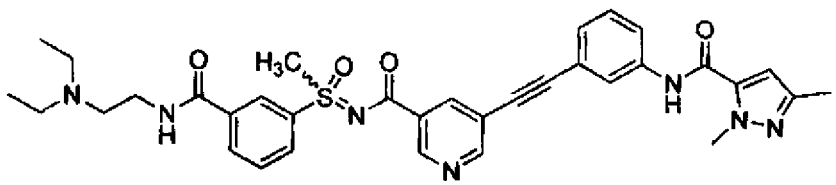

insert -- -- , therefor.

In column 190, line 67, delete "43" and insert -- 43%). --, therefor.

In column 197, line 41, delete "methyl-5-" and insert -- methyl-S- --, therefor.

In column 201, line 40, delete "pH~5" and insert -- pH ~5 --, therefor.

In column 209, line 46, delete "lambda~4~-" and insert -- λ4 --, therefor.

In column 213, line 45, delete "60☐ C." and insert -- 60° C. --, therefor.

In column 214, line 5, delete "65☐C." and insert -- 65° C. --, therefor.

In column 214, line 53, delete "aroyl" and insert -- aryl --, therefor.

In column 215, line 21, delete "aroyl" and insert -- aryl --, therefor.

In column 215, line 62, in claim 1, delete "Wherein:" and insert -- wherein: --, therefor.

In column 216, line 29, in claim 1, delete "(O)R<sub>6</sub>," and insert -- (O)R$^6$, --, therefor.

In column 223, line 15, in claim 13, delete

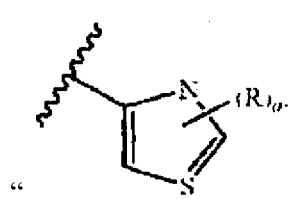

" " and insert --

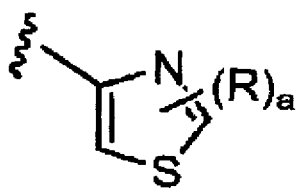

• --, therefor.

In column 224, line 24, in claim 24, delete "(CR$^7$R$^8$)C(O)R$^6$," and insert -- (CR$^7$R$^8$)$_a$C(O)R$^6$, --, therefor.

In column 224, line 37, in claim 24, delete "O(CR$^7$R$^8$)(OR$^6$), N(R$^6$) (CR$^7$R$^8$) (OR$^6$)," and insert -- O(CR$^7$R$^8$)$_a$(OR$^6$), N(R$^6$)(CR$^7$R$^8$)$_a$(OR$^6$), --, therefor.

CERTIFICATE OF CORRECTION (continued)
U.S. Pat. No. 7,915,443 B2

In column 226, line 8, in claim 29, delete "$N(R^6)(CR^7R^8)(OR^6),$" and insert -- $N(R^6)(CR^7R^8)_a(OR^6),$ --, therefor.

In column 228, line 66, in claim 41, delete "S)" and insert -- (S) --, therefor.

In column 229, line 1, in claim 42, delete "aroyl" and insert -- aryl --, therefor.